United States Patent
Chua et al.

(10) Patent No.: US 10,988,513 B2
(45) Date of Patent: Apr. 27, 2021

(54) MALTOSE DEPENDENT DEGRONS, MALTOSE-RESPONSIVE PROMOTERS, STABILIZATION CONSTRUCTS, AND THEIR USE IN PRODUCTION OF NON-CATABOLIC COMPOUNDS

(71) Applicants: AMYRIS, INC., Emeryville, CA (US); TOTAL MARKETING SERVICES, Puteaux (FR)

(72) Inventors: Penelope R. Chua, Emeryville, CA (US); Hanxiao Jiang, Emeryville, CA (US); Adam Leon Meadows, Emeryville, CA (US)

(73) Assignees: AMYRIS, INC., Emeryville, CA (US); TOTAL MARKETING SERVICES, Puteaux (FR)

( * ) Notice: Subject to any disclaimer, the term of this patent is extended or adjusted under 35 U.S.C. 154(b) by 188 days.

(21) Appl. No.: 15/738,918

(22) PCT Filed: Jun. 24, 2016

(86) PCT No.: PCT/US2016/039397
§ 371 (c)(1),
(2) Date: Dec. 21, 2017

(87) PCT Pub. No.: WO2016/210350
PCT Pub. Date: Dec. 29, 2016

(65) Prior Publication Data
US 2018/0171341 A1 Jun. 21, 2018

Related U.S. Application Data

(60) Provisional application No. 62/184,793, filed on Jun. 25, 2015, provisional application No. 62/266,436, filed on Dec. 11, 2015.

(51) Int. Cl.
*C07K 14/395* (2006.01)
*C12N 1/16* (2006.01)
*C12P 19/62* (2006.01)
*C12P 5/02* (2006.01)
*C12P 7/64* (2006.01)
*C12P 21/00* (2006.01)
*C12N 15/52* (2006.01)
*C12N 15/63* (2006.01)
*C12N 15/65* (2006.01)
*C12P 21/02* (2006.01)

(52) U.S. Cl.
CPC .............. *C07K 14/395* (2013.01); *C12N 1/16* (2013.01); *C12N 15/52* (2013.01); *C12N 15/635* (2013.01); *C12N 15/65* (2013.01); *C12P 5/02* (2013.01); *C12P 5/026* (2013.01); *C12P 7/64* (2013.01); *C12P 19/62* (2013.01); *C12P 21/00* (2013.01); *C12P 21/02* (2013.01); *C07K 2319/95* (2013.01); *C12N 2330/51* (2013.01); *C12Y 503/03002* (2013.01)

(58) Field of Classification Search
None
See application file for complete search history.

(56) References Cited

FOREIGN PATENT DOCUMENTS

WO  WO 2014/025941 A1  2/2014
WO  WO 2015/020649 A1  2/2015

OTHER PUBLICATIONS

International Search report and written opinion dated Aug. 29, 2016 for PCT/US2016/039397, 15 pages.
Choi et al., "Design of protein switches based on an ensemble model of allostery", Nature Communications, 6:6968, Apr. 22, 2015, pp. 1-9, XP002760503, DOI: 10.1038/ncomms7968.
Jiang et al., "Controlling isoprenoid production using a microaerobic-responsive switch in yeast", Genetics Society of America Conferences, Yeast Genetics Meeting, 2014, University of Washington, Seattle, Abstracts Book, 2014, p. Cover + 109, Retrieved from the Internet: URL:http://www.genetics-gsa.org/yeast/2014/asp/Content/Yeast 2014 Abstracts_Book.pdf [retrieved on Aug. 2, 2016].
New et al., "Different levels of catabolite repression optimize growth in stable and variable environments", Plos Biology, vol. 12, 2014, pp. 1-22.
Rienzo et al., "Different mechanisms confer gradual control and memory at nutrient- and stress-regulated genes in yeast", Molecular And Cellular Biology, vol. 35, Aug. 17, 2015, pp. 3669-3683.
Sandoval et al., "Use of pantothenate as a metabolic switch increases the genetic stability of farnesene producing *Saccharomyces cerevisiae*", Metabolic Engineering, vol. 25, 2014, pp. 215-226.

(Continued)

Primary Examiner — Channing S Mahatan
(74) Attorney, Agent, or Firm — Squire Patton Boggs (US) LLP

(57) ABSTRACT

The present disclosure relates to the use of a maltose dependent degron to control stability of a protein of interest fused thereto at the post-translational level. The present disclosure also relates to the use of a maltose dependent degron in combination with a maltose-responsive promoter to control gene expression at the transcriptional level and to control protein stability at the post-translational level. The present disclosure also relates to the use of a stabilization construct that couples expression of a cell-growth-affecting protein with the production of non-catabolic compounds. The present disclosure further relates to the use of a synthetic maltose-responsive promoter. The present disclosure further provides compositions and methods for using a maltose dependent degron, a maltose-responsive promoter, and a stabilization construct, either alone or in various combinations, for the production of non-catabolic compounds in genetically modified host cells.

25 Claims, 26 Drawing Sheets
Specification includes a Sequence Listing.

(56) References Cited

OTHER PUBLICATIONS

Walker et al., "Mutations in maltose-binding protein that alter affinity and solubility properties", Applied Microbiology and Biotechnology, vol. 88, 2010, pp. 187-197.
Weinhandl et al., "Carbon source dependent promoters in yeast", Microbial Cell Factories, vol. 13, 2014, pp. 1-17.

Global DNA alignment. Reference molecule: pMAL12_1, Region 1 to 11
Sequences : 7. Scoring matrix: Linear (Mismatch 2, OpenGap 4, ExtGap 1 )

Sequence View: Similarity Format, Color areas of high matches at same base position

```
pMAL12_1   1 gataatatttc--
pMAL12_2   1 --gaaaatttcgc
pMAL12_3   1 gttaaagtttac-
pMAL12_4   1 --gaaattttcgc
pMAL32_1   1 tataatatttc--
pMAL32_3   1 gtttaagtttac-
pMAL32_4   1 --gaagttttcgc
```

Global DNA alignment. Reference molecule: pMAL12_1, Region 1 to 11
Sequences : 8. Scoring matrix: Linear (Mismatch 2, OpenGap 4, ExtGap 1 )

Sequence View: Similarity Format, Color areas of high matches at same base position

```
pMAL12_1   1 gataatatttc--
pMAL12_2   1 --gaaaatttcgc
pMAL12_3   1 gttaaagtttac-
pMAL12_4   1 --gaaattttcgc
pMAL12_1r  1 -gaaatattatc-
pMAL12_2r  1 gcgaaatttc--
pMAL12_3r  1 -gtaaacttaac-
pMAL12_4r  1 gcgaaaatttc--
```

FIG. 13B

| Promoter | Induced<br><br>In sucrose and maltose | Un-induced<br><br>In raffinose | Un-induced<br><br>In sucrose |
|---|---|---|---|
| pGAL1 | 11595% | 21869% | 12448% |
| pGMAL_v16 | 9193% | 177% | 182% |
| pGMAL_v17 | 6659% | 184% | 148% |
| pGMAL_v10 | 5842% | 158% | 172% |
| pGMAL_v12 | 4626% | 117% | 125% |
| pTDH3 | 4116% | 7700% | 4649% |
| pGMAL_v13 | 3994% | 131% | 123% |
| pGMAL_v18 | 3485% | 160% | 134% |
| pGMAL_v11 | 3021% | 94% | 115% |
| pG7MAL_v8 | 2973% | 124% | 113% |
| pGMAL_v9 | 2623% | 150% | 150% |
| pGMAL_v11 | 2575% | 108% | 107% |
| pG2MAL_V10 | 2188% | 113% | 113% |
| pGMAL_v6 | 1768% | 128% | 133% |
| pMAL11 | 1480% | 601% | 171% |
| pMAL12 | 1418% | 491% | 185% |
| pG7MAL_v4 | 1405% | 171% | 120% |
| pG712_MAL_V14 | 1352% | 164% | 113% |
| pG271_MAL_V12 | 1330% | 141% | 111% |
| pMAL32 | 1223% | 209% | 138% |
| pGMAL_v15 | 1208% | 141% | 106% |

FIG. 14A

| Promoter | Induced In sucrose and maltose | Un-induced In raffinose | Un-induced In sucrose |
|---|---|---|---|
| pG7MAL_v9 | 1176% | 136% | 112% |
| pG7MAL_v6 | 1043% | 128% | 104% |
| pG2MAL_V6 | 954% | 159% | 124% |
| pG721_MAL_v11 | 885% | 170% | 114% |
| pG2MAL_V8 | 873% | 112% | 107% |
| pGMAL_v14 | 820% | 90% | 100% |
| pG2MAL_V7 | 640% | 170% | 113% |
| pG2MAL_V3 | 479% | 167% | 130% |
| pG2MAL_V5 | 448% | 103% | 95% |
| pG2MAL_V9 | 432% | 139% | 116% |
| pGMAL_v5 | 330% | 112% | 116% |
| pGMAL_v7 | 322% | 106% | 120% |
| pMAL31 | 279% | 169% | 121% |
| pG172_MAL_V13 | 192% | 124% | 108% |
| pG2MAL_V1 | 186% | 126% | 113% |
| pG2MAL_V2 | 126% | 109% | 103% |
| pG7MAL_v2 | 108% | 121% | 105% |

FIG. 14B

SEQUENCE LISTING

```
<160> NUMBER OF SEQ ID NOS: 110

<210> SEQ ID NO 1
<211> LENGTH: 1113
<212> TYPE: DNA
<213> ORGANISM: Escherichia coli
<220> FEATURE:
<221> NAME/KEY: misc_feature
<222> LOCATION: (1)..(1113)
<223> OTHER INFORMATION: wild-type MBP Nucleotide sequence

<400> SEQUENCE: 1
atgaaaatcg aagaaggtaa gttagtcatt tggatcaacg gtgacaaggg ttacaatggt       60
ttggctgaag ttggtaagaa gtttgaaaaa gacactggta tcaaggttac cgtcgaacat      120
ccagataagt tggaagaaaa gttcccacaa gtcgccgcta ctggtgatgg tccagatatt      180
atcttctggg ctcacgacag attcggtggt tacgctcaat ctggtttgtt agccgaaatt      240
actcctgaca aggctttcca agacaaatta tacccattca cctgggatgc tgtcagatat      300
aacggtaaat tgatcgctta cccaatcgct gtcgaagctt tgtccttgat ctacaacaag      360
gatttgttac ctaacccacc aaaaacttgg gaagaaatcc cagctttgga caaggaattg      420
aaagctaaag gtaaatccgc tttgatgttc aacttacaag aaccatattt cacttggcct      480
ttgattgctg ctgatggtgg ttatgccttt aagtacgaaa acggtaagta cgatattaag      540
```

-continued

```
gacgtcggtg ttgacaacgc cggtgctaag gctggtttaa cttctcttggt cgatttgatc   600
aagaacaagc atatgaacgc cgacactgac tactctatcg ctgaagccgc tttcaataag    660
ggtgagactg ctatgactat taacggtcct tgggcttggt ctaatatcga tacttctaag    720
gtcaactacg gtgttaccgt tttgccaacc ttcaaaggtc aaccatccaa gccatttgtt    780
ggtgttttgt ccgctggtat caacgctgct tctcctaaca aggaattggc taaggaattc    840
ttggaaaact atttgttgac tgatgaaggt ttagaagctg ttaacaagga caagccattg    900
ggtgccgttg ccttgaagtc ttacgaagaa gaattggcca aggacctag aattgctgct     960
actatggaaa atgcccaaaa aggtgagatc atgccaaaca ttccacaaat gtctgctttc   1020
tggtatgctg ttagaactgc cgtcattaac gctgcttccg gtagacaaac tgttgatgaa   1080
gccttgaaag atgcccaaac taactcctct tcc                                1113
```

<210> SEQ ID NO 2
<211> LENGTH: 370
<212> TYPE: PRT
<213> ORGANISM: Escherichia coli
<220> FEATURE:
<221> NAME/KEY: misc_feature
<222> LOCATION: (1)..(370)
<223> OTHER INFORMATION: wild-type MBP Amino acid sequence

<400> SEQUENCE: 2

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255
```

```
Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser
    370

<210> SEQ ID NO 3
<211> LENGTH: 1098
<212> TYPE: DNA
<213> ORGANISM: Artificial Sequence
<220> FEATURE:
<223> OTHER INFORMATION: Synthetic: 3A6 Nucleotide sequence

<400> SEQUENCE: 3
atgaaaatcg aagaaggtaa gttagtcact tggatcaacg gtgacaaggg ttacaatggt      60
ttggctgaag ctggtaagaa gtttgaaaaa gacactggta tcaaggttac cgtcgaacat     120
ccagttgagt tggaagaaaa attcccacaa gtcgccgcta ctggtgatgg tccagatatt     180
atcttctggg ctcacgacag attcggtggt tacgctcaat ctggtttgtt agccgaaatt     240
actcctggca aggctttcca agacaaatta tacacattca cctgggatgc tgtcagatat     300
aacggtaaat tgatcgctta cccaatcgct gtcgaagctt gtccttgat ctacaacaag      360 gatttgttac ctaacccacc aaaaacttgg aagaaaatcc cagctttgga caaggaattg     420
aaagctaaag gtaaatccgc tttgatcttc aacttacaag aaccatattt cacttggcct     480
ttgattgctg ctgatggtgg taatgccttt aagtacgaaa acggtaagta cgatattaag     540
gacgtcggtg ttgacagcgc cggtgctaag gctggtttaa cttcttggt cgatttgatc     600 aagaacaagc atatgaacgc cgacactgac tactctatcg ctgaagtcgc tttcaataag     660
ggtgagactg ctatgactat taacggtcct tgggcttggt ctaatatcga tacttctaag     720
gtcaactacg gtgttaccgt tttgccaaca ttcaaaggtc aaccatccaa gccatttgtt     780
ggtgttttgt ccgctggtat caacgctgct tctcctaaca aggaattggc taaggaattc     840
ttggaaaact atttgttgac tgatgaaggt ttagaagctg ttaacaagga caagccattg     900
ggtgccgttg ccttgaagtc ttacgaagaa gaattggcca aggacctag aattgctgct     960 actatggaaa atgcccaaaa aggtgagatc atgccaaaca ttccacaaat gtctgctttc    1020
tggtatgctg ttagaactgc cgtcattaac gctgcttccg gtagacaaag tgttgatgaa    1080
gccttgaaag atgcctaa                                                  1098

<210> SEQ ID NO 4
<211> LENGTH: 365
<212> TYPE: PRT
<213> ORGANISM: Artificial Sequence
<220> FEATURE:
```

<223> OTHER INFORMATION: Synthetic: 3A6 Amino acid sequence

<400> SEQUENCE: 4

```
Met Lys Ile Glu Glu Gly Lys Leu Val Thr Trp Ile Asn Gly Asp Lys
1               5                   10                  15

Gly Tyr Asn Gly Leu Ala Glu Ala Gly Lys Lys Phe Glu Lys Asp Thr
            20                  25                  30

Gly Ile Lys Val Thr Val Glu His Pro Val Glu Leu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Gly Lys Ala Phe Gln Asp Lys Leu Tyr Thr Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Ile Phe Asn Leu Gln Glu Pro Tyr Phe Thr Trp Pro
145                 150                 155                 160

Leu Ile Ala Ala Asp Gly Gly Asn Ala Phe Lys Tyr Glu Asn Gly Lys
                165                 170                 175

Tyr Asp Ile Lys Asp Val Gly Val Asp Ser Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Val Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Ser Val Asp Glu Ala Leu Lys Asp Ala
        355                 360                 365
```

<210> SEQ ID NO 5
<211> LENGTH: 1098
<212> TYPE: DNA
<213> ORGANISM: Artificial Sequence
<220> FEATURE:

<223> OTHER INFORMATION: Synthetic: 4D3 Nucleotide sequence

<400> SEQUENCE: 5

```
atgaaaatcg aagaaggtaa gttagtcact tggatcaacg gtgacaaggg ttacaatggt      60
ttggctgaag ctggtaagaa gtttgaaaaa gacactggta tcaaggttac cgtcgaacat     120
ccagttgagt tggaagaaaa gttcccacaa gtcgccgcta ctggtgatgg tccagatatt     180
atcttctggg ctcacgacag attcggtggt tacgctcaat ctggtttgtt agccgaaatt     240
actcctggca aggctttcca agacaaatta tacccattca cctgggatgc tgtcagatat     300
aacggtaaat tgatcgctta cccaatcgct gtcgaagctt tgtccttgat ctacaacaag     360
gatttgttac ctaacccacc aaaaacttgg gaagaaatcc cagctttgga caaggaattg     420
aaagctaaag gtaaatccgc tttgatcttc aacttacaag aaccatattt cacttggcct     480
ttgattgctg ctgatggtgg taatgccttt aagtacgaaa acggtaagta cgatattaag     540
gacgtcggtg ttgacagcgc cggtgctaag gctggtttaa ctttcttggt cgatttgatc     600
aagaacaagc atatgaacgc cgacactgac tactctatcg ctgaagtcgc ttcaataag      660
ggtgagactg ctatgactat taacggtcct tgggcttggt ctaatatcaa tacttctaag     720
gtcaactacg gtgttaccgt tttgccaacc ttcaaaggtc aaccatccaa gccatttgtt     780
ggtgttttgt ccgctggtat caacgctgct tctcctaaca aggaattggc taaggaattc     840
ttggaaaact atttgttgac tgatgaaggt ttagaagctg ttaacaagga caagccattg     900
ggtgccgttg ccttgaagtc ttacgaagaa gaattggcca aggacctag aattgctgct     960
actatggaaa atgcccaaaa aggtgagatc atgccaaaca ttccacaaat gtctgctttc    1020
tggtatgctg ttagaactgc cgtcattaac gctgcttccg gtagacaaac tgttgatgaa    1080
gccttgaaag atgcctaa                                                  1098
```

<210> SEQ ID NO 6
<211> LENGTH: 365
<212> TYPE: PRT
<213> ORGANISM: Artificial Sequence
<220> FEATURE:
<223> OTHER INFORMATION: Synthetic: 4D3 Amino acid sequence

<400> SEQUENCE: 6

```
Met Lys Ile Glu Glu Gly Lys Leu Val Thr Trp Ile Asn Gly Asp Lys
1               5                   10                  15

Gly Tyr Asn Gly Leu Ala Glu Ala Gly Lys Lys Phe Glu Lys Asp Thr
            20                  25                  30

Gly Ile Lys Val Thr Val Glu His Pro Val Glu Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Gly Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140
```

Lys Ser Ala Leu Ile Phe Asn Leu Gln Glu Pro Tyr Phe Thr Trp Pro
145                 150                 155                 160

Leu Ile Ala Ala Asp Gly Gly Asn Ala Phe Lys Tyr Glu Asn Gly Lys
                165                 170                 175

Tyr Asp Ile Lys Asp Val Gly Val Asp Ser Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Val Ala Phe Asn Lys Gly Glu Thr Ala
    210                 215                 220

Met Thr Ile Asn Gly Pro Trp Ala Trp Ser Asn Ile Asn Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala
        355                 360                 365

<210> SEQ ID NO 7
<211> LENGTH: 1098
<212> TYPE: DNA
<213> ORGANISM: Artificial Sequence
<220> FEATURE:
<223> OTHER INFORMATION: Synthetic: 5A2 Nucleotide sequence

<400> SEQUENCE: 7
atgaaaatcg aagaaggtaa gttagtcact tggatcaacg gtgacaaggg ttacaatggt    60
ttggctgaag ctggtaagaa gtttgaaaaa gacactggta tcaaggttac cgtcgaacat    120
ccagttgagt ggaagaaaaa gttcccacaa gtcgccgcta ctggtgatgg tccagatatt    180
atcttctggg ctcacgacag attcggtggt tacgctcaat ctggtttgtt agccgaaatt    240
actcctggca aggctttcca agacaaatta tacccattca cctgggatgc tgtcagatat    300
aacggtaaat tgatcgctta cccaatcgct gtcgaagctt gtccttgat ctacaacaag    360 gatttgttac ctaacccacc aaaaacttgg gaagaaatcc cagctttgga caaggaattg    420
aaagctaaag gtaaatccgc tttgatcttc aacttacaag aaccatattt cacttggcct    480
ttgattgctg ctgatggtgg taatgccttt aagtacgaaa acggtaagta cgatattaag    540
gacgtcggtg ttgacagcgc cggtgctaag gctggtttaa cttccttggt cgatttgatc    600
aagaacaagc atatgaacgc cgacactgac tactctatcg ctgaagtcgc tttcaataag    660
ggtgagactg ctatgactat taacggtcct tgggcttggt ctaatatcga tacttctaag    720
gtcaactacg gtgttaccgt tttgccaacc ttcaaaggtc aaccatccaa gccatttgtt    780
ggtgttttgt ccgctggtat caacgctgct tctcctaaca aggaattggc taaggaattc    840

```
ttggaaaact atttgttgac tgatgaaggt ttagaagctg ttaacaagga caagccattg    900
ggtgccgttg ccttgaagtc ttacgaagaa gaattggcca aggaccctag aattgctgct    960
actatggaaa atgcccaaaa aggtgagatc atgccaaaca ttccacaaat gtctactttc   1020
tggtatgctg ttagaactgc cgtcattaac gctgcttccg gtagacaaac tgttgatgaa   1080
gccttgaaag atgcctaa                                                 1098
```

<210> SEQ ID NO 8
<211> LENGTH: 365
<212> TYPE: PRT
<213> ORGANISM: Artificial Sequence
<220> FEATURE:
<223> OTHER INFORMATION: Synthetic: 5A2 Amino acid sequence

<400> SEQUENCE: 8

```
Met Lys Ile Glu Glu Gly Lys Leu Val Thr Trp Ile Asn Gly Asp Lys
1               5                   10                  15

Gly Tyr Asn Gly Leu Ala Glu Ala Gly Lys Lys Phe Glu Lys Asp Thr
            20                  25                  30

Gly Ile Lys Val Thr Val Glu His Pro Val Glu Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Gly Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Ile Phe Asn Leu Gln Glu Pro Tyr Phe Thr Trp Pro
145                 150                 155                 160

Leu Ile Ala Ala Asp Gly Gly Asn Ala Phe Lys Tyr Glu Asn Gly Lys
                165                 170                 175

Tyr Asp Ile Lys Asp Val Gly Val Asp Ser Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Val Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
```

```
                305                 310                 315                 320

Thr Met Glu Asn Ala Gln Lys Gly Glu Ile Met Pro Asn Ile Pro Gln
                325                 330                 335

Met Ser Thr Phe Trp Tyr Ala Val Arg Thr Ala Val Ile Asn Ala Ala
                340                 345                 350

Ser Gly Arg Gln Thr Val Asp Glu Ala Leu Lys Asp Ala
                355                 360                 365

<210> SEQ ID NO 9
<211> LENGTH: 1098
<212> TYPE: DNA
<213> ORGANISM: Artificial Sequence
<220> FEATURE:
<223> OTHER INFORMATION: Synthetic: 5F3 Nucleotide sequence

<400> SEQUENCE: 9
atgaaaatcg aagaaggtaa gttagtcact tggatcaacg gtgacaaggg ttacaatggt      60
ttggctgaag ctggtaagaa gtttgaaaaa gacactggta tcaaggttac cgtcgaacat     120
ccagttgagt tggaagaaaa gttcccacaa gtcgccgcta ctggtgatgg tccagatatt     180
atcttctggg ctcacgacag attcggtggt tacgctcaat ctggtttgtt agccgaaatt     240
actcctggca aggctttcca agacaaatta tacccattca cctgggatgc tgtcagatat     300
aacggtaaat tgatcgctta cccaatcgct gtcgaagctt tgtccttgat ctacaacaag     360
gatttgttac ctaacccacc aaaaacttgg gaagaaatcc agctttggac aaggaattg     420 aaagctaaag gtaaatccgc tttgatcttc aacttacaag aaccatattt cacttggcct     480
ttgattgctg ctgatggtgg taatgccttt aagtacgaaa acggtaagta cgatattaag     540
gacgtcggtg ttgacagcgc cggtgctaag gctggtttaa cttctcttggt cgatttgatc     600 aagaacaagc atatgaacgc cgacactgac tactctatcg ctgaagtcgc tttcaataag     660
ggtgagactg ctatgactat taacggtcct tgggcttggt ctaatatcga tacttctaag     720
gtcgactacg tgttaccgt tttgccaacc ttcaaaggtc aaccatccaa gccatttgtt     780
ggtgttttgt ccgctggtat caacgctgct tctcctaaca aggaattggc taaggaattc     840
ttggaaaact atttgttgac tgatgaaggt ttagaagctg ttaacaagga caagccattg     900
ggtgccgttg ccttgaagtc ttacgaagaa gaattggcca aggacctag aattgctgct     960 actatggaaa tgcccaaaa aggtgagatc atgccaaaca ttccacaaat gtctgctttc    1020
tggtatgctg ttagaactgc cgtcattaac gctgcttccg gtagacaaac tgttgatgaa    1080
gccttgaaag atgcctaa                                                 1098

<210> SEQ ID NO 10
<211> LENGTH: 365
<212> TYPE: PRT
<213> ORGANISM: Artificial Sequence
<220> FEATURE:
<223> OTHER INFORMATION: Synthetic: 5F3 Amino acid sequence

<400> SEQUENCE: 10

Met Lys Ile Glu Glu Gly Lys Leu Val Thr Trp Ile Asn Gly Asp Lys
1               5                   10                  15

Gly Tyr Asn Gly Leu Ala Glu Ala Gly Lys Lys Phe Glu Lys Asp Thr
                20                  25                  30

Gly Ile Lys Val Thr Val Glu His Pro Val Glu Leu Glu Glu Lys Phe
            35                  40                  45

Pro Gln Val Ala Ala Thr Gly Asp Gly Pro Asp Ile Ile Phe Trp Ala
```

```
             50                  55                  60
His Asp Arg Phe Gly Gly Tyr Ala Gln Ser Gly Leu Leu Ala Glu Ile
 65                  70                  75                  80

Thr Pro Gly Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Ile Phe Asn Leu Gln Glu Pro Tyr Phe Thr Trp Pro
145                 150                 155                 160

Leu Ile Ala Ala Asp Gly Gly Asn Ala Phe Lys Tyr Glu Asn Gly Lys
                165                 170                 175

Tyr Asp Ile Lys Asp Val Gly Val Asp Ser Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Val Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asp Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala
            355                 360                 365

<210> SEQ ID NO 11
<211> LENGTH: 1164
<212> TYPE: DNA
<213> ORGANISM: Artificial Sequence
<220> FEATURE:
<223> OTHER INFORMATION: Synthetic: L8 Nucleotide sequence

<400> SEQUENCE: 11
atgaaaatcg aagaaggtaa gttagtcact tggatcaacg gtgacaaggg ttacaatggt     60
ttggctgaag ctggtaagaa gtttgaaaaa gacactggta tcaaggttac cgtcgaacat    120
ccagttaagt tggaagaaaa gttcccacaa gtcgccgcta ctggtgatgg tccagatatt    180
atcttctggg ctcacgacag attcggtggt tacgctcaat ctggtttgtt agccgaaatt    240
actcctgaca aggctttcca agacaaatta tacccattca cctgggatgc tgtcagatat    300
```

```
aacggtaaat tgatcgctta cccaatcact gtcgaagctt tgtccttgat ctacaacaag    360
gatttgttac ctaacccacc aaaaacttgg gaagaaatcc cagctttgga caaggaattg    420
aaagctaaag gtaaatccgc tttgatcttc aacttacaag aaccatattt cacttggcct    480
ttgattgctg ctgatggtgg ttatgccttt aagtacgaaa acggtaagta cgatattaag    540
gacgtcggtg ttgacaacgc cggtgctaag gctggtttaa ctttcttggt cgatttgatc    600
aagaacaagc atatgaacgc cgacactgac tactctatcg ctgaagtcgc tttcaataag    660
ggtgagactg ctatgactat taacggtcct tgggcttggt ctaatatcga tacttctaag    720
gtcaactacg gtgttaccgt tttgccaacc ttcaaaggtc aaccatccaa gccatttgtt    780
ggtgttttgt ccgctggtat caacgctgct tctcctaaca aggaattggc taaggaattc    840
ttggaaaact atttgttgac tgatgaaggt ttagaagctg ttaacaagga caagccattg    900
ggtgccgttg ccttgaagtc ttacgaagaa gaattggcca aggacctag aattgctgct    960 actatggaaa atgcccaaaa aggtgagatc atgccaaaca ttccacaaat gtctgctttc   1020
tggtatgctg ttagaactgc cgtcattaac gctgcttccg gtagacaaac tgttgatgaa   1080
gccttgaaag atgcctaaac taactcctct tccaacaaca ataataacaa caacaacaac   1140
aacttgggta tcgaaggtag ataa                                         1164
```

<210> SEQ ID NO 12
<211> LENGTH: 365
<212> TYPE: PRT
<213> ORGANISM: Artificial Sequence
<220> FEATURE:
<223> OTHER INFORMATION: Synthetic: L8 Amino acid sequence

<400> SEQUENCE: 12

```
Met Lys Ile Glu Glu Gly Lys Leu Val Thr Trp Ile Asn Gly Asp Lys
1               5                   10                  15

Gly Tyr Asn Gly Leu Ala Glu Ala Gly Lys Lys Phe Glu Lys Asp Thr
                20                  25                  30

Gly Ile Lys Val Thr Val Glu His Pro Val Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Thr Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Ile Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205
```

```
Thr Asp Tyr Ser Ile Ala Glu Val Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala
        355                 360                 365
```

<210> SEQ ID NO 13
<211> LENGTH: 1098
<212> TYPE: DNA
<213> ORGANISM: Artificial Sequence
<220> FEATURE:
<223> OTHER INFORMATION: Synthetic: L8_v4d nucleotide sequence

<400> SEQUENCE: 13

```
atgaaaatcg aagaaggtaa gttagtcact tggatcaacg gtgacaaggg ttacaatggt     60
ttggctgaag ctggtaagaa gtttgaaaaa gacactggta tcaaggttac cgtcgaacat    120
ccagttgagt tggaagaaaa gttcccacaa gtcgccgcta ctggtgatgg tccagatatt    180
atcttctggg ctcacgacag attcggtggt tacgctcaat ctggtttgtt agccgaaatt    240
actcctggca aggcttttcca agacaaatta tacccattca cctgggatgc tgtcagatat    300
aacggtaaat tgatcgctta cccaatcgct gtcgaagctt tgtccttgat ctacaacaag    360
gatttgttac ctaacccacc aaaaacttgg gaagaaatcc cagctttgga caaggaattg    420
aaagctaaag gtaaatccgc tttgatcttc aacttacaag aaccatattt cacttggcct    480
ttgattgctg ctgatggtgg taatgccttt aagtacgaaa acgtaagta cgatattaag    540
gacgtcggtg ttgacagcgc cggtgctaag gctggtttaa cttcttggt cgatttgatc    600
aagaacaagc atatgaacgc cgacactgac tactctatcg ctgaagtcgc tttcaataag    660
ggtgagactg ctatgactat taacggtcct tgggcttggt ctaatatcga tacttctaag    720
gtcaactacg gtgttaccgt tttgccaacc ttcaaaggtc aaccatccaa gccatttgtt    780
ggtgttttgt ccgctggtat caacgctgct tctcctaaca aggaattggc taaggaattc    840
ttggaaaact atttgttgac tgatgaaggt ttagaagctg ttaacaagga caagccattg    900
ggtgccgttg ccttgaagtc ttacgaagaa gaattggcca aggacctag aattgctgct    960
actatggaaa atgcccaaaa aggtgagatc atgccaaaca ttccacaaat gtctgctttc   1020
tggtatgctg ttagaactgc cgtcattaac gctgcttccg gtagacaaac tgttgatgaa   1080
gccttgaaag atgcctaa                                                 1098
```

<210> SEQ ID NO 14
<211> LENGTH: 365
<212> TYPE: PRT
<213> ORGANISM: Artificial Sequence
<220> FEATURE:
<223> OTHER INFORMATION: Synthetic: L8_v4d Amino acid sequence

<400> SEQUENCE: 14

```
Met Lys Ile Glu Glu Gly Lys Leu Val Thr Trp Ile Asn Gly Asp Lys
1               5                   10                  15

Gly Tyr Asn Gly Leu Ala Glu Ala Gly Lys Lys Phe Glu Lys Asp Thr
            20                  25                  30

Gly Ile Lys Val Thr Val Glu His Pro Val Glu Leu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Gly Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Ile Phe Asn Leu Gln Glu Pro Tyr Phe Thr Trp Pro
145                 150                 155                 160

Leu Ile Ala Ala Asp Gly Gly Asn Ala Phe Lys Tyr Glu Asn Gly Lys
                165                 170                 175

Tyr Asp Ile Lys Asp Val Gly Val Asp Ser Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Val Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala
        355                 360                 365
```

<210> SEQ ID NO 15
<211> LENGTH: 1164
<212> TYPE: DNA
<213> ORGANISM: Artificial Sequence
<220> FEATURE:
<223> OTHER INFORMATION: Synthetic: H8 Nucleotide sequence

<400> SEQUENCE: 15

```
atgaaaatcg aagaaggtaa gttagtcatt tggatcaacg gtgacaaggg ttacaatggt      60
tcggctgaag ttggtaagaa gtttgaaaaa gacactggta tcaaggttac cgtcgaacat     120
ccagataagt tggaagaaaa gttcccacaa gtcgccgcta ctggtgatgg tccagatatt     180
atcttctgga ctcacgacag attcggtggt tacgctcaat ctggtttgtt agccgaaatt     240
actcctgaca aggctttcca agacaaatta tacccattca cctgggatgc tgtcagatat     300
aacggtaaat tgatcgctta cccaatcgct gtcgaagctt tgtccttgat ctacaacaag     360
gatttgttac taacccacc aaaaacttgg aagaaatcc cagctatgga caaggaattg      420
aaagctaaag gtaaatccgc tttgatgttc aacttacaag aaccatattt cacttggcct     480
ttgattgctg ctgatggtgg ttatgccttt aagtacgaaa acggtaagca cgatattaag     540
gacgtcggtg ttgacaaccc cggtgctaag gctggtttaa cttctcttggt cgatttgatc     600
aagaacaagc atatgaacgc cgacactgac tactctatcg ctgaagccgc tttcaataag     660
ggtgagactg ctatgactat taacggtcct tgggcttggt ctaatatcga tacttctaag     720
gtcaactacg gtgttaccgt tttgccaacc ttcaaaggtc aaccatccaa gccatttgtt     780
ggtgttttgt ccgctggtat caacgctgct tctcctaaca aggaattggc taaggaattc     840
ttggaaaact atttgttgac tgatgaaggt ttagaagctg ttaacaagga caagccattg     900
ggtgccgttt ccttgaagtc ttacgaagaa gaattggcca aggacccag aattgctgct     960
aatatggaga atgcccaaaa aggtgagatc atgccaaaca ttccacaaat gtctgctttc    1020
tggtatgctg ttagaactgc cgtcattaac actgcttccg gtagcaaaac tgttgatgaa    1080
gccttgaaag atgcccaaac taactcctct tccaacaaca ataataacaa caacaacaac    1140
aacttgggta tcgaaggtag ataa                                           1164
```

<210> SEQ ID NO 16
<211> LENGTH: 387
<212> TYPE: PRT
<213> ORGANISM: Artificial Sequence
<220> FEATURE:
<223> OTHER INFORMATION: Synthetic: H8 Amino acid sequence

<400> SEQUENCE: 16

```
Met Lys Ile Glu Glu Gly Lys Leu Val Ile Trp Ile Asn Gly Asp Lys
1               5                   10                  15

Gly Tyr Asn Gly Ser Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Thr
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110
```

Ala Leu Ser Leu Ile Tyr Asn Lys Asp Leu Leu Pro Asn Pro Pro Lys
            115                 120                 125

Thr Trp Glu Glu Ile Pro Ala Met Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

His Asp Ile Lys Asp Val Gly Val Asp Asn Pro Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ser
290                 295                 300

Leu Lys Ser Tyr Glu Glu Leu Ala Lys Asp Pro Arg Ile Ala Ala
305                 310                 315                 320

Asn Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Thr Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg
385

<210> SEQ ID NO 17
<211> LENGTH: 1164
<212> TYPE: DNA
<213> ORGANISM: Artificial Sequence
<220> FEATURE:
<223> OTHER INFORMATION: Synthetic: H9 Nucleotide sequence

<400> SEQUENCE: 17
atgaaaatcg aagaaggtag gttagtcatt tggatcaacg gtgacaaggg ttacaatggt     60
ttggctgaag ttggtaagaa gtttgaaaaa gacactggta tcaaggttac cgtcgaacat    120
ccagataagt tggaagaaaa gttcccacaa gtcgccgcta ctggtgatgg tccagatatt    180
atcttctggg ctcacgacag attcggtggt tacgctcaat ctggtttgtt agccgaaatt    240
actcctggca aggctttcca agacaaatta tacccattca cctgggatgc tatcagatat    300
aacggtaaat tgatcgctta ccccatcgct gtcgaagctt tgtccttgat ctacaacaag    360
gatttgttac ctaacccacc aaaaacttgg gaagaaatcc cagctttgga caaggaattg    420

```
aaagctaaag gtaaatccgc tttgatgttc aacttacaag aaccatattt cacttggcct      480
ttgattgctg ctgatggtgg ttatgccttt aagtacgaaa acggtaagta cgatattaag      540
gacgtcggtg ttgacaacgc cggtgctaag gctggttcaa ctttcttggt cgatttgatc      600
aagaacaagc atatgaacgc cgacactgac tactctatcg ctgaagccgc tttcaataag      660
ggtgagactg ctatgactat aacggtcct tgggcttggt ctaataacga tacttctaag       720
```

```
ggtgagactg ctatgactat aacggtcct  tgggcttggt ctaataacga tacttctaag      720
gtcaactacg gtgttaccgt tttgccaacc ttcaaaggtc aaccatccaa gccatttgtt      780
ggtgttttgt ccgctggtat caacgctgct tctcctaaca aggaattggc taaggaattc      840
ttggaaaact atttgttgac tgatgaaggt ttagaagctg ttaacaagga caagccattg      900
ggtgccgttg ccttgaagtc ttacgaagaa gaattggcca aggacctag  aattgctgct      960 actatggaaa atgcccaaaa aggtgagatc atgccaaaca ttccacaaat gtctgctttc     1020
tggtatgctg ttagaactgc cgtcattaac gctgcttccg gtagacaaac tgttgatgaa     1080
gccttgaaag atgcccaaac taactcctct tccaacaaca gtaataacaa caacaacaac     1140
aacttgggta tcgaaggtag ataa                                             1164
```

<210> SEQ ID NO 18
<211> LENGTH: 387
<212> TYPE: PRT
<213> ORGANISM: Artificial Sequence
<220> FEATURE:
<223> OTHER INFORMATION: Synthetic: H9 Amino acid sequence

<400> SEQUENCE: 18

```
Met Lys Ile Glu Glu Gly Arg Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Gly Lys Ala Phe Gln Asp Lys Leu Tyr Pro Phe Thr Trp Asp
                85                  90                  95

Ala Ile Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Ser Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Asn Asp Thr Ser Lys
```

```
            225                 230                 235                 240
Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
            290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
                355                 360                 365

Ser Ser Ser Asn Asn Ser Asn Asn Asn Asn Asn Asn Leu Gly Ile
            370                 375                 380

Glu Gly Arg
385

<210> SEQ ID NO 19
<211> LENGTH: 1164
<212> TYPE: DNA
<213> ORGANISM: Artificial Sequence
<220> FEATURE:
<223> OTHER INFORMATION: Synthetic: H10 Nucleotide sequence

<400> SEQUENCE: 19
atgaaaatcg aagaaggtaa gttagtcatt gggatcaacg gtgacaaggg ttacaatggt      60
ttggctgaag taggtaagaa gtttgaaaaa gacactggta tcaaggttac cgtcgaacat     120
ccagataagt tggaagaaaa gttcccacaa gtcgccgcta ctggtgatgg tccagatatt     180
atcttctggg ctcacgacag attcggtggt tacgctcaat ctggcttgtt agccgaaatt     240
actcctgaca aggctttcca aaacaaatta tacccattca cctgggatgc tgtcagatat     300
aacggtaaat tgatcgctta cccaatcgct gtcgaagctt gtccttgat ctacaacaag     360 gatttgttac ctaacccacc aaaaacttgg gaagaaatct caactttgga caaggaattg     420
aaagctaaag gtaaatccgc tttgatgttc aacttacaag aaccatattt cacttggcct     480
ttgattgctg ctgatggtgg ttatgccttt aagtacgaaa acggtaagta cgatattaag     540
gacgtcggtg ttgacaacgc cggtgctaag gctggtttaa cttttcttggt cgatttgatc     600 aagaacaagc atatgaacgc cgacactgag tactctatcg ctgaagccgc tttcaataag     660
ggtgagactg ctatgactat taacggtcct tgggcttggt ctaatatcga tacttctaag     720
gtcaactacg gtgttaccgt tttgccaacc ttcaaaggtc aaccatccaa gccatttgtt     780 ggtgtttttgt ccgctggtat caacgctgct tctcctaaca aggaattggc taaggaattc     840
ttggaaaact atttgttgac tgatgaaggt ttagaagctg ttaacaagga caagccattg     900
ggtgccgttg ccttgaagtc ttacgaagaa gaattggcca aggacctag aattgctgct     960 accttggaaa atgcccaaaa aggtgagatc atgccaaaca ttccacaaat gtctgctttc    1020
tggtatgctg ttagaactgc cgtcattaac gctgcttccg gtagacaaac tgttgacgaa    1080 gcccttgaaag atgcccaaac taactcctca tccaacaaca ataataacaa caacaacaac    1140
```
aacttgggta tcgaaggtag ataa                                            1164

<210> SEQ ID NO 20
<211> LENGTH: 387
<212> TYPE: PRT
<213> ORGANISM: Artificial Sequence
<220> FEATURE:
<223> OTHER INFORMATION: Synthetic: H10 Amino acid sequence

<400> SEQUENCE: 20

```
Met Lys Ile Glu Glu Gly Lys Leu Val Ile Gly Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asn Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Ser Thr Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Glu Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Leu Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350
```

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Leu Gly Ile
    370                 375                 380

Glu Gly Arg
385

<210> SEQ ID NO 21
<211> LENGTH: 1164
<212> TYPE: DNA
<213> ORGANISM: Artificial Sequence
<220> FEATURE:
<223> OTHER INFORMATION: Synthetic: M1 Nucleotide sequence

<400> SEQUENCE: 21

| | | | |
|---|---|---|---|
| atgaaaatcg aagaaggtaa gttagtcatt tggatcaacg gtgacaaggg ttacaatggt | 60 |
| ttggctgaag ttggtaagaa gtttgaaaaa gacactggta tcaaggttac cgtcgaacat | 120 |
| ccagataagt tggaagaaaa gttcccacaa gtcgccgcta ctggtgatgg tccagatatt | 180 |
| atcttctggg ctcacgacag attcggtggt tacgctcaat ctggtttgtt agccgaaatt | 240 |
| actcctgaca aggctttcca agacaaatta tatccattca cctgggatgc tgtcagatat | 300 |
| aacggtaaat tgatcgctta cccaatcgct gtcgaagctt tgtccttggt ctacaacaag | 360 |
| gatttgttac ctaacccacc aaaaacttgg gaagaaatcc cagctttgga caaggaattg | 420 |
| aaagctaaag gtaaatccgc tttgatgttc aacttacaag aaccatattt cacttggcct | 480 |
| ttgattgctg ctgatggtgg taatgccttt aagtacgaaa acggtaagta cgatattaag | 540 |
| gacgtcggtg ttgacaacgc cggtgctaag gctggtttaa ctttcttggt cgatttgatc | 600 |
| aagaacaagc atatgaacgc cgacactgac tactctatcg ctgaagccgc tttcaataag | 660 |
| ggtgagactg ctatgactat taactgtcct tgggcttggt ctaatatcga tacttctaag | 720 |
| gtcaactacg tgttaccgt tttgccaacc ttcaaaggtc aaccatccaa gccatttgtt | 780 |
| ggtgttatgt ccgctggtat caacgctgct tctcctaaca aggaattggc taaggaattc | 840 |
| ttggaaaact atttgttgac tgatgaaggt ttagaagctg ttaacaagga caagccattg | 900 |
| ggtgccgttg ccttgaagtc ttacgaagaa gaattggcca aggacctag aattgctgct | 960 |
| actatggaaa atgcccaaaa aggtgagatc atgccaaaca ttccacaaat gtctgctttc | 1020 |
| tggtatgctg ttagaactgc cgtcattaac gctgcttccg gtagacaaac tgttgatgaa | 1080 |
| gccttgaaag atgcccaatc taactcccct tccaacaaca ataataacaa caacaacaac | 1140 |
| aacttgggta tcgaaggtag ataa | 1164 |

<210> SEQ ID NO 22
<211> LENGTH: 387
<212> TYPE: PRT
<213> ORGANISM: Artificial Sequence
<220> FEATURE:
<223> OTHER INFORMATION: Synthetic: M1 Amino acid sequence

<400> SEQUENCE: 22

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala

```
            50                  55                  60
His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Val Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Asn Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Cys Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Met Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Ser Asn
        355                 360                 365

Ser Pro Ser Asn Asn Asn Asn Asn Asn Asn Asn Asn Leu Gly Ile
    370                 375                 380

Glu Gly Arg
385

<210> SEQ ID NO 23
<211> LENGTH: 1164
<212> TYPE: DNA
<213> ORGANISM: Artificial Sequence
<220> FEATURE:
<223> OTHER INFORMATION: Synthetic: M5 Nucleotide sequence

<400> SEQUENCE: 23
atgaaaatcg aagaaggtaa gttagtcatt tggatcaacg gtgacaaggg ttacaatggt      60
ttggctgaag ttggtaagaa gtttgaaaaa gacactggta tcaaggttac cgtcgaacat     120
```

```
ccagataagt tggaagaaaa gttcccacaa gtcgccgcta ctggtgatgg tccagatatt    180
atcttctggg ctcacgacag atccggtggt tacgctcaat ctggtttgtt agccgaaatt    240
actcctgaca aggctttcca agacaaatta tacccattca ccagggatgc tgtcagatat    300
aacggtaaat tgatcgctta cccaatcgct gtcgaagcat tgtccttgat ctacaacaag    360
gatttgttac ctaacccacc aaaaacttgg gaagaaatcc cagctttgga caaggaattg    420
aaagctaaag gtaaatccgc tttgatgttc aacttacaag aaccatattt cacttggcct    480
ttgattgctg ctgatggtgg ttatgccttt aagtacgaaa acggtaagta cgatattaag    540
gacgtcggtg ttgacagcgc cggtgctaag gctggtttaa ctttcttggt cgttttgatc    600
aagaacaagc atatgaacgc cgacactgac tactctatcg ctgaagccgc tttcaataag    660
ggtgagactg ctatgactat taacggtcct tgggcttggt ctaatatcga tacttctaag    720
gtcaactacg gtgttaccgt tttgccaacc ttcaaaggtc aaccatccaa gccatttgtt    780
ggtgttttgt ccgctggtat caacgctgct tctcctaaca aggaattggc taaggaattc    840
ttggaaaact atttgttgac tgatgaaggt ttagaagctg ttaacaagga caagccattg    900
ggtgccgttg ccttgaagtc ttacgaagaa gaattggcca aggacctag aattgctgct    960 actatggaaa atgcccaaaa aggtgagatc atgccaaaca ttccacaaat gtctgctttc    1020
tggtatgctg ttagaactgc cgtcattaac gctgcttccg gtagacaaac tgttgatgaa    1080
gccttgaaag atgcccaaac taactcctct ccaacaaca ataataacaa caacaacaac    1140
aacttgggta tcgaaggtag ataa                                           1164
```

<210> SEQ ID NO 24
<211> LENGTH: 387
<212> TYPE: PRT
<213> ORGANISM: Artificial Sequence
<220> FEATURE:
<223> OTHER INFORMATION: Synthetic: M5 Amino acid sequence

<400> SEQUENCE: 24

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Ser Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Arg Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175
```

Tyr Asp Ile Lys Asp Val Gly Val Asp Ser Ala Gly Ala Lys Ala Gly
                180                 185                 190

Leu Thr Phe Leu Val Val Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg
385

<210> SEQ ID NO 25
<211> LENGTH: 1164
<212> TYPE: DNA
<213> ORGANISM: Artificial Sequence
<220> FEATURE:
<223> OTHER INFORMATION: Synthetic: M13 Nucleotide sequence

<400> SEQUENCE: 25
atgaaaatcg aagaaggtaa gttagtcatt tggatcaacg gtgacaaggg ttacaatggt      60
ttggctgaag ttggtaagaa gtatgaaaaa gacactggta tcaaggttac cgtcgaacat     120
ccagatgagt tggaagaaaa gttcccacaa gtcgccgcta ctggtgatgg tccagatatt     180
atcttctggg ctcacgacag attcggtggt tacgctcaat ctggtttgtt agccgaaatt     240
actcctgaca aggctttcca agacaaatta tacccattca cctgggatgc tgtcagatat     300
atcggtaaat tgatcgctta cccaatcgct gtcgaagctt tgtccttgat ctacaacaag     360
gatttgttac ctaacccacc aaaaacttgg gaagaaatcc cagctttgga caaggaattg     420
aaagctaaag gtaaatccgc tttgatgttc aacttacaag aaccatattt cacttggcct     480
ttgattgctg ctgatggtgg ttgtgccttt aagtacgaaa acggtaagta cgatattaag     540
gacgtcggtg ttgacaacgc cggtgctaag gctggtttaa cttttcttggt cgatttgatc     600 aagaacaagc atatgaacgc cgacactgac tactctatcg ctgaagccga tttcaataag     660
ggtgagactg ctatgactat taacggtcct tgggcttggt ctaatatcga tacttctaag     720
gtcaactacg gtgtaaccgt tttgccaacc ttcaaaggtc aaccatccaa gccatttgtt     780
ggtgttttgt ccgctggtat caacgctgct tctcctaaca aggaattggc taaggaattc     840

-continued

```
ttggaaaact atttgttgac tgatgaaggt gtagaagctg ttaacaagga caagccattg    900
ggtgccgttg ccttgaagtc ttacgaagaa gaattggcca aggaccctag aattgctgct    960
actatggaaa atgcccaaaa aggtgagatc atgccaaaca ttccacaaat gtctgctttc   1020
tggtatgctg ttagaactgc cgtcattaac gctgcttccg gtagacaaac tgttgatgaa   1080
gccttgaaag atgcccaaac taactcctct tccaacaaca ataataacaa caacaacaac   1140
aacttgggta tcgaaggtag ataa                                          1164
```

<210> SEQ ID NO 26
<211> LENGTH: 387
<212> TYPE: PRT
<213> ORGANISM: Artificial Sequence
<220> FEATURE:
<223> OTHER INFORMATION: Synthetic: M13 Amino acid sequence

<400> SEQUENCE: 26

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Tyr Glu Lys Asp Thr
            20                  25                  30

Gly Ile Lys Val Thr Val Glu His Pro Asp Glu Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Ile Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Cys Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Asp Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Val Glu Ala Val Asn Lys Asp Lys Pro Leu Gly Ala Val Ala
    290                 295                 300
```

| Leu | Lys | Ser | Tyr | Glu | Glu | Leu | Ala | Lys | Asp | Pro | Arg | Ile | Ala | Ala |
| | | | | 310 | | | | 315 | | | | | 320 | |
| 305 | | | | | | | | | | | | | | |

| Thr | Met | Glu | Asn | Ala | Gln | Lys | Gly | Glu | Ile | Met | Pro | Asn | Ile | Pro | Gln |
| | | | | 325 | | | | | 330 | | | | | 335 | |

| Met | Ser | Ala | Phe | Trp | Tyr | Ala | Val | Arg | Thr | Ala | Val | Ile | Asn | Ala | Ala |
| | | | 340 | | | | | 345 | | | | | 350 | | |

| Ser | Gly | Arg | Gln | Thr | Val | Asp | Glu | Ala | Leu | Lys | Asp | Ala | Gln | Thr | Asn |
| | | 355 | | | | | 360 | | | | | 365 | | | |

| Ser | Ser | Ser | Asn | Asn | Asn | Asn | Asn | Asn | Asn | Asn | Asn | Leu | Gly | Ile |
| | 370 | | | | | 375 | | | | | 380 | | | |

Glu Gly Arg
385

<210> SEQ ID NO 27
<211> LENGTH: 1164
<212> TYPE: DNA
<213> ORGANISM: Artificial Sequence
<220> FEATURE:
<223> OTHER INFORMATION: Synthetic: wild-type MBP Nucleotide sequence + linker

<400> SEQUENCE: 27

```
atgaaaatcg aagaaggtaa gttagtcatt tggatcaacg gtgacaaggg ttacaatggt     60
ttggctgaag ttggtaagaa gtttgaaaaa gacactggta tcaaggttac cgtcgaacat    120
ccagataagt tggaagaaaa gttcccacaa gtcgccgcta ctggtgatgg tccagatatt    180
atcttctggg ctcacgacag attcggtggt tacgctcaat ctggtttgtt agccgaaatt    240
actcctgaca aggctttcca agacaaatta tacccattca cctgggatgc tgtcagatat    300
aacggtaaat tgatcgctta cccaatcgct gtcgaagctt tgtccttgat ctacaacaag    360
gatttgttac ctaacccacc aaaaacttgg gaagaaatcc cagctttgga caaggaattg    420
aaagctaaag gtaaatccgc tttgatgttc aacttacaag aaccatattt cacttggcct    480
ttgattgctg ctgatggtgg ttatgccttt aagtacgaaa acggtaagta cgatattaag    540
gacgtcggtg ttgacaacgc cggtgctaag gctggtttaa cttctcttggt cgatttgatc    600
aagaacaagc atatgaacgc cgacactgac tactctatcg ctgaagccgc tttcaataag    660
ggtgagactg ctatgactat taacggtcct tgggcttggt ctaatatcga tacttctaag    720
gtcaactacg gtgttaccgt tttgccaacc ttcaaaggtc aaccatccaa gccatttgtt    780
ggtgttttgt ccgctggtat caacgctgct tctcctaaca aggaattggc taaggaattc    840
ttggaaaact atttgttgac tgatgaaggt ttagaagctg ttaacaagga caagccattg    900
ggtgccgttg ccttgaagtc ttacgaagaa gaattggcca aggaccctag aattgctgct    960
actatggaaa atgcccaaaa aggtgagatc atgccaaaca ttccacaaat gtctgctttc   1020
tggtatgctg ttagaactgc cgtcattaac gctgcttccg gtagacaaac tgttgatgaa   1080
gccttgaaag atgcccaaac taactcctct ccaacaaca ataataacaa caacaacaac   1140
aacttgggta tcgaaggtag ataa                                         1164
```

<210> SEQ ID NO 28
<211> LENGTH: 389
<212> TYPE: PRT
<213> ORGANISM: Artificial Sequence
<220> FEATURE:
<223> OTHER INFORMATION: Synthetic: wild-type Amino acid sequence + linker

<400> SEQUENCE: 28

```
Ala Ala Met Lys Ile Glu Glu Gly Lys Leu Val Ile Trp Ile Asn Gly
1               5                   10                  15

Asp Lys Gly Tyr Asn Gly Leu Ala Glu Val Gly Lys Lys Phe Glu Lys
                20                  25                  30

Asp Thr Gly Ile Lys Val Thr Val Glu His Pro Asp Lys Leu Glu Glu
            35                  40                  45

Lys Phe Pro Gln Val Ala Ala Thr Gly Asp Gly Pro Asp Ile Ile Phe
    50                  55                  60

Trp Ala His Asp Arg Phe Gly Gly Tyr Ala Gln Ser Gly Leu Leu Ala
65                  70                  75                  80

Glu Ile Thr Pro Asp Lys Ala Phe Gln Asp Lys Leu Tyr Pro Phe Thr
                85                  90                  95

Trp Asp Ala Val Arg Tyr Asn Gly Lys Leu Ile Ala Tyr Pro Ile Ala
            100                 105                 110

Val Glu Ala Leu Ser Leu Ile Tyr Asn Lys Asp Leu Leu Pro Asn Pro
        115                 120                 125

Pro Lys Thr Trp Glu Glu Ile Pro Ala Leu Asp Lys Glu Leu Lys Ala
    130                 135                 140

Lys Gly Lys Ser Ala Leu Met Phe Asn Leu Gln Glu Pro Tyr Phe Thr
145                 150                 155                 160

Trp Pro Leu Ile Ala Ala Asp Gly Gly Tyr Ala Phe Lys Tyr Glu Asn
                165                 170                 175

Gly Lys Tyr Asp Ile Lys Asp Val Gly Val Asp Asn Ala Gly Ala Lys
            180                 185                 190

Ala Gly Leu Thr Phe Leu Val Asp Leu Ile Lys Asn Lys His Met Asn
        195                 200                 205

Ala Asp Thr Asp Tyr Ser Ile Ala Glu Ala Ala Phe Asn Lys Gly Glu
    210                 215                 220

Thr Ala Met Thr Ile Asn Gly Pro Trp Ala Trp Ser Asn Ile Asp Thr
225                 230                 235                 240

Ser Lys Val Asn Tyr Gly Val Thr Val Leu Pro Thr Phe Lys Gly Gln
                245                 250                 255

Pro Ser Lys Pro Phe Val Gly Val Leu Ser Ala Gly Ile Asn Ala Ala
            260                 265                 270

Ser Pro Asn Lys Glu Leu Ala Lys Glu Phe Leu Glu Asn Tyr Leu Leu
        275                 280                 285

Thr Asp Glu Gly Leu Glu Ala Val Asn Lys Asp Lys Pro Leu Gly Ala
    290                 295                 300

Val Ala Leu Lys Ser Tyr Glu Glu Glu Leu Ala Lys Asp Pro Arg Ile
305                 310                 315                 320

Ala Ala Thr Met Glu Asn Ala Gln Lys Gly Glu Ile Met Pro Asn Ile
                325                 330                 335

Pro Gln Met Ser Ala Phe Trp Tyr Ala Val Arg Thr Ala Val Ile Asn
            340                 345                 350

Ala Ala Ser Gly Arg Gln Thr Val Asp Glu Ala Leu Lys Asp Ala Gln
        355                 360                 365

Thr Asn Ser Ser Ser Asn Asn Asn Asn Asn Asn Asn Asn Asn Asn Leu
    370                 375                 380

Gly Ile Glu Gly Arg
385
```

<210> SEQ ID NO 29

<211> LENGTH: 1253
<212> TYPE: DNA
<213> ORGANISM: Artificial Sequence
<220> FEATURE:
<223> OTHER INFORMATION: Synthetic: pMAL1 Nucleotide sequence

<400> SEQUENCE: 29

```
gatgatggac actagtgtgt cgagaatgta tcaactatat atagtcctaa tgccacacaa      60
atatgaagtg ggggaagccc attcttaatc cggctcaatt ttggtgcgtg atcgcggcct     120
atgtttgctt ccagaaaaag cttagaataa tatttctcac ctttgatgga atgctcgcga     180
gtgctcgttt tgattacccc atatgcattg ttgcagcatg caagcactat tgcaagccac     240
gcatggaaga aatttgcaaa cacctatagc cccgcgttgt tgaggaggtg acttggtgt      300
aggaccataa agctgtgcac tactatggtg agctctgtcg tctggtgacc ttctatctca     360
ggcacatcct cgttttttgtg catgaggttc gagtcacgcc cacggcctat taatccgcga    420
aataaatgcg aaatctaaat tatgacgcaa ggctgagaga ttctgacacg ccgcatttgc     480
ggggcagtaa ttatcgggca gttttccggg gttcgggatg gggtttggag agaaagttca    540
acacagacca aaacagcttg ggaccacttg gatggaggtc cccgcagaag agctctggcg    600
cgttggacaa acattgacaa tccacggcaa aattgtctac agttccgtgt atgcggatag    660
ggatatcttc gggagtatcg caataggata caggcactgt gcagattacg cgacatgata    720
gctttgtatg ttctacagac tctgccgtag cagtctagat ataatatcgg agttttgtag    780
cgtcgtaagg aaaacttggg ttacacaggt ttcttgagag ccctttgacg ttgattgctc    840
tggcttccat ccaggccctc atgtggttca ggtgcctccg cagtggctgg caagcgtggg    900
ggtcaattac gtcacttcta ttcatgtacc ccagactcaa tgttgacag caatttcagc     960
gagaattaaa ttccacaatc aattctcgct gaaataatta ggccgtgatt taattctcgc   1020
tgaaacagaa tcctgtctgg ggtacagata acaatcaagt aactattatg gacgtgcata   1080
ggaggtggag tccatgacgc aaagggaaat attcatttta tcctcgcgaa gttgggatgt   1140
gtcaaagcgt cgcgctcgct atagtgatga gaatgtcttt agtaagctta agccatataa   1200
agaccttccg cctccatatt tttttttatc cctcttgaca atattaattc ctt          1253
```

<210> SEQ ID NO 30
<211> LENGTH: 1253
<212> TYPE: DNA
<213> ORGANISM: Artificial Sequence
<220> FEATURE:
<223> OTHER INFORMATION: Synthetic: pMAL2 Nucleotide sequence

<400> SEQUENCE: 30

```
aaggaattaa tattgtcaag agggataaaa aaaatatgg aggcggaagg tctttatatg      60
gcttaagctt actaaagaca ttctcatcac tatagcgagc gcgacgcttt gacacatccc    120
aacttcgcga ggataaaatg aatatttccc tttgcgtcat ggactccacc tcctatgcac    180
gtccataata gttacttgat tgttatctgt accccagaca ggattctgtt tcagcgagaa    240
ttaaatcacg gcctaattat ttcagcgaga attgattgtg gaatttaatt ctcgctgaaa    300
ttgctgtcaa caattgagtc tggggtacat gaatagaagt gacgtaattg accccacgc     360
ttgccagcca ctgcggaggc acctgaacca catgagggcc tggatggaag ccagagcaat    420
caacgtcaaa gggctctcaa gaaacctgtg taacccaagt tttccttacg acgctacaaa    480
actccgatat tatatctaga ctgctacggc agagtctgta gaacatacaa agctatcatg    540
tcgcgtaatc tgcacagtgc ctgtatccta ttgcgatact cccgaagata tccctatccg    600
```

-continued

```
catacacgga actgtagaca attttgccgt ggattgtcaa tgtttgtcca acgcgccaga      660
gctcttctgc ggggacctcc atccaagtgg tcccaagctg ttttggtctg tgttgaactt      720
tctctccaaa ccccatcccg aaccccggaa aactgcccga taattactgc cccgcaaatg      780
cggcgtgtca gaatctctca gccttgcgtc ataatttaga tttcgcattt atttcgcgga      840
ttaataggcc gtgggcgtga ctcgaacctc atgcacaaaa acgaggatgt gcctgagata      900
gaaggtcacc agacgacaga gctcaccata gtagtgcaca gctttatggt cctacaccaa      960
gtccacctcc tcaacaacgc ggggctatag gtgtttgcaa atttcttcca tgcgtggctt     1020
gcaatagtgc ttgcatgctg caacaatgca tatggggtaa tcaaaacgag cactcgcgag     1080
cattccatca aggtgagaa atattattct aagcttttc tggaagcaaa cataggccgc      1140
gatcacgcac caaaattgag ccggattaag aatgggcttc ccccacttca tatttgtgtg     1200
gcattaggac tatatatagt tgatacattc tcgacacact agtgtccatc atc            1253

<210> SEQ ID NO 31
<211> LENGTH: 785
<212> TYPE: DNA
<213> ORGANISM: Artificial Sequence
<220> FEATURE:
<223> OTHER INFORMATION: Synthetic: pMAL11 Nucleotide sequence

<400> SEQUENCE: 31
ttatgtaatt tagttacgct tgactgatgt acatttgaga ttatcaaaaa aactgcttaa       60
gagatggatg attttaatttt ttagagacgt attaatggaa cttttttatac cttgcccaga     120 gcgcctcaag aaaatgatgc tgcaagaaga attgaggaag gaactattca tcttacgttg      180
tttgtatcat cccacgatcc aaatcatgtt acctacgtta ggtacgctag gaactaaaaa      240
aagaaaagaa aagtatgcgt tatcactctt cgagccaatt cttaattgtg tggggtccgc      300
gaaaatttcc ggataaatcc tgtaaacttt aacttaaacc ccgtgtttag cgaaattttc      360
aacgaagcgc gcaataagga gaaatattat ctaaaagcga gagtttaagc gagttgcaag     420
aatctctacg gtacagatgc aacttactat agccaaggtc tattcgtatt actatggcag      480
cgaaaggagc tttaaggttt taattacccc atagccatag attctactcg gtctatctat     540
catgtaacac tccgttgatg cgtactagaa aatgacaacg taccgggctt gagggacata     600
cagagacaat tacagtaatc aagagtgtac ccaactttaa cgaactcagt aaaaaataag     660
gaatgtcgac atcttaattt tttatataaa gcggtttggt attgattgtt tgaagaattt      720
tcgggttggt gtttctttct gatgctacat agaagaacat caaacaacta aaaaaatagt     780
ataat                                                                  785

<210> SEQ ID NO 32
<211> LENGTH: 785
<212> TYPE: DNA
<213> ORGANISM: Artificial Sequence
<220> FEATURE:
<223> OTHER INFORMATION: Synthetic: pMAL12 Nucleotide sequence

<400> SEQUENCE: 32
attatactat tttttagtt gtttgatgtt cttctatgta gcatcagaaa gaaacaccaa       60
cccgaaaatt cttcaaacaa tcaataccaa accgctttat ataaaaaatt aagatgtcga     120
cattccttat tttttactga gttcgttaaa gttgggtaca ctcttgatta ctgtaattgt      180
ctctgtatgt ccctcaagcc cggtacgttg tcattttcta gtacgcatca acggagtgtt      240
```

```
acatgataga tagaccgagt agaatctatg gctatggggt aattaaaacc ttaaagctcc    300
tttcgctgcc atagtaatac gaatagacct tggctatagt aagttgcatc tgtaccgtag    360
agattcttgc aactcgctta aactctcgct tttagataat atttctcctt attgcgcgct    420
tcgttgaaaa tttcgctaaa cacggggttt aagttaaagt ttacaggatt tatccggaaa    480
ttttcgcgga ccccacacaa ttaagaattg gctcgaagag tgataacgca tacttttctt    540 ttctttttt agttcctagc gtacctaacg taggtaacat gatttggatc gtgggatgat    600
acaaacaacg taagatgaat agttccttcc tcaattcttc ttgcagcatc attttcttga    660
ggcgctctgg gcaaggtata aaaagttcca ttaatacgtc tctaaaaaat taaatcatcc    720
atctcttaag cagttttttt gataatctca aatgtacatc agtcaagcgt aactaaatta    780
cataa                                                                785

<210> SEQ ID NO 33
<211> LENGTH: 875
<212> TYPE: DNA
<213> ORGANISM: Artificial Sequence
<220> FEATURE:
<223> OTHER INFORMATION: Synthetic: pMAL31 Nucleotide sequence

<400> SEQUENCE: 33
ttatgtattt tagttacgct tgactgatgt acatttgaga ttatcaaaaa aactgcttaa     60
gagatagatg gtttaatttt ttagagacgt attaatggaa cttttatac cttgcccaga    120 gcgcctcaag aaaatgatgc tgaaagaaga attgaggaag gaactactca tcttacgttg    180
tttgtatcat cccacgatcc aaatcatgtt acctacgtta ggtacgctag gaactgaaaa    240
aagaaaagaa agtatgcgt tatcactctt cgagccaatt cttaattgtg tggggtccgc    300
gaaaacttcc ggataaatcc tgtaaactta aacttaaacc ccgtgtttag cgaaattttc    360
aacgaagcgc gcaataagga gaaatattat ataaaagcga gagtttaagc gaggttgcaa    420
gaatctctac ggtacagatg caacttacta tagccaaggt ctattcgtat tggtatccaa    480
gcagtgaagc tactcagggg aaaacatatt ttcagagatc aaagttatgt cagtctcttt    540
ttcatgtgta acttaacgtt tgtgcaggta tcataccggc ctccacataa tttttgtggg    600
gaagacgttg ttgtagcagt ctccttatac tctccaacag gtgtttaaag acttcttcag    660
gcctcatagt ctacatctgg agacaacatt agatagaagt ttccacagag gcagctttca    720
atatactttc ggctgtgtac atttcatcct gagtgagcgc atattgcata agtactcagt    780
atataaagag acacaatata ctccatactt gttgtgagtg gttttagcgt attcagtata    840
acaataagaa ttacatccaa gactattaat taact                                875

<210> SEQ ID NO 34
<211> LENGTH: 875
<212> TYPE: DNA
<213> ORGANISM: Artificial Sequence
<220> FEATURE:
<223> OTHER INFORMATION: Synthetic: pMAL32 Nucleotide sequence

<400> SEQUENCE: 34
agttaattaa tagtcttgga tgtaattctt attgttatac tgaatacgct aaaaccactc     60
acaacaagta tggagtatat tgtgtctctt tatatactga gtacttatgc aatatgcgct    120
cactcaggat gaaatgtaca cagccgaaag tatattgaaa gctgcctctg tggaaacttc    180
tatctaatgt tgtctccaga gtagactat gaggcctgaa gaagtcttta aacacctgtt    240
ggagagtata aggagactgc tacaacaacg tcttccccac aaaaattatg tggaggccgg    300
```

```
tatgatacct gcacaaacgt taagttacac atgaaaaaga gactgacata actttgatct    360
ctgaaaatat gttttcccct gagtagcttc actgcttgga taccaatacg aatagacctt    420
ggctatagta agttgcatct gtaccgtaga gattcttgca acctcgctta aactctcgct    480
tttatataat atttctcctt attgcgcgct tcgttgaaaa tttcgctaaa cacggggttt    540
aagtttaagt ttacaggatt tatccggaag ttttcgcgga ccccacacaa ttaagaattg    600
gctcgaagag tgataacgca tacttttctt ttcttttttc agttcctagc gtacctaacg    660
taggtaacat gatttggatc gtgggatgat acaaacaacg taagatgagt agttccttcc    720
tcaattcttc tttcagcatc atttcttga ggcgctctgg gcaaggtata aaaagttcca    780
ttaatacgtc tctaaaaaat taaaccatct atctcttaag cagtttttt gataatctca     840 aatgtacatc agtcaagcgt aactaaaata cataa    875
```

<210> SEQ ID NO 35
<211> LENGTH: 643
<212> TYPE: DNA
<213> ORGANISM: Artificial Sequence
<220> FEATURE:
<223> OTHER INFORMATION: Synthetic: pGMAL_v5 Nucleotide sequence

<400> SEQUENCE: 35

```
ttatattgaa ttttcaaaaa ttcttacttt ttttttggat ggacgcaaag aagtttaata     60
atcatattac atggcaatac caccatatac atatccatat ctaatcttac ttatatgttg    120
tggaaatgta aagagcccca ttatcttagc ctaaaaaaac cttctctttg gaactttcag    180
taatacgctt aactgctcat tgctatattg aagtcttgca acctcgctta aactctcgct    240
tttatataat atttcttccg tgcgtcctgg tcttcaccgg tcgcgttcct gaaacgcaga    300
tgtgcctaac aataaagatt tatccggaag ttttcgcgga cgattctaca atactagctt    360
ttatggttat gaagaggaaa aattggcagt aacctggccc cacaaacctt caaatcaacg    420
aatcaaatta acaaccatag gataataatg cgattagttt tttagcctta tttctggggt    480
aattaatcag cgaagcgatg attttgatc tattaacaga tatataaatg caaaagctgc    540
ataaccactt taactaatac tttcaacatt tcggtttgt attacttctt attcaaatgt     600
cataaaagta tcaacaaaaa attgttaata tacctctata ctt    643
```

<210> SEQ ID NO 36
<211> LENGTH: 709
<212> TYPE: DNA
<213> ORGANISM: Artificial Sequence
<220> FEATURE:
<223> OTHER INFORMATION: Synthetic: pGMAL_v6 Nucleotide sequence

<400> SEQUENCE: 36

```
ttatattgaa ttttcaaaaa ttcttacttt ttttttggat ggacgcaaag aagtttaata     60
atcatattac atggcaatac caccatatac atatccatat ctaatcttac ttatatgttg    120
tggaaatgta aagagcccca ttatcttagc ctaaaaaaac cttctctttg gaactttcag    180
taatacgctt aactgctcat tgctatattg aagagaaata ttatctaaaa gcgagagttt    240
aagcgagttg caagaagaaa tattatctaa agcgagagtt taagcgagt tgcaagatcc     300 gtgcgtcctg gtcttcaccg gtcgcgttcc tgaaacgcag atgtgcctaa caataaagtc    360
cgcgaaaatt tccggataaa tcgtccgcga aatttccgg ataaatcgat tctacaatac     420 tagctttat ggttatgaag aggaaaaatt ggcagtaacc tggccccaca aaccttcaaa     480
```

```
tcaacgaatc aaattaacaa ccataggata ataatgcgat tagttttta gccttatttc    540 tggggtaatt aatcagcgaa gcgatgattt ttgatctatt aacagatata taaatgcaaa    600
agctgcataa ccactttaac taatactttc aacattttcg gtttgtatta cttcttattc    660
aaatgtcata aaagtatcaa caaaaaattg ttaatatacc tctatactt                709

<210> SEQ ID NO 37
<211> LENGTH: 709
<212> TYPE: DNA
<213> ORGANISM: Artificial Sequence
<220> FEATURE:
<223> OTHER INFORMATION: Synthetic: pGMAL_v7 Nucleotide sequence

<400> SEQUENCE: 37
ttatattgaa ttttcaaaaa ttcttacttt ttttttggat ggacgcaaag aagtttaata     60
atcatattac atggcaatac caccatatac atatccatat ctaatcttac ttatatgttg    120
tggaaatgta aagagcccca ttatcttagc ctaaaaaaac cttctctttg gaactttcag    180
taatacgctt aactgctcat tgctatattg aagagaaata ttatctaaaa gcgagagttt    240
aagcgagttg caagatcttg caactcgctt aaactctcgc ttttagataa tatttcttcc    300
gtgcgtcctg gtcttcaccg gtcgcgttcc tgaaacgcag atgtgcctaa caataaagtc    360
cgcgaaaatt tccggataaa tcgatttatc cggaaatttt cgcggacgat tctacaatac    420
tagcttttat ggttatgaag aggaaaaatt ggcagtaacc tggccccaca aaccttcaaa    480
tcaacgaatc aaattaacaa ccataggata ataatgcgat tagttttta gccttatttc    540 tggggtaatt aatcagcgaa gcgatgattt ttgatctatt aacagatata taaatgcaaa    600
agctgcataa ccactttaac taatactttc aacattttcg gtttgtatta cttcttattc    660
aaatgtcata aaagtatcaa caaaaaattg ttaatatacc tctatactt                709

<210> SEQ ID NO 38
<211> LENGTH: 776
<212> TYPE: DNA
<213> ORGANISM: Artificial Sequence
<220> FEATURE:
<223> OTHER INFORMATION: Synthetic: pGMAL_v9 Nucleotide sequence

<400> SEQUENCE: 38
ttatattgaa ttttcaaaaa ttcttacttt ttttttggat ggacgcaaag aagtttaata     60
atcatattac atggcaatac caccatatac atatccatat ctaatcttac ttatatgttg    120
tggaaatgta aagagcccca ttatcttagc ctaaaaaaac cttctctttg gaactttcag    180
taatacgctt aactgctcat tgctatattg aagagaaata ttatctaaaa gcgagagttt    240
aagcgagttg caagaagaaa tattatctaa aagcgagagt ttaagcgagt tgcaagaaga    300
aatattatct aaaagcgaga gtttaagcga gttgcaagat ccgtgcgtcc tggtcttcac    360
cggtcgcgtt cctgaaacgc agatgtgcct aacaataaag tccgcgaaaa tttccggata    420
aatcgtccgc gaaaatttcc ggataaatcg tccgcgaaaa tttccggata aatcgattct    480
acaatactag cttttatggt tatgaagagg aaaaattggc agtaacctgg ccccacaaac    540
cttcaaatca acgaatcaaa ttaacaacca taggataata atgcgattag ttttttagcc    600
ttatttctgg ggtaattaat cagcgaagcg atgattttg atctattaac agatatataa    660
atgcaaaagc tgcataacca ctttaactaa tactttcaac attttcggtt tgtattactt    720
cttattcaaa tgtcataaaa gtatcaacaa aaaattgtta atatacctct atactt        776
```

<210> SEQ ID NO 39
<211> LENGTH: 843
<212> TYPE: DNA
<213> ORGANISM: Artificial Sequence
<220> FEATURE:
<223> OTHER INFORMATION: Synthetic: pGMAL_v10 Nucleotide sequence

<400> SEQUENCE: 39

```
ttatattgaa ttttcaaaaa ttcttacttt tttttggat ggacgcaaag aagtttaata      60
atcatattac atggcaatac caccatatac atatccatat ctaatcttac ttatatgttg    120
tggaaatgta aagagcccca ttatcttagc ctaaaaaaac cttctctttg gaactttcag    180
taatacgctt aactgctcat tgctatattg aagagaaata ttatctaaaa gcgagagttt    240
aagcgagttg caagaagaaa tattatctaa agcgagagt ttaagcgagt tgcaagaaga    300
aatattatct aaaagcgaga gtttaagcga gttgcaagaa gaaatattat ctaaaagcga    360
gagtttaagc gagttgcaag atccgtgcgt cctggtcttc accggtcgcg ttcctgaaac    420
gcagatgtgc ctaacaataa agtccgcgaa aatttccgga taaatcgtcc gcgaaaattt    480
ccggataaat cgtccgcgaa aatttccgga taaatcgtcc gcgaaaattt ccggataaat    540
cgattctaca atactagctt ttatggttat gaagaggaaa aattggcagt aacctggccc    600
cacaaacctt caaatcaacg aatcaaatta acaaccatag gataataatg cgattagttt    660
tttagcctta tttctggggt aattaatcag cgaagcgatg attttgatc tattaacaga    720
tatataaatg caaaagctgc ataaccactt taactaatac tttcaacatt ttcggtttgt    780
attacttctt attcaaatgt cataaaagta tcaacaaaaa attgttaata tacctctata    840
ctt                                                                  843
```

<210> SEQ ID NO 40
<211> LENGTH: 776
<212> TYPE: DNA
<213> ORGANISM: Artificial Sequence
<220> FEATURE:
<223> OTHER INFORMATION: Synthetic: pGMAL_v11 Nucleotide sequence

<400> SEQUENCE: 40

```
ttatattgaa ttttcaaaaa ttcttacttt tttttggat ggacgcaaag aagtttaata      60
atcatattac atggcaatac caccatatac atatccatat ctaatcttac ttatatgttg    120
tggaaatgta aagagcccca ttatcttagc ctaaaaaaac cttctctttg gaactttcag    180
taatacgctt aactgctcat tgctatattg aaggtccgcg aaaatttccg gataaatcgt    240
ccgcgaaaat ttccggataa atcgtccgcg aaaatttccg gataaatctc cgtgcgtcct    300
ggtcttcacc ggtcgcgttc ctgaaacgca gatgtgccta acaataaaag aaatattatc    360
taaaagcgag agtttaagcg agttgcaaga agaaatatta tctaaaagcg agagtttaag    420
cgagttgcaa gaagaaatat tatctaaaag cgagagttta agcgagttgc aagagattct    480
acaatactag cttttatggt tatgaagagg aaaaattggc agtaacctgg ccccacaaac    540
cttcaaatca acgaatcaaa ttaacaacca taggataata atgcgattag ttttttagcc    600
ttatttctgg ggtaattaat cagcgaagcg atgattttg atctattaac agatatataa    660
atgcaaaagc tgcataacca ctttaactaa tactttcaac attttcggtt tgtattactt    720
cttattcaaa tgtcataaaa gtatcaacaa aaaattgtta atatacctct atactt       776
```

<210> SEQ ID NO 41
<211> LENGTH: 843
<212> TYPE: DNA

<213> ORGANISM: Artificial Sequence
<220> FEATURE:
<223> OTHER INFORMATION: Synthetic: pGMAL_v12 Nucleotide sequence

<400> SEQUENCE: 41

```
ttatattgaa ttttcaaaaa ttcttacttt ttttttggat ggacgcaaag aagtttaata      60
atcatattac atggcaatac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aaggtccgcg aaaatttccg gataaatcgt     240
ccgcgaaaat ttccggataa atcgtccgcg aaaatttccg gataaatcgt ccgcgaaaat     300
ttccggataa atctccgtgc gtcctggtct tcaccggtcg cgttcctgaa acgcagatgt     360
gcctaacaat aaaagaaata ttatctaaaa gcgagagttt aagcgagttg caagaagaaa     420
tattatctaa aagcgagagt ttaagcgagt tgcaagaaga aatattatct aaaagcgaga     480
gtttaagcga gttgcaagaa gaaatattat ctaaaagcga gagtttaagc gagttgcaag     540
agattctaca atactagctt ttatggttat gaagaggaaa aattggcagt aacctggccc     600
cacaaacctt caaatcaacg aatcaaatta acaaccatag gataataatg cgattagttt     660
tttagcctta tttctggggt aattaatcag cgaagcgatg attttgatc tattaacaga      720
tatataaatg caaaagctgc ataaccactt aactaatac tttcaacatt ttcggtttgt       780
attacttctt attcaaatgt cataaaagta tcaacaaaaa attgttaata tacctctata     840
ctt                                                                    843
```

<210> SEQ ID NO 42
<211> LENGTH: 776
<212> TYPE: DNA
<213> ORGANISM: Artificial Sequence
<220> FEATURE:
<223> OTHER INFORMATION: Synthetic: pGMAL_v13 Nucleotide sequence

<400> SEQUENCE: 42

```
ttatattgaa ttttcaaaaa ttcttacttt ttttttggat ggacgcaaag aagtttaata      60
atcatattac atggcaatac caccatatac atatccatat ctaatcttac ttatatgttg     120
tggaaatgta aagagcccca ttatcttagc ctaaaaaaac ctagaaatat tatctaaaag     180
cgagagttta agcgagttgc aagatctctt tggaactttc agtaatacgc ttgtccgcga     240
aaatttccgg ataaatcaac tgctcattgc tatattgaag tccgtgcgtc ctggtcttca     300
ccggtcgcgt tcctgaaacg cagatgtgcc taacaataaa gattctaaga atatattatct    360
aaaagcgaga gtttaagcga gttgcaagac aatactagct tttatggtta tgagtccgcg     420
aaatttccg gataaatcag aggaaaaatt ggcagtaacc agaaatatta tctaaaagcg       480
agagtttaag cgagttgcaa gatggccccaa caaaccttca aatcaacgaa tcaaattaac    540
gtccgcgaaa atttccggat aaatcaacca taggataata atgcgattag ttttttagcc     600
ttatttctgg ggtaattaat cagcgaagcg atgattttg atctattaac agatatataaa    660
atgcaaaagc tgcataacca ctttaactaa tactttcaac attttcggtt tgtattactt     720
cttattcaaa tgtcataaaa gtatcaacaa aaaattgtta atatacctct atactt         776
```

<210> SEQ ID NO 43
<211> LENGTH: 708
<212> TYPE: DNA
<213> ORGANISM: Artificial Sequence
<220> FEATURE:
<223> OTHER INFORMATION: Synthetic: pGMAL_v14 Nucleotide sequence

<400> SEQUENCE: 43

```
ttatattgaa ttttcaaaaa ttcttacttt ttttttggat ggacgcaaag aagtttaata    60
atcatattac atggcaatac caccatatac atatccatat ctaatcttac ttatatgttg   120
tggaaatgta aagagcccca ttatcttagc ctaaaaaaac ctagaaatat tatctaaaag   180
cgagagttta agcgagttgc aagatctctt tggaactttc agtaatacgc ttgtccgcga   240
aaatttccgg ataaatcaac tgctcattgc tatattgaag tccgtgcgtc ctggtcttca   300
ccggtcgcgt tcctgaaacg cagatgtgcc taacaataaa gattctaaga aatattatct   360
aaaagcgaga gtttaagcga gttgcaagac aatactagct tttatggtta tgagtccgcg   420
aaaatttccg ataaatcag aggaaaaatt ggcagtaacc tggccccaca aaccttcaaa    480
tcaacgaatc aaattaaaac cataggataa taatgcgatt agttttttag ccttatttct   540
ggggtaatta atcagcgaag cgatgatttt tgatctatta acagatatat aaatgcaaaa   600
gctgcataac cactttaact aatactttca acattttcgg tttgtattac ttcttattca   660
aatgtcataa aagtatcaac aaaaaattgt taatatacct ctatactt                708
```

<210> SEQ ID NO 44
<211> LENGTH: 709
<212> TYPE: DNA
<213> ORGANISM: Artificial Sequence
<220> FEATURE:
<223> OTHER INFORMATION: Synthetic: pGMAL_v15 Nucleotide sequence

<400> SEQUENCE: 44

```
ttatattgaa ttttcaaaaa ttcttacttt ttttttggat ggacgcaaag aagtttaata    60
atcatattac atggcaatac caccatatac atatccatat ctaatcttac ttatatgttg   120
tggaaatgta aagagcccca ttatcttagc ctaaaaaaac cttctctttg gaactttcag   180
taatacgctt aactgctcat tgctatattg aagtccgtgc gtcctggtct tcaccggtcg   240
cgttcctgaa acgcagatgt gcctaacaat aaagattcta agaaatatta tctaaaagcg   300
agagtttaag cgagttgcaa gacaatacta gcttttatgg ttatgagtcc gcgaaaattt   360
ccggataaat cagaggaaaa attggcagta accagaaata ttatctaaaa gcgagagttt   420
aagcgagttg caagatggcc ccacaaacct tcaaatcaac gaatcaaatt aacgtccgcg   480
aaaatttccg gataaatcaa ccataggata ataatgcgat tagttttta gccttatttc    540
tggggtaatt aatcagcgaa gcgatgattt tgatctatt aacagatata taaatgcaaa    600
agctgcataa ccactttaac taatactttc aacattttcg gtttgtatta cttcttattc   660
aaatgtcata aagtatcaa caaaaaattg ttaatatacc tctatactt                709
```

<210> SEQ ID NO 45
<211> LENGTH: 843
<212> TYPE: DNA
<213> ORGANISM: Artificial Sequence
<220> FEATURE:
<223> OTHER INFORMATION: Synthetic: pGMAL_v16 Nucleotide sequence

<400> SEQUENCE: 45

```
ttatattgaa ttttcaaaaa ttcttacttt ttttttggat ggacgcaaag aagtttaata    60
atcatattac atggcaatac caccatatac atatccatat ctaatcttac ttatatgttg   120
tggaaatgta aagagcccca ttatcttagc ctaaaaaaac cttctctttg gaactttcag   180
taatacgctt aactgctcat tgctatattg aagtccgtgc gtcctggtct tcaccggtcg   240
```

```
cgttcctgaa acgcagatgt gcctaacaat aaagattcta caatactagc ttttatggtt      300
atgaagagga aaaattggca gtaacctggc cccacaaacc ttcaaatcaa cgaatcaaat      360
taacagaaat attatctaaa agcgagagtt aagcgagtt gcaagaagaa atattatcta       420
aaagcgagag tttaagcgag ttgcaagaag aaatattatc taaaagcgag agtttaagcg      480
agttgcaaga agaaatatta tctaaaagcg agagtttaag cgagttgcaa gaaaccatag      540
gataataatg cgattagttt gtccgcgaaa atttccggat aaatcgtccg cgaaaatttc      600
cggataaatc gtccgcgaaa atttccggat aaatcgtccg cgaaaatttc cggataaatc      660
tttagcctta tttctggggt aattaatcag cgaagcgatg attttgatc tattaacaga      720 tatataaatg caaaagctgc ataaccactt taactaatac tttcaacatt ttcggtttgt      780
attacttctt attcaaatgt cataaaagta tcaacaaaaa attgttaata tacctctata      840
ctt                                                                    843

<210> SEQ ID NO 46
<211> LENGTH: 776
<212> TYPE: DNA
<213> ORGANISM: Artificial Sequence
<220> FEATURE:
<223> OTHER INFORMATION: Synthetic: pGMAL_v17 Nucleotide sequence

<400> SEQUENCE: 46
ttatattgaa ttttcaaaaa ttcttacttt tttttttggat ggacgcaaag aagtttaata     60
atcatattac atggcaatac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aagtccgtgc gtcctggtct tcaccggtcg     240
cgttcctgaa acgcagatgt gcctaacaat aaagattcta caatactagc ttttatggtt      300
atgaagagga aaaattggca gtaacctggc cccacaaacc ttcaaatcaa cgaatcaaat      360
taacagaaat attatctaaa agcgagagtt aagcgagtt gcaagaagaa atattatcta       420
aaagcgagag tttaagcgag ttgcaagaag aaatattatc taaaagcgag agtttaagcg      480
agttgcaaga aaccatagga taataatgcg attagtttgt ccgcgaaaat ttccggataa      540
atcgtccgcg aaaatttccg gataaatcgt ccgcgaaaat ttccggataa atctttagcc      600
ttatttctgg ggtaattaat cagcgaagcg atgattttg atctattaac agatatataa      660
atgcaaaagc tgcataacca ctttaactaa tactttcaac attttcggtt tgtattactt     720
cttattcaaa tgtcataaaa gtatcaacaa aaaattgtta atatacctct atactt          776

<210> SEQ ID NO 47
<211> LENGTH: 709
<212> TYPE: DNA
<213> ORGANISM: Artificial Sequence
<220> FEATURE:
<223> OTHER INFORMATION: Synthetic: pGMAL_v18 Nucleotide sequence

<400> SEQUENCE: 47
ttatattgaa ttttcaaaaa ttcttacttt tttttttggat ggacgcaaag aagtttaata     60
atcatattac atggcaatac caccatatac atatccatat ctaatcttac ttatatgttg     120
tggaaatgta aagagcccca ttatcttagc ctaaaaaaac cttctctttg gaactttcag     180
taatacgctt aactgctcat tgctatattg aagtccgtgc gtcctggtct tcaccggtcg     240
cgttcctgaa acgcagatgt gcctaacaat aaagattcta caatactagc ttttatggtt      300
atgaagagga aaaattggca gtaacctggc cccacaaacc ttcaaatcaa cgaatcaaat      360
```

```
taacagaaat attatctaaa agcgagagtt taagcgagtt gcaagaagaa atattatcta    420
aaagcgagag tttaagcgag ttgcaagaaa ccataggata taatgcgat tagtttgtcc    480 gcgaaaattt ccggataaat cgtccgcgaa aatttccgga taaatcttta gccttatttc    540
tggggtaatt aatcagcgaa gcgatgattt ttgatctatt aacagatata taaatgcaaa    600
agctgcataa ccactttaac taatactttc aacattttcg gtttgtatta cttcttattc    660
aaatgtcata aaagtatcaa caaaaaattg ttaatatacc tctatactt                709
```

<210> SEQ ID NO 48
<211> LENGTH: 711
<212> TYPE: DNA
<213> ORGANISM: Artificial Sequence
<220> FEATURE:
<223> OTHER INFORMATION: Synthetic: pG2MAL_v1 Nucleotide sequence

<400> SEQUENCE: 48

```
cagaaggcac atctattaca tttactgagc ataacgggct gtactaatcc aaggaggttt     60
acggaccaga ggaactttcc agattcagat cacagcaata taggactgga aaacatcagg    120
tagccgcact caacttgtaa ctggcaacta ctttgcatta aactccaatt aaatgcggta    180
gaatcttttc agaaaaggta ttcaacgtca attgaatggc ttaagtaggt tgcaatttct    240
ttttctatta gtagctaaaa atgggtcacg tgatctatat tcgaaagggg cggttgcctc    300
aggaaggcac agaaatatta tctaaaagcg agagtttaag cgagttgcaa gattcagggg    360
tccatgtgcc ttggacgata ttaaggcaga aggcagtatg tccgcgaaaa tttccggata    420
aatcagatta gttaagccct tcccatctca agatggggag caaatggcat tatactcctg    480
ctagaaagtt aactgtgcac atattcttaa attatacaat gttctggaga gctattgttt    540
aaaaaacaaa catttcgcag gctaaaatgt ggagatagga ttagttttgt agacatatat    600
aaacaatcag taattggatt gaaaatttgg tgttgtgaat tgctcttcat tatgcacctt    660
attcaattat catcaagaat agcaatagtt aagtaaacac aagattaaca t             711
```

<210> SEQ ID NO 49
<211> LENGTH: 711
<212> TYPE: DNA
<213> ORGANISM: Artificial Sequence
<220> FEATURE:
<223> OTHER INFORMATION: Synthetic: pG2MAL_v2 Nucleotide sequence

<400> SEQUENCE: 49

```
cagaaggcac atctattaca tttactgagc ataacgggct gtactaatcc aaggaggttt     60
acggaccaga ggaactttcc agattcagat cacagcaata taggactgga aaacatcagg    120
tagccgcact caacttgtaa ctggcaacta ctttgcatta aactccaatt aaatgcggta    180
gaatcttttc agaaaaggta ttcaacgtca attgaatggc ttaagtaggt tgcaatttct    240
ttttctatta gtagctaaaa atgggtcacg tgatctatat tcgaaagggg cggttgcctc    300
aggaaggcac gtccgcgaaa atttccggat aaatcttcag gggtccatgt gccttggacg    360
atattaaggc agaaggcagt atagaaatat tatctaaaag cgagagttta agcgagttgc    420
aagaagatta gttaagccct tcccatctca agatggggag caaatggcat tatactcctg    480
ctagaaagtt aactgtgcac atattcttaa attatacaat gttctggaga gctattgttt    540
aaaaaacaaa catttcgcag gctaaaatgt ggagatagga ttagttttgt agacatatat    600
aaacaatcag taattggatt gaaaatttgg tgttgtgaat tgctcttcat tatgcacctt    660
```
attcaattat catcaagaat agcaatagtt aagtaaacac aagattaaca t     711

<210> SEQ ID NO 50
<211> LENGTH: 778
<212> TYPE: DNA
<213> ORGANISM: Artificial Sequence
<220> FEATURE:
<223> OTHER INFORMATION: Synthetic: pG2MAL_v3 Nucleotide sequence

<400> SEQUENCE: 50
cagaaggcac atctattaca tttactgagc ataacgggct gtactaatcc aaggaggttt     60
acggaccaga ggaactttcc agattcagat cacagcaata taggactgga aaacatcagg    120
tagccgcact caacttgtaa ctggcaacta ctttgcatta aactccaatt aaatgcggta    180
gaatcttttc agaaaaggta ttcaacgtca atttcttgca actcgcttaa actctcgctt    240
ttagataata tttctgaatg gcttaagtag gttgcaattt cttttctat tagtagctaa     300
aaatgggtca cgtgatctat attcgaaagg ggcggttgcc tcaggaaggc acgtccgcga    360
aaatttccgg ataaatcttc agggtccat gtgccttgga cgatattaag gcagaaggca     420
gtatagaaat attatctaaa agcgagagtt taagcgagtt gcaagaagat tagttaagcc    480
cttcccatct caagatgggg agcaaatggc attatactcc tgctaggatt tatccggaaa    540
ttttcgcgga caaagttaac tgtgcacata ttcttaaatt atacaatgtt ctggagagct    600
attgtttaaa aaacaaacat ttcgcaggct aaaatgtgga gataggatta gttttgtaga    660
catatataaa caatcagtaa ttggattgaa aatttggtgt tgtgaattgc tcttcattat    720
gcaccttatt caattatcat caagaatagc aatagttaag taaacacaag attaacat     778

<210> SEQ ID NO 51
<211> LENGTH: 778
<212> TYPE: DNA
<213> ORGANISM: Artificial Sequence
<220> FEATURE:
<223> OTHER INFORMATION: Synthetic: pG2MAL_v5 Nucleotide sequence

<400> SEQUENCE: 51
cagaaggcac atctattaca tttactgagc ataacgggct gtactaatcc aaggaggttt     60
acggaccaga ggaactttcc agattcagat cacagcaata taggactgga aaacatcagg    120
tagccgcact caacttgtaa ctggcaacta ctttgcatta aactccaatt aaatgcggta    180
gaatcttttc agaaaaggta ttcaacgtca atttcttgca actcgcttaa actctcgctt    240
ttagataata tttctgaatg gcttaagtag gttgcaattt cttttctat tagtagctaa     300
aaatgggtca cgtgatctat attcgaaagg ggcggttgcc tcaggaaggc acgtccgcga    360
aaatttccgg ataaatcttc agggtccat gtgccttgga cgatattaag gcagaaggca     420
gtatgattta tccggaaatt ttcgcggaca gattagttaa gcccttccca tctcaagatg    480
gggagcaaat ggcattatac tcctgctaga gaaatattat ctaaaagcga gagtttaagc    540
gagttgcaag aaagttaac tgtgcacata ttcttaaatt atacaatgtt ctggagagct     600
attgtttaaa aaacaaacat ttcgcaggct aaaatgtgga gataggatta gttttgtaga    660
catatataaa caatcagtaa ttggattgaa aatttggtgt tgtgaattgc tcttcattat    720
gcaccttatt caattatcat caagaatagc aatagttaag taaacacaag attaacat     778

<210> SEQ ID NO 52
<211> LENGTH: 794
<212> TYPE: DNA
<213> ORGANISM: Artificial Sequence
<220> FEATURE:
<223> OTHER INFORMATION: Synthetic: pG2MAL_v6 Nucleotide sequence

<400> SEQUENCE: 52

| | |
|---|---|
| aataccagtt tcgctgcaga aggcacatct attacattta ctgagcataa cgggctgtac | 60 |
| taatccaagg aggtttacgg accagaggaa ctttccagat tcagatcaca gcaatatagg | 120 |
| actggaaaac atcaggtagc cgcactcaac ttgtaactgg caactacttt gcattaaact | 180 |
| ccaattaaat gcggtagaat cttttcagaa aaggtattca acgtcaattg aatggcttaa | 240 |
| gtaggttgca atttcttttt ctattagtag ctaaaaatgg gtcacgtgat ctatattcga | 300 |
| aaggggcggt tgcctcagga aggcacttca ggggtccatg tgccttggac gatattaagg | 360 |
| cagaaggcag tattcttgca actcgcttaa actctcgctt ttagataata tttctagatt | 420 |
| agttaagccc ttcccagtcc gcgaaaattt ccggataaat ctctcaagat ggggagcaaa | 480 |
| tggcattata ctcctgctag gatttatccg gaaattttcg cggacaaagt taactgtgca | 540 |
| catattctta aattatacaa tgttctggag agctattgtt taaaaaacaa acatttcgca | 600 |
| gaaatattat ctaaaagcga gagtttaagc gagttgcaag aaggctaaaa tgtggagata | 660 |
| ggattagttt tgtagacata tataaacaat cagtaattgg attgaaaatt tggtgttgtg | 720 |
| aattgctctt cattatgcac cttattcaat tatcatcaag aatagcaata gttaagtaaa | 780 |
| cacaagatta acat | 794 |

<210> SEQ ID NO 53
<211> LENGTH: 778
<212> TYPE: DNA
<213> ORGANISM: Artificial Sequence
<220> FEATURE:
<223> OTHER INFORMATION: Synthetic: pG2MAL_v7 Nucleotide sequence

<400> SEQUENCE: 53

| | |
|---|---|
| cagaaggcac atctattaca tttactgagc ataacgggct gtactaatcc aaggaggttt | 60 |
| acggaccaga ggaactttcc agattcagat cacagcaata taggactgga aaacatcagg | 120 |
| tagccgcact caacttgtaa ctggcaacta ctttgcatta aactccaatt aaatgcggta | 180 |
| gaatcttttc agaaaaggta ttcaacgtca attagaaata ttatctaaaa gcgagagttt | 240 |
| aagcgagttg caagagaatg gcttaagtag gttgcaattt cttttctat tagtagctaa | 300 |
| aaatgggtca cgtgatctat attcgaaagg ggcggttgcc tcaggaaggc acgtccgcga | 360 |
| aaatttccgg ataaatcttc aggggtccat gtgccttgga cgatattaag gcagaaggca | 420 |
| gtatagaaat attatctaaa agcgagagtt taagcgagtt gcaagaagat tagttaagcc | 480 |
| cttcccatct gtccgcgaaa atttccggat aaatccaaga tggggagcaa atggcattat | 540 |
| actcctgcta gaaagttaac tgtgcacata ttcttaaatt atacaatgtt ctggagagct | 600 |
| attgtttaaa aaacaaacat ttcgcaggct aaaatgtgga gataggatta gttttgtaga | 660 |
| catatataaa caatcagtaa ttggattgaa aatttggtgt tgtgaattgc tcttcattat | 720 |
| gcaccttatt caattatcat caagaatagc aatagttaag taaacacaag attaacat | 778 |

<210> SEQ ID NO 54
<211> LENGTH: 845
<212> TYPE: DNA
<213> ORGANISM: Artificial Sequence
<220> FEATURE:
<223> OTHER INFORMATION: Synthetic: pG2MAL_v8 Nucleotide sequence

<400> SEQUENCE: 54

```
cagaaggcac atctattaca tttactgagc ataacgggct gtactaatcc aaggaggttt     60
acggaccaga ggaactttcc agattcagat cacagcaata taggactgga aaacatcagg    120
tagccgcact caacttgtaa ctggcaacta ctttgcatta aactccaatt aaatgcggta    180
gaatcttttc agaaaggta ttcaacgtca attgtccgcg aaaatttccg gataaatcgt    240
ccgcgaaaat ttccggataa atcgtccgcg aaaatttccg gataaatcga atggcttaag    300
taggttgcaa tttcttttc tattagtagc taaaaatggg tcacgtgatc tatattcgaa    360
aggggcggtt gcctcaggaa ggcacttcag gggtccatgt gccttggacg atattaaggc    420
agaaggcagt atagaaatat tatctaaaag cgagagttta agcgagttgc aagaagaaat    480
attatctaaa agcgagagtt taagcgagtt gcaagaagaa atattatcta aaagcgagag    540
tttaagcgag ttgcaagaag attagttaag cccttcccat ctcaagatgg ggagcaaatg    600
gcattatact cctgctagaa agttaactgt gcacatattc ttaaattata caatgttctg    660
gagagctatt gtttaaaaaa caaacatttc gcaggctaaa atgtggagat aggattagtt    720
ttgtagacat atataaacaa tcagtaattg gattgaaaat ttggtgttgt gaattgctct    780
tcattatgca ccttattcaa ttatcatcaa gaatagcaat agttaagtaa acacaagatt    840
aacat                                                                845

<210> SEQ ID NO 55
<211> LENGTH: 778
<212> TYPE: DNA
<213> ORGANISM: Artificial Sequence
<220> FEATURE:
<223> OTHER INFORMATION: Synthetic: pG2MAL_v9 Nucleotide sequence

<400> SEQUENCE: 55
cagaaggcac atctattaca tttactgagc ataacgggct gtactaatcc aaggaggttt     60
acggaccaga ggaactttcc agattcagat cacagcaata taggactgga aaacatcagg    120
tagccgcact caacttgtaa ctggcaacta ctttgcatta aactccaatt aaatgcggta    180
gaatcttttc agaaaggta ttcaacgtca attgtccgcg aaaatttccg gataaatcga    240
atggcttaag taggttgcaa tttcttttc tattagtagc taaaaatggg tcacgtgatc    300
tataagaaat attatctaaa agcgagagtt taagcgagtt gcaagattcg aaaggggcgg    360
ttgcctcagg aaggcacgtc gcgaaaatt tccggataaa tcttcagggg tccatgtgcc    420
ttggacgata ttaaggcaga aggcagtata gaaatattat ctaaaagcga gagtttaagc    480
gagttgcaag aagattagtt aagcccttcc catctcaaga tggggagcaa atggcattat    540
actcctgcta gaaagttaac tgtgcacata ttcttaaatt atacaatgtt ctggagagct    600
attgtttaaa aaacaaacat ttcgcaggct aaaatgtgga gataggatta gttttgtaga    660
catatataaa caatcagtaa ttggattgaa aatttggtgt tgtgaattgc tcttcattat    720
gcaccttatt caattatcat caagaatagc aatagttaag taaacacaag attaacat    778

<210> SEQ ID NO 56
<211> LENGTH: 845
<212> TYPE: DNA
<213> ORGANISM: Artificial Sequence
<220> FEATURE:
<223> OTHER INFORMATION: Synthetic: pG2MAL_v10 Nucleotide sequence

<400> SEQUENCE: 56
cagaaggcac atctattaca tttactgagc ataacgggct gtactaatcc aaggaggttt     60
acggaccaga ggaactttcc agattcagat cacagcaata taggactgga aaacatcagg    120
```

```
tagccgcact caacttgtaa ctggcaacta ctttgcatta aactccaatt aaatgcggta      180
gaatcttttc agaaaaggta ttcaacgtca attagaaata ttatctaaaa gcgagagttt      240
aagcgagttg caagagaatg gcttaagtag gttgcaattt cttttctat tagtagctaa       300 aaatgggtca cgtgatctat agtccgcgaa aatttccgga taaatcttcg aaaggggcgg      360
ttgcctcagg aaggcacaga aatattatct aaaagcgaga gtttaagcga gttgcaagat      420
tcaggggtcc atgtgccttg gacgatatta aggcagaagg cagtatgtcc gcgaaaattt      480
ccggataaat cagattagtt aagcccttcc agaaatatta tctaaaagcg agagtttaag      540
cgagttgcaa gacatctcaa gatggggagc aaatggcatt atactcctgc tagaaagtta      600
actgtgcgtc cgcgaaaatt tccggataaa tcacatattc ttaaattata caatgttctg      660
gagagctatt gtttaaaaaa caaacatttc gcaggctaaa atgtggagat aggattagtt      720
ttgtagacat atataaacaa tcagtaattg gattgaaaat ttggtgttgt gaattgctct      780
tcattatgca ccttattcaa ttatcatcaa gaatagcaat agttaagtaa acacaagatt      840
aacat                                                                 845

<210> SEQ ID NO 57
<211> LENGTH: 752
<212> TYPE: DNA
<213> ORGANISM: Artificial Sequence
<220> FEATURE:
<223> OTHER INFORMATION: Synthetic: pG7MAL_v2 Nucleotide sequence

<400> SEQUENCE: 57
tttgccagct tactatcctt cttgaaaata tgcactctat atcttttagt tcttaattgc       60
aacacataga tttgctgtat aacgaatttt atgctatttt ttaaatttgg agttcagtga      120
taaaagtgtc acagcgaatt tcctcacatg tagggaccga attgtttaca agttctctgt      180
accaccatgg agacatcaaa gattgaaaat ctatggaaag atatggacgg tagcaacaag      240
aatatagcac gagccgcgaa gttcatttcg ttacttttga tatcgctcac aactattgcg      300
aagcgcttca gtgaaaaaat cataaggaaa agttgtaaat attattggta gtattcgttt      360
ggtaaagtag aggggtaat ttttcccctt tattttgttc atacattctt aaattgcttt       420
gcctctcctt ttggaaagct atagtccgcg aaaatttccg gataaatcgc tcattagata      480
tattttctgt cattttcctt aacccaaaaa taagggaaag ggtccaaaaa gcgctagaaa      540
tattatctaa aagcgagagt ttaagcgagt tgcaagatga tccgaaggac tggctataca      600
gtgttcacaa aatagccaag ctgaaaataa tgtgtagcta tgttcagtta gtttggctag      660
caaagatata aaagcaggtc ggaaatattt atgggcatta ttatgcagag catcaacatg      720
ataaaaaaaa acagttgaat attccctcaa aa                                   752

<210> SEQ ID NO 58
<211> LENGTH: 819
<212> TYPE: DNA
<213> ORGANISM: Artificial Sequence
<220> FEATURE:
<223> OTHER INFORMATION: Synthetic: pG7MAL_v4 Nucleotide sequence

<400> SEQUENCE: 58
tttgccagct tactatcctt cttgaaaata tgcactctat atcttttagt tcttaattgc       60
aacacataga tttgctgtat aacgaatttt atgctatttt ttaaatttgg agttcagtga      120
taaaagtgtc acagcgaatt tcctcacatg tagggaccga attgtttaca agttctctgt      180
```

```
accaccatgg agacatcaaa gattgaaaat ctatggaaag atatggacgg tagcaacaag    240
aatatagcac gagccgcgaa gttcatttcg ttacttttga tatcgctcac aactattgcg    300
aagcgcttca gtgaaaaaat cataaggaaa agttgtaaat attattggta gtattcgttt    360
ggtaaagtag aggggtaat ttttcccctt tattttgttc atacattctt aaattgcttt     420
gcctctcctt ttggaaagct atagctcatt agatatattt tctgtcattt tccttaaccc    480
aaaaataagg gaaagggtcc aaaaagcgct tcttgcaact cgcttaaact ctcgctttta    540
gataatattt cttgatccga aggactggct agtccgcgaa atttccgga taaatctaca     600 gtgttcacaa ataagaaat attatctaaa gcgagagtt taagcgagtt gcaagagcca      660
agctgaaaat aatgtggatt tatccggaaa ttttcgcgga ctagctatgt tcagttagtt    720
tggctagcaa agatataaaa gcaggtcgga aatatttatg ggcattatta tgcagagcat    780
caacatgata aaaaaaaca gttgaatatt ccctcaaaa                            819

<210> SEQ ID NO 59
<211> LENGTH: 819
<212> TYPE: DNA
<213> ORGANISM: Artificial Sequence
<220> FEATURE:
<223> OTHER INFORMATION: Synthetic: pG7MAL_v6 Nucleotide sequence

<400> SEQUENCE: 59
tttgccagct tactatcctt cttgaaaata tgcactctat atctttagt tcttaattgc      60 aacacataga tttgctgtat aacgaatttt atgctatttt ttaaatttgg agttcagtga    120
taaaagtgtc acagcgaatt tcctcacatg tagggaccga attgtttaca agttctctgt    180
accaccatgg agacatcaaa gattgaaaat ctatggaaag atatggacgg tagcaacaag    240
aatatagcac gagccgcgaa gttcatttcg ttacttttga tatcgctcac aactattgcg    300
aagcgcttca gtgaaaaaat cataaggaaa agttgtaaat attattggta gtattcgttt    360
ggtaaagtag aggggtaat ttttcccctt tattttgttc atacattctt aaattgcttt     420
gcctctcctt ttggaaagct atagctcatt agatatattt tctgtcattt tccttaaccc    480
aaaaataagg gaaagggtcc aaaaagcgct tcttgcaact cgcttaaact ctcgctttta    540
gataatattt cttgatccga aggactggct agtccgcgaa atttccgga taaatctaca     600 gtgttcacaa atagattta tccggaaatt ttcgcggacg ccaagctgaa ataatgtga      660 gaaatattat ctaaagcga gagtttaagc gagttgcaag atagctatgt tcagttagtt     720
tggctagcaa agatataaaa gcaggtcgga aatatttatg ggcattatta tgcagagcat    780
caacatgata aaaaaaaca gttgaatatt ccctcaaaa                            819

<210> SEQ ID NO 60
<211> LENGTH: 886
<212> TYPE: DNA
<213> ORGANISM: Artificial Sequence
<220> FEATURE:
<223> OTHER INFORMATION: Synthetic: pG7MAL_v8 Nucleotide sequence

<400> SEQUENCE: 60
tttgccagct tactatcctt cttgaaaata tgcactctat atctttagt tcttaattgc      60 aacacataga tttgctgtat aacgaatttt atgctatttt ttaaatttgg agttcagtga    120
taaaagtgtc acagcgaatt tcctcacatg tagggaccga attgtttaca agttctctgt    180
accaccatgg agacatcaaa gattgaaaat ctatggaaag atatggacgg tagcaacaag    240
aatatagcac gagccgcgaa gttcatttcg ttacttttga tatcgctcac aactattgcg    300
```

| | |
|---|---|
| aagcgcttca gtgaaaaaat cataaggaaa agttgtaaat attattggta gtattcgttt | 360 |
| ggtaaagtag aggggtaat ttttcccctt tattttgttc atacattctt aaattgcttt | 420 |
| gcctctcctt ttggaaagct atagtccgcg aaaatttccg gataaatcgt ccgcgaaaat | 480 |
| ttccggataa atcgtccgcg aaaatttccg gataaatcgc tcattagata tattttctgt | 540 |
| cattttcctt aacccaaaaa taagggaaag ggtccaaaaa gcgctagaaa tattatctaa | 600 |
| aagcgagagt ttaagcgagt tgcaagaaga aatattatct aaaagcgaga gtttaagcga | 660 |
| gttgcaagaa gaaatattat ctaaaagcga gagtttaagc gagttgcaag atgatccgaa | 720 |
| ggactggcta tacagtgttc acaaaatagc caagctgaaa ataatgtgta gctatgttca | 780 |
| gttagtttgg ctagcaaaga tataaaagca ggtcggaaat atttatgggc attattatgc | 840 |
| agagcatcaa catgataaaa aaaaacagtt gaatattccc tcaaaa | 886 |

<210> SEQ ID NO 61
<211> LENGTH: 819
<212> TYPE: DNA
<213> ORGANISM: Artificial Sequence
<220> FEATURE:
<223> OTHER INFORMATION: Synthetic: pG7MAL_v9 Nucleotide sequence

<400> SEQUENCE: 61

| | |
|---|---|
| tttgccagct tactatcctt cttgaaaata tgcactctat atcttttagt tcttaattgc | 60 |
| aacacataga tttgctgtat aacgaatttt atgctatttt ttaaatttgg agttcagtga | 120 |
| taaaagtgtc acagcgaatt tcctcacatg tagggaccga attgtttaca agttctctgt | 180 |
| accaccatgg agacatcaaa gattgaaaat ctatggaaag atatggacgg tagcaacaag | 240 |
| aatatagcac gagccgcgaa gttcatttcg ttacttttga tatcgctcac aactattgcg | 300 |
| aagcgcttca gtgaaaaaat cataaggaaa agttgtaaat attattggta gtattcgttt | 360 |
| ggtaaagtag aggggtaat ttttcccctt tattttgttc atacattctt aaattgcttt | 420 |
| gcctctcctt ttggaaagct atagtccgcg aaaatttccg gataaatcgc tcattagata | 480 |
| tattttctgt cattttcctt aacccaaaaa taagggaaag ggtccaaaaa gcgctagaaa | 540 |
| tattatctaa aagcgagagt ttaagcgagt tgcaagatga tccgaaggac tggctagtcc | 600 |
| gcgaaaattt ccggataaat ctacagtgtt cacaaaatag cagaaatatt atctaaaagc | 660 |
| gagagtttaa gcgagttgca agacaagctg aaaataatgt gtagctatgt tcagttagtt | 720 |
| tggctagcaa agatataaaa gcaggtcgga aatatttatg gcattatta tgcagagcat | 780 |
| caacatgata aaaaaaaaca gttgaatatt ccctcaaaa | 819 |

<210> SEQ ID NO 62
<211> LENGTH: 694
<212> TYPE: DNA
<213> ORGANISM: Artificial Sequence
<220> FEATURE:
<223> OTHER INFORMATION: Synthetic: pG172_MAL_v13 Nucleotide sequence

<400> SEQUENCE: 62

| | |
|---|---|
| ttatattgaa ttttcaaaaa ttcttacttt tttttggat ggacgcaaag aagtttaata | 60 |
| atcatattac atggcaatac caccatatac atatccatat ctaatcttac ttatatgttg | 120 |
| tggaaatgta aagagcccca ttatcttagc ctaaaaaac cttctctttg gaactttcag | 180 |
| taatacgctt aactgctcat tgctatattg aagagaaata ttatctaaaa gcgagagttt | 240 |
| aagcgagttg caagaggtag tattcgtttg gtaaagtaga gggggtaatt tttccccttt | 300 |

```
attttgttca tacatgtccg cgaaaatttc cggataaatc agattagtta agcccttccc    360
atctcaagat ggggagcaaa tggcattaga aatattatct aaaagcgaga gtttaagcga    420
gttgcaagaa tactcctgct agaaagttaa ctgtgcacat attcttaaat tatacaatgt    480
tctgggtccg cgaaaatttc cggataaatc agagctattg tttaaaaaac aaacatttcg    540
caggctaaaa tgtggagata ggattagttt tgtagacata tataaacaat cagtaattgg    600
attgaaaatt tggtgttgtg aattgctctt cattatgcac cttattcaat tatcatcaag    660
aatagcaata gttaagtaaa cacaagatta acat                                694
```

<210> SEQ ID NO 63
<211> LENGTH: 716
<212> TYPE: DNA
<213> ORGANISM: Artificial Sequence
<220> FEATURE:
<223> OTHER INFORMATION: Synthetic: pG271_MAL_v12 Nucleotide sequence

<400> SEQUENCE: 63

```
aataccagtt tcgctgcaga aggcacatct attacattta ctgagcataa cgggctgtac     60
taatccaagg aggtttacgg accagaggaa ctttccagat tcagatcaca gcaatatagg    120
actggaaaac atcaggtagc cgcactcaac ttgtaactgg caactacttt gcattaaact    180
ccaattaaat gcggtagaat cttttcagaa aaggtattca agaaatatta tctaaaagcg    240
agagtttaag cgagttgcaa gaggtagtat tcgtttggta aagtagaggg ggtaattttt    300
cccctttatt ttgttcatac atgtccgcga aaatttccgg ataaatcgat tctacaatac    360
tagcttttat ggttaagaaa tattatctaa agcgagagt ttaagcgagt tgcaagatga    420
agaggaaaaa ttggcgtccg cgaaaatttc cggataaatc agtaacctgg ccccacaaac    480
cttcaaatca acgaatcaaa ttaacaacca taggataata atgcgattag ttttttagcc    540
ttatttctgg ggtaattaat cagcgaagcg atgattttg atctattaac agatatataa    600
atgcaaaagc tgcataacca ctttaactaa tactttcaac attttcggtt tgtattactt    660
cttattcaaa tgtcataaaa gtatcaacaa aaaattgtta atatacctct atactt        716
```

<210> SEQ ID NO 64
<211> LENGTH: 762
<212> TYPE: DNA
<213> ORGANISM: Artificial Sequence
<220> FEATURE:
<223> OTHER INFORMATION: Synthetic: pG721_MAL_v11 Nucleotide sequence

<400> SEQUENCE: 64

```
tttgccagct tactatcctt cttgaaaata tgcactctat atcttttagt tcttaattgc     60
aacacataga tttgctgtat aacgaatttt atgctatttt ttaaatttgg agttcagtga    120
taaaagtgtc acagcgaatt tcctcacatg tagggaccga attgtttaca agttctctgt    180
accaccatgg agacatcaaa gattgaaaat ctatggaaag atatggacgg tagcaacaag    240
aatatagcac gagccgcgaa gttcatagaa atattatcta aaagcgagag tttaagcgag    300
ttgcaagatt ttctattagt agctaaaaat gggtcacgtg atctatattc gaaggggcg    360 gttgcctcgt ccgcgaaaat ttccggataa atcgattcta caatactagc ttttaagaaa    420
tattatctaa agcgagagt ttaagcgagt tgcaagatgg ttatgaagag gaaaaattgg    480
cagtagtccg cgaaaatttc cggataaatc acctggcccc acaaacctt aaatcaacga    540 atcaaattaa caaccatagg ataataatgc gattagtttt ttagcctat ttctggggta    600 attaatcagc gaagcgatga ttttgatct attaacagat atataaatgc aaaagctgca    660
```

```
taaccactتt aactaatact ttcaacattt tcggtttgta ttacttctta ttcaaatgtc      720
ataaaagtat caacaaaaaa ttgttaatat acctctatac tt                         762
```

<210> SEQ ID NO 65
<211> LENGTH: 807
<212> TYPE: DNA
<213> ORGANISM: Artificial Sequence
<220> FEATURE:
<223> OTHER INFORMATION: Synthetic: pG712_MAL_v14 Nucleotide sequence

<400> SEQUENCE: 65

```
tttgccagct tactatcctt cttgaaaata tgcactctat atcttttagt tcttaattgc      60
aacacataga tttgctgtat aacgaattتt atgctatttt ttaaatttgg agttcagtga     120
taaaagtgtc acagcgaatt tcctcacatg tagggaccga attgtttaca agttctctgt     180
accaccatgg agacatcaaa gattgaaaat ctatggaaag atatggacgg tagcaacaag     240
aatatagcac gagccgcgaa gttcatتttt ctattagtag ctaaaaatgg gtcacgtgat     300
ctatattcga aggggcggt tgcctcagaa atattatcta aaagcgagag tttaagcgag      360
ttgcaagatc cgtgcgtcct ggtcttcacc ggtcgcgttc ctgaaacgca gatgtgccta    420
acaataaagt ccgcgaaaat ttccggataa atcagattag ttaagcccتt cccatctcaa    480 gatggggagc aaatggcatt atactcctgc tagaaagaga atattatcta aaaagcgaga    540 gتttaagcga gتtgcaagat taactgtgca catattctta aattatacaa tgttcgtccg    600
cgaaaatttc cggataaatc tggagagcta tgtttaaaa acaaacatt tcgcaggcta     660 aaatgtggag ataggattag tttgtagac atatataaac aatcagtaat tggattgaaa    720 atttggtgتt gtgaattgct cttcattatg caccttatتc aattatcatc aagaatagca    780
atagttaagt aaacacaaga ttaacat                                        807
```

<210> SEQ ID NO 66
<211> LENGTH: 24
<212> TYPE: DNA
<213> ORGANISM: Artificial Sequence
<220> FEATURE:
<223> OTHER INFORMATION: Synthetic: PC542 a forward primer used to
      mutagenize MBP from DNA construct

<400> SEQUENCE: 66

```
cgttagcaat atctcgcatt atag                                            24
```

<210> SEQ ID NO 67
<211> LENGTH: 20
<212> TYPE: DNA
<213> ORGANISM: Artificial Sequence
<220> FEATURE:
<223> OTHER INFORMATION: Synthetic: PC543 a reverse primer to
      mutagenize MBP from DNA construct

<400> SEQUENCE: 67

```
ccaagcacag ggcaagatgc                                                 20
```

<210> SEQ ID NO 68
<211> LENGTH: 4799
<212> TYPE: DNA
<213> ORGANISM: Artificial Sequence
<220> FEATURE:
<223> OTHER INFORMATION: Synthetic: DNA construct comprises a Gal80
      fused in frame to wild-type MBP with a linker sequence

<400> SEQUENCE: 68

```
gacggcacgg ccacgcgttt aaaccgccta cgccatcatt aaagacctgg tcaactataa       60
aataatacaa tcaatacttg cttgaacgct tgatttract gatattctat ccaaaagcaa      120
gtagaccaga aactctcaag atgttgcaaa taccgttcga tgttttggt ttagattgtt       180 ttaatgttga tgcttttta cttattttg gaagcgtctt tttaatttag ttttatatta       240
taggtatatg aatgtgttta tgccaataag ggtttttttg tacagttatg tgattataaa       300
cagtcttttg tctagtttt ttcaccagta tcggcctcta tttataaaaa acggagcagc       360
tttcggtgtc agtaattctg aaaaaatttg tgtcactctg attgtaaatg aattaattta       420
gctagatagt tgcgagcccc aacgagaaga ttgtcagaca aagacaacat tcaacaacct       480
acatccgtta ctattcgtta actcgaggta cttgaaactt ttcagttaag tcgctcgtcc       540
aacgccggcg gaccttatta acttcttcac tataagaaaa tcacacgagc gcccggacga       600
tgtctctgtt taaatggcgc aagttttccg ctttgtaata tatatttata ccccttttctt      660 ctctcccctg caatataata gtttaattct aatattaata atatcctata ttttcttcat       720
ttaccggcgc actctcgccc gaacgacctc aaaatgtctg ctacattcat aataaccaaa       780
agctcataac ttttttttt gaacctgaat atatatacat cacatgtcac tgctggtcct       840
tgccgaccag cgtatacaat ctcgatagtt ggacctcccg cgacctccaa aatcgaacta       900
ccttcacaat ggactacaac aagagatctt cggtctcaac cgtgcctaat gcagctccca       960
taagagtcgg attcgtcggt ctcaacgcag ccaaaggatg ggcaatcaag acacattacc      1020
ccgccatact gcaactatcg tcacaatttc aaatcactgc cttatacagt ccaaaaattg      1080
agacttctat tgccaccatc cagcgtctaa aattgagtaa tgccactgct tttcccactt      1140
tagagtcatt tgcatcatct tccactatag atatgatagt gatagctatc caagtggcca      1200
gtcattatga cgttgttatg cctctcttgg aattctccaa aaataatccg aacctcaagt      1260
atcttttcgt agaatgggcc cttgcatgtt cactagatca agccgaatcc atttataagg      1320
ctgctgctga acgtggggtt caaaccatca tctctttaca aggtcgtaaa tcaccatata      1380
ttttgagagc aaaagaatta atatctcaag gctatatcgg cgacattaat tctatcgaga      1440
ttgctggaaa tggcggttgg tacggctacg aaaggcctgt taaatcacca aaatacatct      1500
atgaaatcgg gaacggtgta gatctggtaa ccacaacatt tggtcacaca atcgatattt      1560
tacaatacat gacaagttcg tacttttcca ggataaatgc aatggttttc aataatattc      1620
cagagcaaga gctgatagat gagcgtggta accgattggg ccagcgagtc ccaaagacag      1680
taccggatca tctttattc caaggcacat tgttaaatgg caatgttcca gtgtcatgca      1740
gtttcaaagg tggcaaacct accaaaaaat ttaccaaaaa tttggtcatt gatattcacg      1800
gtaccaaggg agatttgaaa cttgaaggcg atgccggatt cgcagaaatt tcaaatctgg      1860
tcctttacta cagtggaact agagcaaacg acttcccgct agctaatgga caacaagctc      1920
ctttagaccc ggggtatgat gcaggtaaag aaatcatgga agtatatcat ttacgaaatt      1980
ataatgccat tgtcggtaat attcatcgac tgtatcaatc tatctctgac ttccacttca      2040
atacaaagaa aattcctgaa ttaccctcac aatttgtaat gcaaggtttc gatttcgaag      2100
gctttcccac cttgatggat gctctgatat tacacaggtt aatcgagagc gtttataaaa      2160
gtaacatgat gggctccaca ttaaacgtta gcaatatctc gcattatagt ttaatgaaaa      2220
tcgaagaagg taagttagtc atttggatca acggtgacaa gggttacaat ggtttggctg      2280
aagttggtaa gaagtttgaa aaagacactg gtatcaaggt taccgtcgaa catccagata      2340
```

-continued

```
agttggaaga aaagttccca caagtcgccg ctactggtga tggtccagat attatcttct    2400
gggctcacga cagattcggt ggttacgctc aatctggttt gttagccgaa attactcctg    2460
acaaggcttt ccaagacaaa ttatacccat tcacctggga tgctgtcaga tataacggta    2520
aattgatcgc ttacccaatc gctgtcgaag ctttgtcctt gatctacaac aaggatttgt    2580
tacctaaccc accaaaaact tgggaagaaa tcccagcttt ggacaaggaa ttgaaagcta    2640
aaggtaaatc cgctttgatg ttcaacttac aagaaccata tttcacttgg cctttgattg    2700
ctgctgatgg tggttatgcc tttaagtacg aaaacggtaa gtacgatatt aaggacgtcg    2760
gtgttgacaa cgccggtgct aaggctggtt aactttctt ggtcgatttg atcaagaaca    2820
agcatatgaa cgccgacact gactactcta tcgctgaagc cgctttcaat aagggtgaga    2880
ctgctatgac tattaacggt ccttgggctt ggtctaatat cgatacttct aaggtcaact    2940
acggtgttac cgttttgcca accttcaaag gtcaaccatc caagccattt gttggtgttt    3000
tgtccgctgg tatcaacgct gcttctccta caaggaatt ggctaaggaa ttcttggaaa    3060
actatttgtt gactgatgaa ggtttagaag ctgttaacaa ggacaagcca ttgggtgccg    3120
ttgccttgaa gtcttacgaa gaagaattgg ccaaggaccc tagaattgct gctactatgg    3180
aaaatgccca aaaaggtgag atcatgccaa acattccaca aatgtctgct ttctggtatg    3240
ctgttagaac tgccgtcatt aacgctgctt ccggtagaca aactgttgat gaagccttga    3300
aagatgccca aactaactcc tcttccaaca acaataataa caacaacaac aacaacttgg    3360
gtatcgaagg tagataaaag catcttgccc tgtgcttggc ccccagtgca gcgaacgtta    3420
taaaaacgaa tactgagtat atatctatgt aaaacaacca tatcatttct tgttctgaac    3480
tttgtttacc taactagttt taaatttccc tttttcgtgc atgcgggtgt tcttatttat    3540
tagcatacta catttgaaat atcaaatttc cttagtagaa aagtgagaga aggtggcact    3600
gacacaatcc ccgcgtgctt ggccggccgt acgaaaatcg ttattgtctt gaaggtgaaa    3660
tttctactct tattaatggt gaacgttaag ctgatgctat gatggaagct gattggtctt    3720
aacttgcttg tcatcttgct aatggtcatt ggctcgtgtt attacttaag ttatttgtac    3780
tcgttttgaa cgtaatgcta atgatcatct tatggaataa tagtgagtgg tttcagggtc    3840
cataaagctt ttcaattcat ctttttttt tttgttcttt tttttgattc cggtttcttt    3900
gaaattttt tgattcggta atctccgagc agaaggaaga acgaaggaag gagcacagac    3960
ttagattggt atatatacgc atatgtggtg ttgaagaaac atgaaattgc ccagtattct    4020
taacccaact gcacagaaca aaaacctgca ggaaacgaag ataaatcatg tcgaaagcta    4080
catataagga acgtgctgct actcatccta gtcctgttgc tgccaagcta tttaatatca    4140
tgcacgaaaa gcaaacaaac ttgtgtgctt cattggatgt tcgtaccacc aaggaattac    4200
tggagttagt tgaagcatta ggtcccaaaa tttgtttact aaaaacacat gtggatatct    4260
tgactgattt ttccatggag ggcacagtta agccgctaaa ggcattatcc gccaagtaca    4320
atttttact cttcgaagac agaaaatttg ctgacattgg taatacagtc aaattgcagt    4380
actctgcggg tgtatacaga atagcagaat gggcagacat tacgaatgca cacggtgtgg    4440
tgggcccagg tattgttagc ggtttgaagc aggcggcgga agaagtaaca aggaaccta    4500
gaggcctttt gatgttagca gaattgtcat gcaagggctc cctagctact ggagaatata    4560
ctaagggtac tgttgacatt gcgaagagtg acaaagattt tgttatcggc tttattgctc    4620
aaagagacat gggtggaaga gatgaaggtt acgattggtt gattatgaca cccggtgtgg    4680
gtttagatga caagggagac gcattgggtc aacagtatag aaccgtggat gatgtggtct    4740
```
ctacaggatc tgacattatt attgttggaa gcggtgttta aacccagcg cctggcggg    4799

<210> SEQ ID NO 69
<211> LENGTH: 20
<212> TYPE: DNA
<213> ORGANISM: Artificial Sequence
<220> FEATURE:
<223> OTHER INFORMATION: Synthetic: PC540  a reverse primer for vector
      backbone for Gibson assembly

<400> SEQUENCE: 69
tgactaactt accttcttcg                                              20

<210> SEQ ID NO 70
<211> LENGTH: 21
<212> TYPE: DNA
<213> ORGANISM: Artificial Sequence
<220> FEATURE:
<223> OTHER INFORMATION: Synthetic: PC541  a forward primer for vector
      backbone for Gibson assembly

<400> SEQUENCE: 70
caacaacttg ggtatcgaag g                                            21

<210> SEQ ID NO 71
<211> LENGTH: 2178
<212> TYPE: DNA
<213> ORGANISM: Artificial Sequence
<220> FEATURE:
<223> OTHER INFORMATION: Synthetic: D_GAL80

<400> SEQUENCE: 71
atgcagattt tcgtcaagac tttgaccggt aaaaccataa cattggaagt tgaatcttcc    60
gataccatcg acaacgttaa gtcgaaaatt caagacaagg aaggtatccc tccagatcaa   120
caaagattga tctttgccgg taagcagcta gaagacggta gaacgctgtc tgattacaac   180
attcagaagg agtccacctt acatcttgtg ctaaggctaa gaggtggtag gcacggatcc   240
ggcatcatgg ttcgaccatt gaactgcatc gtcgccgtgt cccaaaatat ggggattggc   300
aagaacggag acctaccctg gcctccgctc aggaacgagt tcaagtactt ccaaagaatg   360
accacaacct cttcagtgga aggtaaacag aatctggtga ttatgggtag gaaaacctgg   420
ttctccattc ctgagaagaa tcgactttta aggacagaa ttaatatagt tctcagtaga   480
gaactcaaag aaccaccacg aggagctcat tttcttgcca aaagtttgga tgatgcctta   540
agacttattg aacaaccgga attggcaagt aaagtagaca tggtttggat agtcggaggc   600
agttctgttt accaggaagc catgaatcaa ccaggccacc tcagactctt tgtgacaagg   660
atcatgcagg aatttgaaag tgacacgttt ttcccagaaa ttgatttggg gaaatataaa   720
cttctcccag aatacccagg cgtcctctct gaggtccagg aggaaaaagg catcaagtat   780
aagtttgaag tctacgagaa gaaagacggt accgaacaaa agcttatttc tgaagaagac   840
ttgggagctg gtgcaggcgc tggagcgggt gccatggact acaacaagag atcttcggtc   900
tcaaccgtgc ctaatgcagc tcccataaga gtcggattcg tcggtctcaa cgcagccaaa   960
ggatgggcaa tcaagacaca ttaccccgcc atactgcaac tatcgtcaca atttcaaatc  1020
actgccttat acagtccaaa aattgagact tctattgcca ccatccagcg tctaaaattg  1080
agtaatgcca ctgcttttcc cactttagag tcatttgcat catcttccac tatagatatg  1140
atagtgatag ctatccaagt ggccagtcat tatgacgttg ttatgcctct cttggaattc  1200

| | |
|---|---:|
| tccaaaaata atccgaacct caagtatctt ttcgtagaat gggcccttgc atgttcacta | 1260 |
| gatcaagccg aatccattta taaggctgct gctgaacgtg gggttcaaac catcatctct | 1320 |
| ttacaaggtc gtaaatcacc atatattttg agagcaaaag aattaatatc tcaaggctat | 1380 |
| atcggcgaca ttaattctat cgagattgct ggaaatggcg gttggtacgg ctacgaaagg | 1440 |
| cctgttaaat caccaaaata catctatgaa atcgggaacg gtgtagatct ggtaaccaca | 1500 |
| acatttggtc acacaatcga tattttacaa tacatgacaa gttcgtactt ttccaggata | 1560 |
| aatgcaatgg ttttcaataa tattccagag caagagctga tagatgagcg tggtaaccga | 1620 |
| ttgggccagc gagtcccaaa gacagtaccg gatcatcttt tattccaagg cacattgtta | 1680 |
| aatggcaatg ttccagtgtc atgcagtttc aaaggtggca aacctaccaa aaaatttacc | 1740 |
| aaaaatttgg tcattgatat tcacggtacc aagggagatt tgaaacttga aggcgatgcc | 1800 |
| ggattcgcag aaatttcaaa tctggtcctt tactacagtg gaactagagc aaacgacttc | 1860 |
| ccgctagcta atggacaaca agctccttta gacccggggt atgatgcagg taaagaaatc | 1920 |
| atggaagtat atcatttacg aaattataat gccattgtcg gtaatattca tcgactgtat | 1980 |
| caatctatct ctgacttcca cttcaataca agaaaattc ctgaattacc ctcacaattt | 2040 |
| gtaatgcaag gtttcgattt cgaaggcttt cccaccttga tggatgctct gatattacac | 2100 |
| aggttaatcg agagcgttta taaaagtaac atgatgggct ccacattaaa cgttagcaat | 2160 |
| atctcgcatt atagttta | 2178 |

<210> SEQ ID NO 72
<211> LENGTH: 3130
<212> TYPE: DNA
<213> ORGANISM: Artificial Sequence
<220> FEATURE:
<223> OTHER INFORMATION: Synthetic: MS71316

<400> SEQUENCE: 72

| | |
|---|---:|
| gacggcacgg ccacgcgttt aaaccgccac aaattgttcg atttcacagc ggacggtgtt | 60 |
| gcgtcaaggg ctgaaaagac aatcaattac tacaaaggaa agcagttgct ttctcctatg | 120 |
| ggaagagctt tctaagtctg aagaagtaaa cagttcttg ctatttcaca cttcctggtt | 180 |
| gatggtcact tgctgcctga atatatata tatgtatgac atatgtactt gttttctttt | 240 |
| ttgtgccttt gttacgtcta tattcattga aactgattat tcgattttct tcttgctgac | 300 |
| cgcttctaga ggcatcgcac agttttagcg aggaaaactc ttcaatagtt ttgccagcgg | 360 |
| aattccactt gcaattacat aaaaaattcc ggcggttttt cgcgtgtgac tcaatgtcga | 420 |
| aatacctgcc taatgaacat gaacatcgcc caaatgtatt tgaagacccg ctgggagaag | 480 |
| ttcaagatat ataagtaaca agcagccaat agtataaaaa aaatctgcg ctcgtccaac | 540 |
| gccggcggac ctacgaaaat cgttattgtc ttgaaggtga atttctact cttattaatg | 600 |
| gtgaacgtta agctgatgct atgatggaag ctgattggtc ttaacttgct tgtcatcttg | 660 |
| ctaatggtca ttggctcgtg ttattactta agttatttgt actcgttttg aacgtaatgc | 720 |
| taatgatcat cttatggaat aatagtgagt ggtttcaggg tccataaagc ttttcaattc | 780 |
| atctttttt tttttgttct ttttttgat tccggtttct ttgaaatttt tttgattcgg | 840 |
| taatctccga gcagaaggaa gaacgaagga aggagcacag acttagattg gtatatatac | 900 |
| gcatatgtgg tgttgaagaa acatgaaatt gcccagtatt cttaacccaa ctgcacagaa | 960 |
| caaaaacctg caggaaacga agataaatca tgtcgaaagc tacatataag gaacgtgctg | 1020 |
| ctactcatcc tagtcctgtt gctgccaagc tatttaatat catgcacgaa aagcaaacaa | 1080 |

| | |
|---|---|
| acttgtgtgc ttcattggat gttcgtacca ccaaggaatt actggagtta gttgaagcat | 1140 |
| taggtcccaa aatttgttta ctaaaaacac atgtggatat cttgactgat ttttccatgg | 1200 |
| agggcacagt taagccgcta aaggcattat ccgccaagta cattttttta ctcttcgaag | 1260 |
| acagaaaatt tgctgacatt ggtaatacag tcaaattgca gtactctgcg ggtgtataca | 1320 |
| gaatagcaga atgggcagac attacgaatg cacacggtgt ggtgggccca ggtattgtta | 1380 |
| gcggtttgaa gcaggcggcg gaagaagtaa caaaggaacc tagaggcctt ttgatgttag | 1440 |
| cagaattgtc atgcaagggc tccctagcta ctggagaata tactaagggt actgttgaca | 1500 |
| ttgcgaagag tgacaaagat tttgttatcg gctttattgc tcaaagagac atgggtggaa | 1560 |
| gagatgaagg ttacgattgg ttgattatga cacccggtgt gggtttagat gacaagggag | 1620 |
| acgcattggg tcaacagtat agaaccgtgg atgatgtggc tctacagga tctgacatta | 1680 |
| ttattgttgg aagaggacta tttgcaaagg aagggatgc taaggtagag ggtgaacgtt | 1740 |
| acagaaaagc aggctgggaa gcatatttga gaagatgcgg ccagcaaaac taaaaaactg | 1800 |
| tattataagt aaatgcatgt atactaaact cacaaattag agcttcaatt taattatatc | 1860 |
| agttattacc acgaaaatcg ttattgtctt gaaggtgaaa tttctactct tattaatggt | 1920 |
| gaacgttaag ctgatgctat gatggaagct gattggtctt aacttgcttg tcatcttgct | 1980 |
| aatggtcata tggctcgtgt tattacttaa gttatttgta ctcgttttga acgtaatgct | 2040 |
| aatgatcatc ttatggaata atagtgaagg tccgccggcg ttggacgagc gtcgcttcgc | 2100 |
| tgattaatta ccccagaaat aaggctaaaa aactaatcgc attattatcc tatggttgtt | 2160 |
| aatttgattc gttgatttga aggtttgtgg ggccaggtta ctgccaattt ttcctcttca | 2220 |
| taaccataaa agctagtatt gtagaatctt tattgttcgg agcagtgcgg cgcgaggcac | 2280 |
| atctgcgttt caggaacgcg accggtgaag accaggacgc acggaggaga gtcttccgtc | 2340 |
| ggagggctgt cgcccgctcg gcggcttcta atccgtactt caatatagca atgagcagtt | 2400 |
| aagcgtatta ctgaaagttc caaagagaag gttttttttag gctaagataa tggggctctt | 2460 |
| tacatttcca caacatataa gtaagattag atatggatat gtatatggtg gtattgccat | 2520 |
| gtaatatgat tattaaactt ctttgcgtcc atccaaaaaa aaagtatgtg aaggtagttc | 2580 |
| gatttttggag gtcgcgggag gtatgactaa cgaaaaggtc tggatagaga agttggataa | 2640 |
| tccaactctt tcagtgttac cacatgactt tttacgccca caacaagaac cttatacgaa | 2700 |
| acaagctaca tattcgttac agctacctca gctcgatgtg cctcatgata gttttctaa | 2760 |
| caaatacgct gtcgctttga gtgtatgggc tgcattgata tatagagtaa ccggtgacga | 2820 |
| tgatattgtt ctttatattg cgaataacaa atcttaaga ttcaatattc aaccaacgtg | 2880 |
| gtcatttaat gagctgtatt ctacaattaa caatgagttg aacaagctca attctattga | 2940 |
| ggccaatttt tcctttgacg agctagctga aaaaattcaa agttgccaag atctggaaag | 3000 |
| gaccccctcag ttgttccgtt tggccttttt ggaaaaccaa gatttcaaat tagacgagtt | 3060 |
| caagcatcat ttagtggact ttgctttgaa tttggatacc agggcggttt aaacgcgtgg | 3120 |
| ccgtgccgtc | 3130 |

<210> SEQ ID NO 73
<211> LENGTH: 4799
<212> TYPE: DNA
<213> ORGANISM: Artificial Sequence
<220> FEATURE:
<223> OTHER INFORMATION: Synthetic: S69250 containing MBP L8 mutant

```
<400> SEQUENCE: 73
gacggcacgg ccacgcgttt aaaccgccta cgccatcatt aaagacctgg tcaactataa      60
aataatacaa tcaatacttg cttgaacgct tgattttact gatattctat ccaaaagcaa     120
gtagaccaga aactctcaag atgttgcaaa taccgttcga tgttttggt ttagattgtt      180
ttaatgttga tgcttttta cttatttttg gaagcgtctt tttaatttag ttttatatta     240
taggtatatg aatgtgttta tgccaataag ggttttttg tacagttatg tgattataaa      300
cagtcttttg tctagttttt ttcaccagta tcggcctcta tttataaaaa acggagcagc    360
tttcggtgtc agtaattctg aaaaaatttg tgtcactctg attgtaaatg aattaattta   420
gctagatagt tgcgagcccc aacgagaaga ttgtcagaca aagacaacat tcaacaacct   480
acatccgtta ctattcgtta actcgaggta cttgaaactt ttcagttaag tcgctcgtcc    540
aacgccggcg gaccttatta acttcttcac tataagaaaa tcacacgagc gcccggacga    600
tgtctctgtt taaatggcgc aagttttccg cttttgtaata tatatttata cccctttctt   660
ctctcccctg caatataata gtttaattct aatattaata atatcctata ttttcttcat    720
ttaccggcgc actctcgccc gaacgacctc aaaatgtctg ctacattcat aataaccaaa    780
agctcataac tttttttttt gaacctgaat atatatacat cacatgtcac tgctggtcct   840
tgccgaccag cgtatacaat ctcgatagtt ggacctcccg cgacctccaa aatcgaacta    900
ccttcacaat ggactacaac aagagatctt cggtctcaac cgtgcctaat gcagctccca     960
taagagtcgg attcgtcggt ctcaacgcag ccaaaggatg ggcaatcaag acacattacc    1020
ccgccatact gcaactatcg tcacaatttc aaatcactgc cttatacagt ccaaaaattg   1080
agacttctat tgccaccatc cagcgtctaa aattgagtaa tgccactgct tttcccactt    1140
tagagtcatt tgcatcatct tccactatag atatgatagt gatagctatc caagtggcca    1200
gtcattatga cgttgttatg cctctcttgg aattctccaa aaataatccg aacctcaagt    1260
atcttttcgt agaatgggcc cttgcatgtt cactagatca agccgaatcc atttataagg    1320
ctgctgctga acgtggggtt caaaccatca tctctcttaca aggtcgtaaa tcaccatata   1380
ttttgagagc aaaagaatta atatctcaag gctatatcgg cgacattaat tctatcgaga    1440
ttgctggaaa tggcggttgg tacggctacg aaaggcctgt taaatcacca aaatacatct    1500
atgaaatcgg gaacggtgta gatctggtaa ccacaacatt tggtcacaca atcgatattt    1560
tacaatacat gacaagttcg tacttttcca ggataaatgc aatggttttc aataatattc    1620
cagagcaaga gctgatagat gagcgtggta accgattggg ccagcgagtc ccaaagacag    1680
taccggatca tctttattc caaggcacat tgttaaatgg caatgttcca gtgtcatgca    1740
gtttcaaagg tggcaaacct accaaaaat ttaccaaaaa tttggtcatt gatattcacg     1800
gtaccaaggg agatttgaaa cttgaaggcg atgccggatt cgcagaaatt tcaaatctgg    1860
tcctttacta cagtggaact agagcaaacg acttcccgct agctaatgga caacaagctc    1920
ctttagaccc ggggtatgat gcaggtaaag aaatcatgga agtatatcat ttacgaaatt    1980
ataatgccat tgtcggtaat attcatcgac tgtatcaatc tatctctgac ttccacttca    2040
atacaaagaa aattcctgaa ttaccctcac aatttgtaat gcaaggtttc gatttcgaag    2100
gctttcccac cttgatggat gctctgatat tacacaggtt aatcgagagc gtttataaaa    2160
gtaacatgat gggctccaca ttaaacgtta gcaatatctc gcattatagt ttaatgaaaa    2220
tcgaagaagg taagttagtc acttggatca acggtgacaa gggttacaat ggtttggctg    2280
aagctggtaa gaagtttgaa aaagacactg gtatcaaggt taccgtcgaa catccagtta    2340
```

-continued

```
agttggaaga aaagttccca caagtcgccg ctactggtga tggtccagat attatcttct      2400
gggctcacga cagattcggt ggttacgctc aatctggttt gttagccgaa attactcctg      2460
acaaggcttt ccaagacaaa ttatacccat tcacctggga tgctgtcaga tataacggta      2520
aattgatcgc ttacccaatc actgtcgaag ctttgtcctt gatctacaac aaggatttgt      2580
tacctaaccc accaaaaact tgggaagaaa tcccagcttt ggacaaggaa ttgaaagcta      2640
aaggtaaatc cgctttgatc ttcaacttac aagaaccata tttcacttgg cctttgattg      2700
ctgctgatgg tggttatgcc tttaagtacg aaaacggtaa gtacgatatt aaggacgtcg      2760
gtgttgacaa cgccggtgct aaggctggtt aactttcttg gtcgatttg atcaagaaca      2820 agcatatgaa cgccgacact gactactcta tcgctgaagt cgctttcaat aagggtgaga      2880
ctgctatgac tattaacggt ccttgggctt ggtctaatat cgatacttct aaggtcaact      2940
acggtgttac cgttttgcca accttcaaag gtcaaccatc caagccattt gttggtgttt      3000
tgtccgctgg tatcaacgct gcttctccta caaggaatt ggctaaggaa ttcttggaaa      3060
actatttgtt gactgatgaa ggtttagaag ctgttaacaa ggacaagcca ttgggtgccg      3120
ttgccttgaa gtcttacgaa gaagaattgg ccaaggaccc tagaattgct gctactatgg      3180
aaaatgccca aaaggtgag atcatgccaa acattccaca aatgtctgct ttctggtatg      3240
ctgttagaac tgccgtcatt aacgctgctt ccggtagaca aactgttgat gaagccttga      3300
aagatgccta aactaactcc tcttccaaca acaataataa caacaacaac aacaacttgg      3360
gtatcgaagg tagataaaag catcttgccc tgtgcttggc ccccagtgca gcgaacgtta      3420
taaaaacgaa tactgagtat atatctatgt aaaacaacca tatcatttct tgttctgaac      3480
tttgtttacc taactagttt taaatttccc ttttttcgtgc atgcgggtgt tcttatttat      3540
tagcatacta catttgaaat atcaaatttc cttagtagaa aagtgagaga aggtggcact      3600
gacacaatcc ccgcgtgctt ggccggccgt acgaaaatcg ttattgtctt gaaggtgaaa      3660
tttctactct tattaatggt gaacgttaag ctgatgctat gatggaagct gattggtctt      3720
aacttgcttg tcatcttgct aatggtcatt ggctcgtgtt attacttaag ttatttgtac      3780
tcgttttgaa cgtaatgcta atgatcatct tatgaataa tagtgagtgg tttcagggtc      3840
cataaagctt ttcaattcat cttttttttt tttgttcttt tttttgattc cggtttcttt      3900
gaaatttttt tgattcggta atctccgagc agaaggaaga acgaaggaag gagcacagac      3960
ttagattggt atatatacgc atatgtggtg ttgaagaaac atgaaattgc ccagtattct      4020
taacccaact gcacagaaca aaaacctgca ggaaacgaag ataaatcatg tcgaaagcta      4080
catataagga acgtgctgct actcatccta gtcctgttgc tgccaagcta tttaatatca      4140
tgcacgaaaa gcaaacaaac ttgtgtgctt cattggatgt tcgtaccacc aaggaattac      4200
tggagttagt tgaagcatta ggtcccaaaa tttgtttact aaaaacacat gtggatatct      4260
tgactgattt ttccatggag ggcacagtta agccgctaaa ggcattatcc gccaagtaca      4320 atttttact cttcgaagac agaaaatttg ctgacattgg taatacagtc aaattgcagt      4380
actctgcggg tgtatacaga atagcagaat gggcagacat tacgaatgca cacggtgtgg      4440
tgggcccagg tattgttagc ggtttgaagc aggcggcgga agaagtaaca aaggaaccta      4500
gaggcctttt gatgttagca gaattgtcat gcaagggctc cctagctact ggagaatata      4560
ctaagggtac tgttgacatt gcgaagagtg acaaagattt tgttatcggc tttattgctc      4620
aaagagacat gggtggaaga gatgaaggtt acgattggtt gattatgaca cccggtgtgg      4680
```

```
gtttagatga caagggagac gcattgggtc aacagtatag aaccgtggat gatgtggtct    4740
ctacaggatc tgacattatt attgttggaa gcggtgttta aaccccagcg cctggcggg     4799

<210> SEQ ID NO 74
<211> LENGTH: 4799
<212> TYPE: DNA
<213> ORGANISM: Artificial Sequence
<220> FEATURE:
<223> OTHER INFORMATION: Synthetic: DNA construct containing MBP M5
      mutant

<400> SEQUENCE: 74
gacggcacgg ccacgcgttt aaaccgccta cgccatcatt aaagacctgg tcaactataa      60
aataatacaa tcaatacttg cttgaacgct tgattttact gatattctat ccaaaagcaa     120
gtagaccaga aactctcaag atgttgcaaa taccgttcga tgttttttggt ttagattgtt    180 ttaatgttga tgcttttttta cttattttttg gaagcgtctt tttaatttag ttttatatta   240
taggtatatg aatgtgttta tgccaataag ggttttttttg tacagttatg tgattataaa    300
cagtcttttg tctagttttt ttcaccagta tcggcctcta tttataaaaa acggagcagc    360
tttcggtgtc agtaattctg aaaaaatttg tgtcactctg attgtaaatg aattaattta    420
gctagatagt tgcgagcccc aacgagaaga ttgtcagaca aagacaacat tcaacaacct    480
acatccgtta ctattcgtta actcgaggta cttgaaactt ttcagttaag tcgctcgtcc    540
aacgccggcg gaccttatta acttcttcac tataagaaaa tcacacgagc gcccggacga    600
tgtctctgtt taaatggcgc aagttttccg ctttgtaata tatatttata ccccttttctt   660 ctctcccctg caatataata gtttaattct aatattaata atatcctata ttttcttcat    720
ttaccggcgc actctcgccc gaacgacctc aaaatgtctg ctacattcat aataaccaaa    780
agctcataac ttttttttttt gaacctgaat atatatacat cacatgtcac tgctggtcct   840
tgccgaccag cgtatacaat ctcgatagtt ggacctcccg cgacctccaa aatcgaacta    900
ccttcacaat ggactacaac aagagatctt cggtctcaac cgtgcctaat gcagctccca    960
taagagtcgg attcgtcggt ctcaacgcag ccaaaggatg ggcaatcaag acacattacc   1020
ccgccatact gcaactatcg tcacaatttc aaatcactgc cttatacagt ccaaaaattg   1080
agacttctat tgccaccatc cagcgtctaa aattgagtaa tgccactgct tttcccactt   1140
tagagtcatt tgcatcatct tccactatag atatgatagt gatagctatc caagtggcca   1200
gtcattatga cgttgttatg cctctcttgg aattctccaa aaataatccg aacctcaagt   1260
atcttttcgt agaatgggcc cttgcatgtt cactagatca agccgaatcc atttataagg   1320
ctgctgctga acgtggggtt caaaccatca tctctttaca aggtcgtaaa tcaccatata   1380
ttttgagagc aaaagaatta atatctcaag gctatatcgg cgacattaat tctatcgaga   1440
ttgctggaaa tggcggttgg tacggctacg aaaggcctgt taaatcacca aaatacatct   1500
atgaaatcgg gaacgtgta gatctggtaa ccacaacatt tggtcacaca atcgatattt    1560
tacaatacat gacaagttcg tacttttcca ggataaatgc aatggttttc aataatattc   1620
cagagcaaga gctgatagat gagcgtggta accgattggg ccagcgagtc ccaaagacag   1680
taccggatca tcttttattc caaggcacat tgttaaatgg caatgttcca gtgtcatgca   1740
gtttcaaagg tggcaaacct accaaaaaat ttaccaaaaa tttggtcatt gatattcacg   1800
gtaccaaggg agatttgaaa cttgaaggcg atgccggatt cgcagaaatt tcaaatctgg   1860
tcctttacta cagtggaact agagcaaacg acttcccgct agctaatgga caacaagctc   1920
```

```
ctttagaccc ggggtatgat gcaggtaaag aaatcatgga agtatatcat ttacgaaatt    1980
ataatgccat tgtcggtaat attcatcgac tgtatcaatc tatctctgac ttccacttca    2040
atacaaagaa aattcctgaa ttaccctcac aatttgtaat gcaaggtttc gatttcgaag    2100
gctttcccac cttgatggat gctctgatat tacacaggtt aatcgagagc gtttataaaa    2160
gtaacatgat gggctccaca ttaaacgtta gcaatatctc gcattatagt ttaatgaaaa    2220
tcgaagaagg taagttagtc atttggatca acggtgacaa gggttacaat ggtttggctg    2280
aagttggtaa gaagtttgaa aaagacactg gtatcaaggt taccgtcgaa catccagata    2340
agttggaaga aaagttccca caagtcgccg ctactggtga tggtccagat attatcttct    2400
gggctcacga cagatccggt ggttacgctc aatctggttt gttagccgaa attactcctg    2460
acaaggcttt ccaagacaaa ttatacccat tcaccaggga tgctgtcaga tataacggta    2520
aattgatcgc ttacccaatc gctgtcgaag cattgtcctt gatctacaac aaggatttgt    2580
tacctaaccc accaaaaact tgggaagaaa tcccagcttt ggacaaggaa ttgaaagcta    2640
aaggtaaatc cgctttgatg ttcaacttac aagaaccata tttcacttgg cctttgattg    2700
ctgctgatgg tggttatgcc tttaagtacg aaaacggtaa gtacgatatt aaggacgtcg    2760
gtgttgacag cgccggtgct aaggctggtt taactttctt ggtcgttttg atcaagaaca    2820
agcatatgaa cgccgacact gactactcta tcgctgaagc cgctttcaat aagggtgaga    2880
ctgctatgac tattaacggt ccttgggctt ggtctaatat cgatacttct aaggtcaact    2940
acggtgttac cgttttgcca accttcaaag gtcaaccatc caagccattt gttggtgttt    3000
tgtccgctgg tatcaacgct gcttctccta caaggaatt ggctaaggaa ttcttggaaa    3060
actatttgtt gactgatgaa ggtttagaag ctgttaacaa ggacaagcca ttgggtgccg    3120
ttgccttgaa gtcttacgaa gaagaattgg ccaaggaccc tagaattgct gctactatgg    3180
aaaatgccca aaaaggtgag atcatgccaa acattccaca aatgtctgct ttctggtatg    3240
ctgttagaac tgccgtcatt aacgctgctt ccggtagaca aactgttgat gaagccttga    3300
aagatgccca aactaactcc tcttccaaca caataataa caacaacaac aacaacttgg    3360
gtatcgaagg tagataaaag catcttgccc tgtgcttggc ccccagtgca gcgaacgtta    3420
taaaaacgaa tactgagtat atatctatgt aaaacaacca tatcatttct tgttctgaac    3480
tttgtttacc taactagttt taaatttccc tttttcgtgc atgcgggtgt tcttatttat    3540
tagcatacta catttgaaat atcaaatttc cttagtagaa aagtgagaga aggtggcact    3600
gacacaatcc ccgcgtgctt ggccggccgt acgaaaatcg ttattgtctt gaaggtgaaa    3660
tttctactct tattaatggt gaacgttaag ctgatgctat gatggaagct gattggtctt    3720
aacttgcttg tcatcttgct aatggtcatt ggctcgtgtt attacttaag ttatttgtac    3780
tcgttttgaa cgtaatgcta atgatcatct tatggaataa tagtgagtgg tttcagggtc    3840
cataaagctt ttcaattcat ctttttttttt tttgttcttt tttttgattc cggtttcttt    3900
gaaattttt tgattcggta atctccgagc agaaggaaga acgaaggaag gagcacagac    3960
ttagattggt atatatacgc atatgtggtg ttgaagaaac atgaaattgc ccagtattct    4020
taacccaact gcacagaaca aaaacctgca ggaaacgaag ataaatcatg tcgaaagcta    4080
catataagga acgtgctgct actcatccta gtcctgttgc tgccaagcta tttaatatca    4140
tgcacgaaaa gcaaacaaac ttgtgtgctt cattggatgt tcgtaccacc aaggaattac    4200
tggagttagt tgaagcatta ggtcccaaaa tttgtttact aaaaacacat gtggatatct    4260
tgactgattt ttccatggag ggcacagtta agccgctaaa ggcattatcc gccaagtaca    4320
```

```
attttttact cttcgaagac agaaaatttg ctgacattgg taatacagtc aaattgcagt      4380
actctgcggg tgtatacaga atagcagaat gggcagacat tacgaatgca cacggtgtgg      4440
tgggcccagg tattgttagc ggtttgaagc aggcggcgga agaagtaaca aaggaaccta      4500
gaggcctttt gatgttagca gaattgtcat gcaagggctc cctagctact ggagaatata      4560
ctaagggtac tgttgacatt gcgaagagtg acaaagattt tgttatcggc tttattgctc      4620
aaagagacat gggtggaaga gatgaaggtt acgattggtt gattatgaca cccggtgtgg      4680
gtttagatga caagggagac gcattgggtc aacagtatag aaccgtggat gatgtggtct      4740
ctacaggatc tgacattatt attgttggaa gcggtgttta accccagcg cctggcggg        4799

<210> SEQ ID NO 75
<211> LENGTH: 4013
<212> TYPE: DNA
<213> ORGANISM: Artificial Sequence
<220> FEATURE:
<223> OTHER INFORMATION: Synthetic: MS85927

<400> SEQUENCE: 75
gacggcacgg ccacgcgttt aaaccgccta cgccatcatt aaagacctgg tcaactataa        60
aataatacaa tcaatacttg cttgaacgct tgattttact gatattctat ccaaaagcaa       120
gtagaccaga aactctcaag atgttgcaaa taccgttcga tgttttttggt ttagattgtt      180 ttaatgttga tgctttttta cttattttg gaagcgtctt tttaatttag ttttatatta       240
taggtatatg aatgtgttta tgccaataag ggttttttg tacagttatg tgattataaa       300
cagtcttttg tctagttttt ttcaccagta tcggcctcta tttataaaaa acggagcagc       360
tttcggtgtc agtaattctg aaaaaatttg tgtcactctg attgtaaatg aattaattta       420
gctagatagt tgcgagcccc aacgagaaga ttgtcagaca aagacaacat tcaacaacct       480
acatccgtta ctattcgtta actcgaggta cttgaaactt tcagttaag tcgctcgtcc        540 aacgccggcg gaccttcag acgcgactgc ctcatcagta agacccgttg aaaagaactt        600
acctgaaaaa aacgaatata tactagcgtt gaatgttagc gtcaacaaca agaagtttaa       660
tgacgcggag gccaaggcaa aaagattcct tgattacgta agggagttag aatcattttg       720
aataaaaaac acgcttttc agttcgagtt tatcattatc aatactgcca tttcaaagaa        780
tacgtaaata attaatagta gtgatttcc taactttatt tagtcaaaa attagccttt        840 taattctgct gtaacccgta catgcccaaa atagggggcg ggttacacag aatatataac       900
atcgtaggtg tctgggtgaa cagtttattc ctggcatcca ctaaatataa tggagcccgc       960
tttttaagct ggcatccaga aaaaaaaga atcccagcac caaatattg ttttcttcac        1020 caaccatcag ttcataggtc cattctctta gcgcaactac agagaacagg gcacaaaca       1080 ggcaaaaaac gggcacaacc tcaatggagt gatgcaacct gcctggagta aatgatgaca      1140
caaggcaatt gacccacgca tgtatctatc tcattttctt acaccttcta ttaccttctg      1200
ctctctctga tttggaaaaa gctgaaaaaa aaggttgaaa ccagttccct gaaattattc      1260
ccctacttga ctaataagta tataaagacg gtaggtattg attgtaattc tgtaaatcta      1320
tttcttaaac ttcttaaatt ctacttttat agttagtctt ttttttagtt ttaaaacacc      1380
aagaacttag tttcgacctc ccgcgacctc caaaatcgaa ctaccttcac aatgacagct      1440
ttaactgaag gggccaagct tttcgaaaaa gagatcccat atatcaccga acttgaaggt      1500
gacgttgagg gtatgaagtt tatcataaaa ggagaaggca caggtgatgc gacaacgggt      1560
```

-continued

```
acaatcaagg caaagtacat ttgtacaact ggggacctgc ctgtcccatg ggccactttg    1620
gtgtctactt tgtcttacgg cgtacaatgt tttgctaagt acccttcaca catcaaagat    1680
ttctttaagt ctgcaatgcc tgaaggatac acacaggaac gtacaatttc atttgagggc    1740
gacggtgtct ataaaacaag agctatggtt acttatgaaa gaggttccat ctacaacaga    1800
gtgacactaa cgggcgaaaa tttcaaaaag gatggacata ttttgcgtaa aaacgtagct    1860
ttccaatgcc caccatcaat actatacatt ctgccagata ctgtaaacaa tggtattaga    1920
gtcgagttta atcaagctta tgatatagaa ggtgtcactg aaaaattggt tacaaaatgc    1980
agccaaatga atagaccatt ggcaggatct gccgctgtgc atatccctag ataccatcac    2040
attacctacc acaccaaatt aagtaaagac agggatgaac gaagagatca tatgtgttta    2100
gttgaggttg ttaaggcagt tgatctcgac acttaccaag atgcacgagc gcaacgctca    2160
caaaatgtgg ctgtggtttc agggtccata aagcttttca attcatcttt tttttttttg    2220
ttcttttttt tgattccggt ttctttgaaa tttttttgat tcggtaatct ccgagcagaa    2280
ggaagaacga aggaaggagc acagacttag attggtatat atacgcatat gtggtgttga    2340
agaaacatga aattgcccag tattcttaac ccaactgcac agaacaaaaa cctgcaggaa    2400
acgaagataa atcatgtcga aagctacata taaggaacgt gctgctactc atcctagtcc    2460
tgttgctgcc aagctatttta atatcatgca cgaaaagcaa acaaacttgt gtgcttcatt    2520
ggatgttcgt accaccaagg aattactgga gttagttgaa gcattaggtc ccaaaatttg    2580
tttactaaaa acacatgtgg atatcttgac tgattttttcc atggagggca cagttaagcc    2640
gctaaaggca ttatccgcca agtacaattt tttactcttc gaagacagaa atttgctga     2700
cattggtaat acagtcaaat tgcagtactc tgcgggtgta tacagaatag cagaatgggc    2760
agacattacg aatgcacacg gtgtggtggg cccaggtatt gttagcggtt tgaagcaggc    2820
ggcagaagaa gtaacaaagg aacctagagg cctttttgatg ttagcagaat tgtcatgcaa    2880
gggctcccta tctactggag aatatactaa gggtactgtt gacattgcga agagtgacaa    2940
agattttgtt atcggctttta ttgctcaaag agacatgggt ggaagagatg aaggttacga    3000
ttggttgatt atgacacccg tgtgggttt agatgacaag ggagacgcat gggtcaaca     3060
gtatagaacc gtggatgatg tggtctctac aggatctgac attattattg ttggaagagg    3120
actatttgca aagggaaggg atgctaaggt agagggtgaa cgttacagaa aagcaggctg    3180
ggaagcatat ttgagaagat gcggccagca aaactaaaaa actgtattat aagtaaatgc    3240
atgtatacta aactcacaaa ttagagcttc aatttaatta tatcagttat tacccgggaa    3300
tctcggtcgt aatgatttct ataatgacga aaaaaaaaa attggaaaga aaagcttca     3360
tggcctttat aaaaaggaac tatccaatac ctcgccagaa ccaagtaaca gtatttgtga    3420
gcgttgcgct cgtgcatcaa aattcattta atattcaatg aagttataaa ttgatagttt    3480
aaataaagtc agtctttttc ctcatgttta gaattgtatt aatgtacgcc gtttacgttg    3540
gagtgtaaat gtgtctattc cagaacgaaa tctaaatgag cagtacaggc agttcagatg    3600
gtactgaagc ggtactaaag atgcatgaat tgaacagatg tggtagttat gtatatgagg    3660
aatatgagtt gtcacattaa aaatataata gctatgatcc cattattata ttcgtgacag    3720
ttcgtaacgt tttaattggc ttatgttttt gagaaatggg tgaattttaa gataattgtt    3780
gggattccat tattgataaa ggctataata ttaggtatac agaatatact ggaagttctc    3840
ctcgaggata taggaatcct caaaatggaa tctatatttc tatttactaa tatcacgatt    3900
attcttcatt ccgttttata tgtttcatta tcctattaca ttatcaatcc ttgcatttca    3960
```
gcttcctcta acttcgatga cagctggcgg tttaaacgcg tggccgtgcc gtc    4013

<210> SEQ ID NO 76
<211> LENGTH: 3608
<212> TYPE: DNA
<213> ORGANISM: Artificial Sequence
<220> FEATURE:
<223> OTHER INFORMATION: Synthetic: S73873 containing MBP mutant L8_v4d

<400> SEQUENCE: 76

```
gacggcacgg ccacgcgttt aaaccgccta cgccatcatt aaagacctgg tcaactataa      60
aataatacaa tcaatacttg cttgaacgct tgattttact gatattctat ccaaaagcaa     120
gtagaccaga aactctcaag atgttgcaaa taccgttcga tgtttttggt ttagattgtt     180
ttaatgttga tgcttttttta cttattttg gaagcgtctt tttaatttag ttttatatta     240
taggtatatg aatgtgttta tgccaataag gttttttttg tacagttatg tgattataaa     300
cagtcttttg tctagttttt tcaccagta tcggcctcta tttataaaaa acggagcagc      360
tttcggtgtc agtaattctg aaaaaatttg tgtcactctg attgtaaatg aattaattta     420
gctagatagt tgcgagcccc aacgagaaga ttgtcagaca aagacaacat tcaacaacct     480
acatccgtta ctattcgtta actcgaggta cttgaaactt tcagttaag tcgctcgtcc      540
aacgccggcg gacctattta acttcttcac tataagaaaa tcacgcgagc gcccggacga     600
tgtctctgtt taaatggcgc aagttttccg ctttgtaata tatatttata cccctttctt     660
ctctcccctg caatataata gtttaattct aatattaata atatcctata ttttcttcat     720
ttaccggcgc actctcgccc gaacgacctc aaaatgtctg ctacattcat aataaccaaa     780
agctcataac ttttttttttt gaacctgaat atatatacat cacatgtcac tgctggtcct     840
tgccgaccag cgtatacaat ctcgatagtt ggacctcccg cgacctccaa aatcgaacta     900
ccttcacaat gacagcttta actgaagggg ccaagctttt cgaaaaagag atcccatata     960
tcaccgaact tgaaggtgac gttgagggta tgaagtttat cataaaagga gaaggcacag    1020
gtgatgcgac aacgggtaca atcaaggcaa agtacatttg tacaactggg gacctgcctg    1080
tcccatgggc cactttggtg tctactttgt cttacggcgt acaatgtttt gctaagtacc    1140
cttcacacat caaagatttc tttaagtctg caatgcctga aggatacaca caggaacgta    1200
caatttcatt tgagggcgac ggtgtctata aacaagagc tatggttact tatgaaagag    1260
gttccatcta acacagagtg acactaacgg gcgaaaattt caaaaaggat ggacatattt    1320
tgcgtaaaaa cgtagctttc caatgcccac catcaatact atacattctg ccagatactg    1380
taaacaatgg tattagagtc gagtttaatc aagcttatga tatagaaggt gtcactgaaa    1440
aattggttac aaaatgcagc caaatgaata gaccattggc aggatctgcc gctgtgcata    1500
tccctagata ccatcacatt acctaccaca ccaaattaag taaagacagg gatgaacgaa    1560
gagatcatat gtgtttagtt gaggttgtta aggcagttga tctcgacact taccaaatga    1620
aaatcgaaga aggtaagtta gtcacttgga tcaacggtga caagggttac aatggtttgg    1680
ctgaagctgg taagaagttt gaaaaagaca ctggtatcaa ggttaccgtc gaacatccag    1740
ttgagttgga agaaaagttc ccacaagtcg ccgctactgg tgatggtcca gatattatct    1800
tctgggctca cgacagattc ggtggttacg ctcaatctgg tttgttagcc gaaattactc    1860
ctggcaaggc tttccaagac aaaattatac cattcacctg ggatgctgtc agatataacg    1920
gtaaattgat cgcttacccca atcgctgtcg aagctttgtc cttgatctac aacaaggatt    1980
```

```
tgttacctaa cccaccaaaa acttgggaag aaatcccagc tttggacaag gaattgaaag    2040
ctaaaggtaa atccgctttg atcttcaact tacaagaacc atatttcact tggcctttga    2100
ttgctgctga tggtggtaat gcctttaagt acgaaaacgg taagtacgat attaaggacg    2160
tcggtgttga cagcgccggt gctaaggctg gtttaacttt cttggtcgat ttgatcaaga    2220
acaagcatat gaacgccgac actgactact ctatcgctga agtcgctttc aataagggtg    2280
agactgctat gactattaac ggtccttggg cttggtctaa tatcgatact tctaaggtca    2340
actacggtgt taccgttttg ccaaccttca aggtcaacc atccaagcca tttgttggtg     2400 tttttgtccgc tggtatcaac gctgcttctc ctaacaagga attggctaag gaattcttgg    2460
aaaactattt gttgactgat gaaggtttag aagctgttaa caaggacaag ccattgggtg    2520
ccgttgcctt gaagtcttac gaagaagaat tggccaagga ccctagaatt gctgctacta    2580
tggaaaatgc ccaaaaaggt gagatcatgc aaacattcc acaaatgtct gctttctggt     2640
atgctgttag aactgccgtc attaacgctg cttccggtag acaaactgtt gatgaagcct    2700
tgaaagatgc ctaaactaac tcctcttcca acaacaataa taacaacaac aacaacaact    2760
tgggtatcga aggtagataa aagcatcttg ccctgtgctt ggcccccagt gcagcgaacg    2820
ttataaaaac gaatactgag tatatatcta tgtaaaacaa ccatatcatt tcttgttctg    2880
aactttgttt acctaactag ttttaaattt ccctttttcg tgcatgcggg tgttcttatt    2940
tattagcata ctcatttga aatatcaaat ttccttagta gaaagtgag agaaggtggc      3000 actgacacaa tccccgcgtg cttggccggc cgtaaaattc atttaatatt caatgaagtt    3060
ataaattgat agtttaaata aagtcagtct ttttcctcat gtttagaatt gtattaatgt    3120
acgccgttta cgttggagtg taaatgtgtc tattccagaa cgaaatctaa atgagcagta    3180
caggcagttc agatggtact gaagcggtac taaagatgca tgaattgaac agatgtggta    3240
gttatgtata tgaggaatat gagttgtcac attaaaaata taatagctat gatcccatta    3300
ttatattcgt gacagttcgt aacgttttaa ttggcttatg ttttgagaa atgggtgaat    3360 tttaagataa ttgttgggat tccattattg ataaaggcta taatattagg tatacagaat    3420
atactggaag ttctcctcga ggatatagga atcctcaaaa tggaatctat atttctattt    3480
actaatatca cgattattct tcattccgtt ttatatgttt cattatccta ttacattatc    3540
aatccttgca tttcagcttc ctctaacttc gatgacagct cggtgtttaa accccagcgc    3600
ctggcggg                                                             3608

<210> SEQ ID NO 77
<211> LENGTH: 6823
<212> TYPE: DNA
<213> ORGANISM: Artificial Sequence
<220> FEATURE:
<223> OTHER INFORMATION: Synthetic: pAM2947

<400> SEQUENCE: 77
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
aaatacacat catcgtccta caagttcatc aaagtgttgg acagacaact ataccagcat    240
ggatctcttg tatcggttct tttctcccgc tctctcgcaa taacaatgaa cactgggtca    300
atcatagcct acacaggtga acagagtagc gtttatacag gtttatacg gtgattccta    360 cggcaaaaat ttttcatttc taaaaaaaaa aagaaaaatt tttctttcca acgctagaag    420
```

```
gaaaagaaaa atctaattaa attgatttgg tgattttctg agagttccct ttttcatata      480
tcgaattttg aatataaaag gagatcgaaa aaattttctt attcaatctg ttttctggtt      540
ttatttgata gttttttttgt gtattattat tatggattag tactggttta tatgggtttt     600
tctgtataac ttcttttttat tttagtttgt ttaatcttat tttgagttac attatagttc     660
cctaactgca agagaagtaa cattaaaaat gggtaaggaa aagactcacg tttcgaggcc      720
gcgattaaat tccaacatgg atgctgattt atatgggtat aaatgggctc gcgataatgt      780
cgggcaatca ggtgcgacaa tctatcgatt gtatgggaag cccgatgcgc cagagttgtt     840
tctgaaacat ggcaaaggta gcgttgccaa tgatgttaca gatgagatgg tcagactaaa    900
ctggctgacg gaatttatgc ctcttccgac catcaagcat tttatccgta ctcctgatga     960
tgcatggtta ctcaccactg cgatccccgg caaaacagca ttccaggtat tagaagaata    1020
tcctgattca ggtgaaaata ttgttgatgc gctggcagtg ttcctgcgcc ggttgcattc    1080
gattcctgtt tgtaattgtc cttttaacag cgatcgcgta tttcgtctcg ctcaggcgca    1140
atcacgaatg aataacggtt tggttgatgc gagtgatttt gatgacgagc gtaatggctg    1200
gcctgttgaa caagtctgga aagaaatgca taagcttttg ccattctcac cggattcagt    1260
cgtcactcat ggtgatttct cacttgataa ccttattttt gacgagggga aattaatagg    1320
ttgtattgat gttggacgag tcggaatcgc agaccgatac caggatcttg ccatcctatg    1380
gaactgcctc ggtgagtttt ctccttcatt acagaaacgg ctttttcaaa aatatggtat    1440
tgataatcct gatatgaata aattgcagtt tcatttgatg ctcgatgagt ttttctaagt    1500
ttaacttgat actactagat ttttttctctt catttataaa attttttggtt ataattgaag   1560 ctttagaagt atgaaaaaat cctttttttt cattctttgc aaccaaaata agaagcttct    1620
tttattcatt gaaatgatga atataaaccct aacaaaagaa aaagactcga atatcaaaca   1680
ttaaaaaaaa ataaaagagg ttatctgttt tcccatttag ttggagtttg cattttctaa    1740
tagatagaac tctcaattaa tgtggattta gtttctctgt tcgtttttttt ttgttttgtt   1800 ctcactgtat ttcatttctc atttagtatt tagttattca tataatctta acttgcggtg   1860
tgaaataccg cacagatgcg taaggagaaa ataccgcatc aggaaattgt aagcgttaat    1920
attttgttaa aattcgcgtt aaattttttgt taaatcagct cattttttaa ccaataggcc   1980
gaaatcggca aaatccctta taaatcaaaa gaatagaccg agataggggtt gagtgttgtt  2040 ccagtttgga acaagagtcc actattaaag aacgtggact ccaacgtcaa agggcgaaaa    2100
accgtctatc agggcgatgg cccactacgt gaaccatcac cctaatcaag tttttttgggg   2160 tcgaggtgcc gtaaagcact aaatcggaac cctaaaggga gccccgatt tagagcttga    2220 cggggaaagc cggcgaacgt ggcgagaaag gaagggaaga aagcgaaagg agcgggcgct    2280
agggcgctgg caagtgtagc ggtcacgctg cgcgtaacca ccacacccgc cgcgcttaat    2340
gcgccgctac agggcgcgtc gcgccattcg ccattcaggc tgcgcaactg ttgggaaggg   2400
cgatcggtgc gggcctcttc gctattacgc cagctggcga aggggggatg tgctgcaagg   2460
cgattaagtt gggtaacgcc agggttttcc cagtcacgac gttgtaaaac gacggccagt    2520
gagcgcgcgt aatacgactc actataggggc ggaataaaaa acacgctttt tcagttcgag   2580
tttatcatta tcaatactgc catttcaaag aatacgtaaa taattaatag tagtgatttt    2640
cctaacttta tttagtcaaa aaattagcct ttaattctg ctgtaacccg tacatgccca     2700
aaataggggg cgggttacac agaatatata acatcgtagg tgtctgggtg aacagtttat    2760
```

```
tcctggcatc cactaaatat aatggagccc gcttttaag  ctggcatcca gaaaaaaaaa   2820
gaatcccagc accaaaatat tgttttcttc accaaccatc agttcatagg tccattctct   2880
tagcgcaact acagagaaca ggggcacaaa caggcaaaaa acgggcacaa cctcaatgga   2940
gtgatgcaac ctgcctggag taaatgatga cacaaggcaa ttgacccacg catgtatcta   3000
tctcattttc ttacaccttc tattaccttc tgctctctct gatttggaaa aagctgaaaa   3060
aaaaggttga aaccagttcc ctgaaattat tcccctactt gactaataag tatataaaga   3120
cggtaggtat tgattgtaat tctgtaaatc tatttcttaa acttcttaaa ttctactttt   3180
atagttagtc tttttttag  ttttaaaaca ccaagaactt agtttcgaat aaacacacat   3240
aaacaaacaa aatgactaag ttgtattctg acttgtacag gacctgcatg acatgcggag   3300
aagaaaaatt gtcaaccgag ttctacgtca ggaacaagaa gaccggagtt agacattcat   3360
catgcaaaga gtgtgacaag gtcagggtca aatcaagaca caaggagaac cctgaaagga   3420
ccaaaaacaa cgacttgaag agattgtacg gaatcacctt ggacgagcat acccaaatgt   3480
atgaggaaca aaatggtgta tgtgcaattt gcaagggaga aggagatgga aagtggaaga   3540
aattgtgtgt tgaccatgat cacgaaacag gaaaggtcag gcagttgttg tgtaggaact   3600
gcaatatgat gttgggtcag gtcaacgaca acgttaactt attatcagaa atgataaagt   3660
atttgaaaag atatcagtaa aacctgcagg ccgcgagcgc cgattaagtg aatttacttt   3720
aaatcttgca tttaaataaa ttttcttttt atagctttat gacttagttt caatttatat   3780
actattttaa tgacatttc  gattcattga ttgaaagctt tgtgttttt  cttgatgcgc   3840 tattgcattg ttcttgtctt tttcgccaca tgtaatatct gtagtagata cctgatacat   3900
tgtggatgct gagtgaaatt ttagttaata atggaggcgc tcttaataat tttggggata   3960
ttggcttaac gcgatcgccg acgccgccga tgggggatcc actagttcta gagcggccgc   4020
caccgcggtg gagctccagc ttttgttccc tttagtgagg gttaattgcg cgcttggcgt   4080
aatcatggtc atagctgttt cctgtgtgaa attgttatcc gctcacaatt ccacacaaca   4140
taggagccgg aagcataaag tgtaaagcct ggggtgccta atgagtgagg taactcacat   4200
taattgcgtt gcgctcactg cccgctttcc agtcgggaaa cctgtcgtgc cagctgcatt   4260
aatgaatcgg ccaacgcgcg gggagaggcg gtttgcgtat tgggcgctct tccgcttcct   4320
cgctcactga ctcgctgcgc tcggtcgttc ggctgcggcg agcggtatca gctcactcaa   4380
aggcggtaat acggttatcc acagaatcag gggataacgc aggaaagaac atgtgagcaa   4440
aaggccagca aaaggccagg aaccgtaaaa aggccgcgtt gctggcgttt ttccataggc   4500
tccgcccccc tgacgagcat cacaaaaatc gacgctcaag tcagaggtgg cgaaacccga   4560
caggactata aagataccag gcgtttcccc ctggaagctc cctcgtgcgc tctcctgttc   4620
cgaccctgcc gcttaccgga tacctgtccg cctttctccc ttcgggaagc gtggcgcttt   4680
ctcatagctc acgctgtagg tatctcagtt cggtgtaggt cgttcgctcc aagctgggct   4740
gtgtgcacga accccccgtt cagcccgacc gctgcgcctt atccggtaac tatcgtcttg   4800
agtccaaccc ggtaagacac gacttatcgc cactggcagc agccactggt aacaggatta   4860
gcagagcgag gtatgtaggc ggtgctacag agttcttgaa gtggtggcct aactacggct   4920
acactagaag gacagtattt ggtatctgcg ctctgctgaa gccagttacc ttcggaaaaa   4980
gagttggtag ctcttgatcc ggcaaacaaa ccaccgctgg tagcggtggt ttttttgttt   5040
gcaagcagca gattacgcgc agaaaaaaag gatctcaaga agatcctttg atcttttcta   5100
cggggtctga cgctcagtgg aacgaaaact cacgttaagg gattttggtc atgagattat   5160
```

-continued

```
caaaaaggat cttcacctag atccttttaa attaaaaatg aagttttaaa tcaatctaaa      5220
gtatatatga gtaaacttgg tctgacagtt accaatgctt aatcagtgag gcacctatct      5280
cagcgatctg tctatttcgt tcatccatag ttgcctgact ccccgtcgtg tagataacta      5340
cgatacggga gggcttacca tctggcccca gtgctgcaat gataccgcga gacccacgct      5400
caccggctcc agatttatca gcaataaacc agccagccgg aagggccgag cgcagaagtg      5460
gtcctgcaac tttatccgcc tccatccagt ctattaattg ttgccgggaa gctagagtaa      5520
gtagttcgcc agttaatagt ttgcgcaacg ttgttgccat tgctacaggc atcgtggtgt      5580
cacgctcgtc gtttggtatg gcttcattca gctccggttc ccaacgatca aggcgagtta      5640
catgatcccc catgttgtgc aaaaaagcgg ttagctcctt cggtcctccg atcgttgtca      5700
gaagtaagtt ggccgcagtg ttatcactca tggttatggc agcactgcat aattctctta      5760
ctgtcatgcc atccgtaaga tgcttttctg tgactggtga gtactcaacc aagtcattct      5820
gagaatagtg tatgcggcga ccgagttgct cttgcccggc gtcaatacgg gataataccg      5880
cgccacatag cagaacttta aaagtgctca tcattggaaa acgttcttcg ggcgaaaac      5940 tctcaaggat cttaccgctg ttgagatcca gttcgatgta acccactcgt gcacccaact      6000
gatcttcagc atcttttact ttcaccagcg tttctgggtg agcaaaaaca ggaaggcaaa      6060
atgccgcaaa aaagggaata agggcgacac ggaaatgttg aatactcata ctcttccttt      6120
ttcaatatta ttgaagcatt tatcagggtt attgtctcat gagcggatac atatttgaat      6180
gtatttagaa aaataaacaa ataggggttc cgcgcacatt tccccgaaaa gtgccacctg      6240 ggtcctttc atcacgtgct ataaaaataa ttataattta aattttttaa tataaatata      6300
taaattaaaa atagaaagta aaaaaagaaa ttaaagaaaa aatagttttt gttttccgaa      6360
gatgtaaaag actctagggg gatcgccaac aaatactacc ttttatcttg ctcttcctgc      6420
tctcaggtat taatgccgaa ttgtttcatc ttgtctgtgt agaagaccac acacgaaaat      6480
cctgtgattt tacattttac ttatcgttaa tcgaatgtat atctatttaa tctgcttttc      6540
ttgtctaata aatatatatg taaagtacgc tttttgttga aatttttaa accttttgtt      6600 attttttttt cttcattccg taactcttct accttcttta tttactttct aaaatccaaa      6660
tacaaaacat aaaaataaat aaacacagag taaattccca aattattcca tcattaaaag      6720
atacgaggcg cgtgtaagtt acaggcaagc gatccgtcct aagaaaccat tattatcatg      6780
acattaacct ataaaaatag gcgtatcacg aggccctttc gtc                        6823
```

<210> SEQ ID NO 78
<211> LENGTH: 808
<212> TYPE: DNA
<213> ORGANISM: Artificial Sequence
<220> FEATURE:
<223> OTHER INFORMATION: Synthetic: pMAL32_v1 from MS85487

<400> SEQUENCE: 78

```
agttaattaa tagtcttgga tgtaattctt attgttatac tgaatacgct aaaaccactc        60
acaacaagta tggagtatat tgtgtctctt tatatactga gtacttatgc aatatgcgct       120
cactcaggat gaaatgtaca cagccgaaag tatattgaaa gctgcctctg tggaaacttc       180
tatctaatgt tgtctccaga gtagactat gaggcctgaa gaagtcttta acacctgtt        240 ggagagtata aggagactgc tacaacaacg tcttccccac aaaaattatg tggaggccgg       300
tatgatacct gcacaaacgt taagttacac atgaaaaaga gactgacata actttgatct      360
```

-continued

```
ctgaaaatat gttttcccct gagtagcttc actgcttgga taccaatacg aatagacctt    420
ggctatagta agttgcatct gtaccgtaga gatccttatt gcgcgcttcg ttgaaaattt    480
cgctaaacac ggggtttaag tttaagttta caggattat ccggaagttt tcgcggaccc    540
cacacaatta agaattggct cgaagagtga taacgcatac ttttcttttc ttttttcagt    600
tcctagcgta cctaacgtag gtaacatgat ttggatcgtg ggatgataca aacaacgtaa    660
gatgagtagt tccttcctca attcttcttt cagcatcatt ttcttgaggc gctctgggca    720
aggtataaaa agttccatta atacgtctct aaaaaattaa accatctatc tcttaagcag    780 ttttttttgat aatctcaaat gtacatca                                      808
```

<210> SEQ ID NO 79
<211> LENGTH: 558
<212> TYPE: DNA
<213> ORGANISM: Artificial Sequence
<220> FEATURE:
<223> OTHER INFORMATION: Synthetic: pGAL7 promoter last 24 bp truncated

<400> SEQUENCE: 79

```
tcacatgtag ggaccgaatt gtttacaagt tctctgtacc accatggaga catcaaagat     60
tgaaaatcta tggaaagata tggacggtag caacaagaat atagcacgag ccgcgaagtt    120
catttcgtta cttttgatat cgctcacaac tattgcgaag cgcttcagtg aaaaaatcat    180
aaggaaaagt tgtaaatatt attggtagta ttcgtttggt aaagtagagg gggtaatttt    240
tcccctttat tttgttcata cattcttaaa ttgctttgcc ctccttttg gaaagctata    300 cttcggagca ctgttgagcg aaggctcatt agatatattt tctgtcattt tccttaaccc    360
aaaaataagg gaaagggtcc aaaaagcgct cggacaactg ttgaccgtga tccgaaggac    420
tggctataca gtgttcacaa aatagccaag ctgaaaataa tgtgtagcta tgttcagtta    480
gtttggctag caaagatata aaagcaggtc ggaaatattt atgggcatta ttatgcagag    540
catcaacatg ataaaaaa                                                  558
```

<210> SEQ ID NO 80
<211> LENGTH: 42
<212> TYPE: DNA
<213> ORGANISM: Artificial Sequence
<220> FEATURE:
<223> OTHER INFORMATION: Synthetic: MAL activator binding sites

<400> SEQUENCE: 80

```
agaaatatta tctaaaagcg agagtttaag cgagttgcaa ga                        42
```

<210> SEQ ID NO 81
<211> LENGTH: 26
<212> TYPE: DNA
<213> ORGANISM: Artificial Sequence
<220> FEATURE:
<223> OTHER INFORMATION: Synthetic: MAL activator binding sites

<400> SEQUENCE: 81

```
gtccgcgaaa atttccggat aaatcg                                          26
```

<210> SEQ ID NO 82
<211> LENGTH: 668
<212> TYPE: DNA
<213> ORGANISM: Artificial Sequence
<220> FEATURE:
<223> OTHER INFORMATION: Synthetic: pGAL1_10 promoter

<400> SEQUENCE: 82

```
ttatattgaa ttttcaaaaa ttcttacttt tttttttggat ggacgcaaag aagtttaata        60
atcatattac atggcaatac caccatatac atatccatat ctaatcttac ttatatgttg       120
tggaaatgta aagagcccca ttatcttagc ctaaaaaaac cttctctttg gaactttcag       180
taatacgctt aactgctcat tgctatattg aagtacggat tagaagccgc cgagcgggcg       240
acagccctcc gacggaagac tctcctccgt gcgtcctggt cttaccggt cgcgttcctg       300 aaacgcagat gtgcctcgcg ccgcactgct ccgaacaata aagattctac aatactagct       360
tttatggtta tgaagaggaa aaattggcag taacctggcc ccacaaacct tcaaatcaac       420
gaatcaaatt aacaaccata ggataataat gcgattagtt ttttagcctt atttctgggg       480
taattaatca gcgaagcgat gattttttgat ctattaacag atatataaat gcaaaagctg       540
cataaccact ttaactaata cttttcaacat tttcggtttg tattacttct tattcaaatg       600
tcataaaagt atcaacaaaa aattgttaat atacctctat actttaacgt caaggagaaa       660
aaactata                                                               668
```

<210> SEQ ID NO 83
<211> LENGTH: 759
<212> TYPE: DNA
<213> ORGANISM: Artificial Sequence
<220> FEATURE:
<223> OTHER INFORMATION: Synthetic: pGAL2 promoter

<400> SEQUENCE: 83

```
aataccagtt tcgctgcaga aggcacatct attacattta ctgagcataa cgggctgtac        60
taatccaagg aggtttacgg accagaggaa cttttccagat tcagatcaca gcaatatagg       120
actggaaaac atcaggtagc cgcactcaac ttgtaactgg caactacttt gcattaaact       180
ccaattaaat gcggtagaat cttttcagaa aaggtattca acgtcaattc ggaaagcttc       240
cttccggaat ggcttaagta ggttgcaatt tcttttcta ttagtagcta aaaatgggtc       300
acgtgatcta tattcgaaag gggcggttgc ctcaggaagg caccggcggt ctttcgtccg       360
tgcggagata tctgcgccgt tcaggggtcc atgtgccttg gacgatatta aggcagaagg       420
cagtatcggg gcggatcact ccgaaccgag attagttaag cccttcccat ctcaagatgg       480
ggagcaaatg gcattatact cctgctagaa agttaactgt gcacatattc ttaaattata       540
caatgttctg gagagctatt gtttaaaaaa caaacatttc gcaggctaaa atgtggagat       600
aggattagtt ttgtagacat atataaacaa tcagtaattg gattgaaaat ttggtgttgt       660
gaattgctct tcattatgca ccttattcaa ttatcatcaa gaatagcaat agttaagtaa       720
acacaagatt aacataataa aaaaaataat tctttcata                              759
```

<210> SEQ ID NO 84
<211> LENGTH: 520
<212> TYPE: DNA
<213> ORGANISM: Artificial Sequence
<220> FEATURE:
<223> OTHER INFORMATION: Synthetic: pGAL2_v3 promoter

<400> SEQUENCE: 84

```
gcaactactt tgcattaaac tccaattaaa tgcggtagaa tcttttcaga aaaggtattc        60
aacgtcaatt gaatggctta agtaggttgc aatttctttt tctattagta gctattcgaa       120
aggggcggtt gcctcaggaa ggcactgcgg agatatctgc gccgttcagg ggtccatgtg       180
ccttggacga tattaaggca gaaggcagta tcggggcgga tcactccgaa ccgagattag       240
```

```
ttaagcccctt cccatctcaa gatggggagc aaatggcatt atactcctgc tagaaagtta    300
actgtgcaca tattcttaaa ttatacaatg ttctggagag ctattgttta aaaaacaaac    360
atttcgcagg ctaaaatgtg gagataggat tagttttgta gacatatata aacaatcagt    420
aattggattg aaaatttggt gttgtgaatt gctcttcatt atgcaccttg ttcaattatc    480
atcaagaata gcaatagtta agtaaacaca agattaacat                          520
```

<210> SEQ ID NO 85
<211> LENGTH: 684
<212> TYPE: DNA
<213> ORGANISM: Artificial Sequence
<220> FEATURE:
<223> OTHER INFORMATION: Synthetic: pGAL7_v1 promoter

<400> SEQUENCE: 85

```
tttgccagct tactatcctt cttgaaaata tgcactctat atcttttagt tcttaattgc     60
aacacataga tttgctgtat aacgaatttt atgctatttt ttaaatttgg agttcagtga    120
taaaagtgtc acagcgaatt tcctcacatg tagggaccga attgtttaca agttctctgt    180
accaccatgg agacatcaaa gattgaaaat ctatggaaag atatggacgg tagcaacaag    240
aatatagcac gagccgcgaa gttcatttcg ttacttttga tatcgctcac aactattgcg    300
aagcgcttca gtgaaaaaat cataaggaaa agttgtaaat attattggta gtattcgttt    360
ggtaaagtag agggggtaat ttttccccct tattttgttc atacattctt aaattgcttt    420
gcctctcctt ttggaaagct atacttcgga gcactgttga gcgaaggctc attagatata    480
ttttctgtca ttttccttaa cccaaaaata agggaaaggg tccaaaaagc gcttgatccg    540
aaggactggc tatacagtgt tcacaaaata gccaagctga aaataatgtg tagctatgtt    600
cagttagttt ggctagcaaa gatataaaag caggtcggaa atatttatgg gcattattat    660
gcagagcatc aacatgataa aaaa                                            684
```

<210> SEQ ID NO 86
<211> LENGTH: 503
<212> TYPE: DNA
<213> ORGANISM: Artificial Sequence
<220> FEATURE:
<223> OTHER INFORMATION: Synthetic: pGAL2_v4 promoter

<400> SEQUENCE: 86

```
gcaactactt tgcattaaac tccaattaaa tgcggtagaa tcttttcaga aaaggtattc     60
aacgtcaatt gaatggctta agtaggttgc aatttctttt tctattagta gctattcgaa    120
aggggcggtt gcctcaggaa ggcactgttc aggggtccat gtgccttgga cgatattaag    180
gcagaaggca gtatcggggc ggatcactcc gaaccgagat tagttaagcc cttcccatct    240
caagatgggg agcaaatggc attatactcc tgctagaaag ttaactgtgc acatattctt    300
aaattataca atgttctgga gagctattgt ttaaaaaaca aacatttcgc aggctaaaat    360
gtggagatag gattagtttt gtagacatat ataaacaatc agtaattgga ttgaaaattt    420
ggtgttgtga attgctcttc attatgcacc ttattcaatt atcatcaaga atagcaatag    480
ttaagtaaac acaagattaa cat                                             503
```

<210> SEQ ID NO 87
<211> LENGTH: 522
<212> TYPE: DNA
<213> ORGANISM: Artificial Sequence
<220> FEATURE:
<223> OTHER INFORMATION: Synthetic: pGAL1_v3 promoter

<400> SEQUENCE: 87

```
tggcaatacc accatataca tatccatatc taatcttact tatatgttgt ggaaatgtaa      60
agagccccat tatcttagcc taaaaaaacc ttctctttgg aactttcagt aatacgctta     120
actgctcatt gctatattga agtaagcggg cgacagccct ccgatgcgtc ctggtcttca     180
ccggtcgcgt tcctgaaacg cagatgtgcc taacaataaa gattctacaa tactagcttt     240
tatggttatg aagaggaaaa attggcagta acctggcccc acaaaccttc aaatcaacga     300
atcaaattaa caaccatagg ataataatgc gattagtttt ttagccttat ttctggggta     360
attaatcagc gaagcgatga tttttgatct attaacagat atataaatgc aaaagctgca     420
taaccacttt aactaatact ttcaacattt tcggtttgta ttacttctta ttcaaatgtc     480
ataaaagtat caacaaaaaa ttgttaatat acctctatac tt                       522
```

<210> SEQ ID NO 88
<211> LENGTH: 424
<212> TYPE: DNA
<213> ORGANISM: Artificial Sequence
<220> FEATURE:
<223> OTHER INFORMATION: Synthetic: pGAL10_v3 promoter

<400> SEQUENCE: 88

```
tcgcttcgct gattaattac cccagaaata aggctaaaaa actaatcgca ttattatcct      60
atggttgtta atttgattcg ttgatttgaa ggtttgtggg gccaggttac tgccaatttt     120
tcctcttcat aaccataaaa gctagtattg tagaatcttt attgttaggc acatctgcgt     180
ttcaggaacg cgaccggtga agaccaggac gcatcggagg gctgtcgccc gcttacttca     240
atatagcaat gagcagttaa gcgtattact gaaagttcca agagaaggt ttttttaggc     300
taagataatg gggctcttta catttccaca acatataagt aagattagat atggatatgt     360
atatggtggt attgccatgt aatatgatta ttaaacttct ttgcgtccat ccaaaaaaaa     420
agta                                                                 424
```

<210> SEQ ID NO 89
<211> LENGTH: 542
<212> TYPE: DNA
<213> ORGANISM: Artificial Sequence
<220> FEATURE:
<223> OTHER INFORMATION: Synthetic: pGAL2_v2 promoter

<400> SEQUENCE: 89

```
gcaactactt tgcattaaac tccaattaaa tgcggtagaa tcttttcaga aaaggtattc      60
aacgtcaatt gaatggctta agtaggttgc aatttctttt tctattagta gctaaaaatg     120
ggtcacgtga tctatattcg aaaggggcgg ttgcctcagg aaggcactgc ggagatatct     180
gcgccgttca ggggtccatg tgccttggac gatattaagg cagaaggcag tatcggggcg     240
gatcactccg aaccgagatt agttaagccc ttcccatctc aagatgggga gcaaatggca     300
ttatactcct gctagaaagt taactgtgca catattctta aattatacaa tgttctggag     360
agctattgtt taaaaacaa acatttcgca ggctaaaatg tggagatagg attagttttg     420
tagacatata taaacaatca gtaattggat tgaaaatttg gtgttgtgaa ttgctcttca     480
ttatgcacct tattcaatta tcatcaagaa tagcaatagt taagtaaaca caagattaac     540
at                                                                   542
```

<210> SEQ ID NO 90

```
<211> LENGTH: 678
<212> TYPE: DNA
<213> ORGANISM: Artificial Sequence
<220> FEATURE:
<223> OTHER INFORMATION: Synthetic: pGAL7_v2 promoter

<400> SEQUENCE: 90
tttgccagct tactatcctt cttgaaaata tgcactctat atcttttagt tcttaattgc      60
aacacataga tttgctgtat aacgaatttt atgctatttt ttaaatttgg agttcagtga     120
taaaagtgtc acagcgaatt tcctcacatg tagggaccga attgtttaca agttctctgt     180
accaccatgg agacatcaaa gattgaaaat ctatggaaag atatggacgg tagcaacaag     240
aatatagcac gagccgcgaa gttcatttcg ttacttttga tatcgctcac aactattgcg     300
aagcgcttca gtgaaaaaat cataaggaaa agttgtaaat attattggta gtattcgttt     360
ggtaaagtag agggggtaat ttttcccctt tattttgttc atacattctt aaattgcttt     420
gcctctcctt ttggaaagct atagctcatt agatatattt tctgtcattt tccttaaccc     480
aaaaataagg gaaagggtcc aaaaagcgct cggacaactg ttgaccgtga tccgaaggac     540
tggctataca gtgttcacaa aatagccaag ctgaaaataa tgtgtagcta tgttcagtta     600
gtttggctag caaagatata aaagcaggtc ggaaatattt atgggcatta ttatgcagag     660
catcaacatg ataaaaaa                                                  678

<210> SEQ ID NO 91
<211> LENGTH: 582
<212> TYPE: DNA
<213> ORGANISM: Artificial Sequence
<220> FEATURE:
<223> OTHER INFORMATION: Synthetic: pGAL7 promoter

<400> SEQUENCE: 91
tcacatgtag ggaccgaatt gtttacaagt tctctgtacc accatggaga catcaaagat      60
tgaaaatcta tggaaagata tggacggtag caacaagaat atagcacgag ccgcgaagtt     120
catttcgtta cttttgatat cgctcacaac tattgcgaag cgcttcagtg aaaaaatcat     180
aaggaaaagt tgtaaatatt attggtagta ttcgtttggt aaagtagagg gggtaatttt     240
tccccttat tttgttcata cattcttaaa ttgctttgcc tctccttttg gaaagctata     300
cttcggagca ctgttgagcg aaggctcatt agatatattt tctgtcattt tccttaaccc     360
aaaaataagg gaaagggtcc aaaaagcgct cggacaactg ttgaccgtga tccgaaggac     420
tggctataca gtgttcacaa aatagccaag ctgaaaataa tgtgtagcta tgttcagtta     480
gtttggctag caaagatata aaagcaggtc ggaaatattt atgggcatta ttatgcagag     540
catcaacatg ataaaaaaaa acagttgaat attccctcaa aa                       582

<210> SEQ ID NO 92
<211> LENGTH: 597
<212> TYPE: DNA
<213> ORGANISM: Artificial Sequence
<220> FEATURE:
<223> OTHER INFORMATION: Synthetic: pGAL1 promoter

<400> SEQUENCE: 92
tggcaatacc accatataca tatccatatc taatcttact tatatgttgt ggaaatgtaa      60
agagccccat tatcttagcc taaaaaaacc ttctctttgg aactttcagt aatacgctta     120
actgctcatt gctatattga agtacggatt agaagccgcc gagcgggcga cagccctccg     180
acggaagact ctcctccgtg cgtcctggtc ttcaccggtc gcgttcctga aacgcagatg     240
```

```
tgcctcgcgc cgcactgctc cgaacaataa agattctaca atactagctt ttatggttat    300
gaagaggaaa aattggcagt aacctggccc cacaaacctt caaatcaacg aatcaaatta    360
acaaccatag gataataatg cgattagttt tttagcctta tttctggggt aattaatcag    420
cgaagcgatg attttgatc tattaacaga tatataaatg caaaagctgc ataaccactt     480
taactaatac tttcaacatt ttcggtttgt attacttctt attcaaatgt cataaaagta    540
tcaacaaaaa attgttaata tacctctata ctttaacgtc aaggagaaaa aactata       597
```

<210> SEQ ID NO 93
<211> LENGTH: 341
<212> TYPE: DNA
<213> ORGANISM: Artificial Sequence
<220> FEATURE:
<223> OTHER INFORMATION: Synthetic: pGAL3 promoter

<400> SEQUENCE: 93

```
cctcatcaat gcgagatccg tttaaccgga ccctagtgca cttaccccac gttcggtcca     60
ctgtgtgccg aacatgctcc ttcactattt taacatgtgg aattcttgaa agaatgaaat    120
cgccatgcca agccatcaca cggtctttta tgcaattgat tgaccgcctg caacacatag    180
gcagtaaaat ttttactgaa acgtatataa tcatcataag cgacaagtga ggcaacacct    240
ttgttaccac attgacaacc ccaggtattc atacttccta ttagcggaat caggagtgca    300
aaaagagaaa ataaaagtaa aaaggtaggg caacacatag t                        341
```

<210> SEQ ID NO 94
<211> LENGTH: 499
<212> TYPE: DNA
<213> ORGANISM: Artificial Sequence
<220> FEATURE:
<223> OTHER INFORMATION: Synthetic: pGAL10 promoter

<400> SEQUENCE: 94

```
tcgcttcgct gattaattac cccagaaata aggctaaaaa actaatcgca ttattatcct     60
atggttgtta atttgattcg ttgatttgaa ggtttgtggg gccaggttac tgccaatttt    120
tcctcttcat aaccataaaa gctagtattg tagaatcttt attgttcgga gcagtgcggc    180
gcgaggcaca tctgcgtttc aggaacgcga ccggtgaaga ccaggacgca cggaggagag    240
tcttccgtcg gagggctgtc gcccgctcgg cggcttctaa tccgtacttc aatatagcaa    300
tgagcagtta agcgtattac tgaaagttcc aaagagaagg ttttttttagg ctaagataat    360 ggggctcttt acatttccac aacatataag taagattaga tatggatatg tatatggtgg    420
tattgccatg taatatgatt attaaacttc tttgcgtcca tccaaaaaaa agtaagaat     480 ttttgaaaat tcaatataa                                                 499
```

<210> SEQ ID NO 95
<211> LENGTH: 477
<212> TYPE: DNA
<213> ORGANISM: Artificial Sequence
<220> FEATURE:
<223> OTHER INFORMATION: Synthetic: pGCY1 promoter

<400> SEQUENCE: 95

```
tgcttgggtg atcatacttc ctggctttag atatttgaaa cttaactctt gtcaacaaac     60
ttcctatgga gtgtataaga attgtaagtt ataacaccgg cgaacaatcg gggcagacta    120
ttccggggaa gaacaaggaa gggcggtctt ttctcccctca ttgtcatagc aaggtcattt    180
```

```
cgccttctca gaaaggggta gaatcaatct agcacgcaga ttgcaaacac ggcttaataa      240
tatgcctatc aggcattcac ccgtgtgacg aatcgcacac cgctgctctc cttaattccc      300
tagagtagaa accgagcttt caggaaaaga ctacggcagt aaagaattgc tttactgggc      360
gtataaaacc gggagaatca agacattcta atgacttgat tcaggatgag agcttaatag      420
gtgcatctta gcaagctaaa atttggacag ctctcattac taaattaaga tagaaaa         477
```

<210> SEQ ID NO 96
<211> LENGTH: 341
<212> TYPE: DNA
<213> ORGANISM: Artificial Sequence
<220> FEATURE:
<223> OTHER INFORMATION: Synthetic: pGAL80 promoter
<400> SEQUENCE: 96

```
tattaacttc ttcactataa gaaaatcaca cgagcgcccg gacgatgtct ctgttttaaat     60 ggcgcaagtt ttccgctttg taatatatat ttatacccct ttcttctctc ccctgcaata     120
taatagttta attctaatat taataatatc ctatattttc ttcatttacc ggcgcactct     180
cgcccgaacg acctcaaaat gtctgctaca ttcataataa ccaaaagctc ataactttt     240 tttttgaacc tgaatatata tacatcacat atcactgctg gtccttgccg accagcgtat    300
acaatctcga tagttggttt cccgttcttt ccactcccgt c                         341
```

<210> SEQ ID NO 97
<211> LENGTH: 11
<212> TYPE: DNA
<213> ORGANISM: Artificial Sequence
<220> FEATURE:
<223> OTHER INFORMATION: Synthetic: pMAL12_1; MAL transcriptional
      activator binding site sequence <400> SEQUENCE: 97

```
gataatattt c                                                           11
```

<210> SEQ ID NO 98
<211> LENGTH: 11
<212> TYPE: DNA
<213> ORGANISM: Artificial Sequence
<220> FEATURE:
<223> OTHER INFORMATION: Synthetic: pMAL12_2; MAL transcriptional
      activator binding site sequence <400> SEQUENCE: 98

```
gaaaatttcg c                                                           11
```

<210> SEQ ID NO 99
<211> LENGTH: 12
<212> TYPE: DNA
<213> ORGANISM: Artificial Sequence
<220> FEATURE:
<223> OTHER INFORMATION: Synthetic: pMAL12_3; MAL transcriptional
      activator binding site sequence <400> SEQUENCE: 99

```
gttaaagttt ac                                                          12
```

<210> SEQ ID NO 100
<211> LENGTH: 11
<212> TYPE: DNA
<213> ORGANISM: Artificial Sequence
<220> FEATURE:
<223> OTHER INFORMATION: Synthetic: pMAL12_4; MAL transcriptional
      activator binding site sequence -continued

<400> SEQUENCE: 100
gaaattttcg c                                                                 11

<210> SEQ ID NO 101
<211> LENGTH: 11
<212> TYPE: DNA
<213> ORGANISM: Artificial Sequence
<220> FEATURE:
<223> OTHER INFORMATION: Synthetic: pMAL12_1r; MAL transcriptional
      activator binding site sequence

<400> SEQUENCE: 101
gaaatattat c                                                                 11

<210> SEQ ID NO 102
<211> LENGTH: 11
<212> TYPE: DNA
<213> ORGANISM: Artificial Sequence
<220> FEATURE:
<223> OTHER INFORMATION: Synthetic: pMAL12_2r; MAL transcriptional
      activator binding site sequence

<400> SEQUENCE: 102
gcgaaatttt c                                                                 11

<210> SEQ ID NO 103
<211> LENGTH: 12
<212> TYPE: DNA
<213> ORGANISM: Artificial Sequence
<220> FEATURE:
<223> OTHER INFORMATION: Synthetic: pMAL12_3r; MAL transcriptional
      activator binding site sequence

<400> SEQUENCE: 103
gtaaacttta ac                                                                12

<210> SEQ ID NO 104
<211> LENGTH: 11
<212> TYPE: DNA
<213> ORGANISM: Artificial Sequence
<220> FEATURE:
<223> OTHER INFORMATION: Synthetic: pMAL12_4r; MAL transcriptional
      activator binding site sequence

<400> SEQUENCE: 104
gcgaaaattt c                                                                 11

<210> SEQ ID NO 105
<211> LENGTH: 11
<212> TYPE: DNA
<213> ORGANISM: Artificial Sequence
<220> FEATURE:
<223> OTHER INFORMATION: Synthetic: pMAL32_1; MAL transcriptional
      activator binding site sequence

<400> SEQUENCE: 105
tataatattt c                                                                 11

<210> SEQ ID NO 106
<211> LENGTH: 12
<212> TYPE: DNA
<213> ORGANISM: Artificial Sequence
<220> FEATURE:
<223> OTHER INFORMATION: Synthetic: pMAL32_3; MAL transcriptional
      activator binding site sequence

```
<400> SEQUENCE: 106
gtttaagttt ac                                                          12

<210> SEQ ID NO 107
<211> LENGTH: 11
<212> TYPE: DNA
<213> ORGANISM: Artificial Sequence
<220> FEATURE:
<223> OTHER INFORMATION: Synthetic: pMAL32_4; MAL transcriptional
      activator binding site sequence

<400> SEQUENCE: 107
gaagttttcg c                                                           11

<210> SEQ ID NO 108
<211> LENGTH: 11
<212> TYPE: DNA
<213> ORGANISM: Artificial Sequence
<220> FEATURE:
<223> OTHER INFORMATION: Synthetic: pMAL32_1r; MAL transcriptional
      activator binding site sequence

<400> SEQUENCE: 108
gaaatattat a                                                           11

<210> SEQ ID NO 109
<211> LENGTH: 12
<212> TYPE: DNA
<213> ORGANISM: Artificial Sequence
<220> FEATURE:
<223> OTHER INFORMATION: Synthetic: pMAL32_3r; MAL transcriptional
      activator binding site sequence

<400> SEQUENCE: 109
gtaaacttaa ac                                                          12

<210> SEQ ID NO 110
<211> LENGTH: 11
<212> TYPE: DNA
<213> ORGANISM: Artificial Sequence
<220> FEATURE:
<223> OTHER INFORMATION: Synthetic: pMAL32_4r; MAL transcriptional
      activator binding site sequence

<400> SEQUENCE: 110
gcgaaaactt c                                                           11
```

MALTOSE DEPENDENT DEGRONS, MALTOSE-RESPONSIVE PROMOTERS, STABILIZATION CONSTRUCTS, AND THEIR USE IN PRODUCTION OF NON-CATABOLIC COMPOUNDS

1. CROSS REFERENCE TO RELATED APPLICATIONS

This application claims benefit of priority to U.S. Provisional Application No. 62/184,793, filed Jun. 25, 2015, and U.S. Provisional Patent Application No. 62/266,436, filed Dec. 11, 2015, both of which are incorporated herein by reference.

2. FIELD OF THE INVENTION

The present disclosure generally relates to maltose dependent degrons, maltose-responsive promoters, and stabilization constructs. The present disclosure also relates to their use in controlling gene expression, protein stability, and production of non-catabolic compounds by genetically modified host cells.

3. BACKGROUND

The advent of synthetic biology has brought about the promise of fermentative microbial production of biofuels, chemicals and biomaterials from renewable sources at industrial scale and quality. For example, functional non-native biological pathways have been successfully constructed in microbial hosts for the production of precursors to the antimalarial drug artemisinin (see, e.g., Martin et al., *Nat Biotechnol* 21:796-802 (2003)); fatty acid derived fuels and chemicals (e.g., fatty esters, fatty alcohols and waxes; see, e.g., Steen et al., *Nature* 463:559-562 (2010)); polyketide synthases that make cholesterol lowering drugs (see, e.g., Ma et al., *Science* 326:589-592 (2009)); and polyketides (see, e.g., Kodumal, *Proc Natl Acad Sci USA* 101:15573-15578 (2004)). However, the commercial success of synthetic biology will depend largely on whether the production cost of renewable products can be made to compete with, or out-compete, the production costs of their respective non-renewable counterparts.

Strain stability can be a major driver of the cost of industrial fermentations, as it affects the length of time that a continuous fermentation can be run productively. Strain stability generally refers to the ability of a microbe to maintain favorable production characteristics (e.g., high yield (grams of compound per gram of substrate) and productivity (grams per liter of fermentation broth per hour) of a non-catabolic fermentation product over extended cultivation times. In particular, genetic stability, which is the propensity of the producing microbial population to have little to no alteration of the intended allelic frequency of genes relevant to the production of product over time, plays a major role in the sustained output of product.

For non-catabolic fermentation of products other than biomass (which products, by definition, consume metabolic energy and carbon that could otherwise be used in the production of more cells), the basis of instability is two-fold: evolutionary mutation and selection. First, loss-of-production mutations arise spontaneously and randomly. Second, a growth rate or "fitness" advantage of cells with reduced product yields leads to an eventual population sweep by low producers, and thereby decreases the overall culture performance. This phenomenon can be referred to as "strain degeneration."

Brazilian fuel ethanol fermentations achieve extremely high yields of ethanol from sugar for long periods of time, i.e., about 90% of maximum theoretical yield. This is in part because the production of ethanol is catabolic: it generates 2 ATP per molecule of sugar produced and is redox balanced without the involvement of oxygen. A cell that mutates to not produce ethanol is less fit under the low oxygen conditions of the fermentor and will not sweep the population. This allows industrial ethanol fermentations to recycle the majority of yeast biomass throughout the season, thereby minimizing conversion of sugar into yeast cell biomass and directing nearly all of the sugar to ethanol production. This extended propagation and reuse of biomass increases the efficiencies of ethanol production: operational expenditures are reduced because less sugar goes to biomass during each cycle (i.e., the yield increases); and capital expenditures are reduced because fewer and smaller fermentors are needed to build biomass for inoculations.

By contrast, the production of acetyl-CoA derived hydrocarbons (e.g., isoprenoids, fatty acids, and polyketides) are generally non-catabolic in nature; they usually require a net input of ATP, NADPH, and carbon, often with large amounts of oxygen supplied to help balance the redox of the system. Such an environment makes evolution towards lower product, higher biomass yielding genotypes more favorable, and leads to a higher rate of strain degeneration.

One way to decrease the negative selective pressure of producing non-catabolic products is to switch off the formation of product during periods when the product is not desired, such as during phases of fermentation where biomass must be generated in order to maximize fermentor productivity. Thus, there is a need in the art for switches that can control the timing of production of non-catabolic compounds during fermentation. There is also a need in the art for methods and compositions that reduce the rate of strain degeneration and stabilize the production of non-catabolic compounds during fermentation. The compositions and methods provided herein meet these needs, and they can be used for other applications beyond a fermentation environment.

4. SUMMARY

Provided herein are compositions and methods that utilize a maltose dependent degron to control the stability of any protein fused to the maltose dependent degron. In an embodiment, maltose dependent degrons are obtained by modifying a protein known to bind maltose (e.g., MBP or maltose binding protein), to become unstable when it is not bound to maltose. Therefore, maltose dependent degrons provided herein are dependent on their binding to its ligand (e.g., maltose) for stability. In some embodiments, the maltose dependent degron can be utilized in combination with a maltose-responsive promoter to simultaneously control the timing of expression and stability of proteins. For example, the expression of enzymes of a biosynthetic pathway for producing a non-catabolic compound can be controlled, directly or indirectly, using the maltose dependent degron and a maltose-responsive promoter by manipulating maltose content in a culture medium. Thus, in some embodiment, the same molecule effector (e.g., maltose) can be utilized to provide both transcriptional and post-translational control for gene expression. Also provided herein are compositions and methods that utilize a stabilization construct that provides a growth advantage to high-product-yielding original strains, and a growth disadvantage to spontaneously mutated cells that have become low producers or non-producers. As a result, the high-product-yielding original strains outgrow mutated cells, and the production of desired products (e.g., non-catabolic compounds) is stabilized during fermentation. A maltose dependent degron, a maltose-responsive promoter, and a stabilization construct can be used, either alone, in combination or in sub-combination, in the compositions and methods provided herein.

In one aspect, provided herein are compositions and methods that utilize maltose dependent degrons as switches to regulate stability of any proteins of interest. In particular embodiments, a maltose dependent degron is fused to a protein of interest, which has an effect on the production of a desired product (e.g., non-catabolic compounds) in a genetically modified host cell. In certain embodiments, one or more mutations are introduced into a maltose binding protein (MBP) to convert it into a maltose dependent degron (also referred to as a maltose binding degron), which is more stable when it is bound to maltose than when it is not. In the absence of maltose, a maltose dependent degron and any protein fused thereto are unstable or inactive, resulting in a faster degradation of the fusion protein. Thus, the stability of any protein of interest fused to a maltose dependent degron can be controlled by manipulating the maltose content.

In some embodiments, the fusion protein's stability in host cells can have downstream effects on target molecules, such as enzymes of a biosynthetic pathway for producing a non-catabolic compounds during fermentation. For example, if a fusion protein comprises a transcriptional regulator fused in frame to a maltose dependent degron, its stability can be controlled by adding or removing maltose from a culture medium. In such embodiments, the maltose dependent degrons and maltose content in the culture medium can be used as a switch to control production of non-catabolic compounds. While maltose dependent degrons are useful during a fermentation process, they can be used in any environment where it is desired to modulate stability of proteins of interest and/or the production of target molecules.

Thus, in one aspect, provided herein is a method for modulating protein stability, wherein the method comprises contacting with maltose, a fusion protein comprising a protein of interest fused in frame to a maltose dependent degron. In certain embodiments, the fusion protein is more stable when the maltose dependent degron is in contact with maltose compared to when the maltose dependent degron is not in contact with maltose. In certain embodiments, the method further comprises removing maltose from contact with the fusion protein. In certain embodiments, a half-life of the fusion protein after removing maltose from contact with the fusion protein is at least about 50% less compared to a half-life of a fusion protein comprising a wild-type maltose binding protein fused in frame to the protein of interest.

In certain embodiments, the method further comprises providing a host cell which comprises heterologous nucleic acids encoding a fusion protein comprising a maltose dependent degron fused in frame to a protein of interest, and culturing the host cell expressing the fusion protein in a culture medium comprising maltose.

In certain embodiments, the fusion protein directly or indirectly modulates the levels of one or more target molecules. In certain embodiments, the host cell further comprises a biomolecule that interacts with the fusion protein in the host cell to modulate the level of one or more target molecules. In certain embodiments, the protein of interest is a transcriptional regulator. In certain embodiments, the biomolecule is a transcriptional regulator.

In certain embodiments, the method comprises providing a host cell which further comprises one or more heterologous nucleic acids encoding one or more target molecules, the levels of which are regulated by the protein of interest fused in frame to the maltose dependent degron. In certain embodiments, one or more target molecules are enzymes in a biosynthetic pathway that produce one or more non-catabolic compounds. In certain embodiments, one or more target molecules are non-catabolic compounds produced by the enzymes in the biosynthetic pathway. In certain embodiments, the protein of interest fused in frame to the maltose dependent degron comprises Gal80p. In certain embodiments, the heterologous nucleic acid sequence encoding the fusion protein is integrated into the host genome.

In certain embodiments, the method for modulating protein stability comprises providing a host cell comprising heterologous nucleic acids encoding the fusion protein operably linked to a maltose-responsive promoter. In certain embodiments, the method for modulating protein stability comprises providing a host cell comprising heterologous nucleic acids encoding the fusion protein operably linked to an endogenous promoter of a gene encoding the protein of interest.

In certain embodiments, the method for modulating protein stability comprises providing a host cell comprising heterologous nucleic acids encoding a fusion protein comprising a protein of interest fused in frame to a maltose dependent degron, wherein the maltose dependent degron comprises an amino acid sequence that has at least about 70%, 75%, 80%, 85%, 90%, or 95% sequence identity to SEQ ID NO: 2 or SEQ ID NO: 28, and comprises one or more variant amino acid residues compared to SEQ ID NO: 2 or SEQ ID NO: 28. In certain embodiments, the method for modulating protein stability can be performed with any maltose dependent degrons described herein.

In another aspect of the invention, a maltose-responsive promoter is used in combination with a maltose dependent degron in methods and compositions provided herein. More specifically, a maltose-responsive promoter may be operably linked to nucleic acids encoding a fusion protein comprising a protein of interest fused in frame to a maltose dependent degron. By combining maltose-dependent transcriptional control and post-translational control, compositions and methods provided herein can impose a very robust and tight control of expression and stability of any gene product.

Thus, provided herein is a method that comprises: (a) culturing a population of a genetically modified host cell in a culture medium comprising a carbon source comprising maltose, wherein the genetically modified host cell comprises a maltose-responsive promoter operably linked to a heterologous nucleic acid encoding a fusion protein comprising a protein of interest fused in frame to a maltose dependent degron; and (b) culturing the population or a subpopulation thereof in a culture medium comprising a carbon source, wherein maltose is absent or in sufficiently low amounts compared to the culture medium in step (a). In certain embodiments, during step (a), the transcription of the heterologous nucleic acid is activated and the fusion protein encoded therefrom is stabilized in the presence of maltose. When maltose is absent or present in sufficiently low amounts during step (b), the maltose-responsive promoter activity and the fusion protein stability are reduced compared to in step (a). The timing of these two culture stages of the method can be controlled by, for example, adding or removing maltose from the culture medium.

In certain embodiments, the host cell further comprises a biomolecule that interacts with the fusion protein in the host cell to modulate the levels of one or more target molecules. In certain embodiments, the protein of interest is a transcriptional regulator. In certain embodiments, the biomolecule is a transcriptional activator. In certain embodiments, the host cell further comprises heterologous nucleic acids encoding one or more target molecules, the levels of which are regulated by the protein of interest. In certain embodiments, one or more target molecules are enzymes of a biosynthetic pathway that are positively regulated by the activity of the maltose-responsive promoter and the fusion protein which is stable in the presence of maltose. In certain embodiments, one or more target molecules are enzymes of a biosynthetic pathway that are negatively regulated by the activity of the maltose-responsive promoter and the fusion protein which is stable in the presence of maltose.

In certain embodiments, the method for providing dual transcription and post-translation control can be performed with any maltose dependent degrons described herein. In certain embodiments, the method for providing dual transcription and translation can be performed with a maltose-responsive promoter comprising a sequence selected from the group consisting of pMAL1 (SEQ ID NO: 29), pMAL2 (SEQ ID NO: 30), pMAL11 (SEQ ID NO: 31), pMAL12 (SEQ ID NO: 32), pMAL31 (SEQ ID NO: 33), pMAL32 (SEQ ID NO: 34), pMAL32_v1 (SEQ ID NO: 78), pGMAL_v5 (SEQ ID NO: 35), pGMAL_v6 (SEQ ID NO: 36), pGMAL_v7 (SEQ ID NO: 37), pGMAL_v9 (SEQ ID NO: 38), pGMAL_v10 (SEQ ID NO: 39), pGMAL_v11 (SEQ ID NO: 40), pGMAL_v12 (SEQ ID NO: 41), pGMAL_v13 (SEQ ID NO: 42), pGMAL_v14 (SEQ ID NO: 43), pGMAL_v15 (SEQ ID NO: 44), pGMAL_v16 (SEQ ID NO: 45), pGMAL_v17 (SEQ ID NO: 46), pGMAL_v18 (SEQ ID NO: 47), pG2MAL_v1 (SEQ ID NO: 48), pG2MAL_v2 (SEQ ID NO: 49), pG2MAL_v3 (SEQ ID NO: 50), pG2MAL_v5 (SEQ ID NO: 51), pG2MAL_v6 (SEQ ID NO: 52), pG2MAL_v7 (SEQ ID NO: 53), pG2MAL_v8 (SEQ ID NO: 54), pG2MAL_v9 (SEQ ID NO: 55), pG2MAL_v10 (SEQ ID NO: 56), pG7MAL_v2 (SEQ ID NO: 57), pG7MAL_v4 (SEQ ID NO: 58), pG7MAL_v6 (SEQ ID NO: 59), pG7MAL_v8 (SEQ ID NO: 60), pG7MAL_v9 (SEQ ID NO: 61), pG172 MAL_v13 (SEQ ID NO: 62), pG271 MAL_v12 (SEQ ID NO: 63), pG721 MAL_v11 (SEQ ID NO: 64), pG712 MAL_v14 (SEQ ID NO: 65), a portion thereof which retains promoter function, or a sequence that has at least about 70%, 75%, 80%, 85%, 90%, 95%, 96%, 97%, 98%, or 99% sequence identity to thereof. In certain embodiments, other synthetic maltose-responsive promoters described herein can be used in the method for providing dual transcription and post-translation control.

In another aspect, provided herein are fermentation process for producing a heterologous non-catabolic compound from a genetically modified host cell. In some embodiments, the processes comprise two phases: a build stage during which non-catabolic compound production is substantially reduced (the "off" stage) while cell biomass is accumulated; and a production stage, during which non-catabolic compound production is turned on (the "on" stage). Thus, the negative selective pressure associated with non-catabolic compound production is alleviated during a stage of fermentation (i.e., a build stage) in which production is not needed. The reduction or elimination of the non-catabolic compound production during the build stage results in (i) an improved growth rate of the cells during the build stage; and (ii) improved production stability of the strain during the production stage. This results in longer sustained non-catabolic compound production, thereby increasing the overall yield and/or productivity of the strain. Advantageously, the "off" and "on" states of non-catabolic compound production in the fermentation methods provided herein are controlled through easily obtained, affordable, and industrially relevant conditions.

The term "off" stage as used herein does not necessarily indicate that the non-catabolic compound production in a genetically modified host cell is zero or near zero during this stage. Rather, the term "off" stage is relative to the "on" stage in that non-catabolic compound production during the "off" stage is substantially reduced compared to the "on" stage (e.g., more than about 10%, 20%, 30%, 40%, 50%, 60%, 70%, 80%, 90%, or 100% less).

In certain embodiments, the "off" and "on" states of non-catabolic compound production in the fermentation culture may be controlled by the amount of sugar maltose in the culture medium, in conjunction with the use of maltose-responsive promoters which regulate gene expression of pathway enzymes that effect heterologous non-catabolic compound production. Advantageously, by coupling pathway gene expression to maltose-sensitive promoters, heterologous non-catabolic compound production can be turned on or off by controlling the amount of maltose in the feedstock. For example, a maltose-responsive promoter can be wired as an "on" switch to induce production of the heterologous non-catabolic compound in the presence of maltose. Alternatively, a maltose-responsive promoter can be wired as an "off" switch to induce expression of a negative regulator of the biosynthetic pathway for compound production in the presence of maltose.

In certain embodiments, the "off" and "on" states of non-catabolic compound production in the fermentation culture may be controlled by the amount of sugar maltose in the culture medium, in conjunction with the use of a maltose dependent degron which regulates the stability of expression of pathway enzymes that effect heterologous non-catabolic compound production. Advantageously, by coupling pathway gene expression to maltose dependent stability of maltose dependent degrons, heterologous non-catabolic compound production can be turned on or off by controlling the amount of maltose in the feedstock. For example, a maltose dependent degron fused to a suitable fusion partner (e.g., a transcriptional regulator) can be wired as an "on" switch to induce production of the heterologous non-catabolic compound in the presence of maltose. Alternatively, a maltose dependent degron fused to a suitable fusion partner can be wired as an "off" switch to induce expression of a negative regulator of the biosynthetic pathway for compound production in the presence of maltose.

In certain embodiments, the "off" and "on" states of non-catabolic compound production in the fermentation culture may be controlled by the amount of sugar maltose in the culture medium, in conjunction with the use of a maltose-responsive promoter and a maltose-dependent degron, which can regulate gene expression of pathway enzymes that effect heterologous non-catabolic compound production. By simultaneously combining transcriptional and post-translational control by the same small molecule effector maltose, the timing and the expression levels of pathway enzymes can be tightly regulated. By imposing two layers of control on genes that are tightly regulated during a long fermentation run, the probability of potential strain degeneration can also be reduced.

Thus, provided herein is a method for producing a heterologous non-catabolic compound in a genetically modified host cell, wherein the method comprises: (a) culturing a population of the genetically modified host cell in a culture medium comprising a carbon source comprising maltose, wherein the genetically modified host cell comprises: (i) one or more heterologous nucleic acids encoding one or more enzymes of a biosynthetic pathway for making the heterologous non-catabolic compound; and (i) one or more heterologous nucleic acids encoding one or more enzymes of a biosynthetic pathway for making the heterologous non-catabolic compound; and (ii) a heterologous nucleic acid encoding a fusion protein comprising a protein of interest fused in frame to a maltose dependent degron, operably linked to a maltose-responsive promoter, wherein transcription of the heterologous nucleic acid encoding the fusion protein is activated and the fusion protein encoded therefrom is stabilized in the presence of maltose, and wherein the stabilized fusion protein regulates expression of the one or more enzymes, which, in turn, controls production of the heterologous non-catabolic compound by the host cells; and (b) culturing the population or a subpopulation thereof in a culture medium comprising a carbon source wherein maltose is absent or in sufficiently low amount compared to the culture medium in step (a). In certain embodiments, maltose-responsive promoter activity and fusion protein stability in step (b) are reduced compared to step (a), which results in changes in an amount of production of the heterologous non-catabolic compound by the host cell compared to step (a). With this method, any maltose dependent degrons and/or maltose-responsive promoters described herein may be used.

Also, provided herein is a method for producing a non-catabolic compound in a genetically modified host cell. In certain embodiments, the method comprises: (a) culturing a population of genetically modified host cells in a culture medium comprising a carbon source comprising maltose, wherein the host cell comprises: (i) one or more heterologous nucleic acids encoding one or more enzymes of a biosynthetic pathway, each operably linked to a Gal4p-responsive promoter; (ii) a nucleic acid encoding Gal4p; and (iii) a nucleic acid encoding a fusion protein comprising Gal80p fused in frame to a maltose dependent degron, operably linked to a maltose-responsive promoter, wherein the maltose in the culture medium limits the amount of heterologous non-catabolic compound produced by the host cells; and (b) culturing the population or a subpopulation thereof in a culture medium comprising a carbon source, wherein maltose is absent or in sufficiently low amount such that production of the heterologous non-catabolic compound by the host cells is increased compared to step (a). In performing this method, any maltose dependent degrons and/or maltose-responsive promoters described herein may be used.

In certain embodiments, the Gal4p-responsive promoter used in the method is selected from the group consisting of pGAL1, pGAL2, pGAL7, pGAL10, pGCY1, pGAL80, and synthetic pGAL promoters.

In certain embodiments, the culturing step (a) is for a period of at least about 12, 24, 36, 48, 60, 72, 84, 96 or more than 96 hours. In certain embodiments, the culturing step (a) is for a period of time sufficient for the population to reach a cell density ($OD_{600}$) of between about 0.01 and 400. In certain embodiments, the culture medium of step (a) comprises at least about 0.1% (w/v) maltose. In certain embodiments, the culture medium of step (a) comprises about 0.25% to 3% (w/v) maltose. In certain embodiments, the culture medium of step (b) comprises no more than about 0.08% (w/v) maltose. In certain embodiments, the population or the subpopulation of genetically modified host cells is cultured for a period of about 3 to 20 days during step (b) during production of the heterologous non-catabolic compound.

In certain embodiments, the heterologous non-catabolic compound production by the population of genetically modified host cell of the duration of culturing of step (b) is improved compared to that achieved in a fermentation process wherein expression of the one or more enzymes of the biosynthetic pathway is not limited by the activity of the maltose-responsive promoter and the fusion protein. In certain embodiments, the production of the non-catabolic compound during step (a) is less than about 50, 40, 30, 20, or 10% of the production of the non-catabolic compound during step (b). In certain embodiments, the non-catabolic compound provided by the method is selected from the group consisting of an amino acid, a fatty acid, an isoprenoid, and a polyketide.

In certain embodiments, the genetically modified host cells provided in the present methods are capable of producing a heterologous isoprenoid and comprises at least one heterologous nucleic acid encoding an isoprenoid pathway enzyme selected from the group consisting of: (a) an enzyme that condenses two molecules of acetyl-coenzyme A to form acetoacetyl-CoA; (b) an enzyme that condenses acetoacetyl-CoA with another molecule of acetyl-CoA to form 3-hydroxy-3-methylglutaryl-CoA (HMG-CoA); (c) an enzyme that converts HMG-CoA into mevalonate; (d) an enzyme that converts mevalonate into mevalonate 5-phosphate; (e) an enzyme that converts mevalonate 5-phosphate into mevalonate 5-pyrophosphate; (0 an enzyme that converts mevalonate 5-pyrophosphate into IPP; (g) an enzyme that converts IPP into DMAPP; (h) a polyprenyl synthase that can condense IPP and/or DMAPP molecules to form polyprenyl compounds containing more than five carbons; (i) an enzyme that condenses IPP with DMAPP to form GPP; (j) an enzyme that condenses two molecules of IPP with one molecule of DMAPP; (k) an enzyme that condenses IPP with GPP to form FPP; (1) an enzyme that condenses IPP and DMAPP to form GGPP; and (m) an enzyme that condenses IPP and FPP to form GGPP.

In certain embodiments, the host cells further comprise a heterologous nucleic acid encoding an enzyme that modifies a polyprenyl, selected from the group consisting of a geraniol synthase, a linalool synthase, a limonene synthase, a myrcene synthase, an ocimene synthase, an α-pinene synthase, β-pinene synthase, a sabinene synthase, a γ-terpinene synthase, a terpinolene synthase, an amorphadiene synthase, an α-farnesene synthase, a β-farnesene synthase, a farnesol synthase, a nerolidol synthase, a patchouliol synthase, a nootkatone synthase, and an abietadiene synthase.

In certain embodiments, the host cells comprise a plurality of heterologous nucleic acids encoding all the enzymes of a mevalonate pathway. In some embodiments, the isoprenoid is selected from the group consisting of a hemiterpene, monoterpene, diterpene, triterpene, tetraterpene, and polyterpene. In some embodiments, the isoprenoid is a $C_5$-$C_{20}$ isoprenoid. In some embodiments, the isoprenoid is a sesquiterpene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene.

In certain embodiments, the host cells are capable of producing a polyketide and comprises at least one heterologous nucleic acid encoding a polyketide synthesis enzyme, wherein the polyketide synthesis enzyme is selected from the group consisting of: (a) an enzyme that condenses at least one of acetyl-CoA and malonyl-CoA with an acyl carrier protein; (b) an enzyme that condenses a first reactant selected from the group consisting of acetyl-CoA and malonyl-CoA with a second reactant selected from the group consisting of malonyl-CoA or methylmalonyl-CoA to form a polyketide product; (c) an enzyme that reduces a β-keto chemical group on a polyketide compound to a β-hydroxy group; (d) an enzyme that dehydrates an alkane chemical group in a polyketide compound to produce an α-β-unsaturated alkene; (e) an enzyme that reduces an α-β-double-bond in a polyketide compound to a saturated alkane; and (f) an enzyme that hydrolyzes a polyketide compound from an acyl carrier protein.

In certain embodiments, the polyketide is a lipid having at least one of antibiotic, antifungal, and antitumor activity. In some embodiments, the polyketide is selected from the group consisting of a macrolid, an antibiotic, an antifungal, a cytostatic compound, an anticholesterolemic compound, an antiparasitic compound, a coccidiostatic compound, an animal growth promoter and an insecticide.

In certain embodiments, the host cells are capable of producing a fatty acid and comprises at least one heterologous nucleic acid encoding a fatty acid synthesis enzyme, wherein the fatty acid synthesis enzyme is selected from the group consisting of: (a) an enzyme that covalently links at least one of acetyl-CoA and malonyl-CoA to an acyl carrier protein (ACP); (b) an enzyme that condenses acetyl-ACP and malonyl-ACP to form acetoacetyl-ACP; (c) reduce the double bond in acetoacetyl-ACP with NADPH to form a hydroxyl group in D-3-hydroxybutyryl hydroxylase-ACP; (d) an enzyme that dehydrates D-3-Hydroxybutyryl hydroxylase-ACP to create a double bond between the beta- and gamma-carbons forming crotonyl-ACP; (e) an enzyme that reduces crotonyl ACP with NADPH to form butyryl-ACP; and (f) an enzyme that hydrolyzes a C16 acyl compound from an acyl carrier protein to form palmitate. In some embodiments, the fatty acid is selected from the group consisting of palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid.

In another aspect, provided herein are recombinant host cells comprising a heterologous nucleic acid encoding a fusion protein comprising a protein of interest fused in frame to a maltose dependent degron, wherein the fusion protein is more stable when the maltose dependent degron is in contact with maltose compared to when the maltose dependent degron is not in contact with maltose. In certain embodiments, the heterologous nucleic acid is operably linked to a maltose-responsive promoter. In certain embodiments, the host cells further comprise one or more heterologous nucleic acids encoding one or more enzymes of a biosynthetic pathway for making a heterologous non-catabolic compound. In certain embodiments, the host cells are selected from the group consisting of a fungal cell, a bacterial cell, a plant cell, and an animal cell. In certain embodiments, the host cells are a yeast cell.

In another aspect, provided herein are fermentation compositions comprising the recombinant host cells described herein in a culture medium comprising maltose.

In another aspect, provided herein are isolated nucleic acid molecules encoding maltose dependent degrons. In certain embodiment, the isolated nucleic acid molecules encode a maltose dependent degron comprising an amino acid sequence that has at least about 70%, 75%, 80%, 85%, 90%, or 95% sequence identity to SEQ ID NO: 2 or SEQ ID NO: 28, wherein the maltose dependent degron comprises one or more variant amino acid residues compared to SEQ ID NO: 2 or SEQ ID NO: 28. In certain embodiments, the isolated nucleic acid molecules encode a maltose dependent degron comprising an amino acid sequence that has at least about 70%, 75%, 80%, 85%, 90%, or 95% sequence identity to SEQ ID NO: 2 or SEQ ID NO: 28, wherein (a) the maltose dependent degron comprises one or more variant amino acid residues compared to SEQ ID NO: 2 or SEQ ID NO: 29; and (b) the one or more variant amino acid residues are located at least one of positions 7, 10, 11, 21, 24, 28, 42, 43, 64, 68, 83, 88, 92, 95, 98, 101, 110, 117, 134, 135, 136, 149, 168, 177, 186, 187, 193, 198, 210, 216, 217, 229, 236, 237, 242, 263, 291, 304, 321, 322, 339, 351, 357, 367, 370, and 374, wherein positions of the one or more variant amino acid residues correspond to amino acid positions of SEQ ID NO: 2 or SEQ ID NO: 28. In certain embodiments, the isolated nucleic acid molecule is a cDNA.

In certain embodiments, the isolated nucleic acid molecules encode a maltose dependent degron comprising one or more variant amino acid residues selected from the group consisting of K7R, I10T, W11G, L21S, V24A, F28Y, D42V, K43E, A64T, F68S, D83G, D88N, P92T, W95R, V98I, N101I, A110T, I117V, P134S, A135T, L136M, M149I, Y168C, Y168N, Y177H, N186S, A187P, L193S, D198V, D210E, A216V, A217D, G229C, I236N, D237N, N242D, L263M, L291V, A304T, T321N, M322L, A339T, A351T, T357S, T367S, S370P, and N374S. The positions of one or more variant amino acid residues correspond to amino acid positions of SEQ ID NO: 2 or SEQ ID NO: 28.

In certain embodiments, the isolated nucleic acid molecules encode a maltose dependent degron comprising at least one set of variant amino acid residues compared to SEQ ID NO: 2 or SEQ ID NO: 28, wherein the at least one set of variant amino acid residues is selected from the group of sets of variant amino acid residues consisting of: (a) I10T, V24A, D42V, K43E, D83G, P92T, M149I, Y168N, N186S, A216V, and T357S; (b) I10T, V24A, D42V, K43E, D83G, M149I, Y168N, N186S, A216V, and D237N; (c) I10T, V24A, D42V, K43E, D83G, M149I, Y168N, N186S, A216V, and A339T; (d) I10T, V24A, D42V, K43E, D83G, M149I, Y168N, N186S, A216V, and N242D; (e) I10T, V24A, D42V, A110T, M149I, and A216V; (f) I10T, V24A, D42V, K43E, D83G, M149I, Y168N, N186S, and A216V; (g) L21S, A64T, L136M, Y177H, A187P, A304T, T321N, and A351T; (h) K7R, D83G, V98I, L193S, I236N, and N374S; (i) W11G, D88N, P134S, A135T, D210E, and M322 L; (j) I117V, Y168N, G229C, L263M, T367S, and S370P; (k) F68S, W95R, N186S, D198V; and (l) F28Y, K43E, N101I, Y168C, A217D, and L291V.

In certain embodiments, the isolated nucleic acid molecules encode a maltose dependent degron that comprises a sequence selected from the group consisting of SEQ ID NOS: 4, 6, 8, 10, 12, 14, 16, 18, 20, 22, 24, and 26. In certain embodiments, the isolated nucleic acid molecules encode a maltose dependent degron that comprises a sequence selected from the group consisting of position 1 to position 365 of SEQ ID NOS: 16, 18, 20, 22, 24, and 26. In certain embodiments, the isolated nucleic acid molecules encode a maltose dependent degron that comprises a sequence selected from the group consisting of position 1 to position 370 of SEQ ID NOS: 16, 18, 20, 22, 24, and 26.

In certain embodiments, the isolated nucleic acid molecule comprises a sequence selected from the group consisting of SEQ ID NOS: 3, 5, 7, 9, 11, 13, 15, 17, 19, 21, 23, and 25. In certain embodiments, the isolated nucleic acid molecule comprises a sequence selected from the group consisting of position 1 to position 1098 of SEQ ID NOS: 11, 15, 17, 19, 21, 23, and 25. In certain embodiments, the isolated nucleic acid molecule comprises a sequence selected from the group consisting of position 1 to position 1113 of SEQ ID NOS: 11, 15, 17, 19, 21, 23, and 25.

In another aspect, provided herein are fusion proteins comprising a protein of interest fused in frame to a maltose dependent degron described herein.

In another aspect, provided herein are DNA constructs comprising a maltose-responsive promoter operably linked to a nucleic acid encoding a fusion protein comprising a protein of interest fused in frame to a maltose dependent degron comprising an amino acid sequence encoded by the isolated nucleic acid sequence described herein.

In another aspect, provided herein are synthetic maltose-responsive promoters comprising a pGAL promoter with at least one or all of Gal4p binding sites replaced with one or more binding sites for a MAL transcriptional activator. In certain embodiments, a synthetic maltose-responsive promoter comprises a sequence selected from the group consisting of pGMAL_v5 (SEQ ID NO: 35), pGMAL_v6 (SEQ ID NO: 36), pGMAL_v7 (SEQ ID NO: 37), pGMAL_v9 (SEQ ID NO: 38), pGMAL_v10 (SEQ ID NO: 39), pGMAL_v11 (SEQ ID NO: 40), pGMAL_v12 (SEQ ID NO: 41), pGMAL_v13 (SEQ ID NO: 42), pGMAL_v14 (SEQ ID NO: 43), pGMAL_v15 (SEQ ID NO: 44), pGMAL_v16 (SEQ ID NO: 45), pGMAL_v17 (SEQ ID NO: 46), pGMAL_v18 (SEQ ID NO: 47), pG2MAL_v1 (SEQ ID NO: 48), pG2MAL_v2 (SEQ ID NO: 49), pG2MAL_v3 (SEQ ID NO: 50), pG2MAL_v5 (SEQ ID NO: 51), pG2MAL_v6 (SEQ ID NO: 52), pG2MAL_v7 (SEQ ID NO: 53), pG2MAL_v8 (SEQ ID NO: 54), pG2MAL_v9 (SEQ ID NO: 55), pG2MAL_v10 (SEQ ID NO: 56), pG7MAL_v2 (SEQ ID NO: 57), pG7MAL_v4 (SEQ ID NO: 58), pG7MAL_v6 (SEQ ID NO: 59), pG7MAL_v8 (SEQ ID NO: 60), pG7MAL_v9 (SEQ ID NO: 61), pG172 MAL_v13 (SEQ ID NO: 62), pG271 MAL_v12 (SEQ ID NO: 63), pG721 MAL_v11 (SEQ ID NO: 64), pG712 MAL_v14 (SEQ ID NO: 65), a portion thereof which retains promoter function, or a sequence that has at least about 70%, 75%, 80%, 85%, 90%, 95%, 96%, 97%, 98%, or 99% sequence identity to thereof. In certain embodiments, other synthetic maltose-responsive promoters provided herein comprise: (a) a core promoter comprising a transcription initiation site; and (b) one or more MAL transcriptional activator binding sites, wherein the promoter activity of the synthetic maltose-responsive promoter during an un-induced condition in the absence of maltose is less than the promoter activity of a native maltose-responsive promoter from which the one or more MAL transcriptional activator binding sites are derived.

In another aspect, provided herein are vectors comprising DNA constructs comprising a maltose-responsive promoter operably linked to a nucleic acid encoding a fusion protein comprising a protein of interest fused in frame to a maltose dependent degron, wherein the maltose-responsive promoter is selected from native maltose-responsive promoters and synthetic maltose-responsive promoters provided herein.

In another aspect, provided herein are methods for gene expression comprising: (a) culturing host cells comprising a DNA construct comprising a pGMAL promoter operably linked to a gene of interest in a culture medium without maltose; and (b) adding maltose to the culture medium to activate or increase the pGMAL promoter activity, wherein the pGMAL promoter comprises a pGAL promoter with at least one or all of Gal4p binding sites replaced with one or more binding sites for a MAL transcriptional activator. In some embodiments, other synthetic maltose-responsive promoter described herein can be operably linked to a gene of interest in the methods for gene expression.

In another aspect, provided herein are methods for producing a heterologous non-catabolic compound in a genetically modified host cell, the method comprising: (a) culturing a population of genetically modified host cells in a culture medium comprising a carbon source comprising maltose, wherein the host cell comprises one or more heterologous nucleic acids encoding one or more enzymes of a biosynthetic pathway for making the heterologous non-catabolic compound, wherein expression of the one or more enzymes is negatively regulated by the activity of a synthetic maltose-responsive promoter, wherein the presence of maltose in the culture medium limits the amount of heterologous non-catabolic compound produced by the host cells; and (b) culturing the population or a subpopulation thereof in a culture medium comprising a carbon source wherein maltose is absent or in sufficiently low amounts such that the synthetic maltose-responsive promoter is less active than in step (a), and production of the heterologous non-catabolic compound by the host cells is increased. In certain embodiments, the synthetic maltose-responsive promoter includes pGMAL promoters provided herein.

In another aspect, provided herein are compositions and methods for stabilizing the production of heterologous non-catabolic compounds using a stabilization construct which can minimize the negative impact of a spontaneous mutation that adds a positive selective pressure to lower the production of non-catabolic compounds. In certain embodiments, the method of producing a heterologous non-catabolic compound comprises culturing, in a culture medium, a genetically modified cell which comprises: (a) a heterologous nucleic acid encoding an enzyme of a biosynthetic pathway for producing a heterologous non-catabolic compound, wherein the heterologous nucleic acid is operably linked to a first promoter; (b) a nucleic acid encoding a cell-growth-affecting protein, wherein the nucleic acid is operably linked to a second promoter; and (c) a nucleic acid encoding a transcriptional regulator. In these embodiments, the first promoter and the second promoter are both regulated by the same transcriptional regulator. Therefore, a functional disruption of the transcriptional regulator (e.g., caused by a spontaneous mutation) negatively impacts expression of both of the heterologous nucleic acid encoding the enzyme of the biosynthetic pathway and the nucleic acid encoding the cell-growth-affecting protein. Reduced expression of the nucleic acid encoding the cell-growth-affecting protein would provide a growth disadvantage and prevent such cells from dominating the population of cells during a long fermentation run.

In certain embodiments, the non-catabolic compound itself is a protein of interest instead of an enzyme of a biosynthetic pathway for producing a heterologous non-catabolic compounds. In these embodiments, the transcriptional regulator co-regulates expression of a heterologous nucleic acid encoding a protein of interest and a nucleic acid encoding a cell-growth-affecting protein.

In certain embodiments, the transcriptional regulator(s) that regulate the first promoter and the second promoter are regulatory proteins of the GAL regulon. For example, genetically modified host cells can comprise a heterologous nucleic acid encoding transcriptional activator Gal4p and/or transcriptional repressor Gal80p. In some embodiments, the first promoter and the second promoter are naturally derived pGAL promoters or pGAL synthetic promoters. In certain embodiments, the heterologous nucleic acid encoding a cell-growth-affecting protein and the heterologous nucleic acid encoding an enzyme of a biosynthetic pathway for producing a non-catabolic compound are chromosomally integrated into a genome of the genetically modified host cell.

In certain embodiments, a heterologous nucleic acid encoding a cell-growth-affecting protein is an essential gene which is absolutely required for life for genetically modified host cells under any culture medium or condition. In other embodiments, a heterologous nucleic acid encoding a cell-growth-affecting protein is a conditional essential gene which is necessary for cell growth when host cells are grown in a culture medium lacking an essential compound. These include, for example, one or more biosynthetic genes that encode one or more enzymes in biosynthetic pathways for producing amino acids, nucleotides, or fatty acids. In certain embodiments, a conditional essential gene encodes an enzyme in a biosynthetic pathway for producing lysine. In other embodiments, a conditional essential gene encodes an enzyme in a biosynthetic pathway for producing methionine.

In certain embodiments, the method of culturing comprises two stages: (a) a cellular biomass build stage where a population of genetically modified host cell is cultured in a culture medium that limits production of heterologous non-catabolic compounds, followed by a production stage where the population or a subpopulation thereof is cultured under culture conditions that promote production of the heterologous non-catabolic compound. During the cellular biomass build stage, expression of the regulon (e.g., nucleic acids encoding enzymes of a biosynthetic pathway for producing non-catabolic compounds and a nucleic acid encoding a conditional essential gene product) in genetically modified host cells is limited and the culture medium is supplemented with an essential compound so that the cells can grow. During the production stage, genetically modified host cells are cultured in a culture medium lacking or containing a sufficiently low amount of essential compound such that only the cells that can synthesize the essential compound can grow. This provides a positive selective pressure for cells that maintain expression of transcriptional regulators, and therefore, expression of the regulon, during the production stage.

In another aspect, provided herein are compositions and methods for producing a heterologous non-catabolic compound, which utilize a combination of a fusion protein comprising a transcriptional regulator fused in frame to a maltose dependent degron and a stabilization construct. When the fusion protein is used in combination with a stabilization construct described herein, the production of heterologous non-catabolic compounds is further stabilized since both constructs can counteract any negative effect of spontaneous mutations. A stabilization construct, which couples cell growth of genetically modified host cells to the production of non-catabolic compounds, mitigates any negative effects of spontaneous mutations at the transcriptional level. A fusion protein comprising a transcriptional regulator fused in frame to a maltose dependent degron mitigates any negative effects of spontaneous mutations at the post-translational level.

In certain embodiments, a method of producing a heterologous non-catabolic compound comprises, culturing in a culture medium, a genetically modified host cell which comprises: (a) a heterologous nucleic acid encoding a fusion protein comprising a transcriptional regulator fused in frame to a maltose dependent degron; (b) one or more heterologous nucleic acids encoding one or more enzymes of a biosynthetic pathway for producing the heterologous non-catabolic compound, wherein each of the heterologous nucleic acid is operably linked to a promoter regulated by the fusion protein; and (c) a nucleic acid encoding a cell-growth-affecting protein, wherein the nucleic acid is operably linked to a promoter regulated by the fusion protein. In an embodiment, the fusion protein comprises a Gal80p fused in frame to a maltose dependent degron, and Gal4p-responsive promoters are operably linked to the heterologous nucleic acids encoding one or more enzymes of the biosynthetic pathway and to the nucleic acid encoding the cell-growth-affecting protein.

These and other embodiments of the invention along with many of its features are described in more detail in conjunction with the text below and attached figures.

5. BRIEF DESCRIPTION OF THE FIGURES

Figure 5:
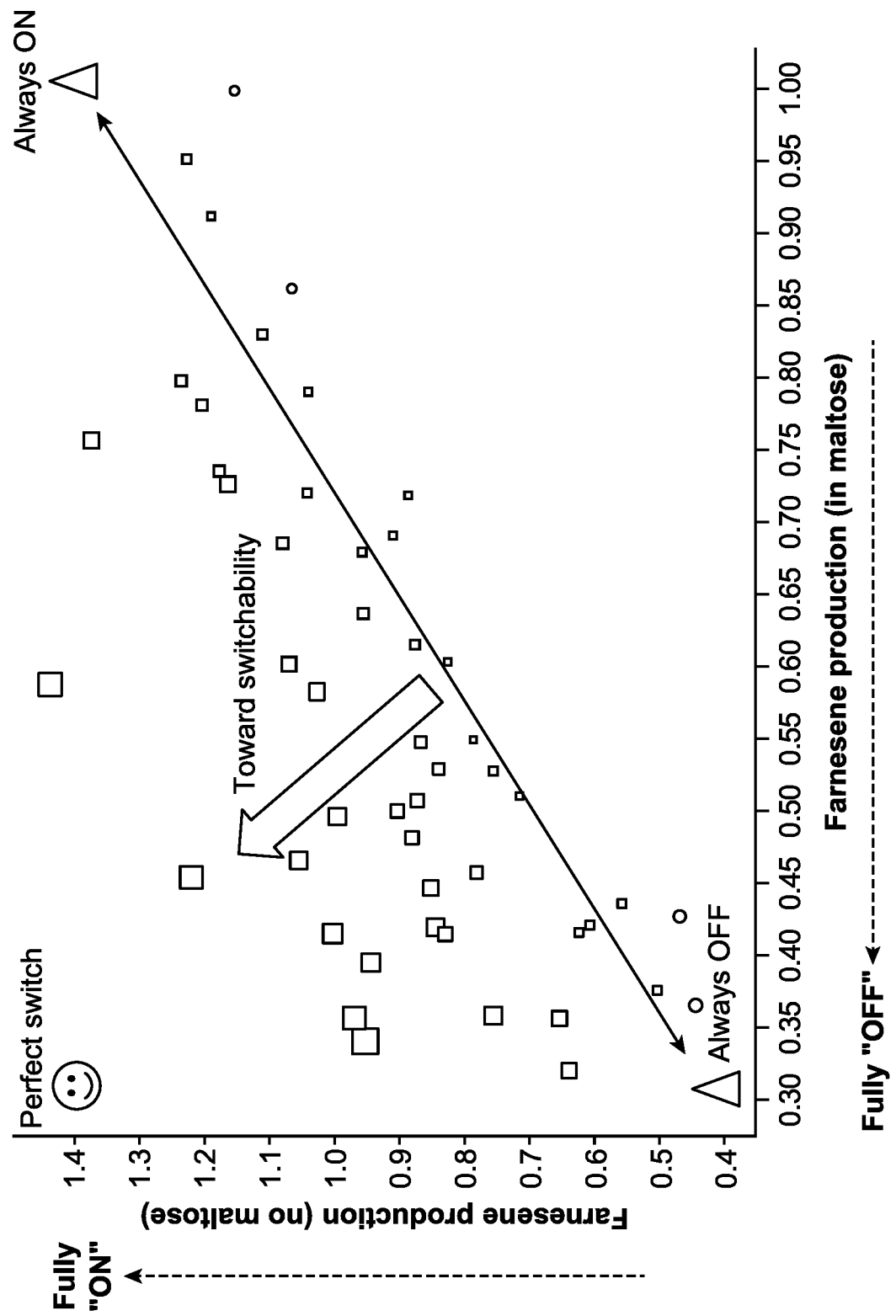

FIG. 5 illustrates a graph representing the farnesene production by strains expressing fusion proteins comprising Gal80p fused in frame to various MBP mutants obtained from the first tier mutagenesis. The X-axis represents the amount of farnesene production from strains cultured in a culture medium comprising maltose, and the Y-axis represents the amount of farnesene production from strains cultured in a culture medium with no maltose. Each MBP mutant strain obtained through the first tier mutagenesis is indicated by a square marker.

Figure 6:
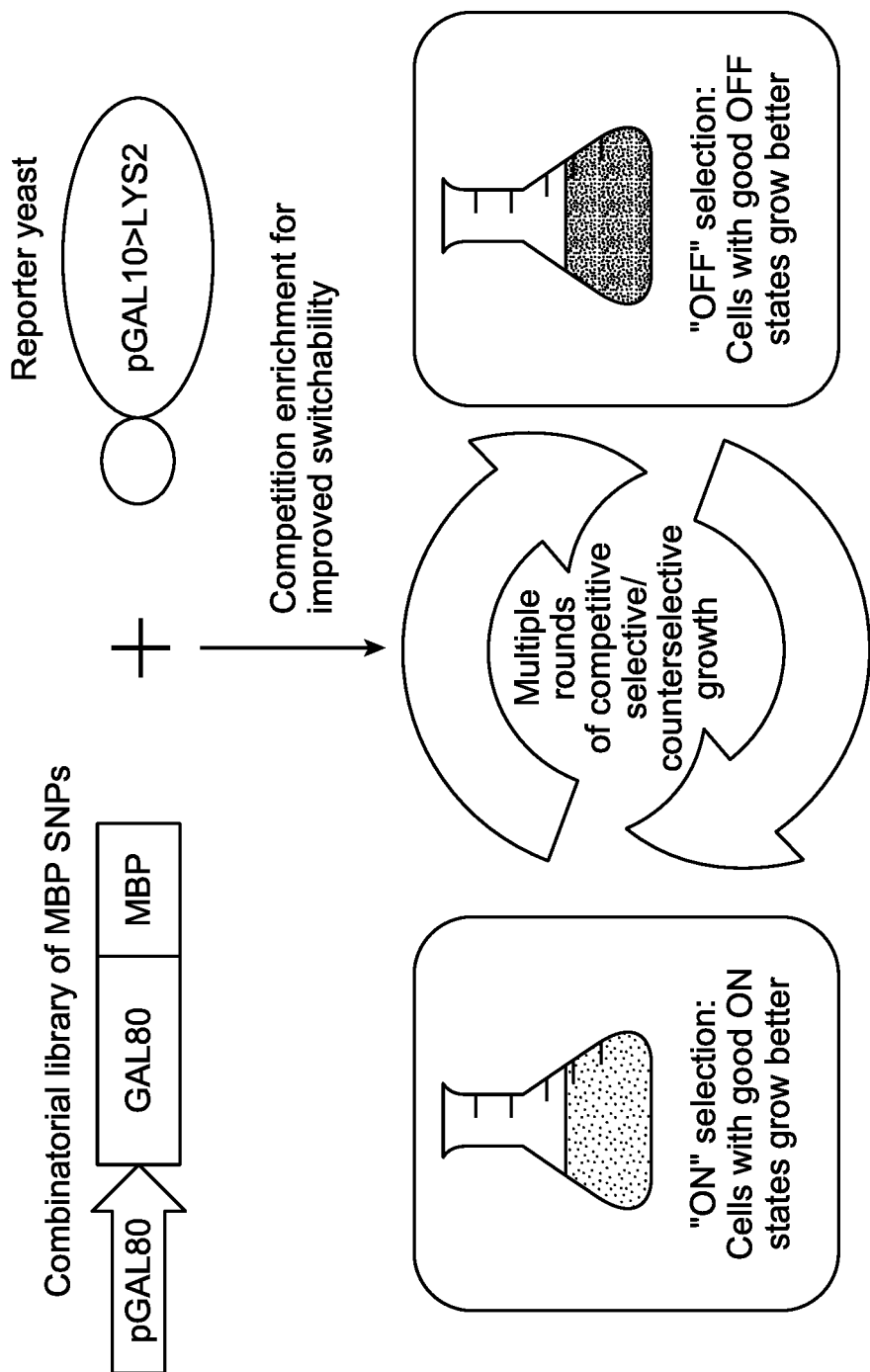

FIG. 6 illustrates a schematic representation of a second tier optimization process showing competition enrichment performed on the first tier MBP mutant strains to improve their maltose dependent switchability.

Figure 7A:
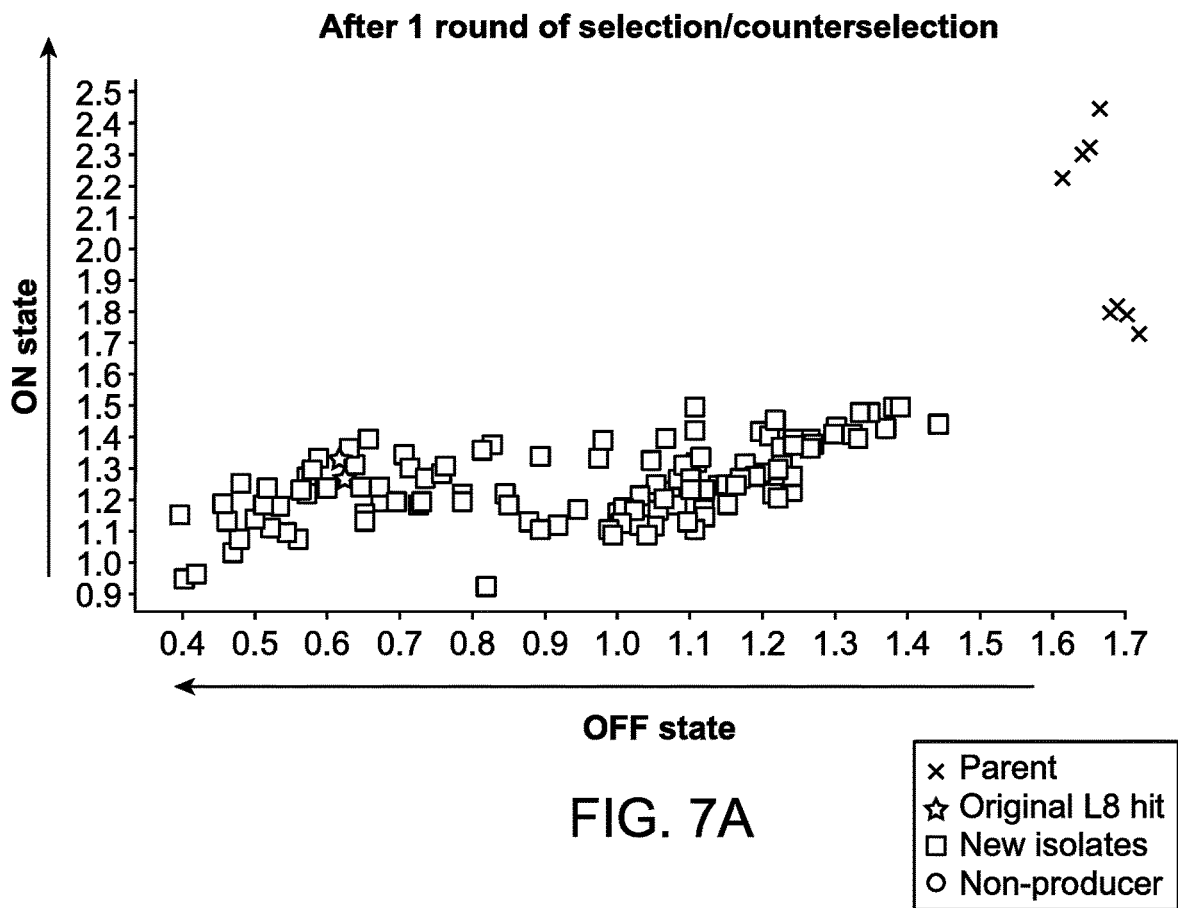
Figure 7B:
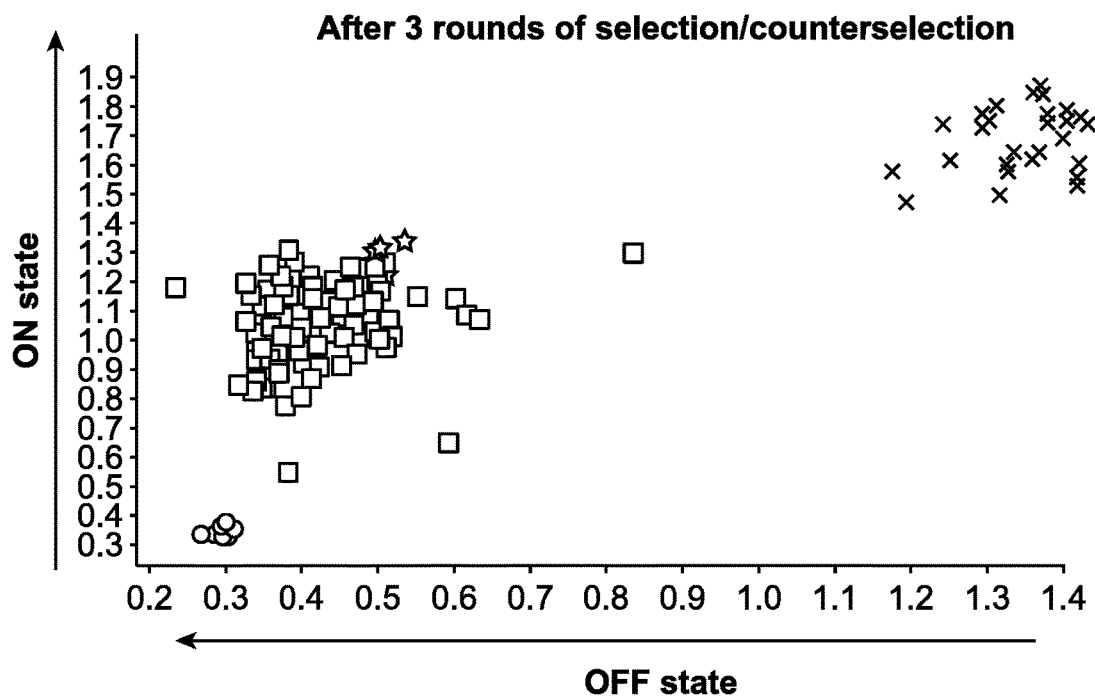

FIGS. 7A and 7B illustrate results of the growth competition selection for combination of MBP mutations from the first tier mutagenesis after one round of selection/counterselection cycle and after three rounds of selection/counterselection cycles. After three rounds of selection/counterselection cycles of the second tier optimization process, strains with improved "off" states were obtained.

Figure 8A:
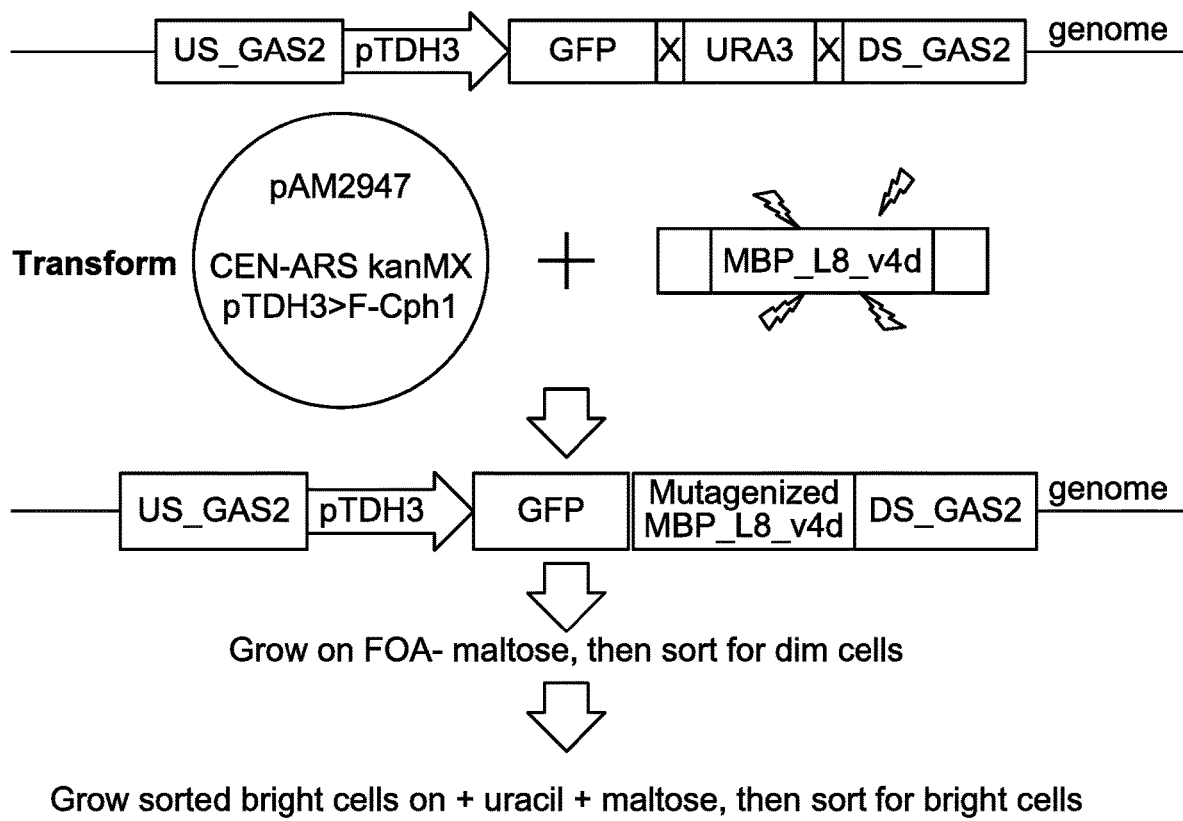

FIG. 8A illustrates a schematic diagram illustrating a cell sorting strategy to screen for MBP mutants with improved instability in the absence of maltose.

Figure 8B:
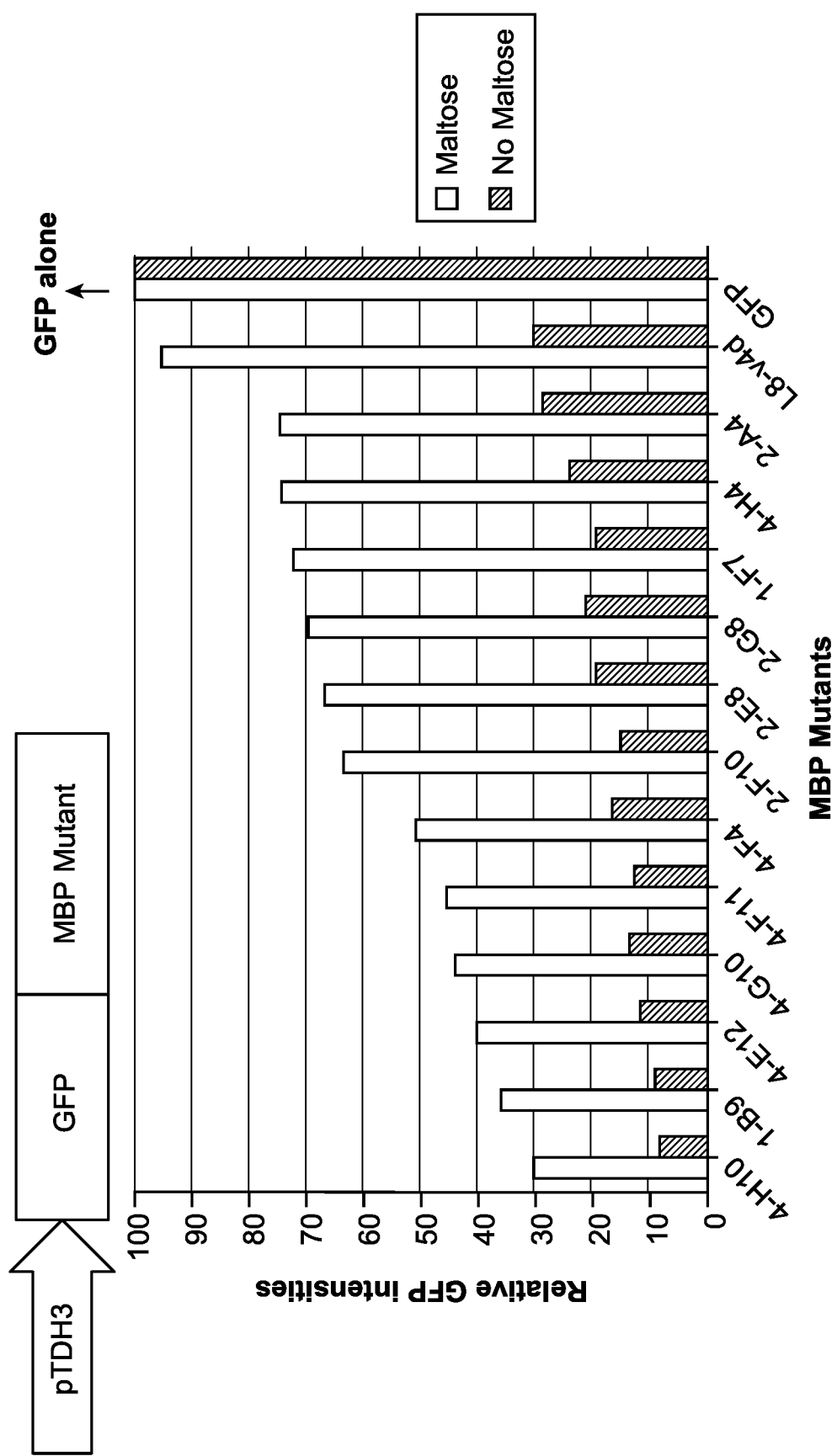

FIG. 8B illustrates relative GFP (green fluorescent protein) intensities from host cells expressing GFP fused to various MBP mutants when the host cells are cultured in a culture medium with maltose or without maltose.

Figure 8C:
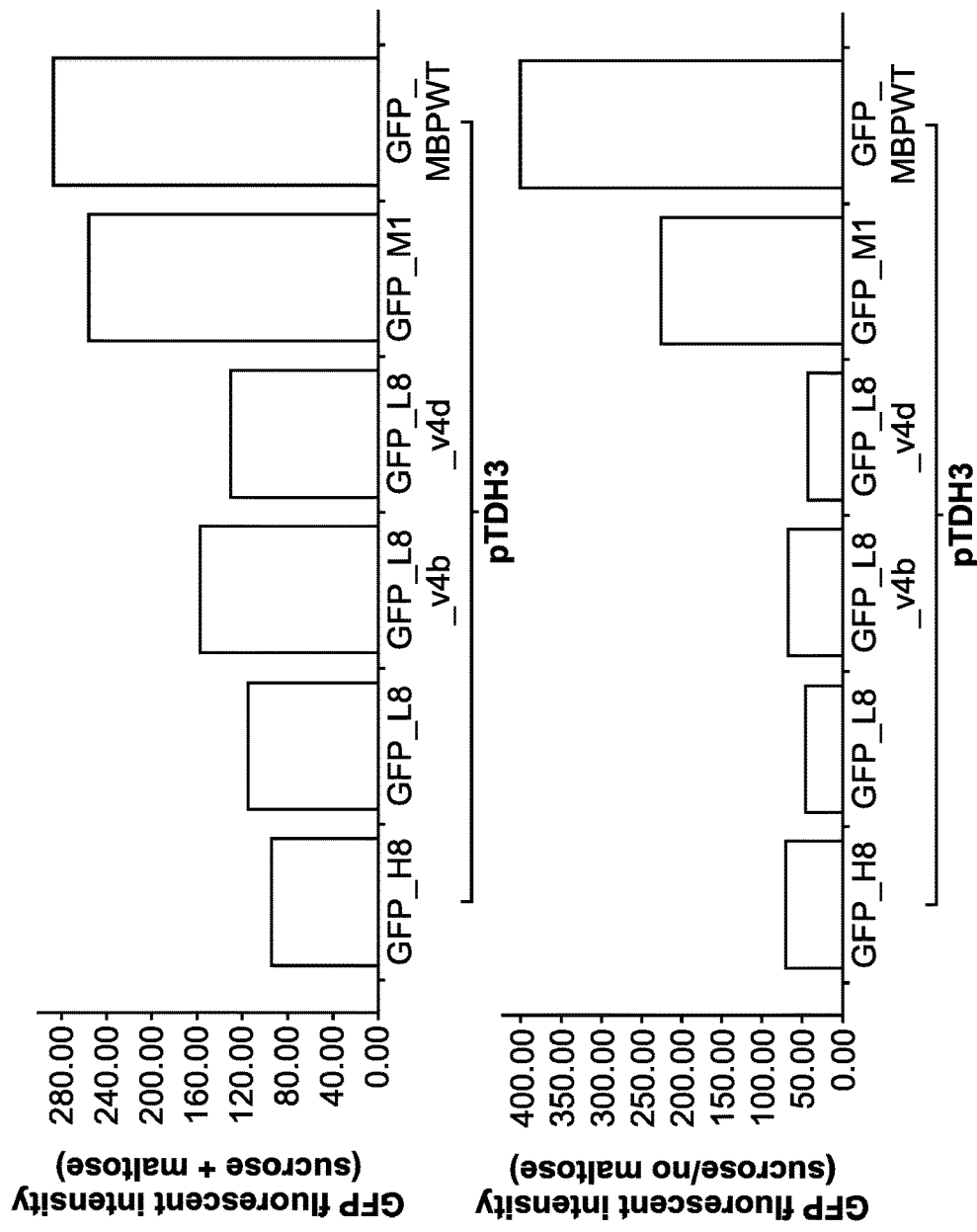

FIG. 8C illustrates GFP fluorescent intensity (in raw units) from host cells expressing GFP fused to various MBP mutants and to wild-type MBP when the host cells are cultured in a culture medium with maltose (top graph) and without maltose (bottom graph). A table at the bottom of FIG. 8C illustrates a ratio of GFP fluorescent intensities from genetically modified host cells cultured in the presence of maltose versus in the absence of maltose.

Figure 9A:
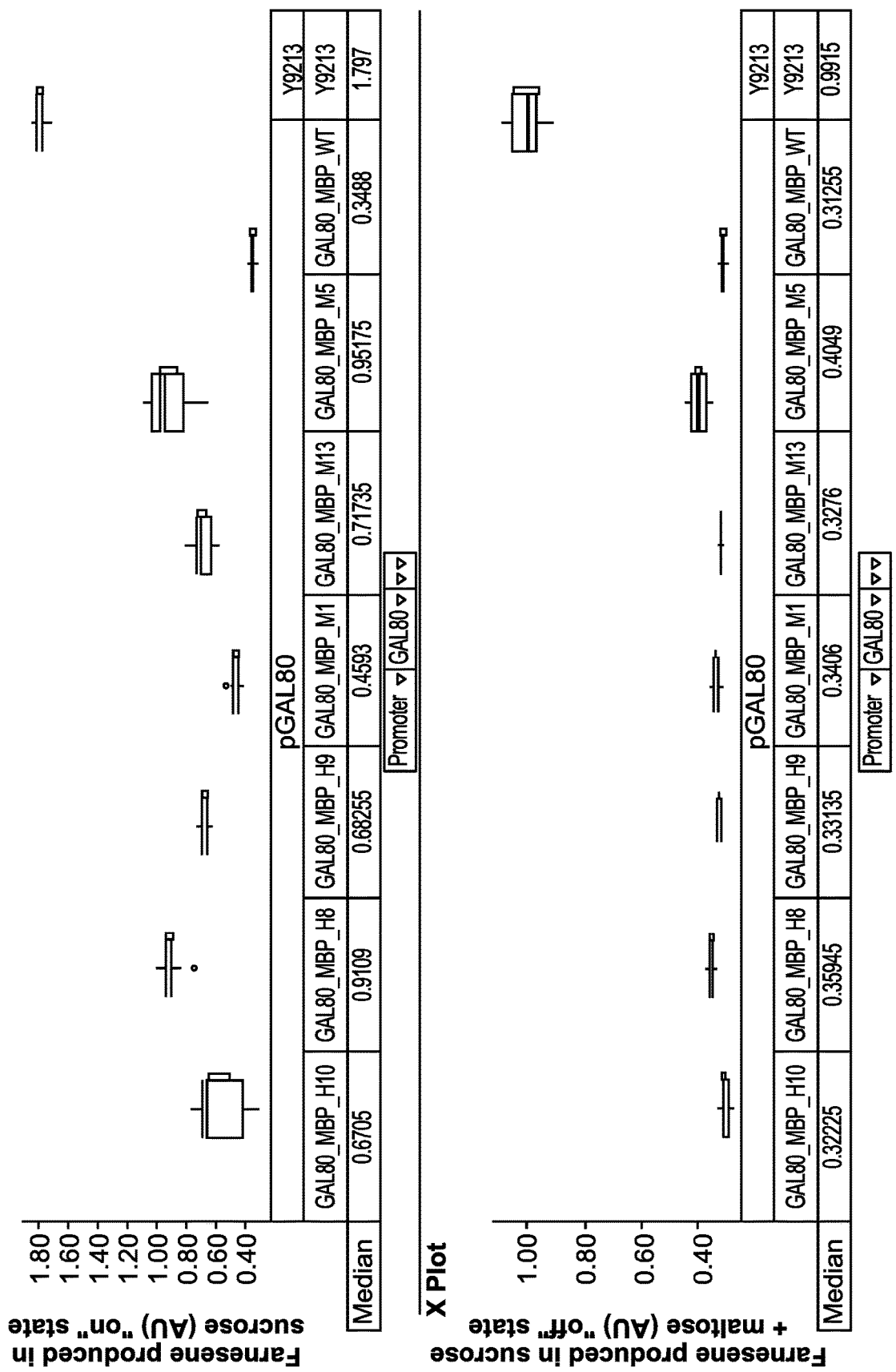
Figure 9B:
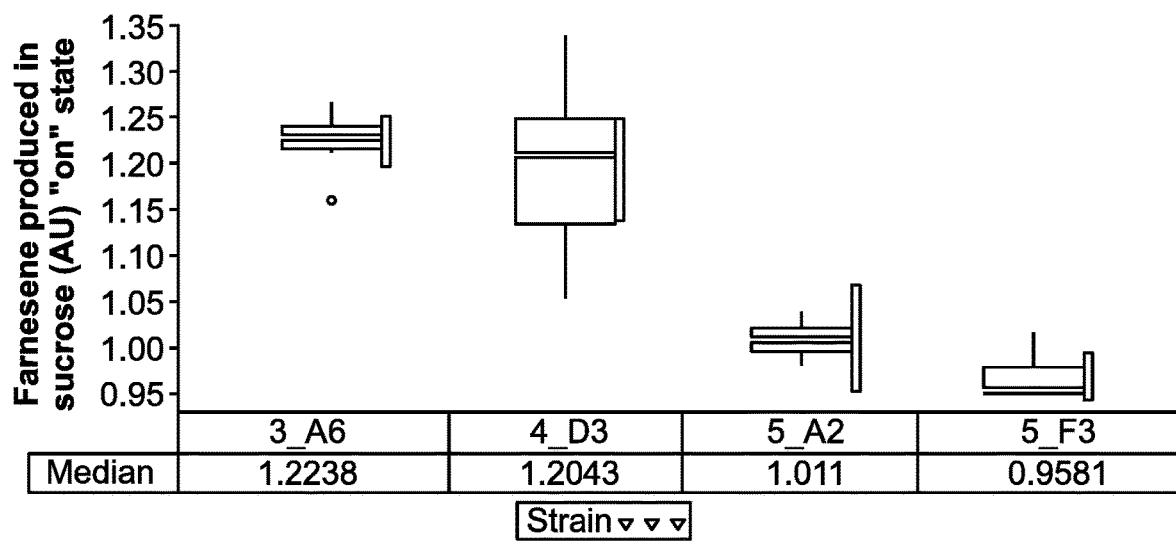
Figure 9B:
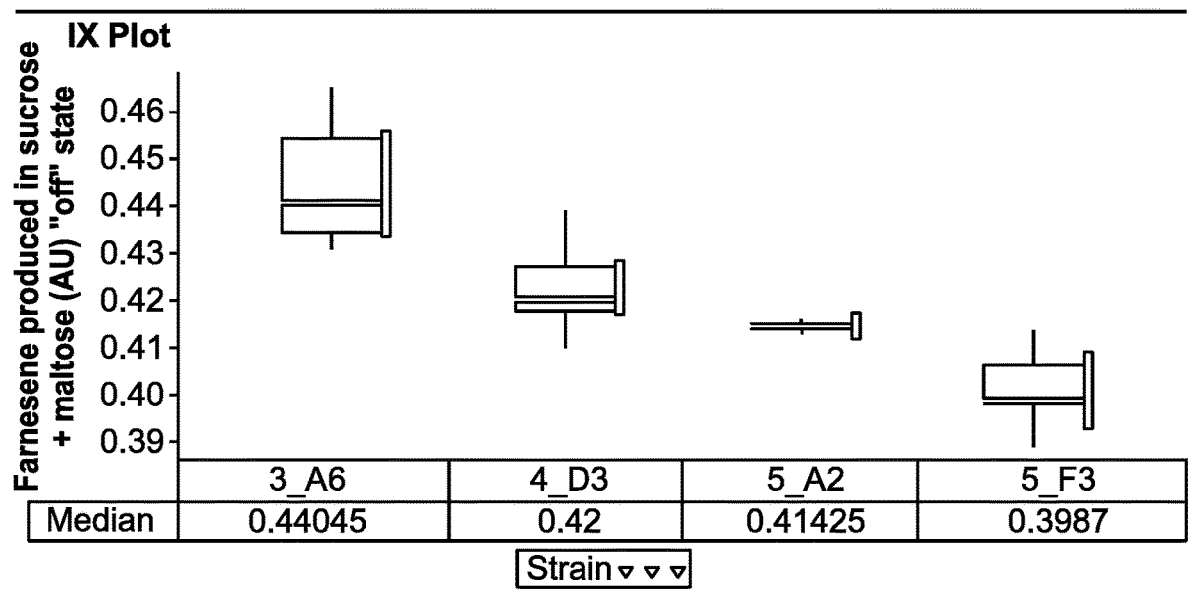
Figure 9C:
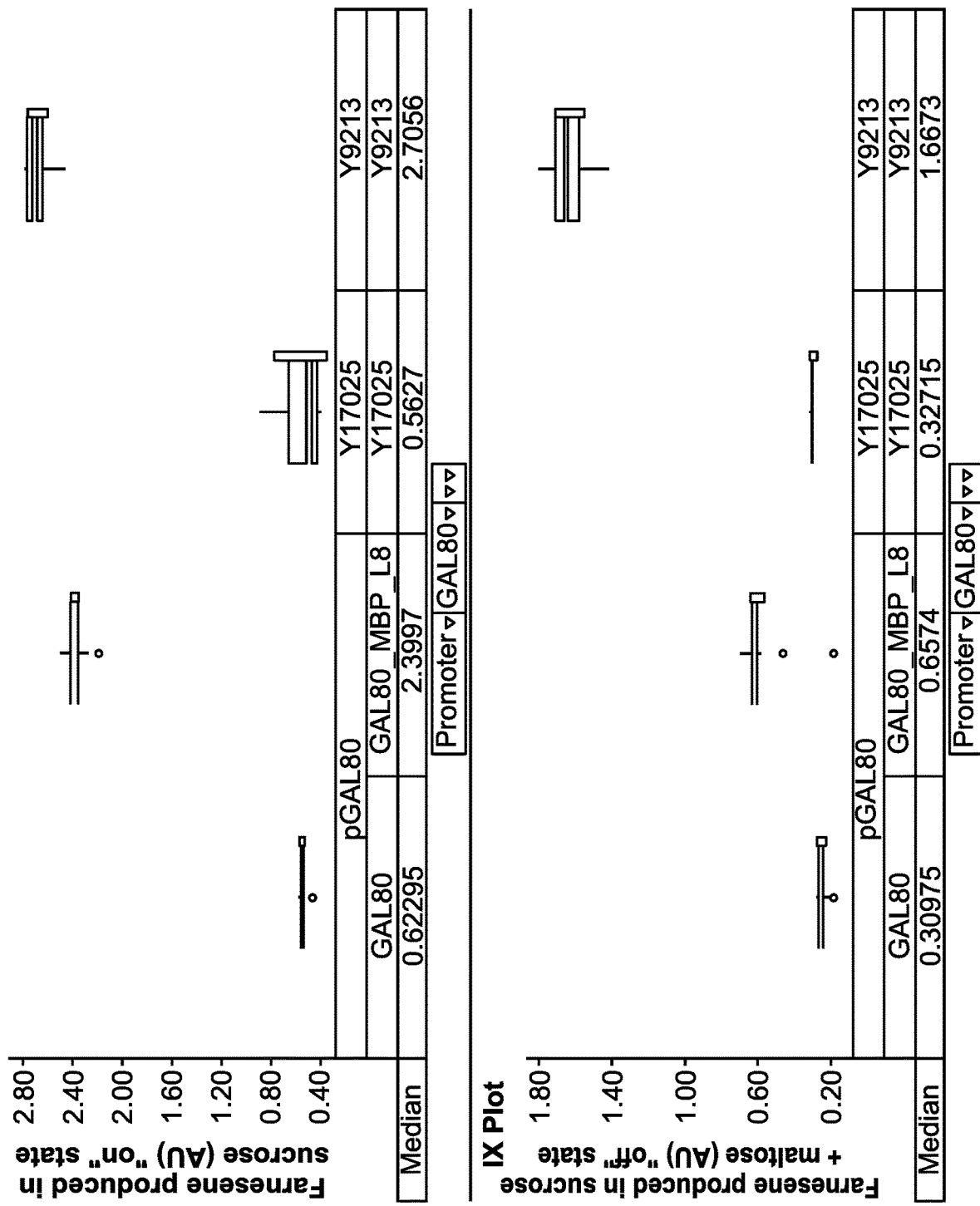

FIGS. 9A to 9C illustrate the maltose dependent farnesene production levels of host cells expressing a fusion protein comprising a Gal80p fused in frame to different MBP mutants.

Figure 9D:
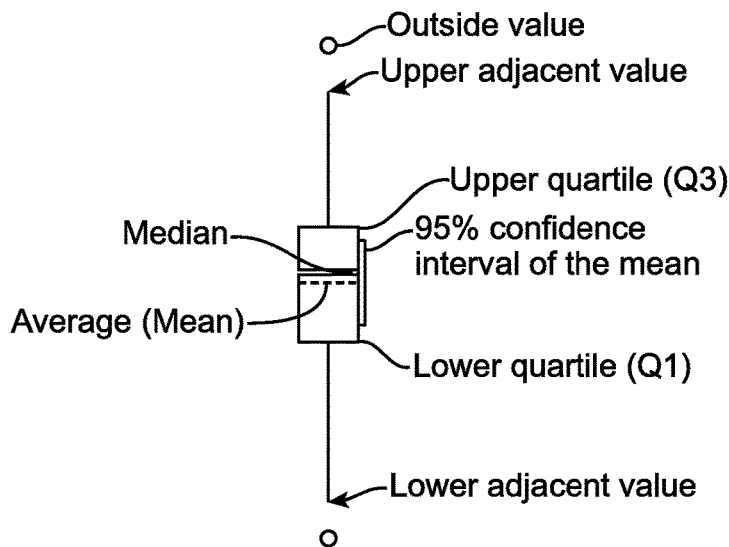

FIG. 9D illustrates a schematic diagram showing how to visualize and interpret data shown as box plots in FIGS. 9A to 9C, 10, and 19. The box plots for these figures were generated using TIBCO® Spotfire® data visualization and analytics software. When measurements for different runs are very precise and close to one another, a box represented by the upper quartile and lower quartile collapses into a line or lines (see, e.g., GAL80_MBP_H9 and GAL80_MBP_M1 data in FIG. 9A).

Figure 10:
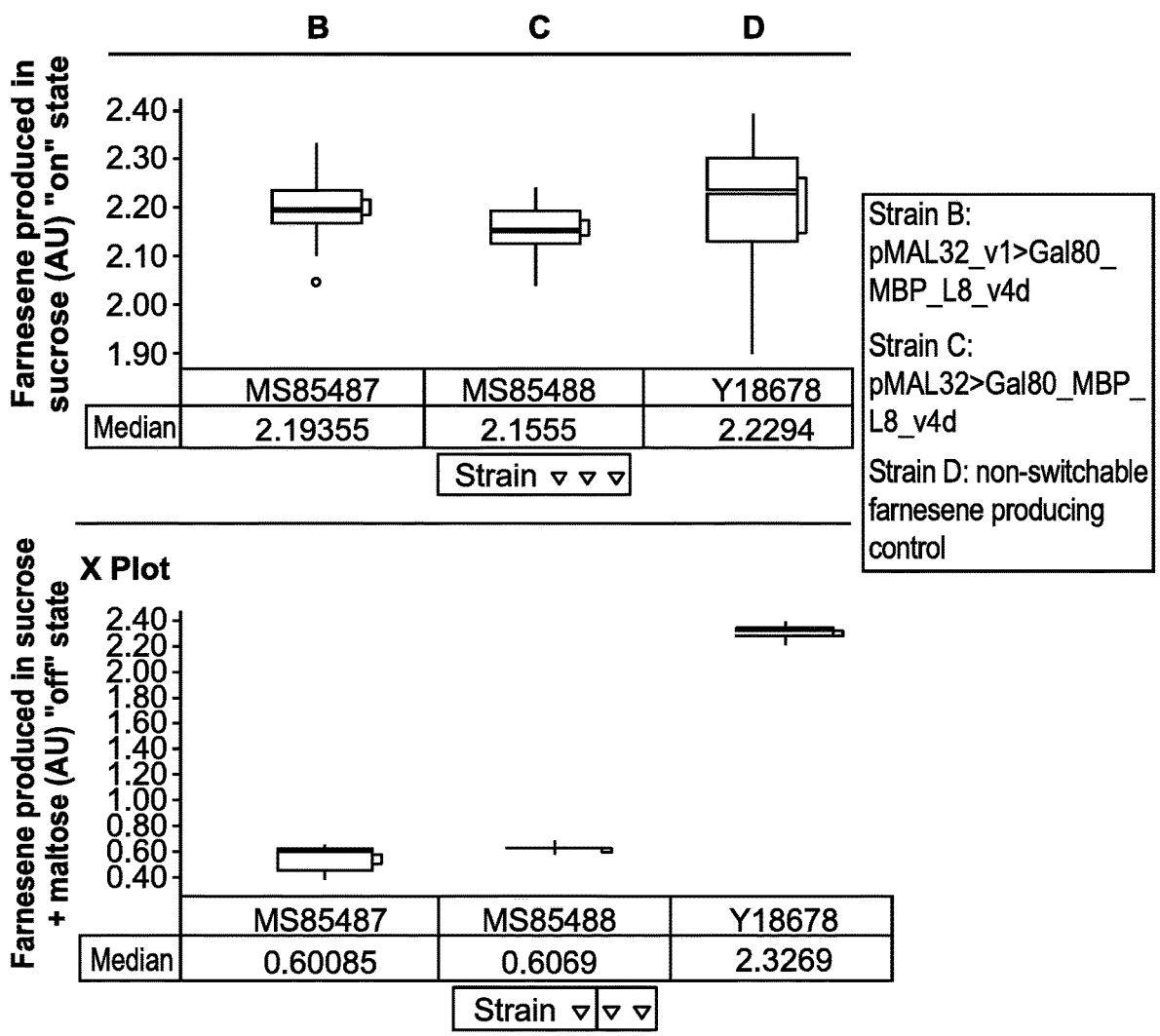

FIG. 10 illustrates switchability of different switch constructs containing MBP. Strains B, C, and D are isogenic strains, and strains B and C comprise specific switch constructs. B=pMAL32_v1>GAL80_MBPL8_v4d (a weaker promoter driving GAL80 fused to the MBP mutant with the best maltose-dependent differential for protein stability); C=pMAL32>GAL80_MBPL8_v4d (same as B except that the promoter is stronger); D=parent strain (constitutive promoter driving expression of mevalonate pathway genes without maltose switch or maltose dependent degron).

Figures 11A, 11B:
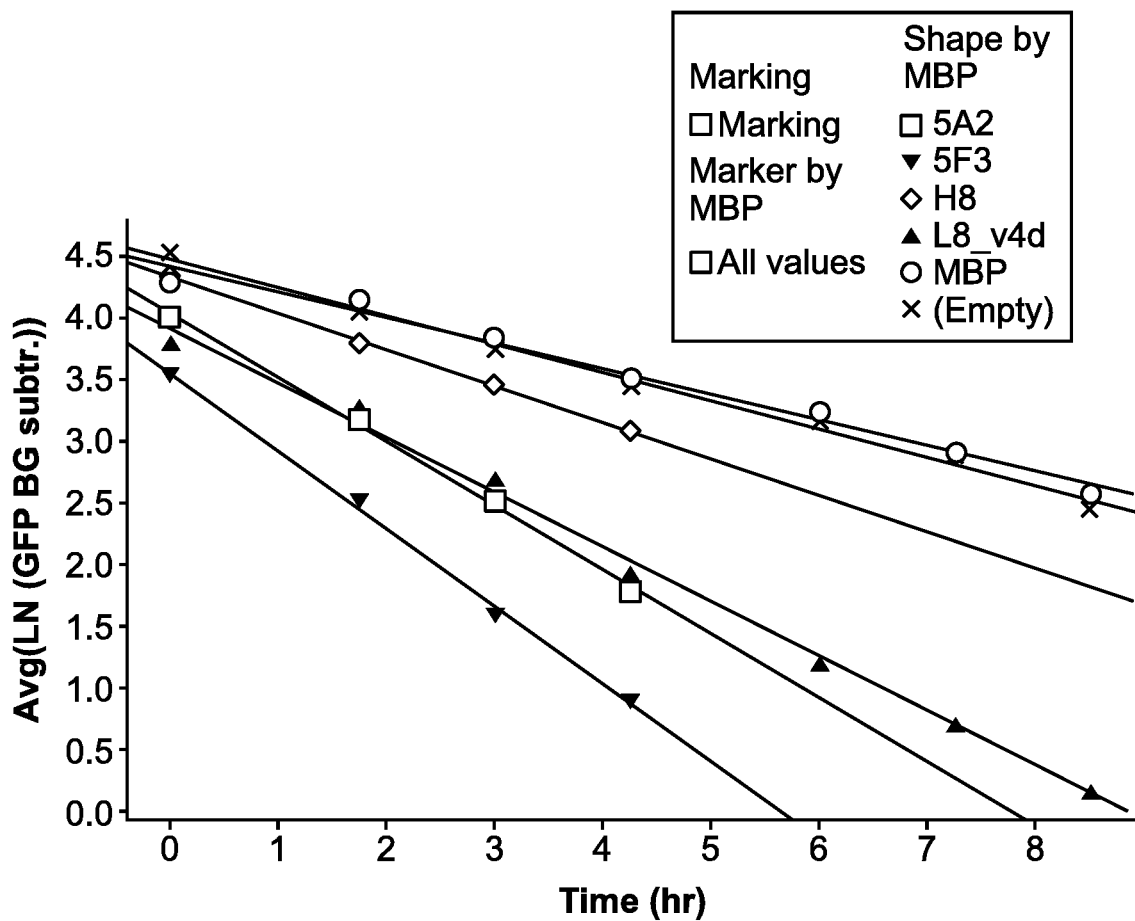

FIG. 11A illustrates degradation of various MBP mutants fused to GFP in BSM sucrose medium. GFP expression was driven by the maltose inducible promoter pMAL32. GFP protein was expressed alone or fused to the N terminus of a wild-type or mutant MBP (no MBP—x; GFP_MBP—o; GFP_5A2—□; GFP_5F3—▼; GFP_H8—◇; GFP_L8_v4d—▲).

FIG. 11B illustrates half-lives of GFP control and GFP fused to various MBP mutants in host cells cultured in BSM sucrose medium.

Figure 12A:
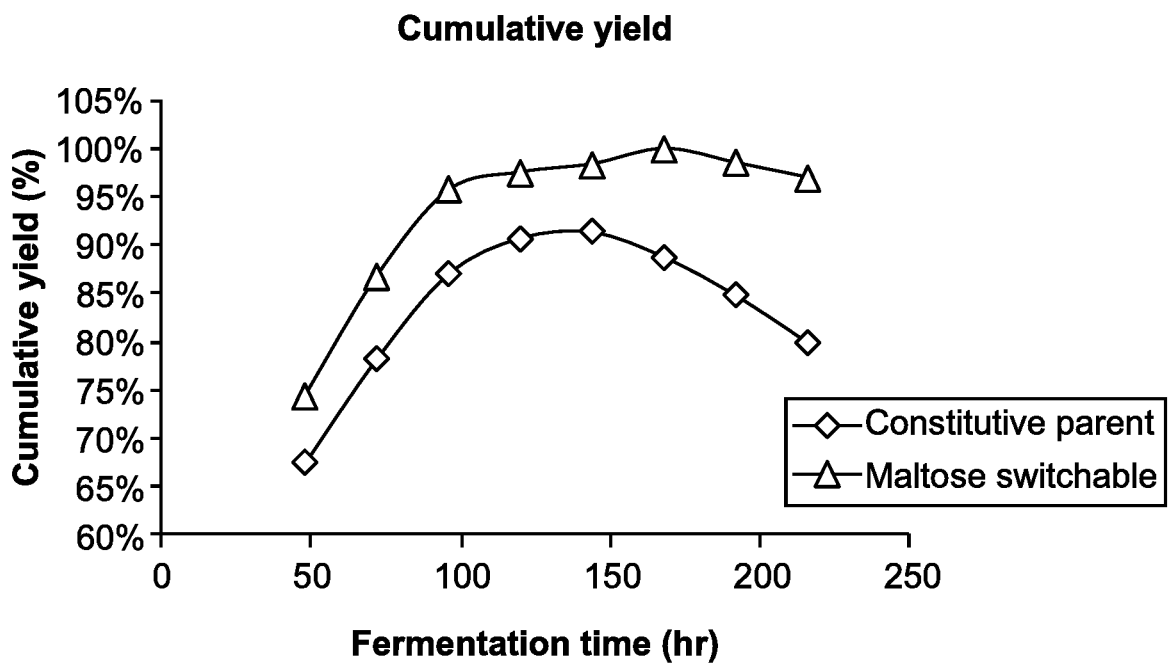
Figure 12B:
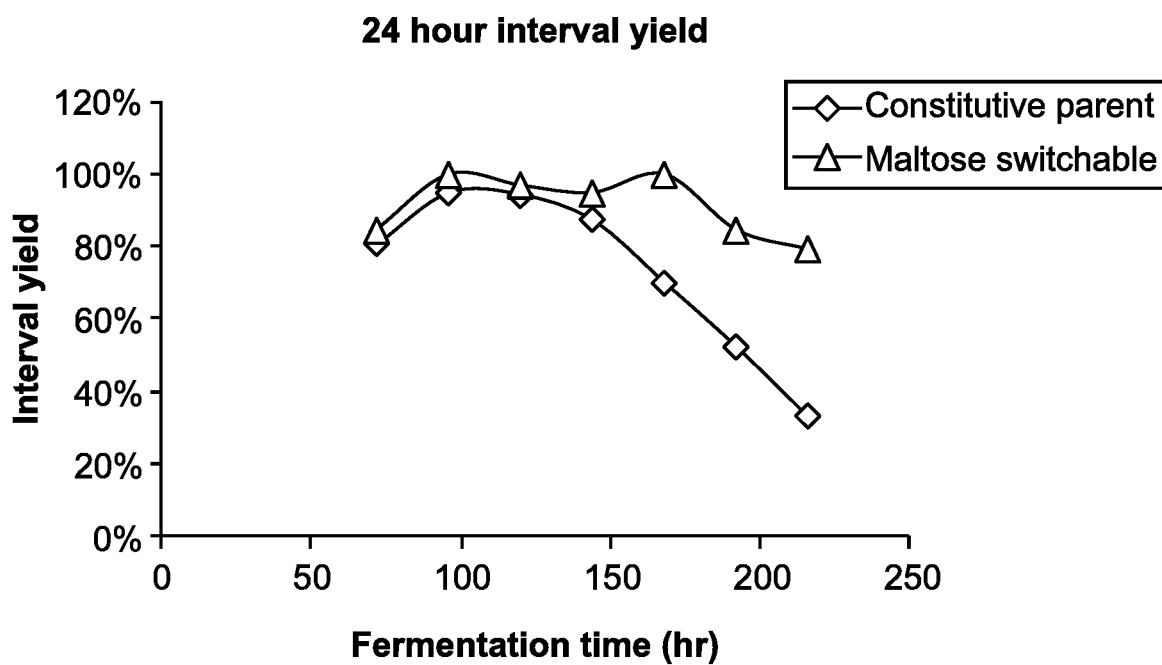

FIGS. 12A and 12B provide results demonstrating that host cells capable of producing the isoprenoid farnesene, and comprising the MEV pathway under negative regulation by a maltose-responsive promoter and a maltose dependent degron, display improved stability of production of farnesene in a long fermentation run when the build stage of the fermentation is performed in the presence of maltose (thereby effecting an "off" state), compared to production from a constitutively producing strain that produced farnesene throughout the build stage.

Figure 13A:
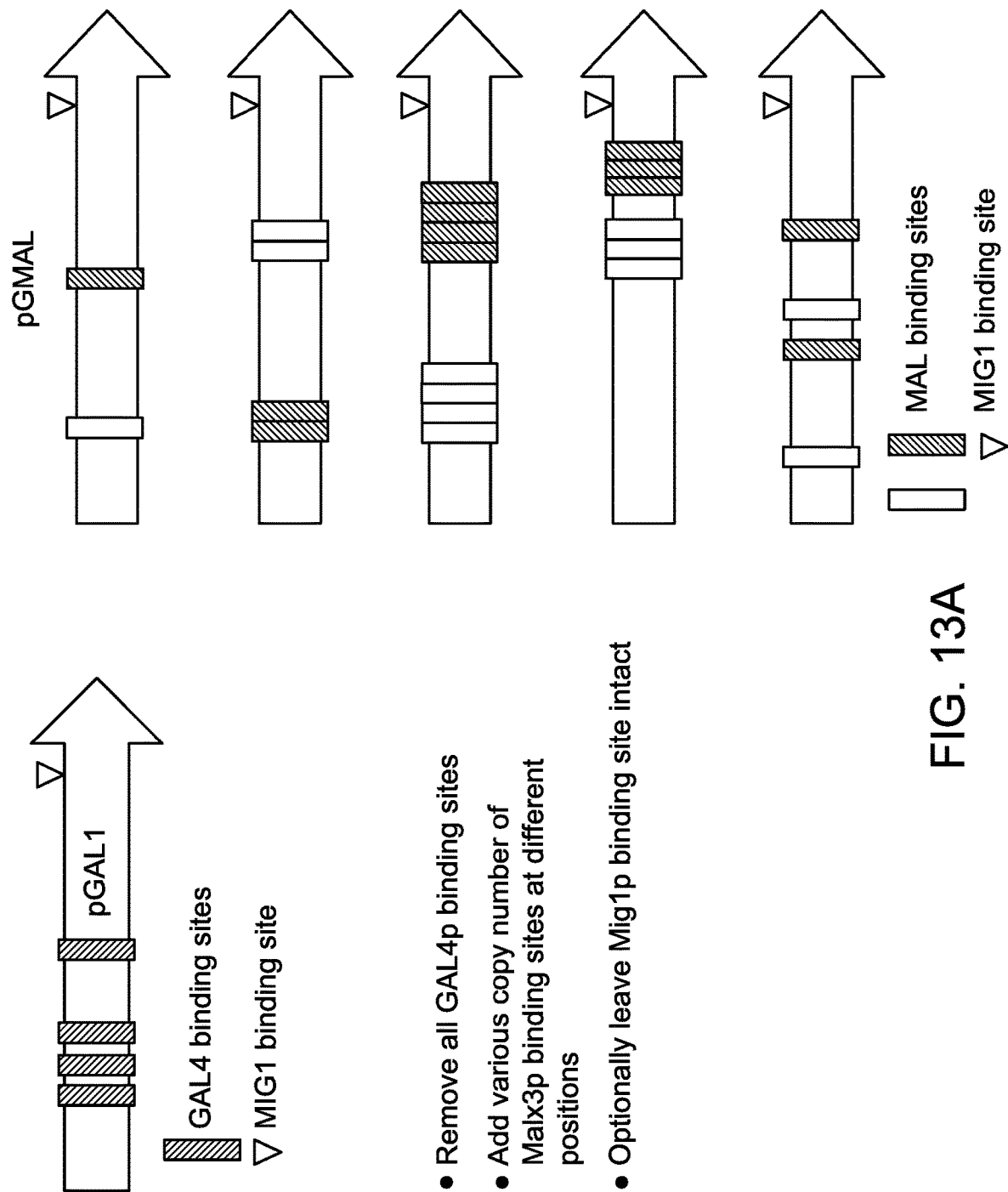

FIG. 13A illustrates a schematic diagram illustrating construction of pGMAL promoters.

FIG. 13B illustrates sequence alignments of MAL transcriptional activator binding sites from pMAL12 and pMAL32. The sequences of the binding sites were aligned using Clone Manager software with scoring matrix: linear (Mismatch 2, OpenGap 4, ExtGap 1).

FIGS. 14A and 14B provide results that pGMAL promoters are maltose inducible and are not affected by growth rate in the absence of maltose.

Figure 15:
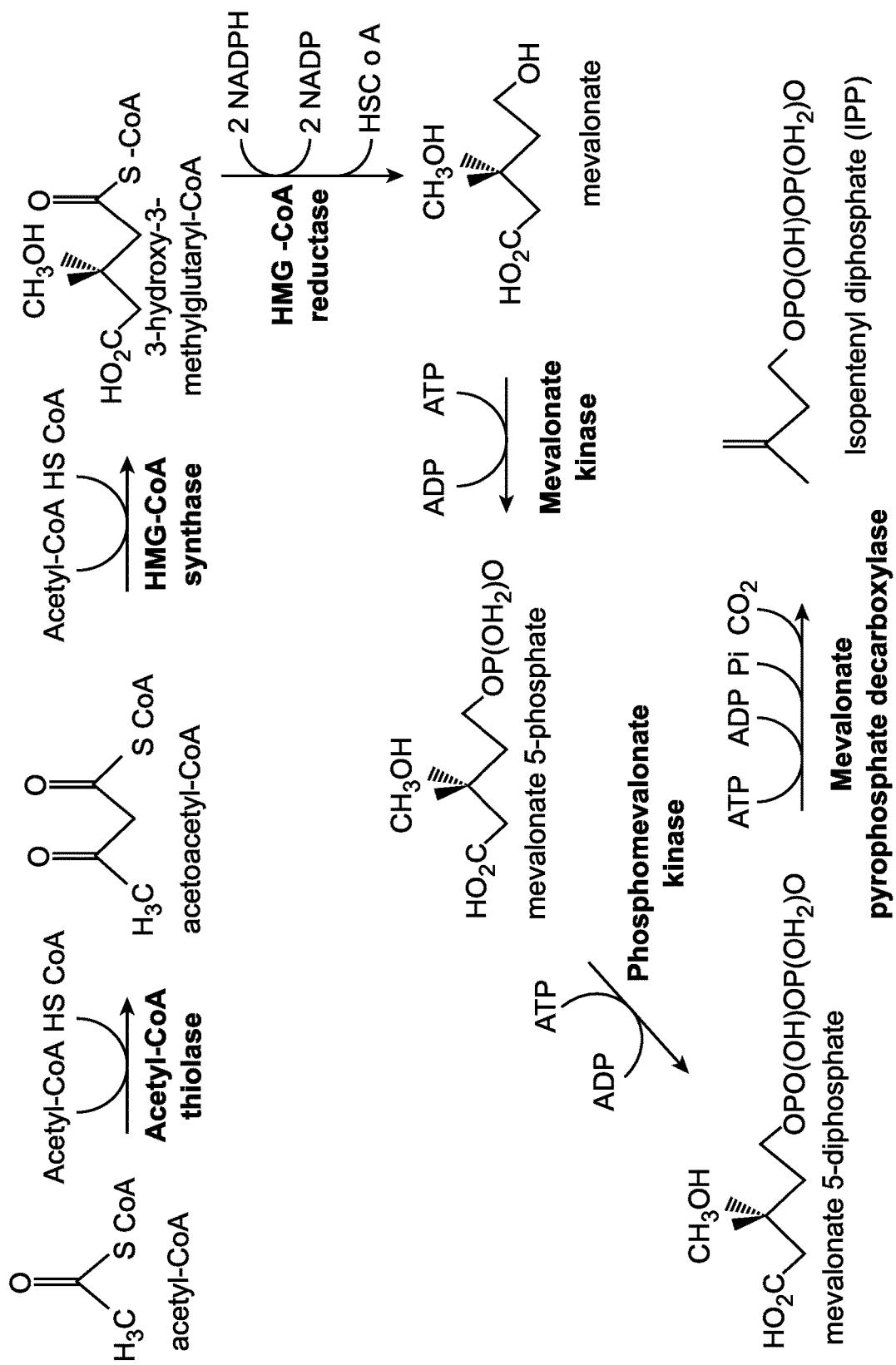

FIG. 15 provides a schematic representation of the mevalonate ("MEV") pathway for the production of isopentenyl diphosphate ("IPP")

Figure 16:
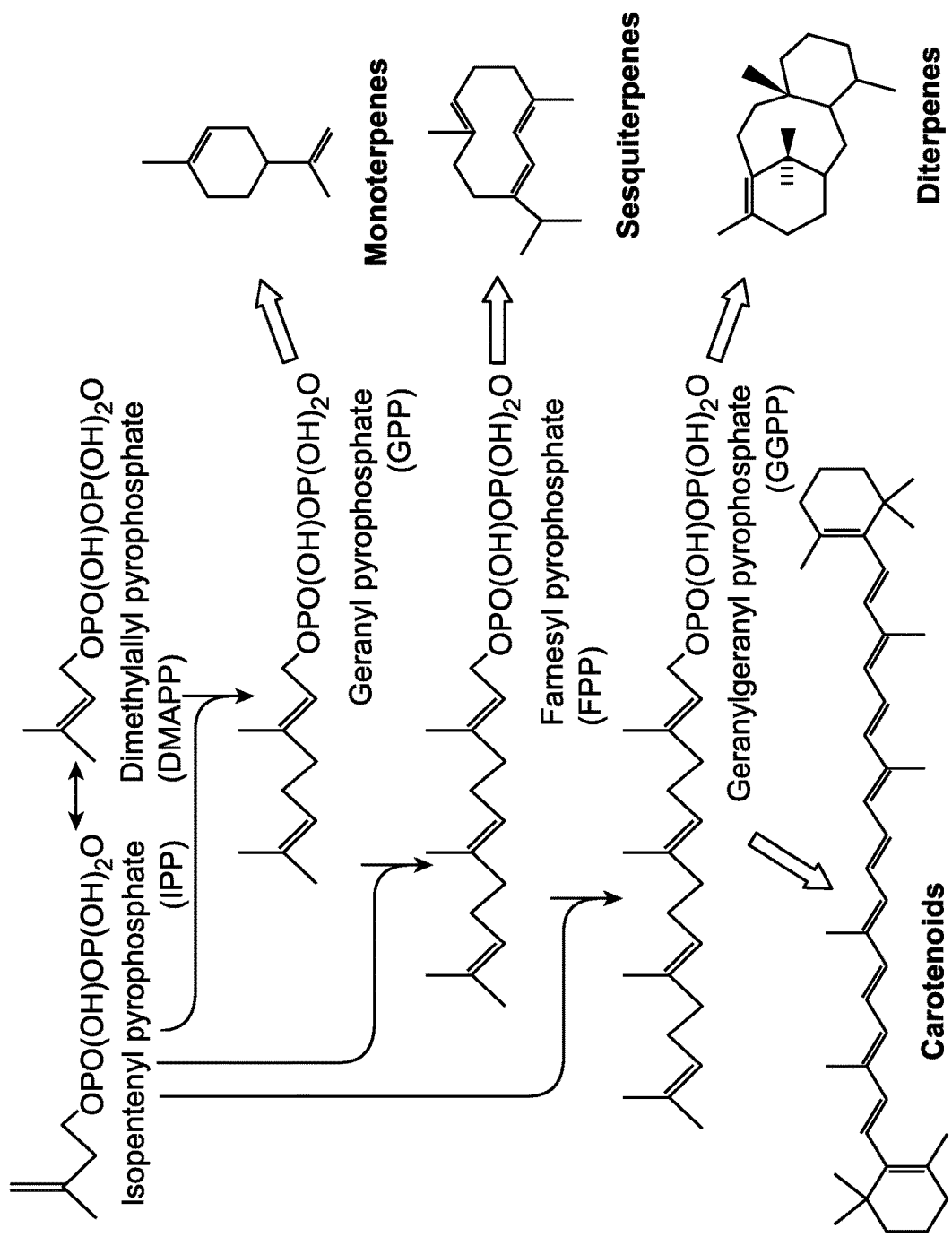

FIG. 16 provides a schematic representation of the conversion of IPP and dimethylallyl pyrophosphate ("DMAPP") to geranyl pyrophosphate ("GPP"), farnesyl pyrophosphate ("FPP"), and geranylgeranyl pyrophosphate ("GGPP").

Figure 17:
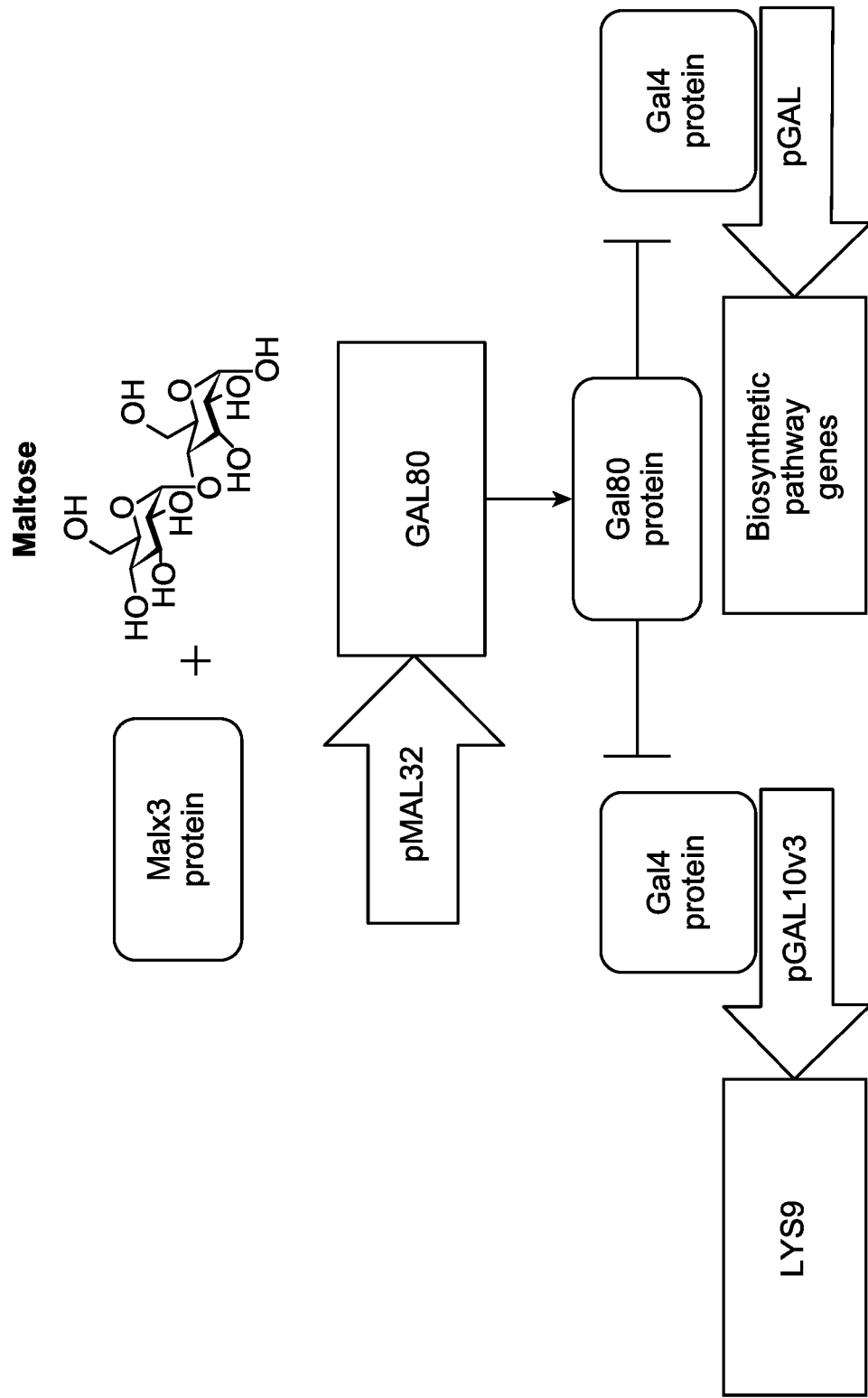

FIG. 17 illustrates a schematic diagram showing the use of a stabilization construct comprising LYS9 operably linked to pGAL10v3 promoter to couple expression of a conditional essential gene, LYS9, with expression of biosynthetic pathway genes for producing a non-catabolic compound. The embodiment shown in FIG. 17 illustrates that a maltose, when present in a culture medium, binds to Malx3 protein, which activates a maltose-responsive promoter, resulting in expression of transcriptional repressor GAL80. Gal80p encoded from GAL80 gene, in turn, represses transcriptional activator Gal4p. Since LYS9 gene and biosynthetic pathway genes for producing a non-catabolic compound are co-regulated as a GAL regulon, the expression of these genes is coupled via transcriptional regulators of the GAL regulon.

Figure 18:
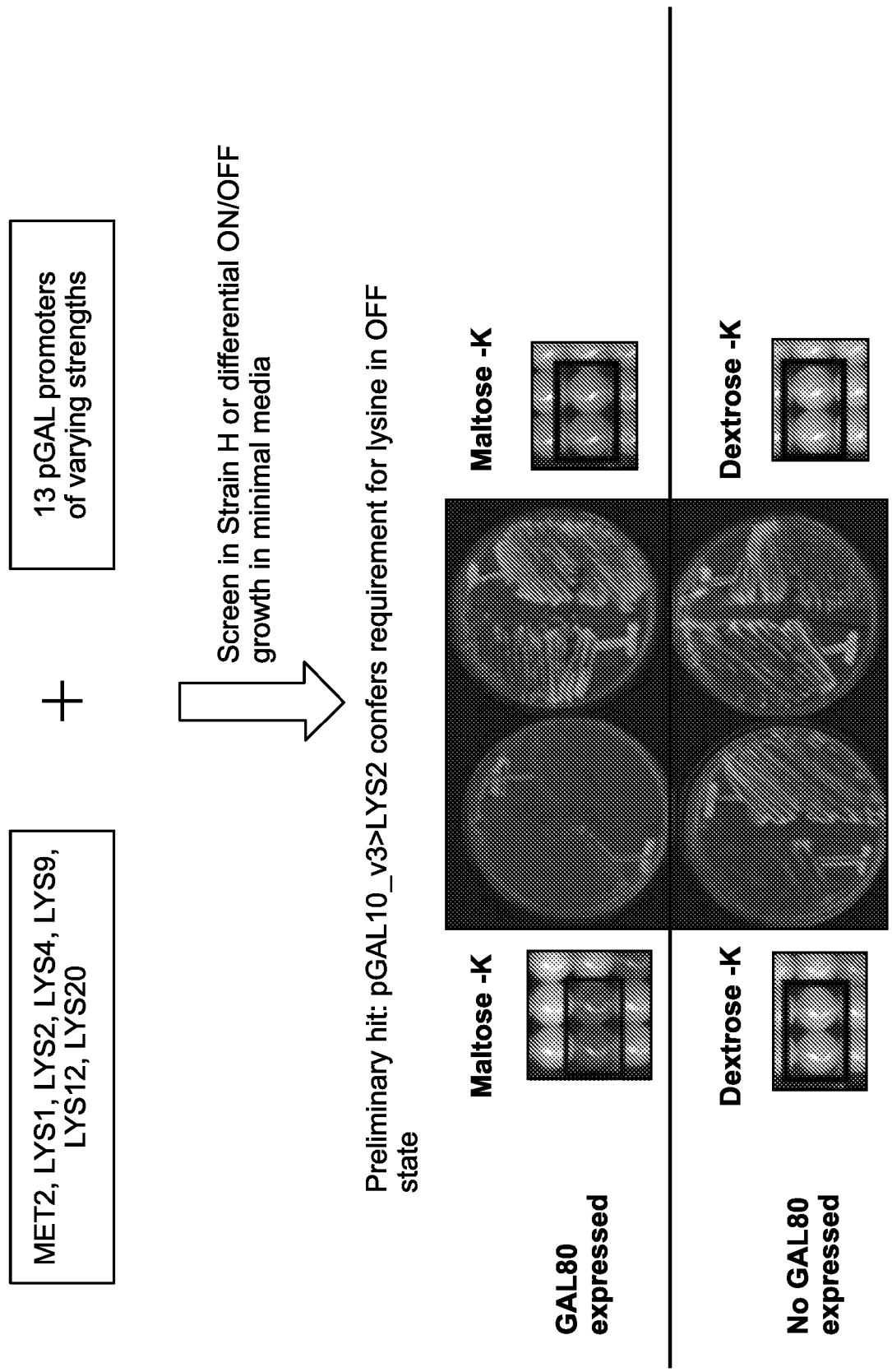

FIG. 18 illustrates a schematic representation showing a selection screen for a combination of an amino acid biosynthetic pathway gene and a pGAL promoter operably linked thereto, which renders genetically modified host cells dependent on its expression for cell growth.

Figure 19:
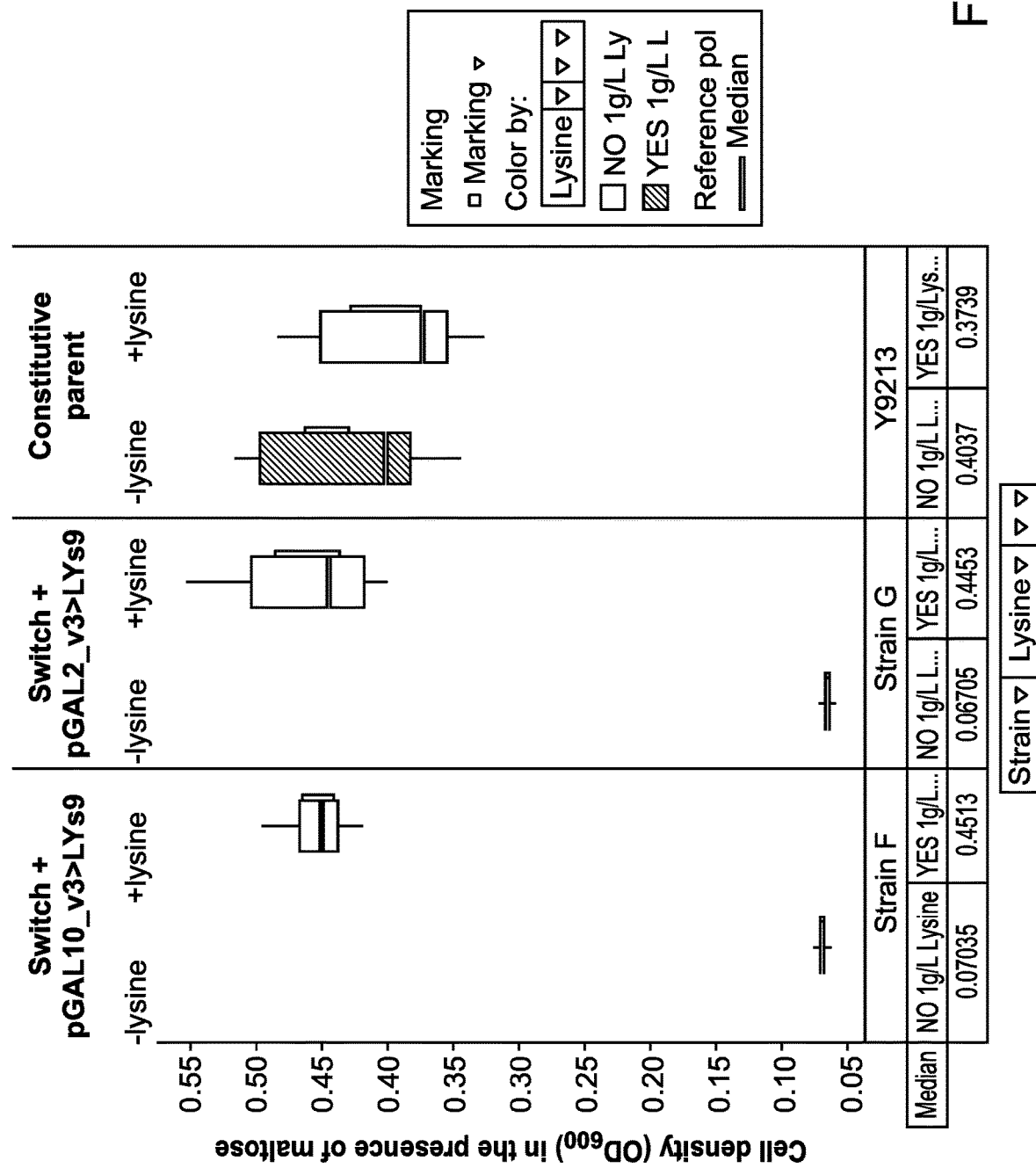

FIG. 19 illustrates two stabilization constructs, each comprising a lysine biosynthetic gene operably linked to a pGAL promoter, which renders genetically modified host cells dependent on its expression for cell growth.

Figure 20:
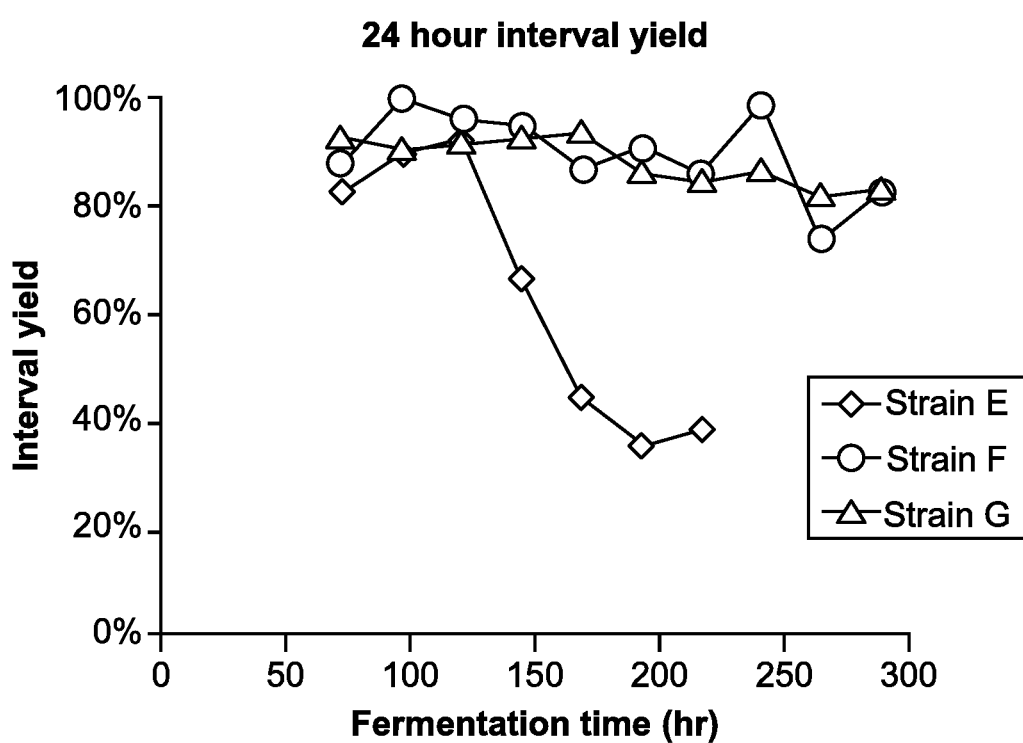

FIG. 20 illustrates results demonstrating that maltose switchable yeast strains comprising a stabilization construct (strain F comprising pGAL10_v3>LYS9; and Strain G comprising pGAL2_v3>LYS1) displays improved stability of production of the isoprenoid farnesene in a long fermentation run, compared to their parent strain which does not comprise a stabilization construct (Strain E).

6. DETAILED DESCRIPTION OF THE EMBODIMENTS

6.1 Definitions

As used herein, the term "maltose-binding protein" or MBP refers a protein that includes a portion that can specifically bind to and interact with maltose. In an embodiment, a MBP includes a protein which is a part of the maltose/maltodextrin system of *Escherichia coli* and other bacteria, which is responsible for the uptake and efficient catabolism of maltodextrins. MBP exhibits the binding affinity to maltose and maltodextrins. Macromolecular alpha (1-4) linked glucans are also bound with high affinities. Ferenci & Klotz, *FEBS Letters*, vol. 94(2): 213-217 (1978).

As used herein, the term "wild-type" MBP includes a MBP which can be isolated from organisms. In an embodiment, the term "wild-type" MBP includes a MBP isolated from bacteria, such as a MPB isolated from *E. coli* comprising an amino acid sequence of SEQ ID NO: 2. SEQ ID NO: 2 is a mature MBP (370 residues) upon cleavage of the N-terminal extension from a precursor polypeptide encoded by the malE gene from *E. coli*. In certain embodiments, the "wild-type" MPB comprises a protein encoded by a nucleic acid sequence of SEQ ID NO: 1. In some embodiments, a "wild-type" MBP refers to a reference sequence which is used as a background sequence to introduce mutations to generate MBP mutants. For example, a "wild-type" MBP can further include a reference sequence which comprises SEQ ID NO: 2 and additional sequences, such as a linker sequence. For example, a "wild-type" MBP comprises a MBP comprising an amino acid sequence of SEQ ID NO: 28, which includes a linker sequence at the C terminal end of SEQ ID NO: 2. A "wild-type" MBP nucleic acid sequence also comprises a nucleic acid sequence comprising a nucleotide sequence of SEQ ID NO: 27, which includes a linker sequence at the C terminal end of SEQ ID NO: 1.

As used herein, the term "MBP mutant" refers to any variant of wild-type MBP. The MBP mutant can include, for example, a wild-type MBP with one or more amino acids added and/or substituted and/or deleted and/or inserted.

The term "degradation domain" or "degron" refers to a protein element that confers instability to another protein to which it is fused.

As used herein, the term "maltose dependent degron," or "maltose binding degron," or "maltose binding protein degron" is a maltose binding protein mutant which has become dependent on binding to maltose for its stability. A maltose dependent degron is more stable when it is in contact with or bound to maltose than when it is not in contact with or bound to maltose. A maltose dependent degron also confers stability to another protein to which it is fused when the maltose dependent degron is in contact or bound to maltose compared to when the maltose dependent degron is not in contact or bound to maltose.

The term "maltose based inducer" includes a maltose or any analogs and derivatives of maltose. The maltose based inducer can bind to MBP, MBP mutants or maltose dependent degrons. In an embodiment, when a maltose based inducer is bound to a maltose dependent degron, it can stabilize the maltose dependent degron. A maltose based inducer can also induce activation of a maltose-responsive promoter. While the term "maltose" is used throughout the specification for simplicity, any maltose based inducer can be used instead of maltose in compositions and methods provided herein, and the term "maltose" can be substituted with a "maltose based inducer" throughout the disclosure.

As used herein, the term "sequence identity" or "percent identity," in the context or two or more nucleic acid or protein sequences, refers to two or more sequences or subsequences that are the same or have a specified percentage of amino acid residues or nucleotides that are the same. For example, the sequence can have a percent identity of at least about 70%, at least about 75%, at least about 80%, at least about 85%, at least about 90%, at least about 91% at least about 92%, at least about 93%, at least about 94%, at least about 95%, at least about 96%, at least about 97%, at least about 98%, at least about 99%, or higher identity over a specified region to a reference sequence when compared and aligned for maximum correspondence over a comparison window, or designated region as measured using a sequence comparison algorithm or by manual alignment and visual inspection. For example, percent of identity is determined by calculating the ratio of the number of identical nucleotides (or amino acid residues) in the sequence divided by the length of the total nucleotides (or amino acid residues) minus the lengths of any gaps.

For convenience, the extent of identity between two sequences can be ascertained using computer program and mathematical algorithms known in the art. Such algorithms that calculate percent sequence identity generally account for sequence gaps and mismatches over the comparison region. Programs that compare and align sequences, like Clustal W (Thompson et al., (1994) *Nucleic Acids Res.*, 22: 4673-4680), ALIGN (Myers et al., (1988) *CABIOS*, 4: 11-17), FASTA (Pearson et al., (1988) *PNAS*, 85:2444-2448; Pearson (1990), *Methods Enzymol.*, 183: 63-98) and gapped BLAST (Altschul et al., (1997) *Nucleic Acids Res.*, 25: 3389-3402) are useful for this purpose. The BLAST or BLAST 2.0 (Altschul et al., *J. Mol. Biol.* 215:403-10, 1990) is available from several sources, including the National Center for Biological Information (NCBI) and on the Internet, for use in connection with the sequence analysis programs BLASTP, BLASTN, BLASTX, TBLASTN, and TBLASTX. Additional information can be found at the NCBI web site.

In certain embodiments, the sequence alignments and percent identity calculations can be determined using the BLAST program using its standard, default parameters. For nucleotide sequence alignment and sequence identity calculations, the BLASTN program is used with its default parameters (Gap opening penalty=5, Gap extension penalty=2, Nucleic match=1, Nucleic mismatch=−3, Expectation value=10.0, Word size=11). For polypeptide sequence alignment and sequence identity calculations, BLASTP program is used with its default parameters (Gap opening=11, Gap extension penalty=2; Nucleic match=1; Nucleic mismatch=−3, Expectation value=10.0; Word size=11; matrix Blosum 62). Alternatively, the following program and parameters are used: Align Plus software of Clone Manager Suite, version 5 (Sci-Ed Software); DNA comparison: Global comparison, Standard Linear Scoring matrix, Mismatch penalty=2, Open gap penalty=4, Extend gap penalty=1. Amino acid comparison: Global comparison, BLOSUM 62 Scoring matrix.

As used herein, the term "homology" refers to the identity between two or more nucleic acid sequences, or two or more amino acid sequences. Sequence identity can be measured in terms of percentage identity (or similarity or homology); the higher the percentage, the more near to identical the sequences are to each other. Homologs or orthologs of nucleic acid or amino acid sequences possess a relatively high degree of sequence identity when aligned using standard methods. For example, a "homolog" of a reference protein or nucleic acid includes a protein or nucleic acid which has at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% sequence identity to the reference protein or nucleic acid, respectively. As discussed above, various programs for sequence alignment and analysis are well known, and can be used to determine whether two sequences are homologs of each other.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at T, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., *Current Protocols in Molecular Biology*, ed. Ausubel et al.

A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (See, e.g., Pearson W. R., 1994, *Methods in Mol. Biol* 25: 365-89).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V); and 6) Phenylalanine (F), Tyrosine (Y), Tryptophan (W).

As used herein, the term "variant amino acid residue" refers to an amino acid change or an amino acid substitution in a variant form of a reference protein. For example, a variant amino acid residue "I10T" refers that position 10 of a reference protein, which normally has isoleucine (I), is substituted with amino acid residue threonine (T) in the variant protein. In another example, a variant amino acid residue "A216V" refers that position 216 of a reference protein, which normally has amino acid residue alanine (A), is substituted with amino acid residue valine (V) in the variant protein.

One example of an algorithm that is suitable for determining percent sequence identity is the algorithm used in the basic local alignment search tool (hereinafter "BLAST"), see, e.g. Altschul et al., *J. Mol. Biol.* 215: 403-410 (1990) and Altschul et al., *Nucleic Acids Res.*, 15: 3389-3402 (1997), which is publicly available through the National Center for Biotechnology Information (hereinafter "NCBI").

As used herein, the term "protein of interest" refers to any protein or polypeptide, the production of which is desirable.

In some embodiments, the term "protein of interest" refers to a protein whose expression is desired within the fusion protein.

As used herein, the term "fusion protein" refers to a protein created through the joining of two or more proteins through a peptide bond formed between the amino terminus of one protein and the carboxyl terminus of another protein. Translation of the "fusion gene" results in a single fusion protein with functional properties derived from each of the original proteins.

The term "protein stability" as used herein is used in a structural context, i.e., relating to the structural integrity of a protein. In an embodiment, the protein stability refers to the net balance of forces, which determine whether a protein will be in its native folded conformation that is protected from degradation or in a denatured state which is subject to degradation. In an embodiment, the protein stability can be measured in a functional context, i.e., relating to the protein's or its fusion protein's state to confer its function and/or activity over time.

The term "stable" in reference to a protein can be used as a relative term to refer to the protein's relative state of being protected from protein degradation. For example, a maltose dependent degron is referred to as being more stable under a condition when it is in contact with or bound to maltose, as compared to a condition when it is not in contact with or bound to maltose. In an embodiment, the maltose dependent degron's stability, in the presence or absence of maltose, is measured by comparing activities of a reporter gene (e.g., green fluorescent protein) fused thereto.

The term "half-life" of a protein typically refers to the time required for the concentration of proteins in host cells or in cell extracts to be reduced by one-half.

As used herein, the maltose dependent degron or fusion protein being "in contact with maltose" or "binding with maltose" refers to either the maltose dependent degron being in physical attachment or close association with maltose. The binding can result from hydrogen bonding, hydrophobic forces, van der Waals forces, covalent, or ionic bonding, for example.

As used herein, the term "biomolecule" refers to any endogenous or heterologous molecules that can exist in cells. The term "biomolecule" can refer to, for example, nucleic acids, proteins, peptides, amino acids, lipids, carbohydrates, metabolites, and metabolic products.

As used herein, the term "target molecule" refers to a molecule of interest, the amount or expression level of which is directly or indirectly influenced by the activity of a fusion protein comprising a protein of interest fused in frame to a maltose dependent degron. The term "target molecule" can refer to, for example, enzymes, other proteins, peptides, amino acids, nucleic acids, lipids, carbohydrates, metabolites, metabolic products, and non-catabolic compounds.

GAL80 gene refers to a gene encoding a transcriptional regulator Gal80p involved in the repression of GAL regulon gene expression. Transcriptional regulation in the galactose regulon of yeast is determined by an interplay between a positive regulatory protein, Gal4p, and a negative regulatory protein, Gal80p. As used herein, Gal80p may refer to a wild-type Gal80p, any variants or modified versions thereof. For example, as used herein, GAL80 gene may encode a wild-type Gal80p or a Gal80p modified with a constitutive degron fused to its N terminus to increase its protein turnover.

As used herein, the phrase to "functionally disrupt" or a "functional disruption" e.g., of a selected gene means that the selected gene is altered in such a way as to decrease in the host cell the activity of the protein encoded by the selected gene. Similarly, to "functionally disrupt" or a "functional disruption" e.g., of a selected protein means that the protein is altered in such a way as to decrease in the host cell the activity of the protein. In some embodiments, the activity of the selected protein encoded by the selected gene is eliminated in the host cell. In other embodiments, the activity of the selected protein encoded by the selected gene is decreased in the host cell. Functional disruption of the selected gene may be achieved by deleting all or a part of the gene so that gene expression is eliminated or reduced, or so that the activity of the gene product is eliminated or reduced. Functional disruption of the selected gene may also be achieved by mutating a regulatory element of the gene, e.g., the promoter of the gene so that expression is eliminated or reduced, or by mutating the coding sequence of the gene so that the activity of the gene product is eliminated or reduced. In some embodiments, functional disruption of the selected gene results in the removal of the complete open reading frame of the selected gene.

As used herein, the term "native" or "endogenous" refers to a substance or process that can occur naturally in a host cell.

As used herein, the term "genetically modified" denotes a host cell that comprises a heterologous nucleotide sequence.

As used herein, the term "heterologous" refers to what is not normally found in nature. For example, the term "heterologous" when used with respect to a nucleic acid (DNA or RNA) or protein refers to a nucleic acid or protein that does not occur naturally as part of the organism, cell, genome, or DNA or RNA sequence in which it is present, or that is found in a cell or location or locations in the genome or DNA or RNA sequence that differ from that in which it is found in nature. The term "heterologous" when used with respect to a nucleic acid (DNA) can also refer to a nucleic acid which is operably linked to a promoter other than an endogenous promoter. The term "heterologous compound" refers to the production of a compound by a cell that does not normally produce the compound, or to the production of a compound at a level at which it is not normally produced by the cell.

As used herein, the phrase "heterologous enzyme" refers to an enzyme that is not normally found in a given cell in nature. The term encompasses an enzyme that is:
(a) exogenous to a given cell (i.e., encoded by a nucleotide sequence that is not naturally present in the host cell or not naturally present in a given context in the host cell); and
(b) naturally found in the host cell (e.g., the enzyme is encoded by a nucleotide sequence that is endogenous to the cell) but that is produced in an unnatural amount (e.g., greater or lesser than that naturally found) in the host cell.

As used herein, the term "naturally occurring" refers to what is found in nature. For example, a maltose binding protein that is present in an organism can be isolated from a source in nature and that has not been intentionally modified by a human in the laboratory is a naturally occurring maltose binding protein (e.g., maltose binding protein sequences in GenBank). Conversely, as used herein, the term "naturally not occurring" refers to what is not found in nature but created by human intervention.

The terms "amino acid sequence," "peptide," "oligopeptide," "polypeptide" and "protein" are used here interchangeably, and refer to a polymeric form of amino acids of any length which may or may not be chemically or biochemically modified.

The terms "polynucleotide" and "nucleic acid" are used here interchangeably, referring to polymeric forms of any length, both ribonucleotides and deoxyribonucleotide.

The term "isolated nucleic acid," when applied to DNA, refers to a DNA molecule that is separated from sequences with which it is immediately contiguous in the naturally occurring genome of the organism in which it originated. An "isolated nucleic acid" also includes non-genomic nucleic acids such as cDNA or other non-naturally occurring nucleic acid molecules.

The term "cDNA" is defined herein as a DNA molecule which can be prepared by reverse transcription from a mature, spliced, mRNA molecule obtained from a cell. cDNA lacks intron sequences that are usually present in the corresponding genomic DNA.

As used herein, the phrase "operably linked" refers to a functional linkage between nucleic acid sequences such that the linked promoter and/or regulatory region functionally control expression of the coding sequence.

As used herein, the term "production" generally refers to an amount of non-catabolic compound produced by a genetically modified host cell provided herein. In some embodiments, production is expressed as a yield of the non-catabolic compound by the host cell. In other embodiments, production is expressed as a productivity of the host cell in producing the non-catabolic compound.

The term "yield" refers to production of a non-catabolic compound by a host cell, expressed as the amount of non-catabolic compound produced per amount of carbon source consumed by the host cell, by weight. In some embodiments, the term "yield" refers to the amount of non-catabolic compound produced per amount of total reducing sugar added to a fermentor vessel or a flask (i.e., grams of non-catabolic produced divided by grams of total reducing sugar added, expressed as percentage). The total reducing sugar is a unit of measurement of sugar in grams. A reducing sugar is any sugar that is capable of acting as a reducing agent because it has a free aldehyde group or a free ketone group. All monosaccharides, such as galactose, glucose, and fructose, are reducing sugars. For example, if 10 grams of non-catabolic compound is produced by feeding host cells 100 grams of glucose (i.e., 100 grams of reducing sugar), then the yield of product per reducing sugar is 10%.

As used herein, the term "productivity" refers to production of a non-catabolic compound by a host cell, expressed as the amount of non-catabolic compound produced (by weight) per amount of fermentation broth in which the host cell is cultured (by volume) over time (per hour).

The term "fermentation" is used to refer to culturing host cells that utilize carbon sources, such as sugar, as an energy source to produce a desired product.

The term "culture medium" refers to a medium which allows growth of cellular biomass and production of metabolites from host cells. It contains a source of carbon and may further contain a source of nitrogen, a source of phosphorus, a source of vitamins, a source of minerals, and the like.

As used herein, the term "fermentation medium" may be used synonymously with "culture medium." Generally, the term "fermentation medium" may be used to refer to a medium which is suitable for culturing host cells for a prolonged time period to produce a desired compound.

The term "medium" refers to a culture medium and/or fermentation medium. The "medium" can be liquid or semi-solid. A given medium may be both a culture medium and a fermentation medium.

The term "whole cell broth" refers to the entire contents of a vessel (e.g., a flask, plate, fermentor and the like), including cells, aqueous phase, compounds produced in hydrocarbon phase and/or emulsion. Thus, the whole cell broth includes the mixture of a culture medium comprising water, carbon source (e.g., sugar), minerals, vitamins, other dissolved or suspended materials, microorganisms, metabolites and compounds produced by host cells, and all other constituents of the material held in the vessel in which a non-catabolic compound is being made by the host cells.

The term "fermentation composition" is used interchangeably with "whole cell broth." The fermentation composition can also include an overlay if it is added to the vessel during fermentation.

The term "biosynthetic pathway" refers to a pathway with a set of anabolic or catabolic biochemical reactions for transmuting one chemical species into another, leading to the biosynthesis of a molecule. Gene products belong to the same "biosynthetic pathway" if they, in parallel or in series, act on the same substrate, produce the same product, or act on or produce a metabolic intermediate (e.g., metabolite) between the same substrate and metabolite end product.

As used herein, the term "promoter" refers to a synthetic or naturally-derived nucleic acid that is capable of conferring, activating or enhancing expression of a DNA coding sequence. A promoter may comprise one or more specific transcriptional regulatory sequences to further enhance expression and/or to alter the spatial expression and/or temporal expression of the coding sequence. A promoter may be positioned 5' (upstream) of the coding sequence under its control. The distance between the promoter and a coding sequence to be expressed may be approximately the same as the distance between that promoter and the native nucleic acid sequence it controls. As is known in the art, variation in this distance may be accommodated without loss of promoter function. In certain embodiments, the regulated promoter used herein generally allows transcription of the nucleic acid sequence encoding a transcriptional regulator (e.g., an activator such as Gal4p, or a repressor such as Gal80p) while in a permissive environment (e.g., the presence of maltose), but ceases transcription of the nucleic acid sequence encoding a transcriptional regulator while in a non-permissive environment (e.g., in the absence of maltose).

The term "maltose-responsive promoter" or "pMAL" promoter refers to a promoter sequence that is bound by and regulated by a transcriptional activator regulated by maltose. For example, the maltose-inducible promoter is regulated by a MAL operon activator (e.g., a MAL transcriptional activator) or functional homologs thereof.

The term "MAL operon activator" or "MAL transcriptional activator" refers to a DNA-binding, maltose-dependent transcriptional activator of the maltose operon or a maltose-responsive promoter.

The term "galactose-inducible promoter" or "pGAL" promoter refers to a promoter sequence that is bound by and regulated by a transcriptional activator regulated by galactose. For example, the galactose-inducible promoter is regulated by Gal4p or functional homologs thereof.

The term "pGMAL" promoter refers to a synthetic promoter which has pGAL promoter sequences with its GAL transcriptional activator (e.g., GAL4p) binding sites replaced with one or more binding sites for a MAL transcriptional activator. Thus, pGMAL promoters are activated by a MAL transcriptional activator instead of a GAL transcriptional activator.

The term "synthetic promoter" refers to a nucleotide sequence having promoter activity and that is not known to be found in nature. In an embodiment, a synthetic promoter is assembled from multiple elements that are heterologous to one another.

The phrase "strain stability" generally refers to the stability of heterologous compound production over extended periods of fermentation by a genetically modified host cell described herein. In particular, stability refers the ability of a microbe to maintain favorable production characteristics (i.e., high yield (grams of compound per gram of substrate) and/or productivity (grams per liter of fermentation broth per hour)) of a non-catabolic fermentation product over extended cultivation times, e.g., about 3 to 20 days. Genetic stability, which is the propensity of the producing microbial population to have little to no alteration of the intended allelic frequency of genes relevant to the production of product over time, plays a major role in the sustained output of product.

Unless indicated otherwise, the concentration unit of maltose or other components in a culture medium or solution is weight/volume percent. It is defined as concentration solute (w/v %)=(weight of solute (g)/volume of solution (mL))×100.

The term "transcriptional regulator" refers to a protein that control gene expression.

The term "transcriptional activator" refers to a transcriptional regulator that activates or positively regulates expression of a gene.

The term "transcriptional repressor" refers to a transcriptional regulator that represses or negatively regulates expression of a gene.

The term "cell-growth-affecting gene" or "nucleic acid encoding a cell-growth-affecting protein" refers to a nucleic acid that encodes a protein which affects cell growth (e.g., growth rate or cellular biomass) of a cell.

The term "essential gene" refers to a gene which is absolutely required to maintain life under optimum conditions where all nutrients are available.

The term "conditional essential gene" refers to a gene that is essential only under certain circumstances or growth conditions.

The term "regulon" refers to a group of genes or nucleic acids that are regulated by the same regulatory proteins (e.g., transcriptional regulators). The genes of a regulon have regulatory binding sites or promoters that are regulated by common transcriptional regulators. The group of genes or nucleic acids comprising a regulon can be located contiguously or non-contiguously in a genome of a host cell.

The term "inducible promoter" refers to a promoter that is activated by an inducer to induce the transcription of the gene(s) it controls.

The phrase "constitutive promoter" refers to a promoter that does not require the presence of an inducer to induce the transcription of the gene(s) it controls.

The term "expression," unless otherwise indicated, refers to the production of mRNA by transcription of the relevant gene and/or, to production of protein via gene transcription and then mRNA translation.

The term "catabolic" as used herein refers to the process of molecule breakdown or degradation of large molecules into smaller molecules.

The term "non-catabolic" refers to the process of constructing molecules from smaller units, and these reactions typically require energy. The term "non-catabolic compound" refers to a compound produced by a non-catabolic process.

The term "a," "an," and "the" means "at least one" unless the context clearly indicates otherwise.

6.2 Maltose Dependent Degrons

6.2.1. Assays to Determine Maltose Dependent Stability of Maltose Dependent Degrons and MBP Mutants Useful maltose dependent degrons in the present invention depend on binding on maltose for their stability and for their fusion proteins. In the compositions and methods provided herein, the maltose dependent stability of maltose dependent degrons and their fusion proteins is conditional in a sense that they are stable when the maltose dependent degrons are in contact with maltose, and they are unstable when maltose is removed from contact with maltose dependent degrons. For instance, when host cells expressing maltose dependent degrons and/or their fusion proteins are cultured in a culture medium comprising maltose, they are more stable compared to when they are cultured in a medium with no maltose. In certain embodiments, when maltose is removed from the culture medium, the half-life of the fusion protein is reduced compared to a control (e.g., a fusion protein comprising a protein of interest fused to a wild-type maltose binding protein or the protein of interest alone).

Any suitable amount of maltose can be contacted with maltose dependent degrons and/or their fusion proteins to maintain their stability. For example, host cells genetically modified to express maltose dependent degrons and/or their fusion proteins may be cultured in a culture medium comprising maltose at a concentration (w/v) of at least about 0.25%, 0.5%, 0.75%, 1.0%, 1.25%, 1.5%, 1.75%, 2.0%, 2.25%, 2.5%, 2.75%, 3.0%, 3.25%, 3.75%, 4.0%, 4.25%, 4.5%, 4.75%, 5.0%, or more. When it is desired to destabilize or degrade maltose dependent degrons and/or their fusion proteins at a faster rate in host cells, the host cells can be cultured in a new culture medium with no or sufficiently low amounts of maltose (e.g., less than about 0.25%, less than about 0.1%, 0%, or the like). Suitable amounts of maltose to maintain stability of maltose dependent degrons and/or their fusion proteins are described in further detail in Section 6.4 below.

In certain embodiments, maltose dependent degrons may be derived from a maltose binding protein (MBP) by introducing destabilizing mutation(s) to a natural protein that already binds maltose. Without wishing to be bound by any theory, the mutation(s) in the MBP cause the mutant protein to depend on the binding energy from maltose to fold properly, and without maltose, the mutant protein may not be able to fold properly and is degraded at a faster rate. When it is fused to another protein, the entire fusion protein becomes targeted for degradation when maltose is absent.

In certain embodiments, MBP mutants may be obtained by mutagenizing nucleic acids encoding a wild-type MBP (e.g., a nucleotide sequence of SEQ ID NO: 1 or a nucleotide sequence of SEQ ID NO: 27 which includes a linker sequence in addition to the nucleotide sequence of SEQ ID NO: 1). In some embodiments, nucleic acids encoding a wild-type MBP may be randomly mutagenized. In other embodiments, nucleic acids encoding a wild-type MBP may be rationally mutagenized based on its known structure and/or function. Additionally, mutations in MBP mutants obtained from random or rational mutagenesis may be combined to generate additional MBP mutants. By introducing one or more mutations that perturb protein conformation in the absence of bound ligand, MBP mutants useful as maltose dependent degrons have been identified and described in Section 6.2.2, and the Examples sections below.

MBP mutants useful as maltose dependent degrons display one or more of the following features. One of the features of useful maltose dependent degrons includes increased stability of their fusion proteins in the presence of maltose compared to in the absence or in sufficiently low amounts of maltose. Without wishing to be bound by any theory, if binding of maltose to a maltose dependent degron renders its fusion protein conformation more stable, then the fusion protein may be degraded by host cells' degradation machinery at a slower rate. Another feature of useful maltose dependent degrons includes their conditional stability to modulate the expression levels or amounts of downstream target molecules by manipulating the maltose content in a culture medium. These and other features of maltose dependent stability of maltose binding proteins and/or their fusion proteins may be determined using any suitable assays described below.

In certain embodiments, a suitable assay for screening MBP mutants (and determining maltose dependent features of maltose dependent degrons) may include determining maltose dependent stability of a fusion protein comprising a reporter protein. For example, a reporter protein fused in frame to a MBP mutant may be used to measure the reporter activity in the presence or in the absence of maltose. As described in Example 7.8 in the Examples section, a reporter, such as a fluorescent marker protein (e.g., GFP), may be used as a fusion partner. In these embodiments, a population of genetically modified host cells comprising reporter fusion proteins may be pre-cultured to express the fusion proteins in a culture medium comprising maltose. Then, the population or a subpopulation of the genetically modified host cells is divided into two groups and cultured in parallel, where one group of cells is cultured in a culture medium comprising maltose and the other group of cells is cultured in a culture medium comprising no maltose. After a suitable time period (e.g., after 48 hours of culturing or when expression of control GFP reporter in host cells is at its maximum), the fluorescence levels from the host cells cultured in the presence of maltose and in the absence of maltose may be compared. A MBP mutant is considered as a maltose dependent degron if the relative GFP intensity of the GFP fusion protein is higher in the presence of maltose than in the absence of maltose (or in low amounts of maltose).

For these comparative experiments, genetically modified host cells are typically cultured in a culture medium comprising the same amount (e.g., molar or weight amount) of carbon source. For example, the culture medium comprising maltose may contain about 2.3% (w/v) sucrose and about 1.7% (w/v) maltose, and the culture medium comprising no maltose may contain about 4% sucrose.

In certain embodiments, a MBP mutant is considered useful as a maltose dependent degron if the relative GFP intensity of the fusion protein is higher in the presence of maltose than in the absence of maltose by at least about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, or more. For example, host cells expressing MBP mutant L8_v4d shown in FIG. 8B exhibit a relative GFP intensity of about 95% in the presence of maltose and a relative GFP intensity of about 30% in the absence of maltose compared to a control (i.e., GPF intensity of GFP alone in the presence of maltose). Since the reporter activity (i.e., fluorescent intensity) of MBP mutant L8_v4d fusion protein is about 316% higher in the presence of maltose than in the absence of maltose, MBP mutant L8_v4d is useful and is considered as a maltose dependent degron.

In FIG. 8B, the relative GFP intensities of fusion proteins are normalized against the GFP intensity of unfused GFP being 100%. In some embodiments, the relative GFP intensities of fusion proteins may be normalized against the GFP intensity of GFP fused to a wild-type MBP expressed in the presence of maltose or in the absence of maltose. For example, the GFP intensity of GFP fused to the wild-type MBP in the presence of maltose may be scaled as having the intensity of 100%, and the GFP intensities of other fusion proteins may be scaled relative the wild-type MBP fusion protein. In another example, as shown in FIG. 8C, the ratios of GFP fluorescence in the presence of maltose and in the absence of maltose can be calculated for the control (e.g., a GFP fused to a wild-type MBP) and for each GFP fused to various MBP mutants. The calculated ratio for each MBP mutant can be compared to the calculated ratio for the control. If the calculated GFP fluorescence ratio of a MBP mutant is greater than that for the control by at least about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, or more, then a MBP mutant is considered useful as a maltose dependent degron.

While the use of GFP as a reporter is described above, the determination of fusion protein stability is not limited to the use of GFP or relative GFP intensity measurements. Other suitable reporters or assay methods deemed suitable by those skilled in the art may be used to compare the fusion protein stability in the presence of maltose or in the absence (or in sufficiently low amounts) of maltose to determine MBP mutants' maltose dependence for their stability.

In another embodiment, a suitable assay for screening MBP mutants (or determining maltose dependent features of maltose dependent degrons) may include determining the expression levels or amounts of target molecules, which are directly or indirectly influenced by the stability of a fusion protein comprising a MBP mutant. Such a screening assay using target molecules can be illustrated using an exemplary embodiment shown in FIGS. 1A and 1B. As shown in the figures, a fusion protein comprises Gal80p fused in frame to a maltose dependent degron (or a MBP mutant). Gal80p is a repressive transcriptional regulator, which binds to Gal4p, a master transcriptional activator of Gal promoters. In the embodiment shown in FIGS. 1A and 1B, one or more pGal promoters are operably linked to biosynthetic pathway genes. If Gal80p fusion protein in host cells is stable with maltose bound to the maltose dependent degron (or MBP mutant) portion, then it will repress Gal4p transcriptional activator, resulting in little or no expression of pathway enzymes. This will, in turn, eliminate or reduce the amount of any heterologous compounds produced by the pathway enzymes. If Gal80p fusion protein is unstable because the maltose dependent degron (or a MBP mutant) is not in contact with maltose as shown in FIG. 1B, then the fusion protein is also unstable or inactive, relieving Gal4p from being repressed by Gal80p. This will result in higher expression levels of pathway enzymes and increased production of heterologous compounds produced by the pathway enzymes. In this exemplary embodiment, the maltose dependent production amount of heterologous compounds can be used as downstream target molecules to screen whether MBP mutants fused to Gal80p are suitable as maltose dependent degrons.

In certain embodiments, the isoprenoid farnesene may be used as a downstream target molecule. In this embodiment, the pathway enzyme genes shown in FIGS. 1A and 1B may include genes encoding the mevalonate pathway enzymes and farnesene synthase, and host cells will produce isoprenoid farnesene as one of the downstream target molecules. The genetically modified host cells will produce no or a small amount of farnesene in a culture medium comprising maltose when stable Gal80p represses the biosynthetic pathway gene expression (see FIG. 1A). When these host cells are cultured in the absence of maltose as shown in FIG. 1B, the host cells will produce farnesene (when unstable or inactive Gal80p no longer represses the biosynthetic pathway gene expression). Thus, in this exemplary embodiment, the amount of farnesene produced from the host cells in the absence or presence of maltose may be used to screen whether a MBP mutant fused to a Gal80p behaves as a maltose dependent degron, which depends on binding to maltose for its stability.

Figure 1A:
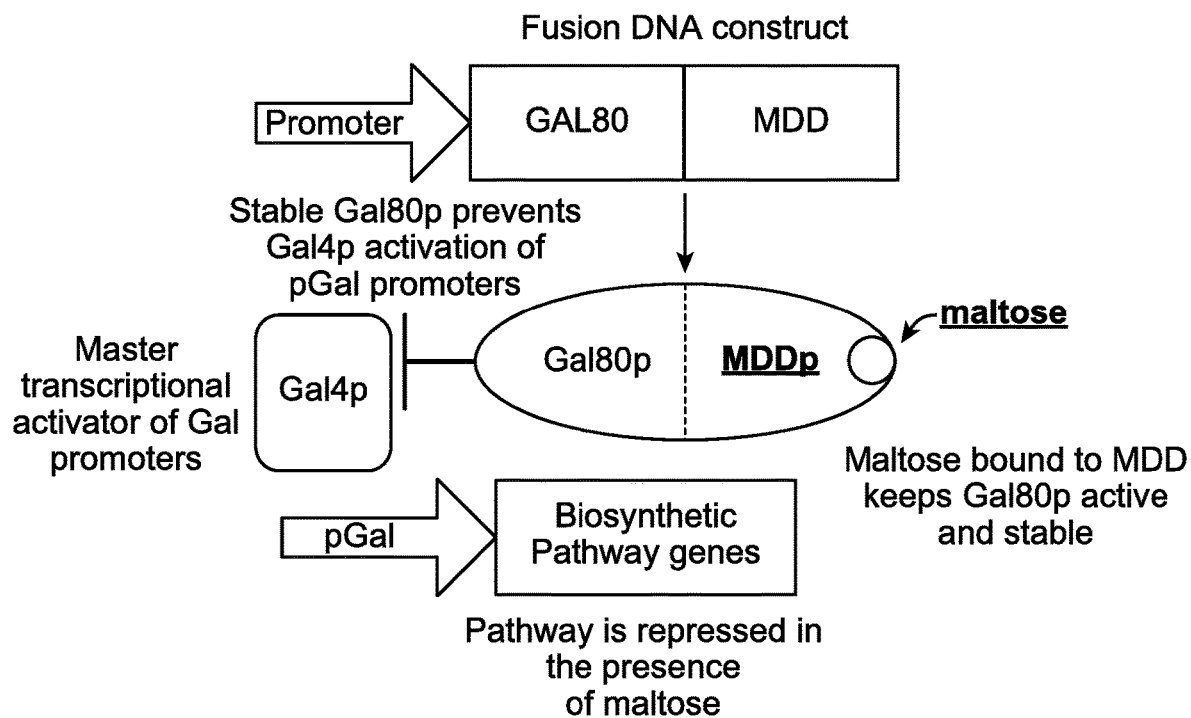
FIGS. 1A and 1B illustrate schematic diagrams showing the use of maltose dependent stability of a fusion protein comprising Gal80p fused in frame to a maltose dependent degron to negatively regulate expression of biosynthetic pathway genes.
Figure 1B:
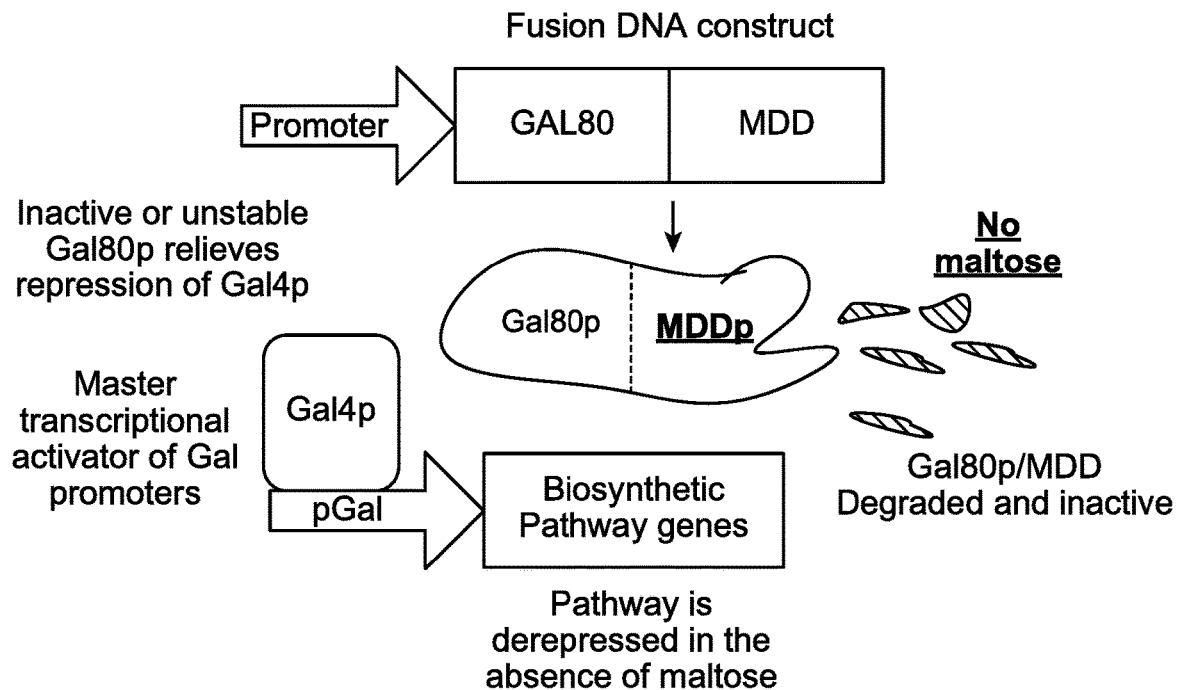

In the exemplary embodiment illustrated in FIGS. 1A and 1B where the fusion protein acts as a negative regulator of target molecules, MBP mutants may be considered as useful maltose dependent degrons if their maltose dependent stability results in host cells producing an increased amount of target molecule (e.g., farnesene) in the absence of maltose than in the presence of maltose. The amount of target molecules (e.g., farnesene) produced in host cells may be measured using any known techniques in the art. For example, the farnesene titer measurement methods described in Example 7.2, 7.3, or 7.4 in the Examples section may be used. In the exemplary embodiment shown in FIGS. 1A and 1B, a MBP mutant is considered as a useful maltose dependent degron if the amount of target molecules (e.g., farnesene) produced from host cells cultured without maltose is higher than the amount of target molecules produced by host cells cultured with maltose by at least about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, or more.

In some embodiments, the percentage of relative increase of the target molecule production discussed above can be calculated by dividing the raw measured value of target molecule production (e.g., UV farnesene titer assay described in Example 7.2) in the absence of maltose by the raw measured value of target molecule production in the presence of maltose. In some embodiments, the amount of target molecule produced by the host cell can be normalized against a control prior to dividing the two values. For example, the control may include the amount of target molecule produced by host cells which constitutively produce target molecules in the presence of maltose. The control amount may be scaled as 100, and all other target molecule production values obtained from host cells comprising MBP mutants may be normalized against this value.

In another embodiment, a suitable assay for screening MBP mutants includes using auxotroph strains and suitable positive and negative selection schemes to screen for MBP mutants that display maltose dependent stability. For example, a genetic strategy can be devised to screen for MBP mutants, which, when fused to constitutively-transcribed Gal80p, would cause Gal80p to switch from a functional (e.g., stable) state in the presence of maltose to a non-functional (e.g., unstable) state in the absence of maltose.

Figure 4:
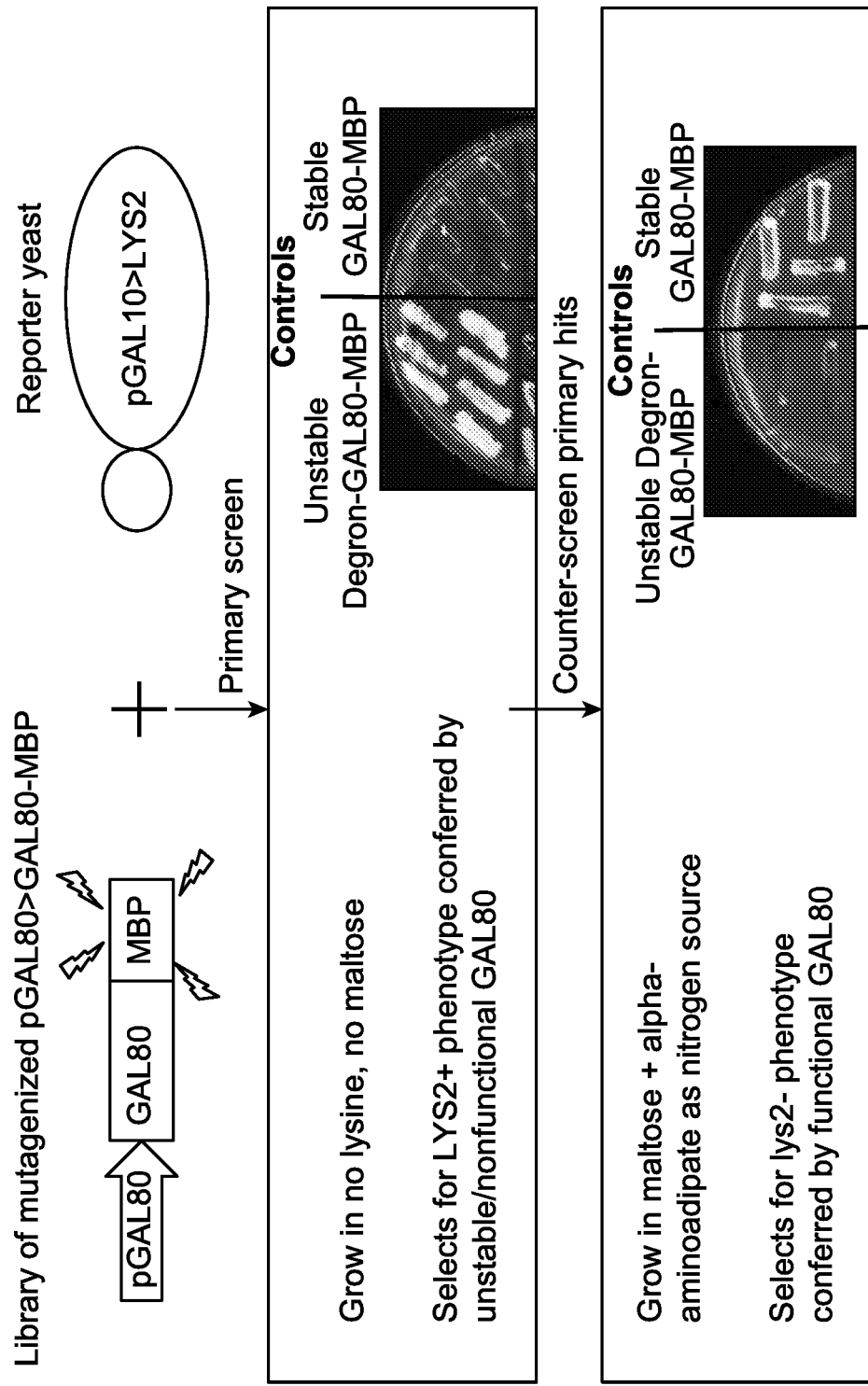
FIG. 4 illustrates a schematic representation illustrating a selection screen for nucleic acids encoding a maltose-dependent Gal80p fused in frame to a MBP mutant.

An exemplary genetic strategy useful as a screening assay is illustrated in FIG. 4 and described in Example 7.6 in the Examples section. As shown in FIG. 4, the GAL80 gene is fused in frame to nucleic acids encoding a MBP mutant. In this exemplary embodiment, a yeast strain, a lysine auxotroph comprising a LYS2 gene operably linked to pGAL10, may be used as a reporter strain to screen for MBP mutants which behave as a maltose dependent degron. If a MBP mutant fused to Gal80p depends on binding of maltose for its stability, then it would impart maltose dependent stability to Gal80p fusion protein. Thus, in the reporter strain, the Gal80p function and its maltose dependent stability can be reported by the phenotypes ascribed to expression or repression of the LYS2 gene from a Gal80-regulated promoter (e.g., pGAL10).

In this exemplary screening assay, the LYS2 gene is operably linked to pGAL10 promoter as shown in FIG. 4. The LYS2 gene encodes an aminoadipate reductase, an enzyme that is required for biosynthesis of lysine. When a MBP mutant has properties of a maltose dependent degron, then Gal80p fused to the MBP mutant will be unstable in the absence of maltose, and it will not repress expression of LYS2 operably linked to pGAL10. As a result, the aminoadipate reductase will be expressed from the LYS2 gene, allowing the reporter yeast to grow on media lacking lysine. To exclude generally destabilizing MBP mutants that exhibit maltose dependent stability, a negative or counter-selection screen may then be performed. In a counter-selection screen, the reporter strain is cultured on media containing α-aminoadipate as the sole nitrogen source. Reporter strains expressing LYS2 will not grow on this media. If a MBP mutant is dependent on maltose for its stability, then Gal80p fused thereto would be stable and functional in the presence of maltose, resulting in repression of pGAL10 and no expression of LYS2. Therefore, during the counter-selection screen, the reporter strains comprising a MBP mutant, which depends on binding to maltose for its stability, can be selected. The positive and negative selection schemes illustrated in FIG. 4 to screen for MBP mutants are merely exemplary. Other suitable auxotroph reporter strains (e.g., URA3 or TRP1 auxotroph) that have positive and counter-selection schemes may be used to screen MBP mutants.

The assays for determining the maltose dependent stability of MBP mutants, maltose dependent degrons, and their fusion proteins described herein are merely exemplary. Those skilled in the art can readily determine other maltose dependent stability assays to screen for MBP mutants which can be utilized as maltose dependent degrons in the compositions and methods provided herein. For example, rounds of competitive selective/counter-selective growth scheme described in Example 7.7 may also be used.

6.2.2. Maltose Dependent Degron Sequences 6.2.2.1 Maltose Dependent Degron Amino Acid Sequences In one aspect, provided herein are amino acid sequences of maltose dependent degrons that exhibit maltose dependent stability. In certain embodiments, maltose dependent degrons are mutants that are derived from any suitable wild-type maltose binding proteins that can bind to maltose. In certain embodiments, the maltose dependent degrons comprise one or more destabilizing mutations (e.g., one or more amino acid additions, substitutions, deletions or insertions), compared to their wild-type counterparts. The maltose dependent degrons are less stable when not bound to maltose, compared to when bound to maltose.

In certain embodiments, a maltose dependent degron comprises an amino acid sequence having a degree of sequence identity to wild-type maltose binding protein having SEQ ID NO: 2. In certain embodiments, a maltose dependent degron comprises an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2. In certain embodiments, a maltose dependent degron comprises an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2, and comprises at least one variant amino acid residue compared to SEQ ID NO: 2.

In certain embodiments, a maltose dependent degron comprises an amino acid sequence having a degree of sequence identity to a wild-type maltose binding protein having SEQ ID NO: 28, which has a linker sequence at its C terminus end of SEQ ID NO: 2. In certain embodiments, a maltose dependent degron comprises an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 28. In certain embodiments, a maltose dependent degron comprises an amino acid sequence that has at least about 70%, at least about 75%, at least about 80%, at least about 85%, at least about 90%, at least about 95%, at least about 96%, at least about 97%, at least about 98%, or at least about 99% sequence identity to SEQ ID NO: 2, and comprises at least one variant amino acid residue compared to SEQ ID NO: 28.

In certain embodiments, a maltose dependent degron comprises an amino acid sequence that comprises at least one or more variant amino acid residues that are located at one or more positions selected from 7, 10, 11, 21, 24, 28, 42, 43, 64, 68, 83, 88, 92, 95, 98, 101, 110, 117, 134, 135, 136, 149, 168, 177, 186, 187, 193, 198, 210, 216, 217, 229, 236, 237, 242, 263, 291, 304, 321, 322, 339, 351, 357, 367, 370, and 374, wherein the positions of these variant amino acid residues correspond to amino acid positions of SEQ ID NO: 2 or SEQ ID NO: 28.

In certain embodiments, a maltose dependent degron comprises an amino acid sequence that comprises one or more variant amino acid residues, wherein the one or more variant amino acid residues are selected from the group consisting of K7R, I10T, W11G, L21S, V24A, F28Y, D42V, K43E, A64T, F68S, D83G, D88N, P92T, W95R, V98I, N101I, A110T, I117V, P134S, A135T, L136M, M149I, Y168C, Y168N, Y177H, N186S, A187P, L193S, D198V, D210E, A216V, A217D, G229C, I236N, D237N, N242D, L263M, L291V, A304S, T321N, M322 L, A339T, A351T, T357S, T367S, S370P, and N374S. The positions of these variant amino acid residues correspond to amino acid positions of SEQ ID NO: 2 or SEQ ID NO: 28.

In certain embodiments, a maltose dependent degron may comprise an amino acid sequence which is truncated in comparison to the wild-type MBP having SEQ ID NO: 2. For example, a maltose dependent degron may comprise an amino acid sequence which is truncated after amino acid position 365 of SEQ ID NO: 2. Thus, in certain embodiments, a maltose dependent degron comprises an amino acid sequence from position 1 to position 365 of SEQ ID NO: 2 and comprises one or more variant amino acid residues at positions selected from the group consisting of 7, 10, 11, 21, 24, 28, 42, 43, 64, 68, 83, 88, 92, 95, 98, 101, 110, 117, 134, 135, 136, 149, 168, 177, 186, 187, 193, 198, 210, 216, 217, 229, 236, 237, 242, 263, 291, 304, 321, 322, 339, 351, and 357, wherein the positions of these variant amino acid residues correspond to SEQ ID NO: 2.

In certain embodiments, a maltose dependent degron comprises an amino acid sequence from position 1 to position 365 of SEQ ID NO: 2, and comprises one or more of the following variant amino acid residues: K7R, I10T, W11G, L21S, V24A, F28Y, D42V, K43E, A64T, F68S, D83G, D88N, P92T, W95R, V98I, N101I, A110T, I117V, P134S, A135T, L136M, M149I, Y168C, Y168N, Y177H, N186S, A187P, L193S, D198V, D210E, A216V, A217D, G229C, I236N, D237N, N242D, L263M, L291V, A304S, T321N, M322 L, A339T, A351T, and T357S, wherein the positions of these variant amino acid residues correspond to amino acid positions of SEQ ID NO: 2. In certain embodiments, a maltose dependent degron may comprise an amino acid sequence shorter than 365 amino acid residues and comprises one or more of variant amino acid residues disclosed herein.

In certain embodiments, a maltose dependent degron comprises an amino acid sequence that has four variant amino acid residues compared to SEQ ID NO: 2 or SEQ ID NO: 28. In certain embodiments, a maltose dependent degron comprises an amino acid sequence that has five variant amino acid residues compared to SEQ ID NO: 2 or SEQ ID NO: 28. In certain embodiments, a maltose dependent degron comprises an amino acid sequence that has six variant amino acid residues compared to SEQ ID NO: 2 or SEQ ID NO: 28. In certain embodiments, a maltose dependent degron comprises an amino acid sequence that has seven variant amino acid residues compared to SEQ ID NO: 2 or SEQ ID NO: 28. In certain embodiments, a maltose dependent degron comprises an amino acid sequence that has eight variant amino acid residues compared to SEQ ID NO: 2 or SEQ ID NO: 28. In certain embodiments, a maltose dependent degron comprises an amino acid sequence that has nine variant amino acid residues compared to SEQ ID NO: 2 or SEQ ID NO: 28. In certain embodiments, a maltose dependent degron comprises an amino acid sequence that has ten variant amino acid residues compared to SEQ ID NO: 2 or SEQ ID NO: 28. In certain embodiments, a maltose dependent degron comprises an amino acid sequence that has eleven variant amino acid residues compared to SEQ ID NO: 2 or SEQ ID NO: 28. In certain embodiments, a maltose dependent degron comprises an amino acid sequence that has less than four variant amino acid residues (e.g., 1, 2, or 3) compared to SEQ ID NO: 2 or SEQ ID NO: 28. In certain embodiments, a maltose dependent degron comprises an amino acid sequence that has more than eleven variant amino acid residues (e.g., 12, 13, 14, 15, or more) compared to SEQ ID NO: 2 or SEQ ID NO: 28.

In certain embodiments, a maltose dependent degron comprises an amino acid sequence that comprises at least five variant amino acid residues that are located at positions 10, 24, 42, 149, and 216, wherein the positions of these variant amino acid residues correspond to positions of SEQ ID NO: 2. In certain embodiments, a maltose dependent degron comprises at least five variant amino acid residues that comprise I10T, V24A, D42V, M149I, and A216V, wherein the positions of these variant amino acid residues correspond to positions of SEQ ID NO: 2. In certain embodiments, a maltose dependent degron comprising an amino acid sequence of these variant amino acid residues is truncated at amino acid position 365 or less.

In certain embodiments, the maltose dependent degron comprises an amino acid sequence comprising at least one set of variant amino acid residues from the following group of variant amino acid residue sets, wherein the positions of the variant amino acid residues correspond to amino acid positions of SEQ ID NO: 2 or SEQ ID NO: 28:

(a) I10T, V24A, D42V, K43E, D83G, P92T, M149I, Y168N, N186S, A216V, and T357S;
(b) I10T, V24A, D42V, K43E, D83G, M149I, Y168N, N186S, A216V, and D237N;
(c) I10T, V24A, D42V, K43E, D83G, M149I, Y168N, N186S, A216V, and A339T;
(d) I10T, V24A, D42V, K43E, D83G, M149I, Y168N, N186S, A216V, and N242D;
(e) I10T, V24A, D42V, A110T, M149I, and A216V;
(f) I10T, V24A, D42V, K43E, D83G, M149I, Y168N, N186S, and A216V;
(g) L21S, A64T, L136M, Y177H, A187P, A304S, T321N, and A351T;
(h) K7R, D83G, V98I, L193S, I236N, and N374S;
(i) W11G, D88N, P134S, A135T, D210E, and M322 L;
(j) I117V, Y168N, G229C, L263M, T367S, and S370P;
(k) F68S, W95R, N186S, and D198V; and
(l) F28Y, K43E, N101I, Y168C, A217D, and L291V.

In certain embodiments, the maltose dependent degron comprises an amino acid sequence of SEQ ID NO: 4 (MBP mutant 3A6). In certain embodiments, the maltose dependent degron comprises an amino acid sequence of SEQ ID NO: 6 (MBP mutant 4D3). In certain embodiments, the maltose dependent degron comprises an amino acid sequence of SEQ ID NO: 8 (MBP mutant 5A2). In certain embodiments, the maltose dependent degron comprises an amino acid sequence of SEQ ID NO: 10 (MBP mutant 5F3). In certain embodiments, the maltose dependent degron comprises an amino acid sequence of SEQ ID NO: 12 (MBP mutant L8). In certain embodiments, the maltose dependent degron comprises an amino acid sequence of SEQ ID NO: 14 (MBP mutant L8_v4d). In certain embodiments, the maltose dependent degron comprises an amino acid sequence of SEQ ID NO: 16 (MBP mutant H8). In certain embodiments, the maltose dependent degron comprises an amino acid sequence of SEQ ID NO: 18 (MBP mutant H9). In certain embodiments, the maltose dependent degron comprises an amino acid sequence of SEQ ID NO: 20 (MBP mutant H10). In certain embodiments, the maltose dependent degron comprises an amino acid sequence of SEQ ID NO: 22 (MBP mutant M1). In certain embodiments, the maltose dependent degron comprises an amino acid sequence of SEQ ID NO: 24 (MBP mutant M5). In certain embodiments, the maltose dependent degron comprises an amino acid sequence of SEQ ID NO: 26 (MBP mutant M13).

A number of MBP mutants mentioned above (e.g., 5A2, 5F3, L8, etc.) are truncated at 365 amino acids in length and are functional as maltose dependent degrons. Thus, in some embodiments, some of longer MBP mutants can be used in the truncated form as maltose dependent degrons. For example, in certain embodiments, a useful maltose dependent degron comprises an amino acid sequence from position 1 to 365 of SEQ ID NO: 16 (MBP mutant H8). In certain embodiments, a maltose dependent degron comprises an amino acid sequence from position 1 to 365 of SEQ ID NO: 18 (MBP mutant H9). In certain embodiments, a maltose dependent degron comprises an amino acid sequence from position 1 to 365 of SEQ ID NO: 20 (MBP mutant H10). In certain embodiments, a maltose dependent degron comprises an amino acid sequence from position 1 to 365 of SEQ ID NO: 22 (MBP mutant M1). In certain embodiments, a maltose dependent degron comprises an amino acid sequence from position 1 to 365 of SEQ ID NO: 24 (MBP mutant M5). In certain embodiments, a maltose dependent degron comprises an amino acid sequence from position 1 to 365 of SEQ ID NO: 26 (MBP mutant M13).

Some of the MBP mutants include additional linker sequences at the C terminus compared to the wild-type MBP having SEQ ID NO: 2. As the linker sequence is not necessarily required for the function of a maltose dependent degron, useful maltose dependent degrons comprise an amino acid sequence which has the same length as the wild-type MBP. For example, in certain embodiments, a useful maltose dependent degron comprises an amino acid sequence from position 1 to 370 of SEQ ID NO: 16 (MBP mutant H8). In certain embodiments, the maltose dependent degron comprises an amino acid sequence from position 1 to 370 of SEQ ID NO: 18 (MBP mutant H9). In certain embodiments, the maltose dependent degron comprises an amino acid sequence from position 1 to 370 of SEQ ID NO: 20 (MBP mutant H10). In certain embodiments, the maltose dependent degron comprises an amino acid sequence from position 1 to 370 of SEQ ID NO: 22 (MBP mutant M1). In certain embodiments, the maltose dependent degron comprises an amino acid sequence from position 1 to 370 of SEQ ID NO: 24 (MBP mutant M5). In certain embodiments, the maltose dependent degron comprises an amino acid sequence from position 1 to 370 of SEQ ID NO: 26 (MBP mutant M13).

In certain embodiments, a maltose dependent degron comprises any suitable amino acid sequence described herein with substitutions, deletions, or insertions. Typically, amino acid changes may be minor such that a maltose dependent degron retains its maltose dependent conditional stability. For instance, the substitutions, deletions, or insertions may include one to about 30 amino acids, and may include, for example, a small peptide linker of about 30 amino acid residues or less at the carboxyl terminal end or at the amino terminal end.

In some embodiments, a maltose dependent degron comprises any suitable amino acid described herein with conservative amino acid substitutions. The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Alanine (A), Valine (V), and 6) Phenylalanine (F), Tyrosine (Y), Tryptophan (W). Amino acid substitutions that do not generally alter specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a maltose dependent degron described herein. A limited number of non-conservative amino acids, amino acids that are not encoded by the genetic code, and unnatural amino acids may be substituted for amino acid residues. Unnatural amino acids can be modified after protein synthesis, and/or have a chemical structure in their side chain(s) different from that of the standard amino acids.

While specific amino acid sequences and specific variant amino acid residues for maltose dependent degrons are described herein, the maltose dependent degron amino acid sequences suitable for use with compositions and methods of the invention are not limited to these specific amino acid sequences or variants. For example, FIG. 8B illustrates a number of other maltose dependent degrons (e.g., 1-B9, 4-E12, 4-G10, 4-F11, 4-F4, 2-F10, 2-E8, 2-G8, 1-F7, 4-H4, and 2-A4), which exhibit maltose dependent stability.

Furthermore, the destabilizing mutations described herein can be introduced to any homologs of MBP comprising SEQ ID NO: 2 or SEQ ID NO: 28. For example, the corresponding positions of destabilizing mutations can be readily determined for other homologs by sequence alignment algorithms known in the art. The amino acid substitutions described herein with reference to SEQ ID NO: 2 or SEQ ID NO: 28 may be applied to their homologs from different species or organisms. For example, the amino acid substitutions described with reference to positions of SEQ ID NO: 2 or SEQ ID NO: 28 may be derived from homologs of E. coli MBP (e.g., MBP from Yersinia pestis, Vibrio cholerae, Thermotoga maritima, Thermococcus litoralis, Pyrococcus furiosus, and the like). In some embodiments, some of these homologs may share at least about 50%, 60%, 70%, 80%, 90%, 95%, 96%, 97%, 98%, or 99% sequence identity to SEQ ID NO: 2 or SEQ ID NO: 28. In other embodiments, maltose dependent degrons can be derived from MBPs which are not homologs of E. coli MBP, but depend on binding to maltose for their stability. Thus, other maltose dependent degrons (e.g., MBP mutants screened using assays described herein) are within the scope of the present invention and may be used in the compositions and methods provided herein.

6.2.2.2 Maltose Dependent Degron Nucleic Acid Sequences

In another aspect, provided herein are isolated nucleic acid molecules encoding maltose dependent degrons. The term "nucleic acid molecule" refers to DNA, RNA, or both in combination or any modification thereof that is known in the state of art. Such nucleic acid molecule(s) are single- or double-stranded, linear or circular and without any size limitation. The nucleic acid molecules of the invention can be obtained by recombinant techniques, such as PCR or may be produced synthetically. In particular embodiments, the nucleic acid molecules of the invention are DNA molecules, such as cDNA.

In certain embodiments, the isolated nucleic acid molecule comprises a nucleotide sequence encoding any maltose dependent degron described herein (e.g., in Section 6.2.2.1). For example, the isolated nucleic acid molecule comprises a nucleic acid sequence encoding a maltose dependent degron that has at least about 70%, at least about 75%, at least about 80%, at least about 85%, at least about 90%, at least about 95%, at least about 96%, at least about 97%, at least about 98%, or at least about 99% sequence identity to SEQ ID NO: 2 or SEQ ID NO: 28, and comprises at least one variant amino acid residue compared to SEQ ID NO: 2 or SEQ ID NO: 28.

In certain embodiments, the isolated nucleic acid molecule comprises a nucleotide sequence encoding a maltose dependent degron that comprises one or more variant amino acid residues that are located at one or more positions selected from the group consisting of 7, 10, 11, 21, 24, 28, 42, 43, 64, 68, 83, 88, 92, 95, 98, 101, 110, 117, 134, 135, 136, 149, 168, 177, 186, 187, 193, 198, 210, 216, 217, 229, 236, 237, 242, 263, 291, 304, 321, 322, 339, 351, 357, 367, 370, and 374, wherein the positions of these variant amino acid residues correspond to the wild-type MBP amino acid position of SEQ ID NO: 2 or SEQ ID NO: 28.

In certain embodiments, the isolated nucleic acid molecule comprises a nucleotide sequence encoding a maltose dependent degron that comprises one or more variant amino acid residues compared to SEQ ID NO: 2 or SEQ ID NO: 28, and wherein the one or more variant amino acid residues selected from the group consisting of K7R, I10T, W11G, L21S, V24A, F28Y, D42V, K43E, A64T, F68S, D83G, D88N, P92T, W95R, V98I, N101I, A110T, I117V, P134S, A135T, L136M, M149I, Y168C, Y168N, Y177H, N186S, A187P, L193S, D198V, D210E, A216V, A217D, G229C, I236N, D237N, N242D, L263M, L291V, A304S, T321N, M322 L, A339T, A351T, T357S, T367S, S370P, and N374S.

In certain embodiments, the isolated nucleic acid molecule comprises a nucleotide sequence encoding a maltose dependent degron which is truncated in comparison to the wild-type MBP having SEQ ID NO: 2. For example, the nucleotide sequence may encode a maltose dependent degron comprising amino acid residue 1 to 365 of SEQ ID NO: 2 and comprises one or more variant amino acid residues described herein. In certain embodiments, the isolated nucleic acid sequence comprises a nucleotide sequence encoding a maltose dependent degron which is truncated at a position shorter than 365 amino acid residues.

In certain embodiments, the isolated nucleic acid molecule comprises a nucleotide sequence encoding a maltose dependent degron comprising an amino acid sequence having at least one set of variant amino acid residues from the following group of variant amino acid residue sets, wherein the positions of the variant amino acid residues correspond to amino acid positions of SEQ ID NO: 2 or SEQ ID NO: 28:
(a) I10T, V24A, D42V, K43E, D83G, P92T, M149I, Y168N, N186S, A216V, and T357S;
(b) I10T, V24A, D42V, K43E, D83G, M149I, Y168N, N186S, A216V, and D237N;
(c) I10T, V24A, D42V, K43E, D83G, M149I, Y168N, N186S, A216V, and A339T;
(d) I10T, V24A, D42V, K43E, D83G, M149I, Y168N, N186S, A216V, and N242D;
(e) I10T, V24A, D42V, A110T, M149I, and A216V;
(f) I10T, V24A, D42V, K43E, D83G, M149I, Y168N, N186S, and A216V;
(g) L21S, A64T, L136M, Y177H, A187P, A304S, T321N, and A351T;
(h) K7R, D83G, V98I, L193S, I236N, and N374S;
(i) W11G, D88N, P134S, A135T, D210E, and M322 L;
(j) I117V, Y168N, G229C, L263M, T367S, and S370P;
(k) F68S, W95R, N186S, and D198V; and
(l) F28Y, K43E, N101I, Y168C, A217D, and L291V.

In certain embodiments, the isolated nucleic acid molecule comprises a nucleic acid molecule which hybridizes with a nucleotide sequence complementary to SEQ ID NO: 1 or SEQ ID NO: 27 under stringent conditions, and encodes a maltose dependent degron that comprises at least one of the above-mentioned specific mutations and retains maltose dependent protein stability. In certain embodiments, the stringent conditions are such that washing is performed at 65° C. in a salt concentration corresponding to 0.1×SSC and 0.1% SDS once, twice, or three times.

In certain embodiments, the maltose dependent degron nucleic acid molecule comprises a nucleotide sequence of SEQ ID NO: 3 (MBP mutant 3A6). In certain embodiments, the maltose dependent degron nucleic acid molecule comprises a nucleotide sequence of SEQ ID NO: 5 (MBP mutant 4D3). In certain embodiments, the maltose dependent degron nucleic acid molecule comprises a nucleotide sequence of SEQ ID NO: 7 (MBP mutant 5A2). In certain embodiments, the maltose dependent degron nucleic acid molecule comprises a nucleotide sequence of SEQ ID NO: 9 (MBP mutant 5F3). In certain embodiments, the maltose dependent degron nucleic acid molecule comprises a nucleotide sequence of SEQ ID NO: 11 (MBP mutant L8). In certain embodiments, the maltose dependent degron nucleic acid molecule comprises a nucleotide sequence of SEQ ID NO: 13 (L8_v4d). In certain embodiments, the maltose dependent degron nucleic acid molecule comprises a nucleotide sequence of SEQ ID NO: 15 (MBP mutant H8). In certain embodiments, the maltose dependent degron nucleic acid molecule comprises a nucleotide sequence of SEQ ID NO: 17 (MBP mutant H9). In certain embodiments, the maltose dependent degron nucleic acid molecule comprises a sequence of SEQ ID NO: 19 (MBP mutant H10). In certain embodiments, the maltose dependent degron nucleic acid molecule comprises a nucleotide sequence of SEQ ID NO: 21 (MBP mutant M1). In certain embodiments, the maltose dependent degron nucleic acid molecule comprises a nucleotide sequence of SEQ ID NO: 23 (MBP mutant M5). In certain embodiments, the maltose dependent degron nucleic acid molecule comprises a nucleotide sequence of SEQ ID NO: 25 (MBP mutant M13).

A number of MBP mutant nucleic acids mentioned above (e.g., 5A2, 5F3, L8, etc.) are truncated at 1098 nucleotides in length, and, when translated into proteins, are functional as maltose dependent degrons. Thus, in some embodiments, maltose dependent degrons with sequences longer than 1098 nucleotides can be used in the truncated form. For example, in certain embodiments, the maltose dependent degron nucleic acid molecule comprises a nucleotide sequence from position 1 to position 1098 of SEQ ID NO: 11. In certain embodiments, the maltose dependent degron nucleic acid molecule comprises a nucleotide sequence from position 1 to position 1098 of SEQ ID NO: 15. In certain embodiments, the maltose dependent degron nucleic acid molecule comprises a nucleotide sequence from position 1 to position 1098 of SEQ ID NO: 17. In certain embodiments, the maltose dependent degron nucleic acid molecule comprises a sequence from position 1 to position 1098 of SEQ ID NO: 19. In certain embodiments, the maltose dependent degron nucleic acid molecule comprises position 1 to position 1098 of a nucleotide sequence of SEQ ID NO: 21. In certain embodiments, the maltose dependent degron nucleic acid molecule comprises a nucleotide sequence from position 1 to position 1098 of SEQ ID NO: 23. In certain embodiments, the maltose dependent degron nucleic acid molecule comprises a nucleotide sequence of SEQ ID NO: 25.

Some of the MBP mutant nucleic acids include additional linker sequences at their C terminus compared to the wild-type MBP nucleic acid having SEQ ID NO: 1. Thus, in some embodiments, these MBP mutant nucleic acids can be used without the additional linker sequences at their C terminal end. For example, in certain embodiments, the maltose dependent degron nucleic acid molecule comprises a nucleotide sequence from position 1 to position 1113 of SEQ ID NO: 11. In certain embodiments, the maltose dependent degron nucleic acid molecule comprises a nucleotide sequence from position 1 to position 1113 of SEQ ID NO: 15. In certain embodiments, the maltose dependent degron nucleic acid molecule comprises a nucleotide sequence from position 1 to position 1113 of SEQ ID NO: 17. In certain embodiments, the maltose dependent degron nucleic acid molecule comprises a sequence from position 1 to position 1113 of SEQ ID NO: 19. In certain embodiments, the maltose dependent degron nucleic acid molecule comprises position 1 to position 1113 of a nucleotide sequence of SEQ ID NO: 21. In certain embodiments, the maltose dependent degron nucleic acid molecule comprises a nucleotide sequence from position 1 to position 1113 of SEQ ID NO:

23. In certain embodiments, the maltose dependent degron nucleic acid molecule comprises a nucleotide sequence of SEQ ID NO: 25.

Mutations can be introduced to any of the sequences disclosed herein (e.g., wild-type MBP having SEQ ID NO: 1) by usual methods such as polymerase chain reaction (PCR, see Sambrook J et al., Molecular cloning: a laboratory manual, Cold Spring Harbor Press, New York (2001), Ausubel F M et al., Current protocols in molecular biology, John Wiley and sons, New York (1999), Adams A et al., Methods in yeast genetics, Cold Spring Harbor Press, New York (1997)), or by random mutagenesis techniques, such as use of mutagenic agents (Ultra-Violet rays or chemical agents like nitrosoguanidine (NTG) or ethylmethanesulfonate (EMS)) or use of PCR techniques (DNA shuffling or error-prone PCR). In certain embodiments, any of the nucleic acid sequences encoding the maltose dependent degrons may be optimized by genetic/protein engineering techniques, such as directed evolution or rational mutagenesis, which are known to those of ordinary skill in the art. The mutants generated using these methods can be screened for their maltose binding stability using any assays described herein or other assays deemed suitable by those skilled in the art. Thus, the scope of the maltose dependent degron nucleic acids is not limited to specific sequences disclosed herein, but further includes any MBP mutant nucleic acids, which, when encoded into proteins, display maltose dependent stability.

Due to the inherent degeneracy of the genetic code, other polynucleotides which encode substantially the same or functionally equivalent polypeptides described in Section 6.2.2.1 can also be used in the compositions and methods provided herein.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, in a process sometimes called "codon optimization" or "controlling for species codon bias."

Optimized coding sequences containing codons preferred by a particular prokaryotic or eukaryotic host (Murray et al., 1989, Nucl Acids Res. 17: 477-508) can be prepared, for example, to increase the rate of translation or to produce recombinant RNA transcripts having desirable properties. Translation stop codons can also be modified to reflect host preference. For example, typical stop codons for S. cerevisiae and mammals are UAA and UGA, respectively. The typical stop codon for monocotyledonous plants is UGA, whereas insects and E. coli commonly use UAA as the stop codon (Dalphin et al., 1996, Nucl Acids Res. 24: 216-8).

While degeneracy of the genetic code and optimizing coding sequences are discussed in the context of maltose dependent degrons, the principle can be applied to any coding sequences described in the present disclosure.

6.2.3. Fusion Proteins

In another aspect, provided herein are maltose dependent degrons that can be fused to any protein of interest to control its stability by manipulating maltose content in a culture medium. For example, proteins of interest may include transcriptional regulators, enzymes, signaling proteins, transport proteins, and the like. In some embodiments, a protein of interest may include those that directly influence cellular functions such as the cell growth rate. In other embodiments, a protein of interest is selected such that the maltose dependent stability of the protein of interest can be utilized to temporally change the level of desired target molecules by manipulating the maltose content.

In certain embodiments, a transcriptional regulator may be selected as a protein of interest to be fused with a maltose dependent degron. A transcriptional regulator fused in frame to a maltose dependent degron can globally affect expression of a number of different downstream target molecules. Examples of transcriptional regulators that can be fused with a maltose dependent degron include Gal80p or Gal4p. The maltose dependent stability of a transcriptional regulator fused in frame to a maltose dependent degron can, in turn, modulate the expression level or amount of target molecules downstream from the transcriptional regulator. For example, the target molecules can include enzymes encoded by biosynthetic genes in a biosynthetic pathway, metabolites, or heterologous compounds produced by enzyme catalytic reactions.

Methods for generating fusion proteins and fusion DNA constructs are well known in the art. Briefly, the methods include linking DNA encoding a gene of interest, or portion thereof, to DNA encoding a maltose dependent degron in the same translational reading frame. The encoded protein of interest may be linked in-frame to the amino- or carboxyl-terminus of the maltose dependent degron. In some embodiments, the coding sequence of a maltose dependent degron may be linked directly to the coding sequence of a protein of interest. In other embodiments, a fusion protein may comprise a linker (e.g., a peptide linker) to connect a maltose dependent degron to a protein of interest.

6.2.4. Nucleic Acid Constructs and Expression Vectors

In another aspect, provided herein are nucleic acid constructs comprising nucleic acids encoding a fusion protein comprising a maltose dependent degron fused in frame to a protein of interest. In certain embodiments, the nucleic acids encoding a fusion protein may be operably linked to one or more control sequences that direct the expression of the fusion protein in a host cell under conditions suitable with the control sequences. The control sequence may include any suitable promoter sequence, transcription terminal sequence, a polyadenylation sequence, and the like. These control sequences may be any nucleotide sequences that regulate transcriptional activity in the host cell of choice and may be obtained from genes encoding proteins of interest homologous or heterologous to the host cell. In some embodiments, nucleic acid constructs used to genetically modify a host cell comprise one or more selectable markers useful for the selection of transformed host cells and for placing selective pressure on the host cell to maintain foreign DNA. Any suitable control sequences or marker sequences known in the art can be used in generating nucleic acid constructs.

In certain embodiments, a promoter sequence operably linked to the fusion nucleic acid may be an endogenous promoter sequence of the nucleic acids encoding the protein of interest. In some situations, it may be desired to match the temporal response of the fusion protein expression level to that of the endogenous expression of the protein of interest. For example, if Gal80p is selected as a protein of interest, then its endogenous promoter may be used to drive the expression of the fusion Gal80p protein.

In certain embodiments, a promoter sequence operably linked to the fusion nucleic acid may be a maltose-responsive promoter. By combining a maltose-responsive promoter together with a nucleic acid construct encoding a fusion protein comprising a maltose dependent degron, the compositions and methods can control both transcription of the fusion nucleic acid construct and post-translational stability of the fusion protein encoded therefrom using a single ligand (e.g., maltose). Examples of suitable maltose-responsive promoters are further described in detail in Section 6.3 below.

In another aspect, provided herein are expression vectors or chromosomal integration constructs comprising nucleic acids encoding fusion proteins comprising proteins of interest and maltose dependent degrons. The recombinant expression vector may be any vector (e.g., a plasmid, viral vector, cosmid) that is suitable for expressing the fusion protein. The choice of vector will depend on the compatibility of the vector with the host cell into which the vector is to be introduced and the end application of the host cells. In some embodiments, the vector may further include element(s) that permit integration of the vector into the host cell's genome. In other embodiments, the vectors may be an autonomously replicating vector which exists extrachromosomally in host cells.

6.2.5. Use of a Maltose Dependent Degron in Methods for Modulating Protein Stability and for Production of Non-Catabolic Compounds In another aspect, provided herein are methods for modulating protein stability using maltose dependent degrons and maltose. The method comprises providing a fusion protein comprising a protein of interest fused in frame to any suitable maltose dependent degron. In certain embodiments, the method comprises contacting the fusion protein with maltose so that the fusion protein is more stable when the maltose dependent degron is in contact (e.g., bound) with maltose compared to when the maltose dependent degron is not in contact with maltose.

In certain embodiments, the methods can be performed in a cell-free system (e.g., cell extracts). For example, cell extracts obtained from host cells genetically modified to express the fusion proteins can be used in the methods provided herein. Fusion proteins in cell extracts without maltose may be unstable and become degraded at a faster rate than desired. When it is desired to increase the stability and reduce the degradation rate of the fusion proteins, maltose may be added to the cell extracts in the methods provided herein. In a cell-free system, the maltose dependent conditional stability of fusion proteins may be measured using any suitable techniques. For example, if the fusion protein comprises a fluorescent marker as a fusion partner to a maltose dependent degron, the fluorescent levels from the cell extracts can be measuring using suitable imaging techniques and/or quantification kits.

In certain embodiments, the methods for modulating protein stability can be performed with genetically modified host cells expressing fusion proteins according to an embodiment of the invention. For example, host cells genetically modified with nucleic acids encoding a fusion protein can be cultured in a culture medium comprising maltose to maintain stability for the fusion protein. When it is desired to eliminate or reduce the fusion protein stability in host cells, the culture medium may be changed such that maltose is absent or present in sufficiently low amounts in the culture medium. For example, the host cells may be transferred to a new fermentor containing a culture medium without maltose. Any residual maltose transferred with the host cells may be consumed by the host cells in the new fermentor, and a carbon source (e.g., sucrose) other than maltose may be added to maintain the host cells.

A suitable amount of maltose to maintain stability of the maltose dependent degron (and the fusion protein) can be empirically determined. For example, a saturating or optimal amount of maltose to maintain stability of maltose dependent degrons and their fusion proteins can be determined by performing the protein stability (maltose dependent degron and/or fusion protein) curve in the presence of increasing amounts of maltose in the culture medium, i.e., maltose titration. For example, a population of genetically modified host cells expressing a maltose dependent degron (or its fusion protein) may be divided into a plurality of subpopulations and cultured in parallel, wherein each subpopulation is grown in culture media comprising a different, e.g., increasing amount of maltose (including no maltose), and the maltose dependent degron or fusion protein expression is assayed after a defined period of time. The maltose titration curve will exhibit at least two concentrations of maltose whereby the maltose dependent degron or fusion protein stability level in the host cells is plateaued at its minimum, and whereby their stability level in the host cells is plateaued at its maximum. A saturating or optimal amount of maltose is an amount or concentration of maltose in a culture medium, whereby the maltose dependent degron or fusion protein stability in the host cells is plateaued at its maximum. Suitable amounts of maltose for stabilizing maltose dependent degrons and their fusion proteins are further described in detail in Section 6.4.

In certain embodiments, host cells are genetically modified to comprise a maltose-responsive promoter operably linked to nucleic acids encoding a fusion protein. These embodiments are described further in detail in Sections 6.2.6 and 6.8. In these embodiments, the saturating or optimal amount of maltose includes an amount that is capable of activating the maltose-responsive promoter to drive the expression of the fusion gene at the maximum level as well as to maintain the maximum post-translational stability of the fusion protein encoded therefrom. Generally, to increase the activity of a maltose-responsive promoter and stability of a fusion protein, maltose is present in a culture medium in the amount of at least about 5 grams/liter, typically at least about 10 grams/liter, more typically at least about 20 grams/liter in the culture medium. Generally, maltose is present in a culture medium less than about 100 grams/liter, typically less than about 60 grams/liter, more typically less than about 50 grams/liter.

In certain embodiments, a fusion protein according to an embodiment of the invention is at least about 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, or more stable when the maltose dependent degron within the fusion protein is in contact with maltose compared to when it is not in contact with maltose. The maltose dependent stability of fusion proteins can be determined using any assays described herein or other assays deemed suitable by those skilled in the art.

For a given fusion protein, its maltose dependent stability can be modulated in a number of different ways. In one embodiment, the concentration of maltose can be adjusted in a culture medium. For example, if the maximum stability is desired for the fusion protein, then the optimal amount of maltose determined from the titration curve may be added to the culture medium. In some embodiments, maltose may be used at a concentration higher than the optimal amount determined from the maltose titration curve to ensure the maximum stability of the fusion protein can be achieved. In another example, if a moderate level of stability is desired for the fusion protein, then a sub-optimal amount of maltose (e.g., a half of the optimal amount) may be added to the culture medium.

In another embodiment, the maltose dependent stability for a fusion protein may be modulated by selecting a suitable maltose dependent degron as a fusion partner to a protein of interest. At a given concentration of maltose or in the absence of maltose, different maltose dependent degrons, when fused to a protein of interest, can confer different levels of stability (e.g., measured in terms of fusion protein activity). For example, as shown in FIG. 8B, the stability level of a fusion protein comprising GFP fused to maltose dependent degron 4-H10 (e.g., H10) is lower than the stability level of a fusion protein comprising GFP and maltose dependent degron L8_v4d, both in the presence of maltose or in the absence of maltose. In an embodiment where a higher stability level of a fusion protein is desired, then a maltose dependent degron, such as L8_v4d, may be used as a fusion partner. In another embodiment where a lower stability level is desired for the fusion protein, then maltose dependent degron 4-H10 may be used as a fusion partner. In some embodiments, it may be desirable to match the stability level of the fusion protein (when in contact with maltose) to the endogenous stability level of protein of interest in host cells. In such embodiments, a suitable maltose dependent degron that imparts an appropriate level of maltose dependent stability may be selected as a fusion partner for the protein of interest.

In some embodiments, a maltose dependent degron may be selected as a fusion partner based on its degradation rate profile. As shown in FIGS. 11A and 11B, some of maltose dependent degrons have a faster degradation rate in cells in the absence of maltose compared to other maltose dependent degrons. For example, maltose dependent degron 5F3, when fused to GFP, degrades the fusion protein at a faster rate in comparison to maltose dependent degron H8. If a slower degradation rate is desired for the protein of interest after removing maltose from the culture medium, then a maltose dependent degron with a slower degradation rate, such as H8, may be used as a fusion partner. On the other hand, if a faster degradation rate is desired for the protein of interest after removing maltose, then a maltose dependent degron with a faster degradation rate, such as 5F3, may be used as a fusion partner for the protein of interest.

In some embodiments, it may be desired to control stability of multiple proteins using maltose dependent degrons in genetically modified host cells. For example, it may be desired to control the stability of two or more enzymes in a biosynthetic pathway using maltose. In these embodiments, the same maltose dependent degron may be used as a fusion partner for all proteins of interest. Alternatively, each protein of interest may be fused with a different maltose dependent degron depending on the stability desired for each protein of interest.

In certain embodiments, the protein of interest selected as a fusion partner to a maltose dependent degron may be endogenously expressed in host cells. Since expression of the endogenous protein of interest may obscure the maltose dependent stability of fusion proteins, in some embodiments, the endogenous gene encoding the protein of interest (e.g., Gal80p) may be functionally disrupted. For example, the endogenous gene may be deleted from the host genome. In another example, a nucleic acid construct which comprises nucleic acids encoding the fusion protein may be integrated at the site of the endogenous gene encoding the protein of interest in the host genome. Any suitable methods known in the art can be used to integrate the nucleic acids encoding the fusion protein at a desired target site within the host genome. For example, the heterologous nucleic acids encoding the fusion protein may be integrated into the selected gene following cleavage by the nuclease, such as a zinc finger nuclease, a TAL-effector domain nuclease, and/or a CRISPR/Cas nuclease system. These techniques are known and described in, for example, U.S. Pat. No. 8,685,737; and Horwitz et al. (2015), *Cell Systems* 1, 1-9, which are incorporated herein by reference in their entirety.

Any suitable protein of interest may be selected as a fusion partner for a maltose dependent degron according to an embodiment of the invention. In certain embodiments, a protein of interest is selected such that when it is fused to a maltose dependent degron, it can directly influence cellular function(s) by manipulating the maltose concentration. For example, the proteins of interest may include gene products that are involved in fatty acid synthesis which can improve cell growth. Such a gene product fused to a maltose dependent degron can be turned on with maltose in the culture medium during the cell biomass build stage of fermentation when cell growth is desired. They can be turned off by removing maltose during the production stage of fermentation when it is desired to reduce cell growth so that the cells' resources can be diverted to manufacturing desired heterologous compounds from host cells. By adjusting the maltose concentration in the culture medium, the stability of fusion proteins comprising such proteins of interest may be directly regulated and temporally adjusted as desired at different stages of the fermentation process.

In other embodiments, a protein of interest is selected as a fusion partner to a maltose dependent degron such that the maltose dependent stability of the protein of interest can be utilized to cascade its effects onto one or more downstream target molecules by manipulating the maltose content. In these embodiments, a fusion protein comprising a maltose dependent degron may interact with one or more biomolecules (e.g., other proteins or nucleic acids) in the host cell to indirectly modulate the expression level or amount of one or more target molecules. For example, indirect regulation of the one or more enzymes of a biosynthetic pathway can be achieved by fusing a maltose dependent degron to a single heterologous transcriptional regulator, the expression of which, in turn, regulates expression of the one or more enzymes (e.g., all the members) of the biosynthetic pathway. Exemplary embodiments of indirect regulation are illustrated by schematic diagrams shown in FIGS. 1A through 2B, which illustrates regulation of a plurality of biosynthetic pathway genes as a GAL regulon.

The GAL regulon in yeast provides an exemplary regulatory network of activators, repressors and promoters that can be utilized in combination with a maltose dependent degron described herein. Yeast can utilize galactose as a carbon source via expression of the GAL genes to import galactose and metabolize it inside the cell. The GAL genes include structural genes GAL1, GAL2, GAL7 and GAL10 genes, which respectively encode galactokinase, galactose permease, α-D-galactose-1-phosphate uridyltransferase, and uridine diphosphogalactose-4-epimerase, and regulator genes GAL4, GAL80, and GAL3. The GAL4 gene product is a positive regulator (i.e., activator) and the GAL80 gene product is a negative regulator (i.e., repressor) of the expression of the GAL1, GAL2, GAL7, and GAL10 genes. Gal4p activates transcription by binding upstream activating sequences (UAS), such as those of the GAL structural genes, i.e., within the pGAL1, pGAL7 and pGAL10 promoters. In the absence of galactose, very little expression of the structural proteins (Gal1p, Gal2p, Gal7p, and Gal10p) is typically detected, due to Gal80p interacting with Gal4p and preventing Gal4p transcriptional activity. In the presence of galactose, however, Gal3p interacts with Gal80p, relieving Gal4p repression by Gal80p. This allows expression of genes downstream of Gal4p binding sequences, such as the GAL1, GAL2, GAL7, and GAL10 gene products.

FIGS. 1A and 1B illustrate an exemplary embodiment where a fusion protein, interacting with one or more biomolecules indirectly and negatively, modulates expression levels or amount of one or more target molecules using the GAL regulon. In the embodiment illustrated in FIGS. 1A and 1B, transcriptional regulator Gal80p is the protein of interest fused in frame to a maltose dependent degron. Gal80p is a repressive co-factor (i.e., transcriptional repressor) of transcriptional activator Gal4p (e.g., a biomolecule), which binds to the pGal promoters, such as pGal1, pGal2, pGal7, or pGAL10 (e.g., a biomolecule). As shown in FIG. 1A, a pGal promoter is operably linked to one or more genes encoding enzymes in a biosynthetic pathway (e.g., target molecules). In the presence of maltose in the culture medium as shown in FIG. 1A, maltose binds to the maltose dependent degron and the fusion protein is stabilized and expressed at a relatively high level. The Gal80p portion of the fusion protein binds to and represses transcriptional activator Gal4p from activating the pGal promoter. This, in turn, represses transcription of the biosynthetic pathway genes from the pGal promoter, lowering the expression level of enzymes and other downstream target molecules resulting from catalytic reactions of the enzymes (e.g., non-catabolic compounds). Thus, in the embodiment shown in FIG. 1A, the fusion protein, when maltose is in contact with the maltose dependent degron, negatively modulates the expression level or amount of target molecules (e.g., enzymes, non-catabolic compounds, and the like).

In FIG. 1B, when maltose is removed from the culture medium, the fusion protein comprising Gal80p in host cells is unstable and degraded at a faster rate, resulting in a lower level of Gal80p expression in host cells compared to the stage shown in FIG. 1A. This relieves repression of transcriptional activator Gal4p, which, in turn, can bind to the pGal promoter and drive the expression of biosynthetic pathway genes. Therefore, the levels of target molecules, such as enzymes, metabolites, heterologous compounds catalyzed from enzyme reactions are increased in comparison to the stage shown in FIG. 1A when maltose is present in the culture medium.

Figure 2A:
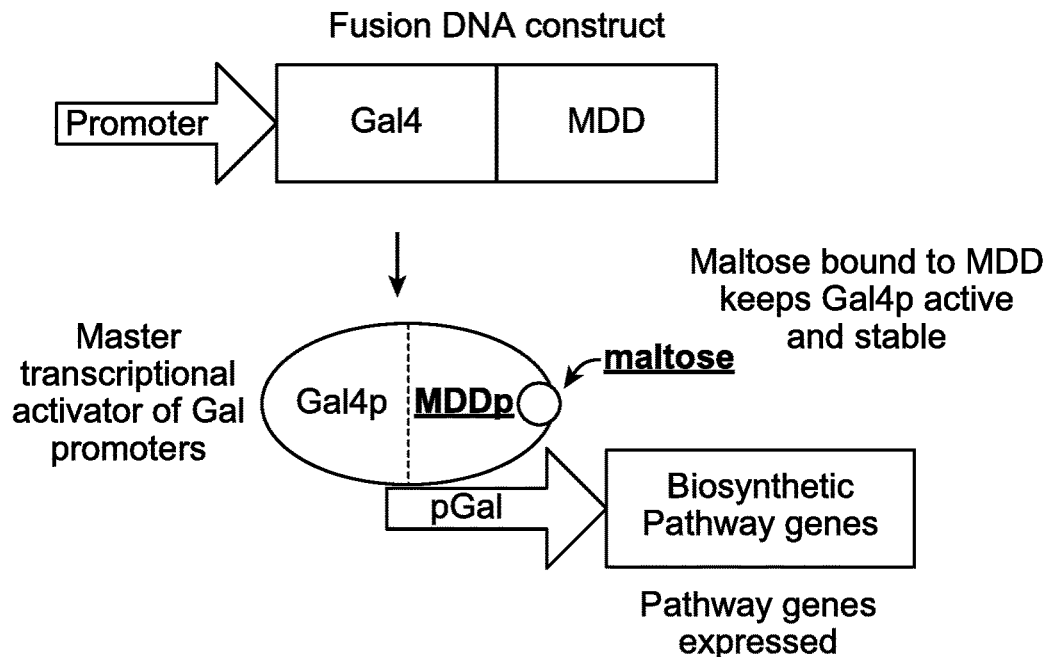
FIGS. 2A and 2B illustrate schematic diagrams showing the use of maltose dependent stability of a fusion protein comprising Gal4p fused in frame to a maltose dependent degron to positively regulate expression of biosynthetic pathway genes.
Figure 2B:
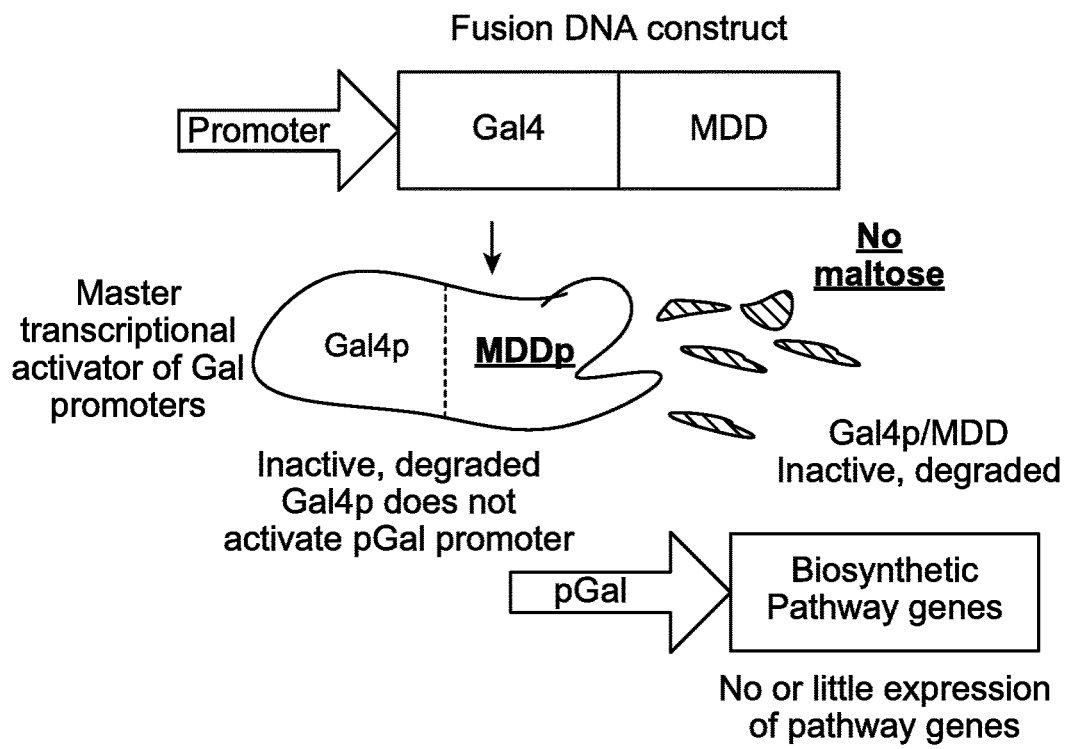

FIGS. 2A and 2B illustrate a fusion protein interacting with one or more biomolecules to indirectly and positively modulate the expression level or amount of one or more target molecules. As shown in FIG. 2A, a host cell comprises transcriptional activator Gal4p as the protein of interest which is fused to a maltose dependent degron. When maltose is added to the culture medium as shown in FIG. 2A, the fusion protein is stabilized with maltose in contact with the maltose dependent degron. This increases the overall stability of the fusion protein comprising Gal4p, which, in turn, binds to the pGal promoter (e.g., biomolecule) to drive the expression of biosynthetic pathway genes (e.g., target molecules). The expression of biosynthetic pathway genes, in turn, increases production of downstream target molecules, such as heterologous compounds which are products of catalytic reactions of these enzymes. In this embodiment, when it is desired to reduce or eliminate the expression level or amount of one or more target molecules produced in the host cells, the maltose content can be lowered or removed as shown in FIG. 2B. In this exemplary embodiment, expression of the endogenous GAL80 gene may be functionally disrupted such that endogenous Gal80p, which is a repressor of Gal4p, is not present to negatively regulate Gal4p activity.

In certain embodiments, different modes of modulation by fusion proteins may co-exist in a single host cell. For example, a host cell may comprise a fusion protein which directly influences cellular functions (e.g., cell growth) and another fusion protein which positively modulates the expression level or amount of one or more target molecules. In another example, a host cell may comprise a fusion protein which directly influences cellular functions and another fusion protein which negatively modulates the expression level or amount of one or more target molecules. In another example, a host cell may comprise a fusion protein which negatively modulates the expression level or amount of one or more target molecules and a fusion protein which positively modulates the expression level or amount of one or more target molecules.

The embodiments illustrated in FIGS. 1A through 2B are merely exemplary, and any suitable combinations of proteins of interest may be used as fusion partners to maltose dependent degrons, and any suitable combinations of modes of modulation may be utilized in the compositions and methods provided herein.

6.2.6. Dual Transcriptional Control and Post-Translational Control with a Maltose-Responsive Promoter and a Maltose Dependent Degron In another aspect, provided herein are methods for providing both transcriptional control of gene expression and post-translational stability control of gene product(s) by manipulating maltose content. By combining a genetic element that can confer maltose dependent post-translational stability to any gene it is fused in frame to with a promoter that is induced by maltose, the compositions and methods provided herein can impart a very robust and tight control over timing of expression and stability of proteins of interest (and any downstream target molecules).

Thus, provided herein are methods of controlling timing of expression and stability of a protein of interest in genetically modified host cell using both maltose dependent degrons and maltose-responsive promoters. In certain embodiments, a host cell comprises a maltose-responsive promoter operably linked to a heterologous nucleic acid encoding a fusion protein comprising a protein of interest fused in frame to a maltose dependent degron. In the presence of a sufficient amount of maltose, the transcription of the heterologous nucleic acid is activated (or increased) and the fusion protein encoded therefrom is stabilized. At a suitable time point, the host cells can be cultured in a culture medium in which maltose is absent or in sufficiently low amounts such that the maltose-responsive promoter activity and the fusion protein stability are reduced as compared to when a culture medium comprises a sufficient amount of maltose. As a result, the heterologous nucleic acid expression can be down-regulated in the absence (or in sufficiently low amounts) of maltose. Therefore, in these embodiments, the same effector molecule (e.g., maltose) can be utilized to provide a simultaneous transcriptional control of a gene of interest and post-translational control of the gene product. In the compositions and methods provided herein, any suitable maltose-responsive promoters (either a natural or synthetic) described in Section 6.3 or others known in the art can be used.

Figure 3A:
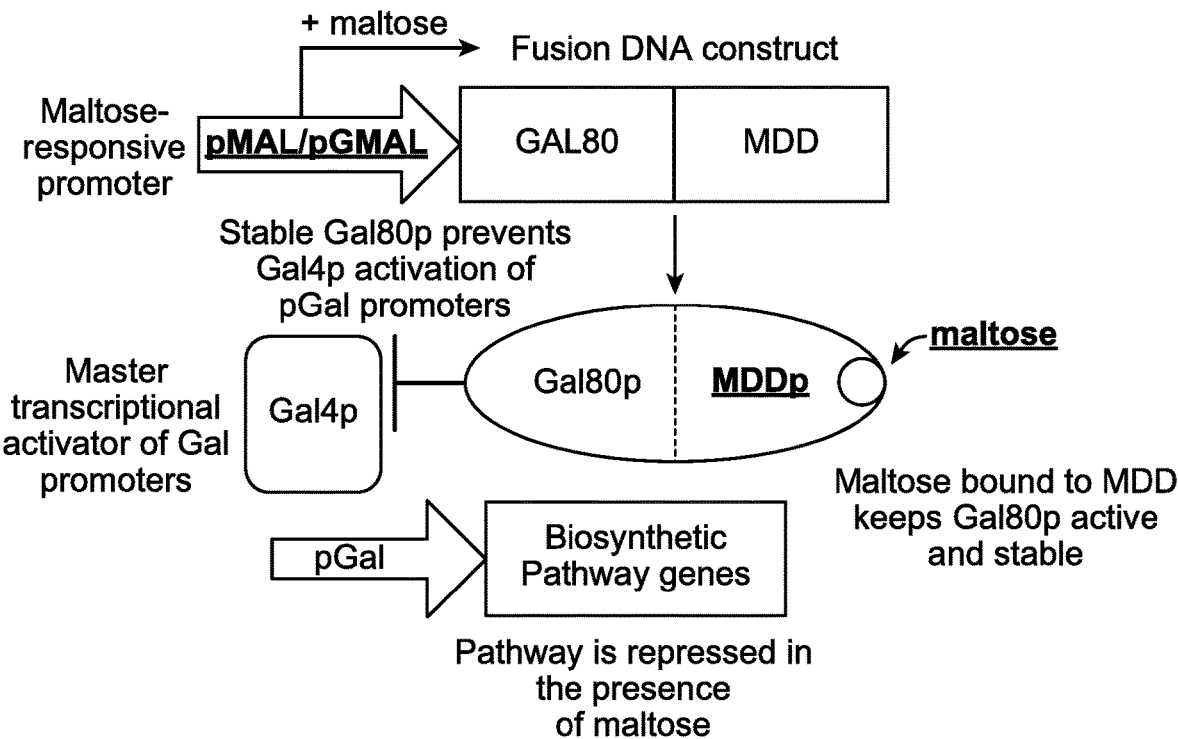
FIGS. 3A and 3B illustrate schematic diagrams showing combining a maltose-responsive promoter and a maltose dependent degron to control transcription of a fusion DNA construct and post-translational stability of the fusion protein by manipulating maltose content in a culture medium.
Figure 3B:
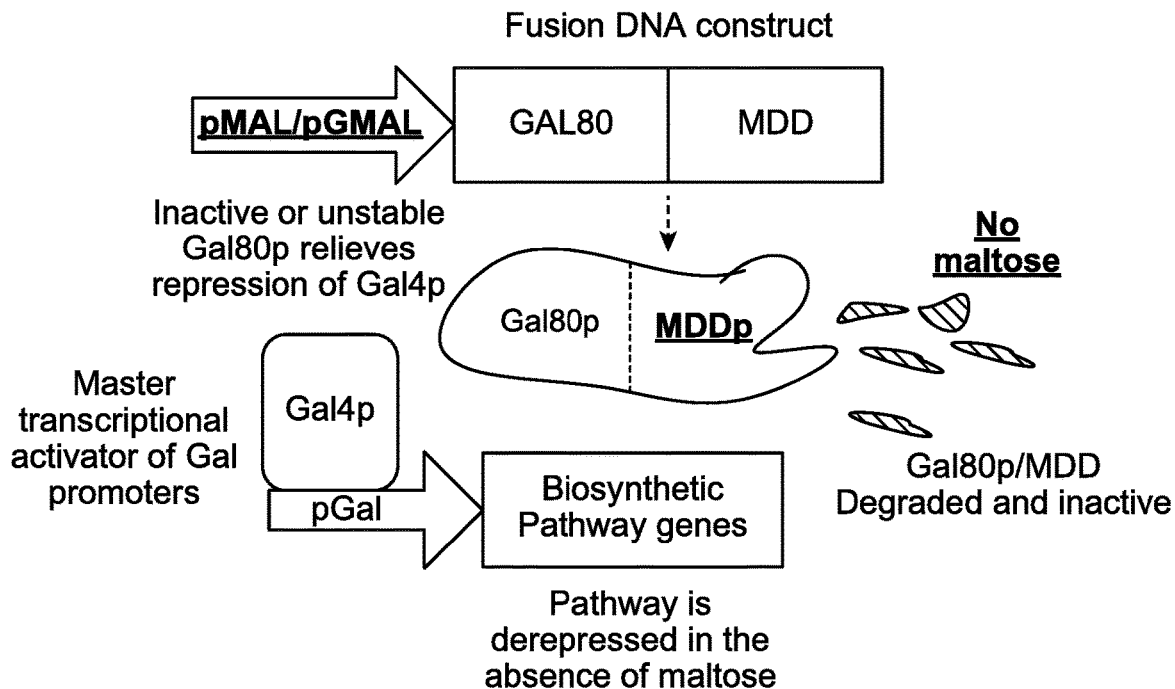

FIGS. 3A and 3B represent a schematic diagram illustrating an exemplary dual transcriptional control of gene expression and post-translational control of gene product(s) with maltose and a maltose dependent degron. As shown in FIGS. 3A and 3B, nucleic acids encoding a fusion protein comprising Gal80p and a maltose dependent degron are operably linked to a maltose-responsive promoter (e.g., native promoter pMAL or synthetic maltose-responsive promoter such as a pGMAL promoter). In the presence of maltose, as shown in FIG. 3A, the pMAL or pGMAL promoter is activated (or its activity increased), and the fusion DNA construct is transcribed to encode a fusion protein comprising Gal80p fused in frame to a maltose dependent degron. In the presence of maltose, the fusion protein is stable with maltose bound to the maltose dependent degron, thereby providing a high level of fusion protein expression and stability. When maltose is removed from the culture medium as shown in FIG. 3B, the maltose-responsive promoter is either inactive or less active and any fusion protein encoded from the fusion DNA construct becomes unstable and degraded at a faster rate.

The embodiment shown in FIGS. 3A and 3B is merely exemplary. The dual transcriptional control and post-translational control using a maltose-responsive promoter and a maltose dependent degron can be applied to any situation where a tight control of timing of expression and stability of fusion proteins and/or downstream target molecules is desired.

6.2.6.1 Use of a Maltose-Responsive Promoter in Combination with a Maltose Dependent Degron and Maltose Content Manipulation as a Switch for Production of Non-Catabolic Compounds In particular embodiments, the methods and compositions provided herein utilize a maltose-responsive promoter and a maltose dependent degron, in combination with manipulation of maltose content in a fermentation medium to regulate, either directly or indirectly, the expression and/or stability of heterologous enzymes capable of effecting non-catabolic compound production in a genetically modified host cell. In these embodiments, the nucleic acids encoding one or more target molecules shown in FIGS. 3A and 3B may include heterologous nucleic acids encoding biosynthetic pathway genes encoding enzymes (e.g., mevalonate pathway enzymes) capable of effecting production of non-catabolic compound (e.g., isoprenoid compounds).

Maltose (or its analogs or derivatives) is inexpensive, non-toxic and stable. It is an attractive molecule to use to control timing of gene expression and protein stability, in particular, for large-scale manufacturing processes. In certain situations, naturally occurring maltose-responsive promoters, when operably linked to a gene of interest, do not always provide a tight transcriptional control required for extended manufacturing processes. Thus, in certain embodiments, a maltose dependent degron can be utilized in combination with a maltose-responsive promoter to concurrently control the timing of gene expression and/or stability of proteins, for example, enzymes of a biosynthetic pathway for producing non-catabolic compounds in genetically modified host cells during fermentation. In other embodiments, a synthetic maltose-responsive promoters can also be used in combination with a maltose dependent degron to concurrently control the timing of gene expression and/or stability of proteins in the production of non-catabolic compounds.

In one embodiment, when fermentation of a host cell is carried out in the presence of maltose (e.g., at least about 0.1% maltose), non-catabolic compound production is substantially reduced or turned off. When the amount of maltose in a fermentation culture medium is reduced or eliminated, non-catabolic compound production is turned on or increased. Thus, in some embodiments, the genetically modified cells described herein comprise heterologous biosynthetic pathway genes that are regulated by a maltose-responsive promoter and a fusion protein comprising a protein of interest fused in frame to a maltose dependent degron. Such a system enables the use of maltose content in a fermentation medium as a switch for the production of non-catabolic compounds. Controlling the timing of non-catabolic compound production to occur only when production is desired redirects the carbon flux during the non-production phase into cell maintenance and biomass. This more efficient use of carbon greatly reduces the metabolic burden on the host cells, improves cell growth, increases the stability of the heterologous genes, reduces strain degeneration, and contributes to better overall health and viability of the cells.

In some embodiments, the fermentation method comprises a two-step process that utilizes maltose as a switch to effect the "off" and "on" stages. In the first step (i.e., the "build" stage, step (a)) wherein production of the compound is not desired, the genetically modified host cells are grown in a growth or "build" medium comprising maltose in an amount sufficient to induce the expression of genes under the control of a maltose-responsive promoter, and the induced gene products act to negatively regulate production of the non-catabolic compound. After transcription of the fusion DNA construct under the control of a maltose-responsive promoter, the stability of the fusion proteins is post-translationally controlled. In the second step (i.e., the "production" stage, step (b)), the fermentation is carried out in a culture medium comprising a carbon source wherein maltose is absent or in sufficiently low amounts such that the activity of a maltose-responsive promoter is reduced or inactive and the fusion proteins are destabilized. As a result, the production of the heterologous non-catabolic compound by the host cells is turned on or increased.

In other embodiments, a maltose-responsive promoter can be operably linked to one or more heterologous nucleic acids encoding one or more enzymes of a biosynthetic pathway. The presence of an activating amount of maltose in the culture medium increases the expression of the one or more enzymes of the biosynthetic pathway. Additionally or alternatively, in certain embodiments, the one or more heterologous nucleic acids encoding the enzymes may be fused in frame to nucleic acids encoding a maltose dependent degron. In these embodiments, the presence of a sufficient amount of maltose in the culture medium will increase expression of one or more enzymes of the biosynthetic pathway, and the fusion enzymes are stabilized in the presence of maltose. In this fashion, the maltose-responsive promoter and maltose dependent degron can be wired to act as a positive regulator of non-catabolic compound production.

6.3 Maltose-Responsive Promoters

In another aspect, provided herein are maltose-responsive promoters useful in compositions and methods provided herein to promote transcription of an operably linked DNA coding sequence in the presence of maltose. In some embodiments, unmodified maltose-responsive promoters derived from the regulatory network for the maltose fermentation system of various organisms (e.g., pMAL promoters) can be utilized to control transcription of the operably linked DNA coding sequence. In other embodiments, synthetic maltose-responsive promoters can be utilized to control transcription of the operably linked DNA coding sequence. As described in detail below, the synthetic maltose-responsive promoters provided herein provide certain advantages in that they can reduce the "leakiness" of gene expression under un-induced conditions (e.g., in the absence of maltose), compared to unmodified maltose-responsive promoters.

6.3.1. pMAL Promoters

In certain embodiments, maltose-responsive promoters useful in the methods and compositions provided herein promote transcription of an operably linked DNA coding sequence in the presence of maltose. In certain embodiments, any maltose-responsive promoters known in the art may be used to regulate expression of enzymes capable of effecting non-catabolic compounds. In some embodiments, the maltose-responsive promoter is selected from the group consisting of pMAL1 (SEQ ID NO: 12), pMAL2 (SEQ ID NO: 13), pMAL11 (SEQ ID NO: 14), pMAL12 (SEQ ID NO: 15), pMAL31 (SEQ ID NO: 16) and pMAL32 (SEQ ID NO: 17). In certain embodiments, pMAL promoters include modified versions of these promoters that have increased or decreased promoter activity compared to unmodified pMAL promoters. An exemplary modified pMAL promoter includes pMAL32_v1 (SEQ ID NO: 78).

Other useful maltose-responsive promoters useful in the methods and compositions provided herein can be derived from the regulatory network for the maltose fermentation system of *S. cerevisiae*. Maltose fermentation in *Saccharomyces* species requires the presence of at least one of five unlinked MAL loci: MAL1, MAL2, MAL3, MAL4, and MAL6. Each of these loci consists of a complex of genes involved in maltose metabolism; the complex includes a maltose permease (MALx1, where x stands for one of the five loci), the maltase (MALx2) responsible for intracellular hydrolysis of the sugar, and a positive regulatory protein (MALx3) that induces the transcription of the two previous genes in the presence of maltose. See, e.g., Cheng & Michels, *J. Bacteriol.* 173: 1817-1820 (1991); Dubin et al., *J. Bacteriol.* 164:605-610 (1985); Chang et al., *Curr. Genet.* 14:201-209 (1988); Higgins et al., *Appl. Environ. Microbiol.* 65: 680-685 (1999). At the MAL6 locus, the activator is encoded by the MAL63 gene. Mal63p is a DNA-binding transcriptional activator required for the maltose-dependent induction of the MAL structural genes encoding maltose permease and maltase.

A MAL activator intermediate complex is stable in the absence of inducer maltose, but addition of maltose causes the release of inducible MAL activator from the complex in an active form capable of DNA binding and transcription activation. See, e.g., Ran, F. and Michels., C. A., *J. Biol. Chem.* 285(18):13850-13862 (2010). Binding sites of the MAL63 protein in the divergently transcribed MAL61-62 promoter have been characterized as an upstream activating sequence for the MAL genes. See, e.g., Ni, B. and Needleman, R., "Identification of the Upstream Activating Sequence of MAL and the Binding Sites for the MAL63 Activator of *Saccharomyces cerevisiae*," *Molecular and Cellular Biology* 10(7):3797-3800 (1990), the contents of which are incorporated by reference in their entirety.

At the MAL1 locus, MAL2 locus, MAL3 locus, and MAL4 locus, the activators are encoded by the MAL13 gene, MAL23 gene, MAL33 gene, and MAL43 gene, respectively. Vidgren et al., *Appl. Environ. Microbiol.* 71(12): 7864-7857 (2005). Mal13p, Mal23p, Mal33p, and Mal43p are DNA binding transcriptional activators encoded by those genes required for the maltose-dependent induction of the MAL structural genes.

Other maltose-responsive promoters useful in the methods and compositions provided herein can be derived from the regulatory network for the maltose/maltodextrin metabolism system of *E. coli*. The malT nucleic acid encodes MalT, a positive regulator of four maltose-responsive promoters ($P_{PQ}$, $P_{EFG}$, $P_{KBM}$, and $P_S$). The combination of malT and a mal promoter creates a tightly regulated expression system that has been shown to work as a strong promoter induced by the addition of maltose. See, e.g., Schleif, "Two Positively Regulated Systems, ara and mal," pp. 1300-1309 in *Escherichia coli and Salmonella Cellular and Molecular Biology*, Second Edition, Neidhardt et al., eds., ASM Press, Washington, D.C., 1996; and Boos, W. and Shuman, H., "Maltose/Maltodextrin System of *Escherichia coli*: Transport, Metabolism and Regulation," *Microbiology and Molecular Biology Reviews*, 62(1):204-229 (1998)), the contents of which are hereby incorporated by reference in their entireties.

Other maltose-responsive promoters useful in the methods and compositions provided herein include those in Berkner et al., "Inducible and constitutive promoters for genetic systems in *Sulfolobus acidocaldarious*," *Extremophiles* 14:249-259 (2010); and U.S. Pat. No. 5,824,545.

6.3.2. Synthetic Maltose-Responsive Promoters

In certain embodiments, useful maltose-responsive promoters comprise synthetic maltose-responsive promoters. In certain situations, a gene operably linked to a native, unmodified maltose-responsive promoter (e.g., pMAL32) may express the gene product at a low level even in the absence of maltose. In addition, expression of a gene operably linked to a native maltose-responsive promoter can be up-regulated when cells are cultured under a condition that promotes a low cell growth rate in the absence of maltose. See Example 7.14 and FIGS. 14A and 14B.

Thus, provided herein are synthetic maltose-responsive promoters which can reduce the leaky expression of a gene product in the absence or in sufficiently low amounts of maltose in comparison to the native, un-modified maltose-responsive promoters. In certain embodiments, the synthetic maltose-responsive promoters are constructed using galactose-inducible pGAL promoters by removing at least one or all of Gal4p binding sites and inserting one or more binding sites for the Mal operon activator (i.e., Mal transcriptional activator). For example, all 4 Gal4p binding sites may be removed from pGAL1 promoter, and various copy numbers of binding sites for the Mal operon activator (e.g., binding sites for Malx3p as shown in FIG. 13, which includes, for example, Mal13p, Mal23p, Mal33p, Mal43p, and Mal63p) may be inserted into the modified pGAL1 promoter. In certain embodiments, a single binding site for the Mal transcriptional activator may be inserted into the modified pGAL promoters. In certain embodiments, 2, 3, 4, 5, 6, 7, 8, 9, 10, or more binding sites for the Mal transcriptional activator may be inserted into the modified pGAL promoters. These modified pGAL promoters with Gal4p binding sites removed and binding sites for the Mal transcriptional activator inserted are herein referred to as pGMAL promoters.

In certain embodiments, pGAL1_GAL10 promoter (SEQ ID NO: 82) may be used as a background promoter to produce pGMAL promoters. In some embodiments, pGAL1 promoter is derived from the divergent GAL1 GAL10 promoter (Johnston & Davis, *Mol. Cell Biol.* 4(8): 1440-1448 (1984)). The pGAL1_GAL10 promoter includes four Gal4p binding sites (at position 216 to 232, at position 235 to 251, at position 253 to 269, and at position 317 and 333 of SEQ ID NO: 82). All of these Gal4p binding sites can be removed from the pGAL1_GAL10 promoter, and one or more Mal transcriptional activator binding sites can be added to generate additional synthetic maltose-responsive promoters. These synthetic promoters originating from the pGAL1_GAL10 promoter include, for example, pGMAL_v5 (SEQ ID NO: 35), pGMAL_v6 (SEQ ID NO: 36), pGMAL_v7 (SEQ ID NO: 37), pGMAL_v9 (SEQ ID NO: 38), pGMAL_v10 (SEQ ID NO: 39), pGMAL_v11 (SEQ ID NO: 40), pGMAL_v12 (SEQ ID NO: 41), pGMAL_v13 (SEQ ID NO: 42), pGMAL_v14 (SEQ ID NO: 43), pGMAL_v15 (SEQ ID NO: 44), pGMAL_v16 (SEQ ID NO: 45), pGMAL_v17 (SEQ ID NO: 46), and pGMAL_v18 (SEQ ID NO: 47).

In certain embodiments, pGAL2 promoter (SEQ ID NO: 83) may be used as a background promoter to produce pGMAL promoters. pGAL2 promoter includes four Gal4p binding sites and two overlapping Gal4p binding sites (at position 230 to 246, at position 344 to 360, at position 363 to 379, at position 427 to 443, and position 432 to 448 of SEQ ID NO: 83). At least one or all of these Gal4p binding sites may be removed from the pGAL2 promoter, and one or more Mal transcriptional activator binding sites may be added to generate additional synthetic maltose-responsive promoters. These synthetic promoters originating from the pGAL2 promoter include, for example, pG2MAL_v1 (SEQ ID NO: 48), pG2MAL_v2 (SEQ ID NO: 49), pG2MAL_v3 (SEQ ID NO: 50), pG2MAL_v5 (SEQ ID NO: 51), pG2MAL_v6 (SEQ ID NO: 52), pG2MAL_v7 (SEQ ID NO: 53), pG2MAL_v8 (SEQ ID NO: 54), pG2MAL_v9 (SEQ ID NO: 55), and pG2MAL_v10 (SEQ ID NO: 56).

In certain embodiments, pGAL7 promoter (SEQ ID NO: 79) may be used as a background promoter to produce pGMAL promoters. The pGAL7 promoter includes two Gal4p binding sites (at position 471 to 487 and at position 558 to 574 of SEQ ID NO: 79). At least one or all of these Gal4p binding sites may be removed from pGAL7 promoter, and one or more Mal transcriptional activator binding sites may be added to generate additional synthetic maltose-responsive promoters. These synthetic promoters originating from the pGAL7 promoter include, for example, pG7MAL_v2 (SEQ ID NO: 57), pG7MAL_v4 (SEQ ID NO: 58), pG7MAL_v6 (SEQ ID NO: 59), pG7MAL_v8 (SEQ ID NO: 60), and pG7MAL_v9 (SEQ ID NO: 61).

In certain embodiments, a hybrid promoter can be constructed by combining sequences from two or more of pGAL1, pGAL2, and pGAL7. From the hybrid promoters, at least one or all of Gal4p binding sites may be removed, and one or more MAL transcriptional activator binding sites may be added to generate additional synthetic maltose-responsive promoters. These synthetic promoters originating from the hybrid promoters include, for example, pG172 MAL_v13 (SEQ ID NO: 62), pG271 MAL_v12 (SEQ ID NO: 63), pG721 MAL_v11 (SEQ ID NO: 64), and pG712 MAL_v14 (SEQ ID NO: 65).

In certain embodiments, pGCY1, pGAL80, or other pGAL promoters may be used as background promoters to produce pGMAL promoters. These promoter sequences and the Gal4p binding sites are well-known. See, e.g., *Saccharomyces* genome database (world wide-web address:yeastgenome.org). The nucleotide sequences for the Gal4p binding sites are also well-known, and can be removed and substituted with MAL transcriptional activator binding sites.

In certain embodiments, a synthetic promoter may comprise a portion of pGMAL promoter sequences disclosed herein, which portion retains the promoter function, instead of the entire sequences associated with SEQ ID numbers. In some embodiments, some of the nucleotide bases in the middle or at the end of the disclosed promoter sequences may not be necessary for their promoter function. Thus, in certain embodiments, synthetic maltose-responsive promoters may generally include at least about 200, 250, 300, 350, 400, 450, 475, 500, 525, 550, 575, 600, 625, 650 nucleotides or more of specific sequences disclosed herein which retain the promoter function. For example, the portions of these sequences may include transcriptional activator and other transcriptional regulator binding sites to retain the promoter function. In certain embodiments, the synthetic maltose-responsive promoter sequences disclosed herein may be further modified by, for example, adding or removing the number of binding sites for the MAL transcriptional activator. In other embodiments, the synthetic maltose-responsive promoter sequences disclosed herein may further comprise additional sequences, such as a linker sequence at the N' terminal and/or C' terminal of a promoter sequence. For example, a linker sequence of 24 or 36 nucleotides may be added to the pGMAL sequences provided herein to provide an adequate space between the promoter sequence and the coding sequence.

In certain embodiments, synthetic promoters or naturally derived promoters do not need to have the exact sequences disclosed herein to retain their promoter function in genetically modified host cells. While many promoter sequences are highly conserved, there are variations in sequences among strains or species even for the same promoter. Thus, in certain embodiments, provided herein are synthetic or naturally derived promoter which have at least about 70%, 75%, 80%, 85%, 90%, 95%, 96%, 97%, 98%, or 99% sequence identity to promoter sequences disclosed herein.

Furthermore, as shown in FIGS. 14A and 14B, each of these pGMAL promoters has different promoter strengths and characteristics. For example, pGMAL_v15, when induced with maltose, is comparable in strength as native promoter pMAL32. In another example, pGMAL_v12 is a stronger promoter than pGMAL_v15 and is comparable in strength to promoter pTDH3. Depending on the promoter strength desired for gene expression, any suitable pGMAL promoter may be selected for the compositions and methods provided herein.

In certain embodiments, promoters other than pGAL promoters may be used as background promoters to generate synthetic maltose-responsive promoters. The selection of a background promoter may depend on the selection of a host cell, an expression level desired, and the like. Thus, in some embodiment, for any selected background promoter, its endogenous transcriptional activator binding sites may be removed, and the binding sites for the MAL transcriptional activator can be inserted. For example, the MAL transcriptional activator binding site sequences from bidirectional promoter pMAL12 can be incorporated into a background promoter (with native transcriptional activator binding sites removed) to generate synthetic maltose-responsive promoters. Exemplary sequences of the four MAL transcriptional activator binding sites from pMAL12 include the following 11 or 12 base pair nucleotide sequences and their reverse complements:

```
pMAL12_1:
                                    (SEQ ID NO: 97)
GATAATATTTC;

pMAL12_2:
                                    (SEQ ID NO: 98)
GAAAATTTCGC;

pMAL12_3:
                                    (SEQ ID NO: 99)
GTTAAAGTTTAC;
```

```
pMAL12_4:
                                       (SEQ ID NO: 100)
GAAATTTTCGC;

pMAL12_1r:
                                       (SEQ ID NO: 101)
GAAATATTATC;

pMAL12_2r:
                                       (SEQ ID NO: 102)
GCGAAATTTTC;

pMAL12_3r:
                                       (SEQ ID NO: 103)
GTAAACTTTAAC;
and pMAL12_4r:
                                       (SEQ ID NO: 104)
GCGAAAATTTC.
```

In certain embodiments, the MAL transcriptional activator binding site sequences from bidirectional promoter pMAL32 can be incorporated into a background promoter (with native transcriptional activator binding sites removed) to generate synthetic maltose-responsive promoters. Exemplary sequences of the MAL transcriptional activator binding sites from pMAL32 include the following 11 or 12 base pair nucleotide sequences and their reverse complements:

```
pMAL32_1:
                                       (SEQ ID NO: 105)
TATAATATTTC;

pMAL32_2:
           (same as pMAL12_2; SEQ ID NO: 98)
GAAAATTTCG;

pMAL32_3:
                                       (SEQ ID NO: 106)
GTTTAAGTTTAC;

pMAL32_4:
                                       (SEQ ID NO: 107)
GAAGTTTTCGC;

pMAL32_1r:
                                       (SEQ ID NO: 108)
GAAATATTATA;

pMAL32_2r:
       (same as 2nd in pMAL12_2r; SEQ ID NO: 102)
GCGAAATTTTC;

pMAL32_3r:
                                       (SEQ ID NO: 109)
GTAAACTTAAAC;
and pMAL32_4r:
                                       (SEQ ID NO: 110)
GCGAAAACTTC.
```

These short 11 or 12 base pair fragments, representing MAL transcriptional activator binding sites, share at least about 45%, 50%, 55%, 60%, 65%, 70%, 75%, 80%, 85%, or 90% sequence identity to one another. Furthermore, as shown in FIG. 13B, these short 11 or 12 base pair fragments, representing MAL transcriptional activator binding sites, comprise one of the following sequence motifs:
DAADDTTTH, DWADDTTTH, DAADDTTWH, or DWADDTTWH.
The symbols of the sequence motifs have the following meanings:
A=nucleotide adenine;
T=nucleotide thymine;
W=nucleotide A (adenine) or T (thymine);
D=nucleotide G (guanine) or A (adenine) or T (thymine); and
H=nucleotide A (adenine) or C (cytosine) or T (thymine).

Thus, in some embodiments, a synthetic maltose-responsive promoter comprises a sequence motif selected from the group consisting of DAADDTTTH, DWADDTTTH, DAADDTTWH, DWADDTTWH, and a combination thereof. In some embodiments, any one or combination of these sequence motifs are incorporated into a background promoter with its native transcriptional activator binding sites removed.

In some embodiments, a synthetic maltose-responsive promoter comprises a core promoter, and one or more MAL transcriptional activator binding sites. As used herein, the core promoter refers to the minimal portion of the promoter required to properly initiate transcription of a selected DNA sequence to which it is operably linked. The term "core promoter" refers to a promoter element providing basal transcription. Optionally it comprises a TATA box or a TATA-like box and complexes with an RNA polymerase. In some embodiments, the synthetic maltose-responsive promoter comprises one or more copies of MAL transcriptional activator binding sites described herein. In some embodiments, the MAL transcriptional activator binding sites comprise a sequence motif selected from the group consisting of DAADDTTTH, DWADDTTTH, DAADDTTWH, DWADDTTWH, and a combination thereof.

In some embodiments, the promoter activity of a synthetic maltose-responsive promoter during an un-induced condition (e.g., a host cell being cultured in a culture medium without maltose) is less than the promoter activity of a native maltose-responsive promoter from which the one or more MAL transcriptional activator binding sites are derived (e.g., pMAL31, pMAL11, pMAL12, and the like). For example, when a host cell comprising a reporter gene (e.g., GFP) operably linked to a synthetic maltose-responsive promoter is cultured in a culture medium lacking maltose, the reporter gene expression under the synthetic maltose-responsive promoter under the un-induced state is at least about 10%, 20%, 30%, 40%, 50%, 60%, 70%, 80%, 90%, 100%, 150%, 200%, 250%, 300% or more, less as compared to a reporter gene operably linked to a native maltose-responsive promoter from which the one or more MAL transcriptional activator binding sites are derived.

The MAL transcriptional activator binding site sequences described herein are merely exemplary, and the MAL transcriptional activator binding sites from other maltose-responsive promoters may be inserted into synthetic maltose-responsive promoters. In some embodiments, synthetic promoters may comprise one or any combination of the MAL transcriptional activator binding sites inserted therein. In some embodiments, 2, 3, 4, 5, 6, 7, 8, 9, 10, or more binding sites for the MAL transcriptional activator may be inserted into the synthetic promoters. In general, the higher copy number of MAL transcriptional activator binding sites in synthetic promoters increases the promoter strengths.

6.3.3. Use of Maltose-Responsive Promoters in Expression of Heterologous Nucleic Acids and in Production of Non-Catabolic Compounds While maltose-responsive promoters described herein can be used together with maltose dependent degrons as described in Section 6.2.6 above, in some embodiments, maltose-responsive promoters can be used without maltose dependent degrons to promote transcription of any operably linked gene in the presence of maltose. For example, any genes that are known to promote cell growth during the cell biomass build phase may be operably linked to a synthetic maltose-responsive promoter so that maltose in a culture medium during this phase can activate transcription of these genes. During the production stage, the maltose can be removed from the culture medium so that expression of these cell growth promoting genes operably linked to a synthetic maltose-responsive promoter can be down-regulated to divert cells' resources towards the production of desired products. Depending on the level of gene products desired, a suitable maltose-responsive promoter with an appropriate promoter strength may be selected in the compositions and methods provided herein.

Thus, provided herein are heterologous nucleic acids encoding a gene of interest operably linked to a maltose-responsive promoter or a portion thereof that retains the promoter function. In certain embodiments, a maltose-responsive promoter is a synthetic maltose-responsive promoter, which is generated from a background promoter (which is not responsive to maltose) with its native transcriptional activator binding sites replaced with MAL transcriptional activator binding sites. In certain embodiments, a synthetic maltose-responsive promoter is a pGMAL promoter. In certain embodiments, the gene of interest operably linked to a synthetic maltose-responsive promoter may include transcriptional regulators. For example, the transcriptional regulators may include Gal80p or Gal4p. In certain embodiments, the gene of interest operably linked to a maltose-responsive promoter may include genes which contribute to the cell growth rate during the biomass build phase of the fermentation process. In certain embodiments, the gene of interest operably linked to a maltose-responsive promoter includes genes that encode pathway enzymes. The application of synthetic maltose-responsive promoters provided herein is not limited to a fermentation environment, and may be used as an inducible promoter to regulate any gene expression.

In some embodiments, a maltose-responsive promoter can be utilized in a fermentation environment in the methods for making the heterologous non-catabolic compound. The methods provided herein utilize genetically modified host cells that comprise a heterologous nucleic acid encoding one or more enzymes of an enzymatic pathway for making the heterologous non-catabolic compound. In some embodiments, expression of the one or more enzymes is under direct control of a maltose-responsive promoter described herein. That is, the one or more heterologous nucleic acid sequences encoding the one or more enzymes of the enzymatic pathway are each operably linked to (i.e., is positioned 3' of) a maltose-responsive promoter, and the maltose-responsive promoter drives expression of each of said one or more heterologous nucleic acids in the presence of maltose.

In other embodiments, expression of the one or more enzymes of an enzymatic pathway is indirectly regulated by the maltose-responsive promoter. For example, indirect regulation of the one or more enzymes of the pathway can be achieved by operably linking a maltose-responsive promoter to a single heterologous transcriptional regulator, the expression of which, in turn, directly regulates expression of the one or more enzymes (e.g., all the members) of the pathway. The GAL regulon in yeast, described in detail above, provides an exemplary regulatory network of activators, repressors and promoters that can be utilized in combination with a maltose-responsive promoter described herein.

In some embodiments, one or more GAL4-activated promoters, e.g., pGAL1, pGAL7, pGAL10, pGCY1 and/or pGAL80 are operably linked to, and are used to drive expression of, the one or more enzymes of an enzymatic pathway for making the heterologous non-catabolic compound. In some embodiments, the host cell further comprises a nucleic acid encoding GAL4. In some embodiments, the GAL4 gene product is constitutively expressed, i.e. is under the control of a constitutive promoter. In some embodiments, the host cell further comprises a nucleic acid encoding GAL80 under the control of a maltose-responsive promoter described herein, and expression of the GAL80 gene product is induced in the presence of maltose. Gal80p, in turn, interacts with Gal4p and prevents Gal4p transcriptional activity. When maltose is removed or sufficiently depleted so that GAL80 expression is no longer induced, Gal4p is relieved of repression by Gal80p, and is free to activate expression of the one or more enzymes of an enzymatic pathway for making the heterologous non-catabolic compound.

In the embodiment described above, if desired, one or more growth-promoting genes can also be placed under the control of a maltose-responsive promoter to further take advantage of a maltose switch to separate cell growth phase from production phase of the heterologous non-catabolic compound. In certain embodiments, one or more genes, which promote production of the heterologous non-catabolic compound, can be operably linked to GAL4-activated promoters such that they will be expressed together with one or more enzymes of an enzymatic pathway for making the heterologous non-catabolic compound.

In other embodiments, the native pGAL4 promoter is replaced by a heterologous nucleic acid comprising a maltose-responsive promoter. In some embodiments, the host cell comprises a heterologous nucleic acid comprising a nucleic acid that encodes Gal4p, operably linked to a heterologous nucleic acid comprising maltose-responsive promoter. In one embodiment, a maltose-responsive promoter is operably linked to a coding sequence for Gal4p, and the coding sequences of the one or more enzymes (e.g., all members) of the enzymatic pathway for making the heterologous non-catabolic compound are operably linked to GAL4-responsive promoters, such that expression of the one or more enzymes are induced in the presence of maltose. In some embodiments, the GAL4-responsive promoter is pGAL1. In some embodiments, the GAL4-responsive promoter is pGAL7. In some embodiments, the GAL4-responsive promoter is pGAL10. In some embodiments, the GAL4-responsive promoter is pGCY1. In some embodiments, the GAL4-responsive promoter is pGAL80.

Detailed description of methods for production of non-catabolic compounds using maltose-responsive promoters are described in Section 6.5 and also in U.S. Patent Publication No. 2015-0299713 and WO2015/020649, which are herein incorporated by reference in its entirety for all purposes. In the compositions and methods described herein, any suitable maltose-responsive promoter, either synthetic or native promoters, can be used to express any gene of interest and/or for the production of non-catabolic compounds.

6.4 Repressing and Non-repressing Amounts of Maltose

Maltose is a disaccharide sugar formed from 2 glucose molecules, as shown below. It has the chemical formula, $C_{12}H_{22}O_{11}$, and a molecular weight of 343 g/mol.

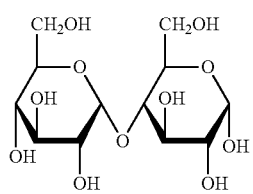

In certain embodiments, in addition or alternative to maltose (shown above and isomers thereof), other substrates which function similarly to maltose in the present methods may be used to stabilize maltose dependent degrons and/or to induce a maltose-responsive promoter. For example, substrates that specifically bind to MBP, MBP mutants, and maltose dependent degrons and that are suitable as their ligands can be selected from the group consisting of maltose, maltodextrins, macromolecular alpha (1→4) linked glucans (e.g., maltotriose), or a combination thereof. In certain embodiments, suitable analogs or derivatives of these substrates (i.e., maltose, maltodextrins, and macromolecular alpha (1→4) linked glucans) may also be used to stabilize maltose dependent degrons (or to induce maltose-responsive promoter). In the present invention, the terms "analog" or "derivative" are used interchangeably to mean a chemical substance that is related structurally and functionally to another substance, in this instance, maintaining the ability to specifically bind to maltose binding proteins and maltose dependent degrons, to stabilize maltose dependent degrons, and/or to induce a maltose-responsive promoter. In some embodiments, unlike maltose, they are not metabolized by host cells. Examples of maltose analogs and derivatives include maltose derivatives, such as methyl-α-maltoside and 5-thiomaltose. Additional examples of maltose analogs and derivatives include maltoheptaose (β-cyclodextrin), maltitol, maltohexaose, maltotetraitol, maltohexaitol, maltohexanoic acid, maltotetraose, and the like. These and other substrates that specifically bind to MBP, MBP mutants, and maltose dependent degrons, that stabilize maltose dependent degrons, and/or that induce a maltose-responsive promoter are collectively referred to as a "maltose based inducer."

While maltose is described as a ligand for MBP mutants and maltose dependent degrons and as an inducer for maltose-responsive promoters throughout the present disclosure, any suitable maltose based inducer (e.g., analogs or derivatives of maltose, maltodextrins, and macromolecular alpha (1→4) linked glucans) may be used instead of maltose in certain embodiments. Thus, any disclosure related to maltose described herein also apply to other maltose based inducers. Similarly, any discussions related to repressing and non-repressing amounts of maltose apply to other maltose based inducers.

In some embodiments, an "inducing" amount of maltose is an amount of maltose sufficient to induce a desired high expression level of a coding sequence operably linked to a maltose-responsive promoter and/or retain stability of a maltose dependent degron and/or fusion protein. In certain embodiments, an "inducing" amount of maltose is a sufficient amount of maltose that allows a maltose dependent degron to be "in contact" with maltose or that a maltose dependent degron (or a fusion protein thereof) is stabilized. In certain embodiments, an "inducing" amount of maltose is an amount of maltose which activates a maltose-responsive promoter or increases the activity of a maltose-responsive promoter compared to the promoter activity in the absence of maltose. In some embodiments, a "non-inducing" amount of maltose is an amount below which expression of a coding sequence operably linked to a maltose-responsive promoter is not induced or reduced compared to when an "inducing" amount of maltose is present in a culture medium. In certain embodiments, a "non-inducing" amount of maltose is an amount of maltose which reduces the activity of a maltose-responsive promoter and/or reduces stability of a maltose dependent degron (and a fusion protein thereof) in comparison to when an "inducing" amount of maltose is present in a culture medium.

The "inducing" amount and "non-inducing" amount of maltose for use in the methods provided herein can be determined for any genetically modified host cell capable of producing a heterologous non-catabolic compound as described above. In some embodiments, a non-inducing amount of maltose is determined by performing a gene expression curve in the presence of increasing amounts of maltose in the culture medium to be used in the fermentation process, i.e., a maltose titration. For example, a population of genetically modified host cells may be divided into a plurality of subpopulations and cultured in parallel, wherein each subpopulation is grown in culture media comprising a different, e.g., increasing amount of maltose (including no maltose), and reporter gene expression or non-catabolic compound production is assayed after a defined period of time.

In some embodiments, where the maltose-responsive promoter (and/or a maltose dependent degron) is wired to effect an "off" state of non-catabolic compound production in the presence of maltose, the maltose titration comprises at least two concentrations of maltose whereby non-catabolic compound production of the host cells is plateaued at a minimum, that is, where no further decrease in production of the compound is observed with an increase in maltose concentration. In some embodiments, the "repressing" amount of maltose is at least the minimum amount of maltose at which non-catabolic compound production of the host cells is plateaued at its minimum (e.g., at about zero). This amount can also be referred to as a "saturating" or "optimal" amount of maltose for repression of non-catabolic compound production for the particular host cell. In some such embodiments, the "repressing" amount of maltose can include any concentration of maltose at which non-catabolic compound production has been decreased relative to an "on" state, even where there is a low level of compound production. In some embodiments, the "non-repressing" amount of maltose, in this configuration of the switch, is any amount of maltose below the "repressing" amount of maltose. In some embodiments, the non-repressing amount of maltose is at least about 2, 3, 4, 5, 6, 7, 8, 9, 10, 20, 30, 40, 50, 60, 70, 80, 90, 100 or greater than about 100 times less than the repressing amount of maltose. In a particular embodiment, the non-repressing amount of maltose is less than about 0.8% (w/v) of the culture medium. In another particular embodiment, the non-repressing amount of maltose is about 0% (w/v) of the culture medium.

In a specific embodiment, the repressing amount of maltose is the optimal or saturating amount for a given host cell, as described above, and the non-repressing amount is no maltose. In another specific embodiment, the repressing amount of maltose is at least about 0.25%, and the non-repressing amount is no maltose. In another specific embodiment, the repressing amount of maltose is an amount of maltose from about 0.25% to 3%, and the non-repressing amount is no maltose. In another specific embodiment, the repressing amount of maltose is in an amount of maltose from about 0.5% to 1%, and the non-repressing amount is no maltose. In another specific embodiment, the repressing amount of maltose is at least about 3%, and the limiting amount is no maltose.

In some embodiments where the maltose-responsive promoter (and/or a maltose dependent degron) is wired to effect an "off" state of non-catabolic compound production in the presence of maltose, the repressing amount of maltose in the culture medium is at least about 0.1% (weight maltose per volume of culture medium). In some embodiments, the repressing amount of maltose in the culture medium is at least about 0.25%. In some embodiments, the repressing amount of maltose in the culture medium is at least about 0.5%. In some embodiments, the repressing amount of maltose in the culture medium is at least about 0.75%. In some embodiments, the repressing amount of maltose in the culture medium is at least about 1.0%. In some embodiments, the repressing amount of maltose in the culture medium is at least about 1.25%. In some embodiments, the repressing amount of maltose in the culture medium is at least about 1.5%. In some embodiments, the repressing amount of maltose in the culture medium is at least about 1.75%. In some embodiments, the repressing amount of maltose in the culture medium is at least about 2.0%. In some embodiments, the repressing amount of maltose in the culture medium is at least about 2.25%. In some embodiments, the repressing amount of maltose in the culture medium is at least about 2.5%. In some embodiments, the repressing amount of maltose in the culture medium is at least about 2.75%. In some embodiments, the repressing amount of maltose in the culture medium is at least about 3.0%. In some embodiments, the repressing amount of maltose in the culture medium is at least about 3.25%. In some embodiments, the repressing amount of maltose in the culture medium is at least about 3.5%. In some embodiments, the repressing amount of maltose in the culture medium is at least about 3.75%. In some embodiments, the repressing amount of maltose in the culture medium is at least about 4.0%. In some embodiments, the repressing amount of maltose in the culture medium is at least about 4.25%. In some embodiments, the repressing amount of maltose in the culture medium is at least about 4.5%. In some embodiments, the repressing amount of maltose in the culture medium is at least about 4.75%. In some embodiments, the repressing amount of maltose in the culture medium is at least about 5.0%. In some embodiments, the repressing amount of maltose in the culture medium is between about 5% and 50%. In some embodiments, the repressing amount of maltose in the culture medium is about 5%, 10%, 15%, 20%, 25%, 30%, 35%, 40% 45% or about 50%.

In some embodiments, the non-repressing amount of maltose is an amount that is at least about 2-fold, 10-fold, 100-fold, 1000-fold, 10,000-fold or about 100,000-fold less than a repressing amount of maltose as determined according to the methods described above. In some embodiments, the non-repressing amount of maltose is an amount that is at least about 2-fold, 10-fold, 100-fold, 1000-fold, 10,000-fold or 100,000-fold less than the saturating amount of maltose as determined according to the methods described above. In some embodiments, the non-repressing amount of maltose is an amount that is less than about 50%, less than about 20%, less than about 10%, less than about 1%, less than about 0.5%, less than about 0.2%, less than about 0.1%, less than about 0.01%, or less than about 0.001% of a repressing amount of maltose as determined according to the methods described above. In some embodiments, the non-repressing amount of maltose is an amount that is less than about 50%, less than about 20%, less than about 10%, less than about 1%, less than about 0.1%, less than about 0.01%, or less than about 0.001% of the saturating amount of maltose as determined according to the methods described above. In a specific embodiment, the non-repressing amount of maltose is about 0 mg/L (0%), i.e., no maltose. Thus, in this specific embodiment, the host cells are grown during the production stage in a cell culture medium that comprises no external source of maltose.

In some embodiments, where the maltose-responsive promoter (and/or a maltose dependent degron) is wired to effect an "on" state of non-catabolic compound production in the presence of maltose, the maltose titration comprises at least two concentrations of maltose whereby non-catabolic compound production of the host cells is plateaued at a maximum, that is, where no further increase in production of the compound is observed with an increase in maltose concentration. In some embodiments, the "non-repressing" amount of maltose is at least the minimum amount of maltose at which non-catabolic compound production of the host cells is plateaued at its maximum. This amount can also be referred to as a "saturating" or "optimal" amount of maltose for induction of non-catabolic compound production for the particular host cell, in this configuration of the switch. In some such embodiments, the "inducing" amount or "non-repressing" amount of maltose can include any concentration of maltose at which non-catabolic compound production has been increased relative to an "off" state, even where compound production is suboptimal. In some embodiments, the "non-inducing" or "repressing" amount of maltose, in this configuration of the switch, is any amount of maltose below the "inducing" or "non-repressing" amount of maltose. In some embodiments, the non-inducing amount or repressing of maltose is at least about 2, 3, 4, 5, 6, 7, 8, 9, 10, 20, 30, 40, 50, 60, 70, 80, 90, 100 or greater than 100 times less than the inducing amount or the non-repressing amount of maltose. In a particular embodiment, the non-inducing amount of maltose is less than about 0.8% (w/v) of the culture medium. In another particular embodiment, the non-inducing amount of maltose is about 0% (w/v) of the culture medium.

In a specific embodiment, the inducing amount of maltose is the optimal or saturating amount for a given host cell, as described above, and the non-inducing amount is no maltose. In another specific embodiment, the inducing amount of maltose is at least about 0.25%, and the non-inducing amount is no maltose. In another specific embodiment, the inducing amount of maltose is an amount of maltose from about 0.25% to 3%, and the non-inducing amount is no maltose. In another specific embodiment, the inducing amount of maltose is an amount of maltose from about 0.5% to 1%, and the non-inducing amount is no maltose. In another specific embodiment, the inducing amount of maltose is at least about 3%, and the limiting amount is no maltose.

In some embodiments where the maltose-responsive promoter (and/or a maltose dependent degron) is wired to effect an "on" state of non-catabolic compound production in the presence of maltose, the inducing amount of maltose in the culture medium is at least about 0.1% (weight maltose per volume of culture medium). In some embodiments, the inducing amount of maltose in the culture medium is at least about 0.25%. In some embodiments, the inducing amount of maltose in the culture medium is at least about 0.5%. In some embodiments, the inducing amount of maltose in the culture medium is at least about 0.75%. In some embodiments, the inducing amount of maltose in the culture medium is at least about 1.0%. In some embodiments, the inducing amount of maltose in the culture medium is at least about 1.25%. In some embodiments, the inducing amount of maltose in the culture medium is at least about 1.5%. In some embodiments, the inducing amount of maltose in the culture medium is at least about 1.75%. In some embodiments, the inducing amount of maltose in the culture medium is at least about 2.0%. In some embodiments, the inducing amount of maltose in the culture medium is at least about 2.25%. In some embodiments, the inducing amount of maltose in the culture medium is at least about 2.5%. In some embodiments, the inducing amount of maltose in the culture medium is at least about 2.75%. In some embodiments, the inducing amount of maltose in the culture medium is at least about 3.0%. In some embodiments, the inducing amount of maltose in the culture medium is at least about 3.25%. In some embodiments, the inducing amount of maltose in the culture medium is at least about 3.5%. In some embodiments, the inducing amount of maltose in the culture medium is at least about 3.75%. In some embodiments, the inducing amount of maltose in the culture medium is at least about 4.0%. In some embodiments, the inducing amount of maltose in the culture medium is at least about 4.25%. In some embodiments, the inducing amount of maltose in the culture medium is at least about 4.5%. In some embodiments, the inducing amount of maltose in the culture medium is at least about 4.75%. In some embodiments, the inducing amount of maltose in the culture medium is at least about 5.0%. In some embodiments, the inducing amount of maltose in the culture medium is between about 5% and 50%. In some embodiments, the inducing amount of maltose in the culture medium is about 5%, 10%, 15%, 20%, 25%, 30%, 35%, 40% 45% or about 50%.

In some embodiments where the maltose-responsive promoter (and/or a maltose dependent degron) is wired to effect an "on" state of non-catabolic compound production in the presence of maltose, the repressing amount of maltose is an amount that is at least about 2-fold, 10-fold, 100-fold, 1000-fold, 10,000-fold or 100,000-fold less than a non-repressing amount of maltose as determined according to the methods described above. In some embodiments, the repressing amount of maltose is an amount that is at least about 2-fold, 10-fold, 100-fold, 1000-fold, 10,000-fold or about 100,000-fold less than the saturating amount of maltose as determined according to the methods described above. In some embodiments, the repressing amount of maltose is an amount that is less than about 50%, less than about 20%, less than about 10%, less than about 1%, less than about 0.5%, less than about 0.2%, less than about 0.1%, less than about 0.01%, or less than about 0.001% of a non-repressing amount of maltose as determined according to the methods described above. In some embodiments, the repressing amount of maltose is an amount that is less than about 50%, less than about 20%, less than about 10%, less than about 1%, less than about 0.1%, less than about 0.01%, or less than about 0.001% of the saturating amount of maltose as determined according to the methods described above. In a specific embodiment, the repressing amount of maltose is about 0 mg/L (0%), i.e., no maltose. Thus, in this specific embodiment, the host cells are grown during the build stage in a cell culture medium that comprises no external source of maltose.

While "inducing" amount, "non-inducing" amount, "repressing" amount, and "non-repressing" amount of maltose are mainly discussed in the context of methods of producing non-catabolic compounds, these terms and their meanings are applicable to any compositions and methods provided herein. For example, an "inducing" amount of maltose includes a sufficient amount of maltose to induce stability of a fusion protein comprising a protein of interest fused in frame to a maltose dependent degron. In another example, a "non-inducing" amount of maltose includes sufficiently low amounts of maltose or no maltose that destabilizes the fusion protein.

6.5 Production of Non-Catabolic Compounds using Maltose Dependent Degrons and/or Maltose-Responsive Promoters In some embodiments of the fermentation methods provided herein, utilizing a maltose-responsive promoter and/or a maltose dependent degron in combination with manipulation of maltose conditions, the production of the non-catabolic compound during the build stage (step (a) of the methods described above) is less than about 50, 40, 30, 20 or 10% of the maximum non-catabolic compound production of the genetically modified host cell, e.g., the amount of non-catabolic compound production when the host cell is cultured during the production stage (step (b) of the methods described above).

The periods of time for during which the build stage and production stage of the fermentation process are carried out can vary, and will depend on factors such as the growth rates of the host cell, the intrinsic rate of growth of the host cell; and other culture conditions such as the pH, temperature, depending on the specific requirements of the host cell, the fermentation, and the process. However, any duration of the build stage is expected to result in some benefit to the final productivity of the fermentation, since some amount of the negative selective pressure associated with non-catabolic compound production is relieved in the "off" state.

In some embodiments, the build stage is carried out for a period of time sufficient to produce an amount of cellular biomass that can support production of the non-catabolic compound during the production stage. In some embodiments, the build stage is carried out for a period of time sufficient for the population present at the time of inoculation to undergo a plurality of doublings until a desired cell density is reached. In some embodiments, the build stage is carried out for a period of time sufficient for the host cell population to reach a cell density ($OD_{600}$) of between about 0.01 and 400 in the fermentation vessel or container in which the build stage is being carried out. In some embodiments, the build stage is carried out until an $OD_{600}$ of at least 0.01 is reached. In some embodiments, the build stage is carried out until an $OD_{600}$ of at least about 0.1 is reached. In some embodiments, the build stage is carried out until an $OD_{600}$ of at least about 1.0 is reached. In some embodiments, the build stage is carried out until an $OD_{600}$ of at least about 10 is reached. In some embodiments, the build stage is carried out until an $OD_{600}$ of at least about 100 is reached. In some embodiments, the build stage is carried out until an $OD_{600}$ of between about 0.01 and 100 is reached. In some embodiments, the build stage is carried out until an $OD_{600}$ of between about 0.1 and 10 is reached. In some embodiments, the build stage is carried out until an $OD_{600}$ of between about 1 and 100 is reached. In other embodiments, the build stage is carried for a period of at least about 12, 24, 36, 48, 60, 72, 84, 96 or more than about 96 hours.

In some embodiments, the production stage is carried out for a period of time sufficient to produce a desired amount of the non-catabolic compound. In some embodiments, the production stage is carried out for a period of at least about 12, 24, 36, 48, 60, 72, 84, 96 or more than about 96 hours.

In some embodiments, the production stage is carried out for a period of between about 3 and 20 days. In some embodiments, the production stage is carried for a period of about 1, 2, 3, 4, 5, 6, 7, 8, 9, 10, 11, 12, 13, 14, 15, 16, 17, 18, 19, 20 or more than about 20 days.

In some embodiment, the method of producing a non-catabolic compound comprises culturing the host cells in separate build and production culture media. For example, the method can comprise culturing the genetically modified host cell in a build stage wherein the cell is cultured under non-producing conditions to produce an inoculum, then transferring the inoculum into a second fermentation medium under conditions suitable to induce compound production, and maintaining steady state conditions in the second fermentation stage to produce a cell culture containing a non-catabolic product. In certain embodiments, maltose is present in a build culture media, and maltose is absent in the fermentation medium to produce a cell culture containing a non-catabolic product. Any residual amount of maltose transferred together with the cells in the build culture media will be metabolized by the cells during the fermentation stage.

In some embodiments, the method provided herein is sufficient for producing one or more non-catabolic compounds in an amount greater than about 10 grams per liter of fermentation medium. In some such embodiments, the non-catabolic derived compound is produced in an amount from about 10 to about 50 grams, more than about 15 grams, more than about 20 grams, more than about 25 grams, or more than about 30 grams per liter of cell culture.

In some embodiments, the method provided herein is sufficient for producing one or more non-catabolic compounds in an amount greater than about 50 milligrams per gram of dry cell weight. In some embodiments, the recombinantly produced non-catabolic compound is produced in an amount from about 50 to about 1500 milligrams, more than about 100 milligrams, more than about 150 milligrams, more than about 200 milligrams, more than about 250 milligrams, more than about 500 milligrams, more than about 750 milligrams, or more than about 1000 milligrams per gram of dry cell weight.

In some embodiments, the practice of the method provided herein results in increased production of the non-catabolic compound by the population of genetically modified host cells, compared to production resulting from a method not comprising a production stage during which the host cells are cultured under non-producing conditions. In some embodiments, the practice of the method results in the production of one or more non-catabolic compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of non-catabolic compound produced by a method not comprising a production stage during which the host cells are cultured under non-producing conditions, on a per unit volume of cell culture basis.

In some embodiments, the practice of the method results in the production of one or more non-catabolic compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of non-catabolic compound produced by a method not comprising a production stage during which the host cells are cultured under non-producing conditions, on a per unit dry cell weight basis.

In some embodiments, the practice of the method results in the production of one or more non-catabolic compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of non-catabolic compound produced by a method not comprising a production stage during which the host cells are cultured under non-producing conditions, on a per unit volume of cell culture per unit time basis.

In some embodiments, the practice of the method results in the production of one or more non-catabolic compounds in an amount that is at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 2-fold, at least about 2.5-fold, at least about 5-fold, at least about 10-fold, at least about 20-fold, at least about 30-fold, at least about 40-fold, at least about 50-fold, at least about 75-fold, at least about 100-fold, at least about 200-fold, at least about 300-fold, at least about 400-fold, at least about 500-fold, or at least about 1,000-fold, or more, higher than the amount of non-catabolic compound produced by a method not comprising a build stage during which the host cells are cultured under non-producing conditions, on a per unit dry cell weight per unit time basis.

6.6 Stabilization Constructs and Their Use in Coupling Cell Growth with Production of Non-Catabolic Compounds In another aspect, provided herein are compositions and methods which can counteract potential negative effects of spontaneous mutations on the production of heterologous non-catabolic compounds by genetically modified host cells. As described above, the production of non-catabolic compounds heterologous to genetically modified host cells typically requires a net input of ATP, NADPH, and carbon, often with large amounts of oxygen supplied to help balance the redox of the system. Such an environment makes evolution towards lower product, higher biomass yielding genotypes more favorable, and mutations arise spontaneously in host cells including loss of production mutations. Thus, mutated host cells with reduced product yields have a "fitness advantage" compared to original, high-product-yielding parental cells, because more of the mutated host cells' metabolic resources go towards building biomass. This results in the mutant, low-product-yielding or no-productyielding cells (referred to as "broken strains") with a higher growth rate outgrowing the original, high-product-yielding parental cells with a slower growth rate. The differential growth rates of these cells, in turn, cause the mutant, low-product-yielding or no-product-yielding mutant cells eventually taking over the population of cells in a fermentation tank (a process called "strain degeneration"), and a substantially reduced product yield over time.

To stabilize production of heterologous non-catabolic compounds, in certain embodiments, expression of a nucleic acid encoding a cell-growth-affecting protein is coupled to the production of heterologous non-catabolic compounds. For example, a nucleic acid encoding a cell-growth-affecting protein and one or more nucleic acids encoding enzymes of a biosynthetic pathway for producing a non-catabolic compound are operably linked to their respective promoters, which are co-regulated by same transcriptional regulator(s). In other words, these nucleic acids, which are not normally regulated by the same transcriptional regulator(s), are co-regulated as a regulon. As a result, any spontaneous mutation that negatively impacts expression or stability of the transcriptional regulator(s) will negatively impact expression of all nucleic acids in the regulon. When expression of the cell-growth-affecting gene in the regulon is reduced due to a spontaneous mutation, it will result in a growth disadvantage for these mutated cells compared to high-product-yielding parental cells. Thus, expression of the regulon, co-regulated by the same transcriptional regulator(s), is more stable to mutations which might otherwise reduce production of heterologous non-catabolic compounds.

Because of its stabilizing effect on the production of non-catabolic compounds, the phrase "stabilization construct" is used herein to refer to a nucleic acid encoding a cell-growth-affecting protein, which is operably linked to a promoter regulated by a common transcriptional regulator of the regulon of interest (i.e., a group of genes of interest that are regulated as a unit). In addition, the term "heterologous nucleic acid encoding a cell-growth-affecting protein" is used in certain embodiments to refer that a nucleic acid encoding a cell-growth-affecting protein is operably linked to a heterologous promoter instead of its endogenous promoter. Similarly, in certain embodiments, the term "heterologous nucleic acid encoding an enzyme of a biosynthetic pathway" is used to refer that a nucleic acid encoding the enzyme is operably linked to a heterologous promoter instead of its endogenous promoter.

In certain embodiments, a promoter responsive to a common transcriptional regulator of the regulon of interest is used to drive expression of a conditional essential gene of a metabolic pathway whose end product is consumable by the genetically modified host cell. For example, a conditional essential gene may be the LYS9 gene in the biosynthetic pathway for producing lysine as an end product. In this embodiment, the conditional essential gene of a metabolic pathway is a cell-growth-affecting gene, since a functional disruption of the conditional essential gene will affect the cell growth or viability. The cell population containing such a genetic design requires a high expression of the regulon of interest (when cultured in the absence of externally added lysine), and therefore, expression of the regulon is more stable to mutations which might otherwise reduce expression of the regulon. This approach to regulon stability is compatible with host cells comprising genetic designs with a genetic switch which conditionally reduces the regulon expression when desired, for example, during the biomass build stage (e.g., the GAL regulon shown in FIG. 17). During the build stage, the resulting auxotrophy caused by reduction of the conditional essential gene expression can be compensated by providing the metabolite of interest (e.g., lysine) to the growth medium. Such an exemplary embodiment is illustrated in FIG. 17, and further described in detail below.

While the exemplary embodiment shown in FIG. 17 relates to the production of heterologous non-catabolic compounds via enzymes of a biosynthetic pathway, the compositions and methods provided herein have broader applications. For example, they can be applied to the production of any heterologous non-catabolic compounds such as proteins of interest, which are encoded by heterologous nucleic acids in host cells. Examples of heterologous proteins of interest include antibodies, vaccines, antibiotics, hormones (e.g., insulin or human growth factors), and the like. Similar to non-catabolic compounds produced via enzymes of a biosynthetic pathway, a heterologous protein of interest, when produced in high quantity, exerts stress on the host cell's metabolic resources. Such an environment can favor evolution towards mutated cells with lower product, higher biomass yielding genotypes, resulting in de-stabilized production of heterologous proteins of interest. Thus, expression of a stabilization construct provided herein can be coupled with expression of a nucleic acid encoding any heterologous protein of interest to stabilize its production during fermentation. Any discussions related to the production of non-catabolic compounds via enzymes of a biosynthetic pathway described herein also apply to the production of any heterologous proteins of interest, which are also non-catabolic compounds.

6.6.1. Common Transcriptional Regulators to Couple Cell Growth and Production of Non-Catabolic Compounds Any suitable transcriptional regulators can be used to couple the expression of a nucleic acid encoding a cell-growth-affecting protein and the production of non-catabolic compounds (or any proteins of interest). In an embodiment, transcriptional regulators of the GAL regulon can be used to couple the expression of one or more heterologous nucleic acids encoding one or more enzymes of the biosynthetic pathway and a heterologous nucleic acid encoding the cell-growth-affecting protein. In an embodiment, transcriptional activator Gal4p can be used as a common transcriptional regulator to regulate expression of all of the heterologous nucleic acids in the regulon. In another embodiment, transcriptional repressor Gal80p can be used as a common transcriptional repressor to repress expression of all of the heterologous nucleic acids in the regulon. In some embodiments, Gal4p and Gal80p are both used as common transcriptional regulators to co-regulate expression of all of the heterologous nucleic acids in the regulon.

The use of transcriptional regulators of the GAL regulon is merely exemplary, and any suitable transcriptional regulators can be used to co-regulate and control expression of the nucleic acids in the regulon. For example, a MAL transcriptional activator may be used as a common transcriptional regulator to regulate expression of nucleic acids in the regulon, where each nucleic acid is operably linked to a maltose-responsive promoter. In another example, the Pho regulon activator may be used as a common transcriptional regulator to regulate expression of nucleic acids in the regulon, when each nucleic acid is operably linked to a Pho regulon promoter.

In certain embodiments, artificial transcriptional regulators may be used to co-regulate expression of nucleic acids in the regulon. For example, LexA fused to an activation domain may be used as an artificial transcriptional regulator. A transcriptional regulator is generally composed of separable functional domains: a DNA-binding domain, which interacts with specific DNA sequences; and an activation domain, which interacts with other proteins to simulate transcription from a promoter. The separable functional domains of a transcriptional regulator enable the replacement of the DNA binding domain and the activation domain with natural and non-natural counterparts leading to the creation of artificial transcriptional regulators.

The selection of a common transcriptional regulator for coupling transcription and expression of heterologous nucleic acids encoding a cell-growth-affecting protein and one or more enzymes of a biosynthetic pathway (or any protein of interest) will depend on the selection of host cells, production levels desired for heterologous non-catabolic compounds, and other parameters associated with the genetically modified host cells.

6.6.2. Nucleic Acids Encoding a Cell-Growth-Affecting Protein Operably Linked to a Co-Regulated Promoter as a Stabilization Construct Any suitable nucleic acid encoding a cell-growth-affecting protein can be used in a stabilization construct so that its expression is coupled, via a common transcriptional regulator, to expression of one or more enzymes of a biosynthetic pathway for producing non-catabolic compounds (or any protein of interest). As used herein, the term "nucleic acid encoding a cell-growth-affecting protein" or "cell-growth-affecting gene" refers to a nucleic acid that encodes a protein which affects cell growth (e.g., growth rate, cellular biomass, or cell viability) of genetically modified host cells. Any spontaneous mutation that negatively impacts the common transcriptional regulator will also negatively impact expression of the nucleic acid encoding the cell-growth-affecting protein, and therefore cell growth. Thus, a genetically modified host cell comprising such a stabilization construct will be more stable to mutations which might otherwise reduce the production of non-catabolic compounds.

In certain embodiments, a heterologous promoter is operably linked to a nucleic acid encoding a cell-growth-affecting protein by replacing or superceding its endogenous promoter in the genome of a host cell. In other embodiments, a heterologous promoter operably linked to a nucleic acid encoding a cell-growth-affecting protein can be chromosomally integrated at a different location, while its endogenous counterpart is functionally disrupted. These methods are merely exemplary, and other suitable methods can be used to incorporate a stabilization construct into a genetically modified host cell.

6.6.2.1 Use of Previously Identified Essential Genes in a Stabilization Construct In certain embodiments, nucleic acids encoding cell-growth-affecting proteins include essential genes which are absolutely required to maintain life under optimum conditions where all nutrients are available. These essential genes can be found in the database of essential genes (DEG), which is publicly available from the website world wide web address: tubic.tju.edu.cn/deg/or world wide web address: essentialgene.org. The essential genes in the DEG database have been identified by the genome-scale gene inactivation technology. The essential genes have been identified in the genomes of various organisms, such as Arabidopsis thaliana, Aspergillus gumigatus, Caenorhabditis elegans, Danio rerio, Drosophila melanogaster, Homo sapiens, Mus musculus, Saccharomyces cerevisiae, Schizosacchromyces pombe, and the like. See, e.g., Meinke et al. (2008) Trends Plant Sci 13:483-91; Hu et al. (2007) PloS Pathog. 3:e24; Kamath et al. (2003) Nature 421:231-7; Amsterdam et al. (2004) Proc Natl Acad Sci USA, 101:12792-7; Spradling et al. (1999) Genetics 153: 135-77; Liao (2008) Proc Natl Acad Sci USA 105:1987-92; Georgi et al. (2013) PLoS genetics 9.5: e1003484; Liao (2007) Trends Genet 23:378-81; Giaever et al. (2002) Nature 418:387-91; and Kim et al. Nature Biotech 28.6 (2010) 617-623. The functions encoded by essential genes are considered a foundation of life, and therefore, are likely to be common to all cells.

There are many categories of essential genes identified in the DEG database. These include genes that are involved in protein synthesis, secretion and quality control, genes involved in cell envelope and cell division, genes involved in metabolism and biosynthesis, genes involved in DNA replication and chromosome maintenance, genes involved in RNA synthesis and degradation, and the like.

Examples of essential genes involved in protein synthesis in yeast include, but are not limited to, EFB1 (translation elongation factor 1 beta; DEG20010002; NCBI NP_009398), RRN6 (protein involved in the transcription of 35S rRNA genes; DEG20010015; NP_009539), RER2 (cis-prenyltransferase involved in dilichol synthesis; DEG20010033; NP_009556), and the like.

Examples of essential genes for secretion and quality control in yeast include, but are not limited to, EXO84 (essential protein in spliceosome assembly and exocytosis; DEG20010050; NP_009660), SEC31 (essential phosphoprotein component of the COPII coat of secretory pathway vesicles; DEG20010148; NP_010086), and the like.

Examples of essential genes for mating and cell division in yeast include, but are not limited to, MTW1 (essential component of the MIND kinetochore complex; DEG20010006; NP_009367), CDC24 (guanine nucleotide exchange factor; DEG20010008; NP_009359), CDC15 (protein kinase of the Mitotic Exit Network; DEG20010012; NP_009411; HTA2 (histone H2A; DEG20010013; NP_009552), CDC27 (DEG20010028; NP_009469); CMD1 (calmodulin; DEG20010051; NP_009667), CKS1 (cyclin-dependent protein kinase regulatory subunit and adaptor; DEG20010055; NP_009693), MEC1 (genome integrity checkpoint protein; DEG20010056; NP_009694), and the like.

Examples of essential genes involved in metabolism or biosynthesis in yeast include, but are not limited to, CDC19 (pyruvate kinase; DEG20010007; NP_009362), GP118 (mannosyltransferase; DEG20010034; NP_009558), TSC3 (protein that stimulates the activity of serine palmitoyltransferase; DEG20010042; NP_116327), ALG14 (DEG20010044; NP_009626), RIB7 (diaminohydroxyphoshoribosylaminopyrimidine deaminase; DEG20010061; NP 0097), RIBS (riboflavin synthase; DEG20010082; NP_009815), FAD1 (flavin adenine dinucleotide synthetase; DEG20010115; NP_010239), HEM13 (coproporphyrinogen III oxidase; DEG20010163; NP_010326), and the like.

Examples of essential genes involved in DNA replication in yeast include, but are not limited to, RFA1 (subunit of heterotrimeric replication protein A which is involved in DNA replication, repair and recombination; DEG20010010; NP_009404), POL30 (proliferating cell nuclear antigen; DEG20010048; NP_009645), POL3 (catalytic subunit of DNA polymerase delta; DEG20010126; NP_010181), CDC9 (DNA ligase; DEG20010144; NP_010117), and the like.

Examples of essential genes involved in RNA synthesis and degradation in yeast include, but are not limited to, TFC3 (largest of six subunits of the RNA polymerase III transcriptional initiation factor; DEG20010001; NP_009400), MAK16 (essential nuclear protein, constituent of 66S pre-ribosomal particles; DEG20010003; NP_009377), PRP45 (protein required for pre-mRNA splicing; DEG20010004; NP_009370), POP5 (subunit of both RNase MRP, which cleaves pre-rRNA and nuclear RNAseP; DEG20010005; NP_009369), PTA1 (subunit of holo-CPF, required for the cleavage and polyadenylation of mRNA and snoRNA 3'ends; involved in pre-tRNA processing; DEG20010009; NP_009356.1), SEN34 (subunit of the rRNA splicing endonuclease; DEG20010011; NP_009405), ABD1 (methyltransferase; DEG20010075; NP_009795), and the like.

The above mentioned essential genes are merely exemplary, and there are a number of other essential genes for yeast as well as for other organisms in the DEG database. Any additional essential genes in other organisms, which are not included in the DEG database, can be further analyzed and identified using the homologous sequence search against DEG. The functions encoded by essential genes are considered to be generally essential for all cells. Therefore, if the query sequences compared using BLAST have homologous genes in DEG, it is likely that the queried genes are also essential. The additional description of the database of essential genes and search for homologous sequences are further described in detail in, e.g., Zhang et al., *Nuc. Acids Res.* 2004 January; 32: D271-272; and Zhang and Lin, *Nuc. Acids. Res.* 2009 January; 37: D455-D458, which are incorporated herein by reference in their entirety. Any one or combination of these essential genes can be used to couple their expression to the production of non-catabolic compounds using a common transcriptional regulator in genetically modified host cells.

6.6.2.2 Use of Conditional Essential Genes in a Stabilization Construct

In certain embodiments, the nucleic acids encoding cell-growth-affecting proteins can include conditional essential genes which are essential only under certain circumstances or growth conditions. Being essential for cell growth or affecting cell growth can be highly dependent on a given culture medium or condition. Examples of conditional essential genes include auxotrophic genes, which are conditional essential. For example, in the absence of uracil in culture media, the orotidine-5'-phosphate decarboxylase gene, URA3, which catalyzes the sixth enzymatic step in the de novo biosynthesis of pyrimidines, becomes essential for a host cell. In another example, in the absence of tryptophan in culture media, the TRP1 gene encoding a phosphoribosylanthranilate isomerase that catalyzes the third step in tryptophan biosynthesis, becomes essential for a host cell. In another example, in the absence of lysine in culture media, the LYS2 gene, which encodes an aminoadipate reductase, can become essential. Any of these conditional essential genes may be operably linked to a promoter regulated by a common transcriptional regulator which also regulates expression of one or more enzymes of a biosynthetic pathway for producing non-catabolic compounds (or any heterologous proteins of interest).

There are a number of other conditional essential genes which encode enzymes for synthesis of essential compounds, which are necessary for cell growth when host cells are grown in culture media lacking these essential compounds. Additional examples of such conditional essential genes include those that encode enzymes in biosynthetic pathways for producing essential amino acids, fatty acids, nucleotides and the like. Genetically modified host cells containing such a conditional essential gene will require high expression of the regulon so that an adequate amount of essential compounds will be produced. Thus, such a regulon will be more stable to mutations which might otherwise reduce production of non-catabolic compounds.

There are a number of databases which provide various biosynthetic pathways including those for synthesizing essential compounds. These include, for example, KEGG pathway database (see, e.g., Kanehisha et al., (2002) *Nucleic Acids Res.,* 30: 42-46); and MetaCyc pathway database (see, e.g., Altman et al. (2013) *BNC Bioinformatics* 14:112). Other useful databases include BRENDA database (see, e.g., Schomburg et al. (2002) *Nucleic Acids Res.* 30: 47-49); SWISS-PROT database (Bairoch and Apweiler (2000) *Nucleic Acids Res.* 28: 45-48); EcoCyc (Karp et al. (2002) *Nucleic Acids Res.* 30: 56-8); and EMP/MPW (Selkov et al. (1998) *Nucleic Acids Res.* 26: 43-45). Many of these pathway databases provide nucleotide sequences of genes encoding enzymes of biosynthetic pathways for producing essential compounds. Any suitable nucleic acids encoding enzymes involved in synthesis of essential compounds can be used in a stabilization construct.

In certain embodiments, amino acid biosynthetic genes encoding essential amino acids can be used as conditional essential genes in a stabilization construct. These include one or more of lysine biosynthetic genes, methionine biosynthetic genes, leucine biosynthetic genes, histidine biosynthetic genes, leucine biosynthetic genes, tryptophan biosynthetic genes, and the like. The biosynthetic pathways for synthesizing these amino acids are well-known. Nucleic acid sequences for many of these amino acid biosynthetic genes are also known and publicly available for many organisms. See, e.g., GenBank sequence database (maintained by National Center for Biotechnology Information).

In some embodiments, a nucleic acid encoding an enzyme in a lysine biosynthetic pathway may be used in a stabilization construct. In yeast, the lysine biosynthetic pathway includes a number of different enzymes to synthesize lysine. These include an enzyme that converts 2-oxoglutarate and acetyl-CoA into homocitrate (e.g., homocitrate synthase; LYS21 or LYS20), an enzyme that converts homocitrate into homoaconitate and homoaconitate into homo-isocitrate (e.g., homoaconitase; LYS4), an enzyme that converts homo-isocitrate into α-ketoadipate (e.g., homo-isocitrate dehydrogenase; LYS12), an enzyme that converts α-ketoadipate into L-2-aminoadipate (e.g., enzyme 2.6.1.39; 2-aminoadipate amino transferase), an enzyme that converts L-2-aminoadipate into L-2-aminoadipate 6-semialdehyde (e.g., alpha aminoadipate reductase; LYS2), an enzyme that converts L-2-aminoadipate 6-semialdehyde into sacchropine (e.g., sacchropine dehydrogenase (NADP+ L-glutamate-forming); LYS9); and an enzyme that converts sacchropine into L-lysine (e.g., sacchropine dehydrogenase (NAD+, L-lysine-forming); LYS1).

Other organisms may use slightly different pathways and enzymes for biosynthesis of lysine. Biosynthetic pathways in other organisms, biosynthetic enzymes, and their corresponding nucleic acid sequences can be found in, for example, the KEGG database and MetaCyc database. For example, a nucleic acid encoding an enzyme that converts 2-oxoglutarate into homocitrate (e.g., homocitrate synthase) from a number of different organisms can be used as a conditional essential gene in a stabilization construct to couple cell growth of genetically modified host cells with the production of heterologous non-catabolic compounds. Illustrative examples of suitable nucleotide sequences include, but are not limited to: (LYS20/YDL182W; *Saccharomyces cerevisiae*), (LYS21/YDL131W, which is a paralog of LYS20; *Saccharomyces cerevisiae*), (AGOS_ADR107W; *Eremothecium gossypii*), (Ecym_8045; *Eremothecium cym-* balariae), (KLLA0E23695g; *Kluveromyces lactis*), (KLLA0F05489g; *Kluveromyces lactis*), (KLTH0E12848g; *Lachancea thermotolerans*), (KLTH0H02486g; *Lachancea thermotolerans*), (Kpol_2000p11; *Vanderwaltozyma polysopora*), (ZYRO0A13222g; *Zygosaccharomyces rouxii*), and the like.

In some embodiments, a nucleic acid encoding an enzyme that converts homocitrate into homo-isocitrate (e.g., homoaconitase) can be used as a conditional essential gene in a stabilization construct to couple cell growth of genetically modified host cells with the production of heterologous non-catabolic compounds. Illustrative examples of suitable nucleotide sequences include, but are not limited to: (LYS4/YDR234W; *Saccharomyces cerevisiae*), (AGOS_ABL106C; *Eremothecium gossypii*), (Ecym_5123; *Eremothecium cymbalariae*), (KLLA0C15125g; *Kluyveromyces lactis*), (KLTH0E10582p; *Lachancea thermotolerans*); (Kpol_1031p57; *Venderwaltozyma polyspora*), (K1705; *Zygosaccharomyces rouxii*), and the like.

In some embodiments, a nucleic acid encoding an enzyme that converts homo-isocitrate to α-ketoadipate (e.g., homo-isocitrate dehydrogenase) can be used as a conditional essential gene in a stabilization construct to couple cell growth of genetically modified host cells with the production of heterologous non-catabolic compounds. Illustrative examples of a suitable nucleotide sequence include, but are not limited to: (LYS12/YIL094C; *Saccharomyces cerevisiae*), and the like.

In some embodiments, a nucleic acid encoding an enzyme that converts α-ketoadipate into L-2-aminoadipate (e.g., enzyme 2.6.1.39; aminoadipate aminotransferase) can be used as a conditional essential gene in a stabilization construct to couple cell growth of genetically modified host cells with the production of heterologous non-catabolic compounds. Illustrative examples of a suitable nucleotide sequence, but are not limited to: (AADAT, KAT2, KATII; *Homo sapiens*), (AADAT; *Pan troglodytes*), (AADAT; *Pan paniscus*), (AADAT; *Pongo abelii*), (AADAT; *Momascus leucogenys*), and the like.

In some embodiments, a nucleic acid encoding an enzyme that converts L-2-amino adipate into L-2-aminoadipate 6-semialdehyde (e.g., alpha aminoadipate reductase) can be used as a conditional essential gene in a stabilization construct to couple cell growth of genetically modified host cells with the production of heterologous non-catabolic compounds. Illustrative examples of a suitable nucleotide sequence include, but are not limited to: (LYS2/YBR115C; *Saccharomyces cerevisiae*), (AGOS_ADL346W; *Eremothecium gossypii*), (Ecym_3457; *Eremothecium cymbalariae*), (KLLA0B09218g; *Kluyvermonyces lactis*), (KLTHOF10384g; *Lachancea thermotolerans*), (Kpol_1006p6; *Vanderwaltozyma polyspora*), (ZYRO0C16566g; *Zygosaccharomyces rouxii*), and the like.

In some embodiments, a nucleic acid encoding an enzyme that converts L-2-aminoadipate 6-semialdhyde into sacchropine (e.g., sacchropine dehydrogenase, NADP+ L-glutamate-forming) can be used as a conditional essential gene in a stabilization construct to couple cell growth of genetically modified host cells with the production of heterologous non-catabolic compounds. Illustrative examples of a suitable nucleotide sequence include, but are not limited to: (LYS9/YNR050C; *Saccharomyces cerevisiae*), (SORBI_03g030510; *Sorghum bicolor*), (AGOS_ABR116c; *Eremothecium gossypii*), (Ecym_7008; *Eremothecium cymbalariae*), (KLAA0C18744g; *Kluyvermyces lactis*), (KLTH0A07590g; *Lachancea thermotolerans*), (Kpol_1028p12; *Vanderwaltozyma polyspora*), (ZYRO0D17578g; *Zygosaccharomyces rouxii*), and the like.

In some embodiments, a nucleic acid encoding an enzyme that converts sacchropine into L-lysine (e.g., sacchropine dehydrogenase, NAD+, L-lysine-forming) can be used as a conditional essential gene in a stabilization construct to couple cell growth of genetically modified host cells with the production of heterologous non-catabolic compounds. Illustrative examples of a suitable nucleotide sequence include, but are not limited to: (LYS1; YIR034c; *Saccharomyces cerevisiae*), (AGOS_ACR167c; *Eremothecium gossypii*), (Ecym_5636; *Eremothecium cymbalariae*), (KLLA0E07987g; *Kluyvermyces lactis*), (KLTH0C00594g; *Lachancea thermotolerans*), (Kpol_1057p13; *Vanderwaltozyma polyspora*), (ZYRO0D00594g; *Zygosaccharomyces rouxii*), and the like.

The use of nucleic acids encoding enzymes in a lysine biosynthetic pathway as conditional essential genes is merely exemplary, and nucleic acids encoding enzymes in other amino acid biosynthetic pathways can be used as conditional essential genes in a stabilization construct. These include, for example, nucleic acids encoding enzymes of a methionine biosynthetic pathway: folypolyglutamate synthetase (e.g., MET7), N5-methyltetrahydropteroyltriglutamate-homocysteine methyltransferase (MET6), L-aspartate 4-P-transferase (HOM3); aspartic beta semi-aldehyde dehydrogenase (e.g., HOM2), homoserine dehydrogenase (e.g., HOM6), homoserine β-trans-acetylase (e.g., MET2), O-acetylhomoserine (thio)-lyase (e.g., MET17), and the like.

Other examples include nucleic acids encoding enzymes of a leucine biosynthetic pathway: alpha-isopropylmalate synthase minor isozyme (LEU9), alpha-isopropylmalate synthase (LEU4); isopropylmalate isomerase (LEU1), beta-IPM dehydrogenase (LEU2); branched-chain amino acid transaminase (e.g., BAT2), branched-chain amino acid aminotransferase (BAT1), and the like.

Other examples include nucleic acids encoding enzymes of a tryptophan biosynthetic pathway: anthranilate synthase (TRP3 and TRP2), anthranilate phosphoribosyl transferase (TRP4), N-(5'-phosphoribosyl)-anthranilate isomerase (TRP), indole-3-glycerol phosphate synthase (TRP3), tryptophan synthetase (TRP5), and the like.

Other examples include nucleic acids encoding enzymes of a histidine biosynthetic pathway: ATP phosphoribosyl-transferase (HIS), phosphoribosyl-ATP pyrophosphatase (HIS4), phosphoribosyl-AMP cyclohydrolase (HIS4), phosphoribosyl-5-amino-1-phosphoribosyl-4-imidazolecarboxi-amide (HIS6), imidazoleglycerol phosphate synthase (HIS7), imidazole glycerol-phosphate dehydratase (HIS3), histidinol-phosphate aminotransferase (HISS), histidinol-phosphatase (HIS2), histidinol dehydrogenase (HIS4), and the like.

Other examples include nucleic acids encoding enzymes of a phenylalanine biosynthetic pathway: chlorismate mutase (ARO7), prephenate dehydratatse (PHA2), aromatic amino acid aminotransferase (ARO8 and ARO9), and the like.

Other examples include nucleic acids encoding enzymes of a threonine biosynthetic pathway: homoserine kinase (THR1), threonine synthase (THR4), and the like.

Other examples include nucleic acids encoding enzymes of an isoleucine biosynthetic pathway: threonine deaminase (ILV1), acetolactate bynthase (ILV6, ILV2), aceohydroxy-acid reductoisomerase (ILV5), dihydroxy-acid dehyrfatase (ILV3), branched-chain amino acid transaminase (BAT2), branched-chain amino acid aminotransferase (BAT1), and the like.

Other examples include nucleic acids encoding enzymes of a valine biosynthetic pathway: acetolactate synthase (ILV6, ILV2), acetohydroxyacid reductoisomerase (ILV5), dihydroxy-acid dehydratase (ILV3), branched-chain amino acid transaminase (BAT2), branched-chain amino acid aminotransferase (BAT1), and the like.

In certain embodiments, nucleic acids encoding enzymes in nucleotide biosynthetic pathways can be used as conditional essential genes in present compositions and methods. These include, for example, nucleic acids encoding enzymes of biosynthetic pathways for producing adenine, thymine, uracil, guanine or cytosine. In other embodiments, nucleic acids encoding enzymes in fatty acid biosynthetic pathways can be used as conditional essential genes in present compositions and methods.

The nucleic acid sequences encoding these enzymes in yeast can be obtained from the *Saccharomyces* genome database, and can be found at world wide web address: yeastgenome.org. The functional homologs from other organisms can also be obtained using the BLAST search. Any other suitable conditional essential genes may be used to generate genetically modified host cells that are conditionally auxotrophic, which can be alleviated by expression of the conditional essential genes.

6.6.2.3 Screening Additional Cell-Growth-Affecting Gene Candidates

Certain nucleic acids, which may not have been identified in the DEG database as essential genes or conditional essential genes, may nonetheless be important for cell growth for particular culture media or conditions selected for fermentation. In some embodiments, the cell-growth-affecting genes may include those that affect cell growth such that their insufficient or lack of expression will cause cells to grow at a substantially slower growth rate, compared to when they are fully expressed under a particular culture medium or condition.

Cell-growth-affecting gene candidates potentially suitable for use in a stabilization construct can be screened using a number of different methods. In an embodiment, cell-growth-affecting gene candidates can be screened using an inducible promoter. An inducible promoter can be operably linked to a cell-growth-affecting gene candidate, and its inducer is used to turn on or off the expression of the cell-growth-affecting gene candidate. After a suitable time period (e.g., about 24, 48 or 72 hours) of culture, the cell growth phenotypes of cells under inducing and non-inducing conditions can be compared. Under non-inducing conditions, the inducible promoter is inactivated, and the cell-growth-affecting gene candidate is no longer transcribed. As the cells divide, the amount of proteins encoded from the cell-growth-affecting gene candidate gradually declines, eventually reaching a state of depletion that mimics a complete loss-of-function mutation. The difference in cell growth phenotype of cells cultured under inducing or non-inducing conditions will indicate whether the cell-growth-affecting gene candidate is important for cell growth.

In certain embodiments, the cell-growth-affecting gene candidates are selected as a cell-growth-affecting gene in a stabilization construct if inactivation of their expression (e.g., under non-inducing conditions) results in a reduction in cellular biomass (e.g., cell count or density) compared to when their expression is activated (e.g., under inducing conditions) by at least about 50%, 55%, 60%, 65%, 70%, 75%, 80%, 85%, 90%, 95% or more after a suitable time period (e.g., about 24 hours, 48, hour, or 72 hours). Cell densities or counts of cultures under non-inducing and inducing conditions can be compared. For example, an optical density ($OD_{600}$) of induced and non-induced cell cultures can be compared. In other embodiments, cell forming units (CFR) can be counted if the cells are grown on agar plates. In other embodiments, maximum specific growth rates can be compared. Other suitable methods which represent cell growth may be used to compare the effects of cell-growth-affecting gene candidate expression under inducing and non-inducing conditions.

In certain embodiments, a cell-growth-affecting gene candidate is screened in combination with a promoter which is regulated by a common transcriptional regulator of the regulon. For example, if a nucleic acid encoding an enzyme of a biosynthetic pathway for producing non-catabolic compounds is operably linked to a pGAL promoter, then a cell-growth-affecting gene candidate is also operably linked to a pGAL promoter to screen its suitability as a stabilization construct. In this example, a screening host cell may be further modified to functionally disrupt expression of repressor GAL80 so that transcriptional activator Gal4p can activate expression of the regulon.

In certain embodiments, a number of different promoters of varying promoter strengths may be tested in expressing these cell-growth-affecting gene candidates. In situations where a low expression level of a cell-growth-affecting gene candidate is required for cell growth, the cell-growth-affecting gene candidate may be operably linked to a relatively weak promoter. In other situations where a high expression level of a cell-growth-affecting gene candidate is required, the cell-growth-affecting gene candidate may be operably linked to a strong promoter. Any naturally derived or synthetic promoters for the regulon may be utilized to drive expression of the cell-growth-affecting gene candidates. For example, if transcriptional regulators of the GAL regulon are used, any promoters of the GAL regulon, pGAL1, pGAL2, pGAL7, pGAL10, pGCY1, pGAL80, or any synthetic promoters generated therefrom, may be utilized during screening of cell-growth-affecting gene candidates.

6.6.3. Fermentation Compositions and Production of Non-Catabolic Compounds Using a Stabilization Construct In another aspect, provided herein are fermentation compositions produced by genetically modified host cells and methods of producing heterologous non-catabolic compounds using a stabilization construct. In certain embodiments, a method of producing heterologous non-catabolic compounds comprises culturing in a culture medium a genetically modified host cell which comprises: (a) a heterologous nucleic acid encoding an enzyme of a biosynthetic pathway for producing the heterologous non-catabolic compound, wherein the heterologous nucleic acid is operably linked to a first promoter; (b) a nucleic acid encoding a cell-growth-affecting protein, wherein the nucleic acid is operably linked to a second promoter; and (c) a nucleic acid encoding a transcriptional regulator, wherein the first promoter and the second promoter are both regulated by the transcriptional regulator. In certain embodiments, the fermentation compositions comprise the genetically modified host cells described herein and heterologous non-catabolic compounds produced therefrom in a culture medium. Generally, genetically modified host cells are cultured in a culture medium comprising a carbon source under suitable conditions for a period of time sufficient to produce a desired biomass of host cells and/or a desired amount of non-catabolic compounds. In certain embodiments, a host cell comprises a heterologous nucleic acid encoding a protein of interest as a non-catabolic compound, instead of a heterologous nucleic acid encoding an enzyme of a biosynthetic pathway for producing a non-catabolic compound.

In the compositions and methods provided herein, the first promoter and the second promoter are both regulated by one or more common transcriptional regulators. Since the common transcriptional regulator(s) regulate expression of both heterologous nucleic acids encoding an enzyme of the biosynthetic pathway and a cell-growth-affecting protein, any spontaneous mutation that negatively affects the transcriptional regulator (e.g., its expression or stability) will negatively impact the expression of both heterologous nucleic acids. These mutated cells will not be viable or will grow at a much slower rate compared to high product-yielding cells, and therefore, high product-yielding cells (e.g., parent cells with the original high-product-yielding genotype) will dominate the cell population during the course of fermentation. Thus, coupling of expression of heterologous nucleic acids encoding an enzyme of a biosynthetic pathway for producing non-catabolic compounds with expression of a cell-growth-affecting protein will stabilize the high-product-yielding genotype of host cells, resulting in stabilized production of non-catabolic compounds over a long fermentation run. Similarly, coupling of expression of a heterologous nucleic acid encoding a protein of interest with expression of a cell-growth-affecting protein will stabilize the production of the protein of interest.

In certain embodiments, at least one of the first promoter or the second promoter is heterologous to these nucleic acids. For example, an endogenous promoter which normally drives expression of a cell-growth-affecting gene in the chromosome can be replaced with a heterologous promoter which is regulated by a common transcriptional regulator. In another example, an endogenous promoter which normally drives expression of a biosynthetic pathway gene for producing non-catabolic compounds can be replaced with a heterologous promoter. In certain embodiments, both first promoter and second promoter are heterologous to their respective nucleic acids. By utilizing heterologous promoters, these nucleic acids, which are not normally regulated by same transcriptional regulator(s), can be co-regulated as a regulon in genetically modified host cells.

The selection of promoter sequences depends on the expression level desired for heterologous nucleic acids encoding a cell-growth-affecting protein or an enzyme of a biosynthetic pathway for producing non-catabolic compounds. In some embodiments, the first promoter sequence and the second promoter sequence are identical. In other embodiments, the first promoter sequence and the second promoter sequence are different. In certain embodiments, the first promoter and the second promoter have different promoter strengths. For example, naturally derived pGal promoters, such as pGAL1, pGAL2, pGAL7 and pGAL10, are generally stronger promoters than synthetic promoters derived from these pGAL promoters (e.g., pGAL2_v3 (SEQ ID NO: 84), pGAL7_v1 (SEQ ID NO: 85), pGAL2_v4 (SEQ ID NO: 86), pGAL1_v3 (SEQ ID NO: 87), pGAL10_v3 (SEQ ID NO: 88), pGAL2_v2 (SEQ ID NO: 89), pGAL7_v2 (SEQ ID NO: 90)). If it is desired to have a higher expression of biosynthetic pathway enzymes compared to cell-growth-affecting proteins, then nucleic acids encoding these enzymes can be operably linked to naturally derived pGAL promoters, whereas nucleic acids encoding a cell-growth-affecting protein can be operably linked to a weaker synthetic promoter of naturally derived pGAL promoters. Generally, promoters are selected so that their promoter strengths are balanced to match the needed expression of a cell-growth-affecting gene in host cells, and the needed expression of a biosynthetic pathway gene for producing non-catabolic compounds.

Additional details related to building of cellular biomass and producing non-catabolic compounds described in Section 6.5 and other sections are also applicable to the compositions and methods comprising a stabilization construct provided herein.

6.6.4. Use of a Stabilization Construct in Constitutive Production of Non-Catabolic Compounds In certain embodiments, heterologous non-catabolic compounds are produced constitutively throughout the fermentation process. For certain heterologous non-catabolic compounds that are relatively non-toxic to cells, genetically modified host cells can tolerate the presence of these compounds throughout the fermentation process (i.e., during both build stage and the production stage of fermentation). Examples of such heterologous compounds include a variety of acetyl-CoA derived compounds, such as some of isoprenoids, fatty acids and polyketides. Specific examples of these compounds are further described in Sections 6.11 to 6.13 below.

To constitutively produce heterologous non-catabolic compounds, any suitable transcriptional regulators and promoters may be used to regulate expression of both heterologous nucleic acids encoding an enzyme of a biosynthetic pathway and a cell-growth-affecting protein. For constitutive production of heterologous non-catabolic compounds, expression of any endogenous transcriptional repressor of the promoters can be reduced or abolished, using known techniques for gene disruption. For example, if heterologous nucleic acids are regulated by transcriptional regulators of the GAL regulon, repressor GAL80, can be functionally disrupted. By functionally disrupting GAL80 expression, Gal80p can no longer repress Gal4p activity.

The use of transcriptional regulators and promoters of the GAL regulon is merely exemplary, and any suitable transcriptional regulators and promoters can be used to co-regulate and control expression of the regulon (i.e., a nucleic acid encoding a cell-growth-affecting protein and a nucleic acid encoding an enzyme of a biosynthetic pathway for producing a non-catabolic compound). For example, a MAL transcriptional activator may be used as a common transcriptional regulator to drive expression of both heterologous nucleic acids, wherein each of the heterologous nucleic acids is operably linked to a maltose-responsive promoter. In another example, the Pho regulon activator may be used as a common transcriptional regulator to drive expression of both heterologous nucleic acids, where each of the heterologous nucleic acids is operably linked to a Pho regulon promoter. In yet another example, artificial transcriptional regulators may be used to activate expression of both heterologous nucleic acids. For example, LexA fused to an activation domain may be used as an artificial transcriptional regulator.

6.6.5. Use of a Stabilization Construct with a Switch to Produce Non-Catabolic Compounds In another aspect, a stabilization construct described herein can be utilized in combination with a switch which separates a growth phase (i.e., a build stage of cellular biomass) and a production phase (i.e., a production stage of heterologous compounds) of fermentation. The production of non-catabolic compounds during a build stage can be undesirable. It can lead to slow growth of cells, and cells cannot reach an optimal cell density for the production stage. On the other hand, biomass production during a production stage of fermentation is undesirable as it diverts metabolic resources away from the production of heterologous non-catabolic compounds. In certain embodiments, a switch can be used in combination with a stabilization construct in genetically modified host cells to separate these two distinct metabolic phases of fermentation and to maximize production of heterologous non-catabolic compounds.

In an embodiment, the build stage is carried out for a period of time sufficient to produce an amount of cellular biomass that can support production of heterologous compounds during the production stage. The build stage is carried out for a period of time sufficient for the population present at the time of inoculation to undergo a plurality of doublings until a desired cell density is reached. In some embodiments, the build stage is carried out for a period of time sufficient for the host cell population to reach a cell density ($OD_{600}$) of between about 0.01 and 400 in the fermentation vessel or container in which the build stage is being carried out. In some embodiments, the build stage is carried out until an $OD_{600}$ of at least about 0.01 is reached. In some embodiments, the build stage is carried out until an $OD_{600}$ of at least about 0.1 is reached. In some embodiments, the build stage is carried out until an $OD_{600}$ of at least about 1.0 is reached. In some embodiments, the build stage is carried out until an $OD_{600}$ of at least about 10 is reached. In some embodiments, the build stage is carried out until an $OD_{600}$ of at least about 100 is reached. In some embodiments, the build stage is carried out until an $OD_{600}$ of between about 0.01 and 100 is reached. In some embodiments, the build stage is carried out until an $OD_{600}$ of between about 0.1 and 10 is reached. In some embodiments, the build stage is carried out until an $OD_{600}$ of between about 1 and 100 is reached. In other embodiments, the build stage is carried for a period of at least about 12, 24, 36, 48, 60, 72, 84, 96 or more than about 96 hours.

In some embodiments, the production stage is carried out for a period of time sufficient to produce a desired amount of heterologous compounds. In some embodiments, the production stage is carried out for a period of at least about 12, 24, 36, 48, 60, 72, 84, 96 or more than about 96 hours. In some embodiments, the production stage is carried out for a period of between about 3 and 20 days. In some embodiments, the production stage is carried for a period of about 1, 2, 3, 4, 5, 6, 7, 8, 9, 10, 11, 12, 13, 14, 15, 16, 17, 18, 19, 20 or more than about 20 days.

In an embodiment where a switch is used to separate two stages of fermentation, a conditional essential gene can be used as a cell-growth-affecting gene in a stabilization construct. For example, a conditional essential gene can encode an enzyme of a metabolic pathway whose end product is an essential compound essential for cell growth, which is consumable by the host cell. Genetically modified host cells containing such a conditional essential gene in a stabilization construct will require high expression of the regulon so that an adequate amount of essential compounds can be produced. An "off" stage of fermentation (i.e., build stage), where the switch turns off expression of both conditional essential gene and biosynthetic pathway genes, will result in conditional auxotrophy for these genetically modified host cells. The conditional auxotrophy can be compensated by adding essential compounds to the culture medium. During an "on" stage of fermentation (i.e., the production stage) wherein the switch turns on expression of both conditional essential gene and biosynthetic pathway genes for producing non-catabolic compounds, an essential compound is not supplemented in a culture medium. Thus, only cells that can express the conditional essential gene and produce a sufficient amount of essential compound can grow. This strategy is compatible with genetically modified host cells with a genetic switch which conditionally reduces the regulon expression when desired, since the resulting auxotrophy caused by the reduction of the regulon expression can be compensated by providing auxotrophically required essential compounds to culture media.

Thus, provided herein is a method for producing a heterologous non-catabolic compound, wherein the method comprises: (a) a build stage where a population of genetically modified host cells is cultured in a culture medium that limits the production of heterologous non-catabolic compounds, wherein the culture medium comprises an essential compound, followed by (b) a production stage where the population or a subpopulation of genetically modified host cells is cultured under culture conditions that promote production of heterologous non-catabolic compounds without supplementing the culture medium with the essential compound (or supplementing with a sufficiently low amount of the essential compound). In this embodiment, genetically modified host cells can comprise: (i) a heterologous nucleic acid encoding a protein of interest (e.g., an enzyme of a biosynthetic pathway for producing a heterologous non-catabolic compound), wherein the heterologous nucleic acid is operably linked to a first promoter; (ii) a nucleic acid encoding a conditional essential gene product of a biosynthetic pathway for producing an essential compound, wherein the heterologous nucleic acid is operably linked to a second promoter; and (iii) a nucleic acid encoding a transcriptional regulator, wherein the first promoter and the second promoter are both regulated by the same transcriptional regulator. During the production stage, only the genetically modified host cells that can express the conditional essential gene can grow since the essential compound is not added to the culture medium (or added in a sufficiently low amount). This adds a selective pressure for functional expression of the transcriptional regulator, which, in turn, improves stability of production of non-catabolic compounds.

Any suitable amount of an essential compound can be added to a culture medium during a build stage. It is generally undesirable for growth to become limited by the concentration of the auxotrophically required essential compound in the medium during a build stage. An essential compound can be added in an amount such that genetically modified auxotrophic host cells comprising a conditional essential gene (expression of which is repressed during the build stage) can grow to a desired concentration of biomass as described in above. In some embodiments, a suitable amount of an essential compound in a build stage culture medium can be determined by performing a titration curve in the presence of increasing amounts of an essential compound in a build stage culture medium. For example, a population of genetically modified host cells may be divided into a plurality of subpopulations and cultured in parallel, wherein each subpopulation is grown in a culture medium comprising a different, e.g., increasing amount of an essential compound (including no essential compound), and a cellular biomass (e.g., $OD_{600}$ reading) can be determined after a defined period time.

In other embodiments, a suitable amount of an essential compound in a build stage culture medium can be determined by measuring a cell growth rate, e.g., a maximum specific growth rate of genetically modified auxotrophic host cells at different concentrations of an essential compound. The term "specific growth rate" refers to the increase of biomass or cell number per time. The term "maximum specific growth rate" refers to "specific growth rate" during the exponential growth phase of a culture. Usually during the exponential growth phase, the specific growth rate is approximately constant as the substrates (or products) are still not exerting a significant inhibition on growth.

In certain embodiments, the essential compound titration may comprise at least one concentration of essential compound whereby host cell biomass (e.g., as measured by $OD_{600}$) or the maximum specific growth rate is plateaued at a maximum, that is, where no further increase in host cell biomass or maximum specific growth rate is observed with an increasing amount of essential compound. In some embodiment, the amount of essential compound added to a build stage culture medium is at least the minimum amount of an essential compound at which the host cell's biomass or maximum specific growth rate is at its maximum. This amount can also be referred to as a "saturating" amount of essential compound.

In certain embodiments, a saturating amount of an essential compound can be added to a build stage culture medium. In some embodiments, an essential compound can be added to a build stage medium in an amount greater than the saturating amount to ensure that genetically modified host cells reach a desired cellular biomass or maximum specific growth rate. For example, an essential compound added to a build stage culture medium is at least about 2, 3, 4, 5, 6, 7, 8, 9, 10, 20, 30, 40, 50, 60, 70, 80, 90, 100, or more than about 100 times greater than the saturating amount determined from an essential compound titration curve. In certain embodiments, if it is desired to grow genetically modified auxotrophic host cells to a lower biomass concentration or maximum specific growth rate, an essential compound can be added to a build stage culture medium in an amount less than the saturating amount. For example, an essential compound added to a build stage culture medium can be at least about 0.1, 0.2, 0.3, 0.4, 0.5, 0.6, 0.7, 0.8, 0.9, 1, 2, 3, 4, 5, 6, 7, 8, 9, 10, 100, or more than about 100 times less than the saturating amount determined from an essential compound titration curve.

In addition, for a given concentration of carbon source (e.g., 20 grams of glucose per a liter of medium) suitable concentrations of essential compounds, such as essential amino acids, for auxotrophic strains are generally known in the art. In some embodiments, the concentration of an essential compound in a build stage culture medium is at least about 0.0001% (weight of essential compound per volume of culture medium). In some embodiments, the concentration of an essential compound in a build stage culture medium is at least about 0.0005% (w/v). In some embodiments, the concentration of an essential compound in a build stage culture medium is at least about 0.001% (w/v). In some embodiments, the concentration of an essential compound in a build stage culture medium is at least about 0.005% (w/v). In some embodiments, the concentration of an essential compound in a build stage culture medium is at least about 0.01% (w/v). In some embodiments, the concentration of an essential compound in a build stage culture medium is at least about 0.05% (w/v). In some embodiments, the concentration of an essential compound in a build stage culture medium is at least about 0.1% (w/v). In some embodiments, the concentration of an essential compound in a build stage culture medium is at least about 0.5% (w/v). In some embodiments, the concentration of an essential compound in a build stage culture medium is at least about 1% (w/v). In some embodiments, the concentration of an essential compound in a build stage culture medium is at least about 5% or 10% (w/v). Designing a culture medium for cultivation of auxotrophic strains are well-known in the art, and described in, for example, Guide to Yeast Genetics and Molecular Biology, 194 (Guthrie et al., Academic Press 1990); Introduction to Yeast Media (Sigma-Aldrich).

After the build stage, a production stage culture medium used to culture genetically modified host cells comprises no externally added essential compound or in sufficiently low amounts. This way, a selective pressure is placed on the host cell to maintain expression of a conditional essential gene so that the cell is capable of producing an auxotrophically required essential compound for cell growth. In certain embodiments, a production stage culture medium comprises no externally added essential compound. In some embodiments, however, an essential compound can be added to a production stage culture medium in a sufficiently low amount. For example, a production stage culture medium can comprise an essential compound in an amount which is at least about 10-fold, 100-fold, 1000-fold, 10,000-fold or about 100,000-fold less than the saturating amount of an essential compound. In some embodiments, a production stage culture medium comprises an essential compound in an amount which is at least about 10-fold, 100-fold, 1000-fold, 10,000-fold or about 100,000-fold less than the amount of essential compound in a build stage culture medium.

In some embodiments, an essential compound is an amino acid, and a conditional essential gene in a stabilization construct encodes an enzyme in an amino acid biosynthetic pathway. For example, an essential compound which is used to supplement a culture medium during the build stage is lysine and any one or combinations of lysine biosynthetic genes, LYS1, LYS2, LY4, LYS9, LYS12, LYS14, LYS20 or LYS21, can be used in a stabilization construct. In another example, an essential compound which is used to supplement a culture medium during the build stage is methionine. Other amino acid biosynthetic genes described in Section 6.6.2 can also be used in a stabilization construct.

In other embodiments, an essential compound that is used to supplement a culture medium during the build stage can be uracil, thymine, guanine or cytosine, and any one or combination of genes that encode enzymes in biosynthetic pathways for these nucleotides can be used in a stabilization construct. In yet other embodiments, an essential compound is a fatty acid, and a conditional essential gene in a stabilization construct encodes an enzyme in a fatty acid biosynthetic pathway.

In certain embodiments, an inducible promoter and its inducer can be used as a switch to turn off the production of heterologous non-catabolic compounds during the build stage and to turn on the production during the production stage. For example, an inducible promoter is operably linked to a nucleic acid encoding a transcriptional activator which can activate expression of both heterologous nucleic acids encoding enzymes of a biosynthetic pathway to produce non-catabolic compounds and conditional essential gene product during the production stage of fermentation. Examples of suitable inducible promoters include maltose-responsive promoters which are inducible by ligands such as maltose based inducers. Additional details of maltose-responsive promoters and maltose based inducers are described in Sections 6.3 and 6.4 above. Other inducible promoters suitable in the present methods include oxygen-sensitive promoters, such as DAN1 promoters, which are inactive under aerobic conditions but highly active under anaerobic conditions. Examples of suitable oxygen-sensitive promoters are described in, e.g., WO2015/020649, which is incorporated herein by reference in its entirety.

In other embodiments, an inducible promoter is operably linked to a nucleic acid encoding a transcriptional repressor which represses expression of both heterologous nucleic acids encoding enzymes of a biosynthetic pathway for producing non-catabolic compounds and conditional essential gene products during the build stage of fermentation. Any suitable inducible promoters including those described above or known in the art can be used in these embodiments to activate transcriptional repressors.

An exemplary embodiment of using an inducible promoter as a switch to turn off or repress expression of heterologous nucleic acids encoding enzymes of a biosynthetic pathway for producing non-catabolic compounds and conditional essential gene products are shown in FIG. 17. As shown in FIG. 17, a nucleic acid encoding a transcriptional repressor of the GAL regulon, Gal80p, is operably linked to a maltose-responsive promoter pMAL32. When an inducing amount of maltose is added to culture medium, Gal80p is expressed, which, in turn, represses activation of transcriptional activator Gal4p and expression of one or more biosynthetic enzymes for producing the heterologous compounds. Gal80p concurrently represses expression of LYS9, a conditional essential gene that encodes an enzyme in the lysine biosynthetic pathway. During the build stage when Gal80p represses the expression of the regulon (including the conditional essential gene expression), lysine is supplemented in a culture medium so that cells can grow.

During the production stage of the exemplary embodiment shown in FIG. 17, the genetically modified host cells are cultured in a culture medium with no maltose or lysine (or in sufficiently low amount thereof). Since GAL80 is no longer expressed, transcriptional activator Gal4p is no longer repressed and therefore activates expression of the biosynthetic pathway genes to produce non-catabolic compounds. Concurrently, Gal4p also activates expression of LYS9, which, in turn, allows the lysine biosynthetic pathway to produce essential compound lysine. Since the genetically modified cells are capable of producing lysine, the cells can be cultured without lysine in a culture medium during the production stage. Absence of lysine in the culture medium adds a selective pressure for Gal4p expression during the production stage. Therefore, any cells that gain spontaneous mutations that negatively affect the GAL regulon will not be able to survive, allowing high product-yielding host cells to dominate the population of cells during a long fermentation run.

6.7 Production of Non-Catabolic Compounds Using a Maltose Dependent Degron and a Stabilization Construct In another aspect, provided herein are fermentation compositions and methods for producing heterologous non-catabolic compounds using a maltose dependent degron and a stabilization construct. A maltose dependent degron fused in frame to a transcriptional regulator can force the transcriptional regulator to become dependent on binding of maltose for its stability. For example, a fusion protein comprising Gal80p fused to a maltose dependent degron in the absence of maltose in a culture medium will become unstable during the production stage. Thus, even if a spontaneous mutation reactivates expression of the fusion protein comprising Gal80p, the fusion protein will become destabilized in the absence of maltose in the culture medium and will not be able to repress the GAL regulon expression during the production stage. When a maltose dependent degron is used in combination with a stabilization construct described herein, the production of heterologous non-catabolic compounds is further stabilized since both constructs can counteract any negative effects of spontaneous mutations.

Thus, provided herein are compositions and methods that provide at least two layers of stabilization on the production of heterologous non-catabolic compounds. In an embodiment, fermentation compositions and methods comprise culturing a genetically modified host cell in a culture medium, wherein the genetically modified host cell comprises: (a) a heterologous nucleic acid encoding a fusion protein comprising a transcriptional regulator fused in frame to a maltose dependent degron; (b) one or more heterologous nucleic acids encoding one or more enzymes of a biosynthetic pathway for producing heterologous non-catabolic compounds, each operably linked to a promoter regulated by the fusion protein; and (c) a stabilization construct which comprises a heterologous nucleic acid encoding a cell-growth-affecting protein, wherein the heterologous nucleic acid is operably linked to a promoter regulated by the fusion protein. The stabilization construct in genetically modified host cell provides a growth advantage to high product-yielding cells and a growth disadvantage to spontaneously mutated cells that are low producers or non-producers, and therefore stabilizes the production of heterologous non-catabolic compounds during fermentation. In addition, a maltose dependent degron provides a post-translational control for the fusion protein comprising a transcriptional regulator fused in frame to a maltose dependent degron. By manipulating the content of maltose in a culture medium, the stability of maltose dependent degron, and therefore, the post-translational stability and activity level of the transcriptional regulator can be controlled. This, in turn, provides an additional layer of stabilization in producing heterologous non-catabolic compounds.

In some embodiments, a fusion protein comprises a transcriptional activator fused in frame to a maltose dependent degron. In one embodiment, transcriptional activator Gal4p is selected as a transcriptional regulator in the fusion protein. For this embodiment, genetically modified host cells comprising heterologous nucleic acids described herein can be cultured in a culture medium comprising maltose during the production stage. The stable fusion protein bound to maltose, in turn, can activate expression of heterologous nucleic acids operably linked to Gal4p-responsive promoters to express enzymes of a biosynthetic pathway for producing non-catabolic compounds and cell-growth-affecting protein. When a maltose dependent degron is fused in frame to a transcriptional activator, any endogenous transcriptional repressor of the regulon (e.g., Gal80p) may be functionally disrupted so that it does not interfere with the activity of the fusion protein.

In other embodiments, a fusion protein comprises a transcriptional repressor fused in frame to a maltose dependent degron. For example, transcriptional repressor Gal80p is selected as a transcriptional regulator in the fusion protein. For this embodiment, genetically modified host cells comprising heterologous nucleic acids described herein can be cultured in a culture medium comprising maltose and an essential compound during a cellular biomass build stage of fermentation. This way, the transcriptional repressor in the fusion protein, bound to maltose, is stable, and therefore, represses the activity of Gal4p. This, in turn, represses expression of heterologous nucleic acids encoding one or more enzymes of a biosynthetic pathway for producing non-catabolic compounds and cell-growth-affecting protein during the cellular biomass build stage of fermentation.

In certain embodiments, any maltose dependent degrons, fusion proteins, maltose based inducers, maltose-responsive promoters, culture conditions and other features related to production of non-catabolic compounds described herein can be used in combination with a stabilization construct to further improve stability and production of non-catabolic compounds from genetically modified host cells. Furthermore, additional details related to the production of non-catabolic compounds and building of cellular biomass described in Section 6.5 and other sections are applicable to the compositions and methods comprising a maltose dependent degron and a stabilization construct provided herein.

6.8 Genetically Modified Host Cells

Provided herein are genetically modified host cells that comprise heterologous nucleic acids encoding a fusion protein described herein. In certain embodiments, genetically modified host cells are microorganisms (e.g., a genetically modified *Saccharomyces cerevisiae* cell) comprising heterologous nucleic acids encoding a fusion protein, which is more stable when a maltose dependent degron within the fusion protein is in contact with maltose compared to when the maltose dependent degron is not contact with maltose.

In certain embodiments, the heterologous nucleic acid encoding a fusion protein is operably linked to a maltose-responsive promoter in host cells. For such host cells, the maltose content in culture media can be adjusted at a suitable time point to activate (or to increase) transcription of the DNA coding sequence of the fusion protein and to increase post-translational stability of the fusion protein encoded therefrom.

The genetically modified host cells according to certain embodiments may be further modified to produce heterologous non-catabolic compounds (e.g., acetyl Co-A derived compound). For example, the genetically modified host cells may further comprise heterologous nucleotide sequences encoding one or more enzymes of a biosynthetic pathway for producing non-catabolic compounds. In these embodiments, the genetically modified host cells produce greater amounts of one or more compounds biosynthesized from acetyl-CoA compared to a parent host cell lacking the genetic modifications described herein.

In certain embodiments, provided herein are genetically modified host cells that comprise a stabilization construct for stabilized production of heterologous non-catabolic compounds. In certain embodiments, the genetically modified host cells provided herein comprise one or more heterologous nucleic acids encoding one or more enzymes of a biosynthetic pathway for producing a heterologous non-catabolic compound, and one or more heterologous nucleic acids encoding one or more cell-growth-affecting proteins, wherein each of the heterologous nucleic acids is operably linked to a commonly regulated promoter.

In certain embodiments, various combinations and subcombinations of nucleic acids and constructs described herein may be introduced into genetically modified host cells to stabilize expression of heterologous nucleic acids encoding biosynthetic enzymes for production of non-catabolic compounds. For example, heterologous non-catabolic compound producing host cells can be further modified to comprise a stabilization construct and a fusion protein described herein.

The heterologous nucleic acids described herein may be introduced into host cells using any suitable vectors described herein or those known in the art. Methods for genetically modifying host cells using expression vectors or chromosomal integration constructs, e.g., to effect increased production of one or more non-catabolic compounds in a host cell, are well known in the art. See, for example, Sherman, F., et al., *Methods Yeast Genetics*, Cold Spring Harbor Laboratory, N.Y. (1978); Guthrie, C., et al. (Eds.) *Guide To Yeast Genetics and Molecular Biology* Vol. 194, Academic Press, San Diego (1991); Sambrook et al., 2001, *Molecular Cloning—A Laboratory Manual*, $3^{rd}$ edition, Cold Spring Harbor Laboratory, Cold Spring Harbor, N.Y.; and Ausubel et al., eds., Current Edition, *Current Protocols in Molecular Biology*, Greene Publishing Associates and Wiley Interscience, NY.; the disclosures of which are incorporated herein by reference. In addition, inhibition of gene expression, e.g., which results in increased production of one or more non-catabolic compounds in the cell, may be accomplished by deletion, mutation, and/or gene rearrangement. It can also be carried out with the use of antisense RNA, siRNA, miRNA, ribozymes, triple stranded DNA, and transcription and/or translation inhibitors. In addition, transposons can be employed to disrupt gene expression, for example, by inserting it between the promoter and the coding region, or between two adjacent genes to inactivate one or both genes.

In some embodiments, increased production of non-catabolic compound in the cell is effected by the use of expression vectors to express a particular protein, e.g., a protein involved in a biosynthetic pathway as described above. Generally, expression vectors are recombinant polynucleotide molecules comprising replication signals and expression control sequences, e.g., promoters and terminators, operably linked to a nucleotide sequence encoding a polypeptide. Expression vectors useful for expressing polypeptide-encoding nucleotide sequences include viral vectors (e.g., retroviruses, adenoviruses and adeno-associated viruses), plasmid vectors, and cosmids. Illustrative examples of expression vectors suitable for use in yeast cells include, but are not limited to CEN/ARS and 2µ, plasmids. Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL7, and GAL10 genes).

Expression vectors and chromosomal integration constructs can be introduced into host cells by any method known to one of skill in the art without limitation. See, for example, Hinnen et al., *Proc. Natl. Acad. Sci. USA* 75:1292-3 (1978); Cregg et al., *Mol. Cell. Biol.* 5:3376-3385 (1985); U.S. Pat. No. 5,272,065; Goeddel et al., eds, 1990, Methods in Enzymology, vol. 185, Academic Press, Inc., CA; Krieger, 1990, *Gene Transfer and Expression—A Laboratory Manual*, Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY. Exemplary techniques include, but are not limited to, spheroplasting, electroporation, PEG 1000 mediated transformation, and lithium acetate or lithium chloride mediated transformation.

6.8.1. Host Cells

Cells useful in the methods and compositions provided herein include any cell capable of producing fusion proteins. In some embodiments, cells are capable of naturally or recombinantly producing a non-catabolic compound, e.g., an isoprenoid, a polyketide, a fatty acid, and the like. In some embodiments, the cell is a prokaryotic cell. In some embodiments, the cell is a bacterial cell. In some embodiments, the cell is an *Escherichia coli* cell. In some embodiments, the cell is a eukaryotic cell. In some embodiments, the cell is a yeast cell. In some embodiments, the cell is a *Saccharomyces cerevisiae* cell. In some embodiments, the cell is a mammalian cell. In some embodiments, the cell is a Chinese hamster ovary (CHO) cell, a COS-7 cell, a mouse fibroblast cell, a mouse embryonal carcinoma cell, or a mouse embryonic stem cell. In some embodiments, the cell is an insect cell. In some embodiments, the cell is a S2 cell, a Schneider cell, a S12 cell, a 5B1-4 cell, a Tn5 cell, or a Sf9 cell. In some embodiments, the cell is a unicellular eukaryotic organism cell, for example, a microbial cell.

In some embodiments, the cell is a mycelial bacterial cell. In some embodiments, the mycelial bacterial cell is of the class actinomycetes. In particular embodiments, the mycelial bacterial cell is of the genera *Streptomyces*, for example, *Streptomyces ambofaciens, Streptomyces avermitilis, Streptomyces azureus, Streptomyces cinnamonensis, Streptomyces coelicolor, Streptomyces curacoi, Streptomyces erythraeus, Streptomyces fradiae, Streptomyces galilaeus, Streptomyces glaucescens, Streptomyces hygroscopicus, Streptomyces lividans, Streptomyces parvulus, Streptomyces peucetius, Streptomyces rimosus, Streptomyces roseofulvus, Streptomyces thermotolerans, Streptomyces violaceoruber.*

In another embodiment, the cell is a fungal cell. In a more particular embodiment, the cell is a yeast cell. Yeasts useful in the methods and compositions provided herein include yeasts that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, SchizoSaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, ZygoSaccharomyces, Zygowilliopsis,* and *Zygozyma,* among others.

In particular embodiments, useful yeasts in the methods and compositions provided herein include *Saccharomyces cerevisiae, Pichia pastoris, SchizoSaccharomyces pombe, Dekkera bruxellensis, Kluyveromyces lactis* (previously called *Saccharomyces lactis*), *Kluveromyces marxianus, Arxula adeninivorans,* or *Hansenula polymorpha* (now known as *Pichia angusta*). In some embodiments, the microbe is a strain of the genus *Candida*, such as *Candida lipolytica, Candida guilliermondii, Candida krusei, Candida pseudotropicalis,* or *Candida utilis.*

In a particular embodiment, the cell is a *Saccharomyces cerevisiae* cell. In some embodiments, the strain of the *Saccharomyces cerevisiae* cell is selected from the group consisting of Baker's yeast, CBS 7959, CBS 7960, CBS 7961, CBS 7962, CBS 7963, CBS 7964, IZ-1904, TA, BG-1, CR-1, SA-1, M-26, Y-904, PE-2, PE-5, VR-1, BR-1, BR-2, ME-2, VR-2, MA-3, MA-4, CAT-1, CB-1, NR-1, BT-1, and AL-1. In some embodiments, the strain of *Saccharomyces cerevisiae* is selected from the group consisting of PE-2, CAT-1, VR-1, BG-1, CR-1, and SA-1. In a particular embodiment, the strain of *Saccharomyces cerevisiae* is PE-2. In another particular embodiment, the strain of *Saccharomyces cerevisiae* is CAT-1. In another particular embodiment, the strain of *Saccharomyces cerevisiae* is BG-1.

In some embodiments, the cell is a haploid microbial cell. In other embodiments, the cell is a diploid microbial cell. In some embodiments, the cell is heterozygous. In other embodiments, the cell is homozygous other than for its mating type allele (i.e., if the cell should sporulate, the resulting four haploid microbial cells would be genetically identical except for their mating type allele, which in two of the haploid cells would be mating type a and in the other two haploid cells would be mating type alpha).

In some embodiments, the cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment.

Exemplary non-catabolic compound producing cells, e.g., cells recombinantly producing isoprenoids, polyketides, and fatty acids, and methods for generating such cells, are provided below.

6.9 Culture Media and Conditions

Materials and methods for the maintenance and growth of cultures are well known to those skilled in the art of microbiology or fermentation science (see, for example, Bailey et al., Biochemical Engineering Fundamentals, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process.

The methods of producing non-catabolic compounds provided herein may be performed in a suitable culture medium in a suitable container, including but not limited to a cell culture plate, a flask, or a fermentor. Further, the methods can be performed at any scale of fermentation known in the art to support industrial production of microbial products. Any suitable fermentor may be used including a stirred tank fermentor, an airlift fermentor, a bubble fermentor, or any combination thereof. In particular embodiments utilizing *Saccharomyces cerevisiae* as the host cell, strains can be grown in a fermentor as described in detail by Kosaric, et al, in Ullmann's Encyclopedia of Industrial Chemistry, Sixth Edition, Volume 12, pages 398-473, Wiley-VCH Verlag GmbH & Co. KDaA, Weinheim, Germany. Further, the methods can be performed at any volume of fermentation, e.g., from lab scale (e.g., about 10 ml to 20 L) to pilot scale (e.g., about 20 L to 500 L) to industrial scale (e.g., about 500 L to ≥500,000 L) fermentations.

In some embodiments, the culture medium for use in the methods of producing non-catabolic compounds as provided herein includes any culture medium in which a genetically modified microorganism capable of producing a non-catabolic compound can subsist, i.e., support and maintain growth and viability. In some embodiments, the culture medium, also promotes the biosynthetic pathway necessary to produce the desired non-catabolic compound.

In some embodiments, the culture medium is an aqueous medium comprising assimilable carbon, nitrogen and phosphate sources. Such a medium can also include appropriate salts, minerals, metals and other nutrients. In some embodiments, the carbon source and each of the essential cell nutrients are added incrementally or continuously to the fermentation media, and each required nutrient is maintained at essentially the minimum level needed for efficient assimilation by growing cells, for example, in accordance with a predetermined cell growth curve based on the metabolic or respiratory function of the cells which convert the carbon source to a biomass.

Suitable conditions and suitable media for culturing microorganisms are well known in the art. In some embodiments, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter), or a selection agent (e.g., an antibiotic to select for microorganisms comprising the genetic modifications).

In some embodiments, the carbon source is a monosaccharide (simple sugar), a disaccharide, a polysaccharide, a non-fermentable carbon source, or one or more combinations thereof. Non-limiting examples of suitable monosaccharides include glucose, galactose, mannose, fructose, ribose, and combinations thereof. Non-limiting examples of suitable disaccharides include sucrose, lactose, maltose, trehalose, cellobiose, and combinations thereof. Non-limiting examples of suitable polysaccharides include starch, glycogen, cellulose, chitin, and combinations thereof. Non-limiting examples of suitable non-fermentable carbon sources include acetate and glycerol. In some embodiments, sugar cane syrup which includes different combinations of carbon source may be used.

The concentration of a carbon source, such as glucose, in the culture medium should promote cell growth, but not be so high as to repress growth of the microorganism used. Typically, cultures are run with a carbon source, such as glucose, being added at levels to achieve the desired level of growth and biomass, but at undetectable levels (with detection limits being about <0.1g/l). In other embodiments, the concentration of a carbon source, such as glucose, in the culture medium is greater than about 1 g/L, typically greater than about 2 g/L, and typically greater than about 5 g/L. In addition, the concentration of a carbon source, such as glucose, in the culture medium is generally less than about 100 g/L, typically less than about 50 g/L, and more typically less than about 20 g/L. Sometimes the concentration of carbon source can be greater than 100 g/L during a brief period, for example, when cells are initially added to the fermentor. It should be noted that references to culture component concentrations can refer to both initial and/or ongoing component concentrations. In some cases, it may be desirable to allow the culture medium to become depleted of a carbon source during culture.

Sources of assimilable nitrogen that can be used in a suitable culture medium include, but are not limited to, simple nitrogen sources, organic nitrogen sources and complex nitrogen sources. Such nitrogen sources include anhydrous ammonia, ammonium salts and substances of animal, vegetable and/or microbial origin. Suitable nitrogen sources include, but are not limited to, protein hydrolysates, microbial biomass hydrolysates, peptone, yeast extract, ammonium sulfate, urea, and amino acids. Any suitable amount of nitrogen sources may be added to the culture medium. Further, in some instances it may be desirable to allow the culture medium to become depleted of the nitrogen sources during culture.

The effective culture medium can contain other compounds such as inorganic salts, vitamins, trace metals or growth promoters. Such other compounds can also be present in carbon, nitrogen or mineral sources in the effective medium or can be added specifically to the medium.

The culture medium can also contain a suitable phosphate source. Such phosphate sources include both inorganic and organic phosphate sources. Preferred phosphate sources include, but are not limited to, phosphate salts such as mono or dibasic sodium and potassium phosphates, ammonium phosphate and mixtures thereof. Any suitable amount of phosphate source may be added to the culture medium.

A suitable culture medium can also include a source of magnesium, preferably in the form of a physiologically acceptable salt, such as magnesium sulfate heptahydrate, although other magnesium sources in concentrations that contribute similar amounts of magnesium can be used. Any suitable amount of magnesium source may be added to the culture medium. Further, in some instances it may be desirable to allow the culture medium to become depleted of a magnesium source during culture.

In some embodiments, the culture medium can also include a biologically acceptable chelating agent, such as the dihydrate of trisodium citrate. Any suitable amount of chelating agent may be added to the culture medium.

The culture medium can also initially include a biologically acceptable acid or base to maintain the desired pH of the culture medium. Biologically acceptable acids include, but are not limited to, hydrochloric acid, sulfuric acid, nitric acid, phosphoric acid and mixtures thereof. Biologically acceptable bases include, but are not limited to, ammonium hydroxide, sodium hydroxide, potassium hydroxide and mixtures thereof. In some embodiments, the base used is ammonium hydroxide.

In some embodiments, the culture medium can also include a biologically acceptable calcium source, including, but not limited to, calcium chloride. In some embodiments, the culture medium can also include sodium chloride. In some embodiments, the culture medium can also include trace metals. Such trace metals can be added to the culture medium as a stock solution that, for convenience, can be prepared separately from the rest of the culture medium. Any suitable amount of calcium source, sodium chloride, and trace metals may be added to the culture medium.

The culture media can include other vitamins, such as biotin, calcium, pantothenate, inositol, pyridoxine-HCl, and thiamine-HCl. Such vitamins can be added to the culture medium as a stock solution that, for convenience, can be prepared separately from the rest of the culture medium. Beyond certain concentrations, however, the addition of vitamins to the culture medium is not advantageous for the growth of the microorganisms.

The fermentation methods described herein can be performed in conventional culture modes, which include, but are not limited to, batch, fed-batch, cell recycle, continuous and semi-continuous. In some embodiments, the fermentation is carried out in fed-batch mode. In such a case, some of the components of the medium are depleted during culture during the production stage of the fermentation. In some embodiments, the culture may be supplemented with relatively high concentrations of such components at the outset, for example, of the production stage, so that growth and/or non-catabolic compound production is supported for a period of time before additions are required. The preferred ranges of these components are maintained throughout the culture by making additions as levels are depleted by culture. Levels of components in the culture medium can be monitored by, for example, sampling the culture medium periodically and assaying for concentrations. Alternatively, once a standard culture procedure is developed, additions can be made at timed intervals corresponding to known levels at particular times throughout the culture. As will be recognized by those in the art, the rate of consumption of nutrient increases during culture as the cell density of the medium increases. Moreover, to avoid introduction of foreign microorganisms into the culture medium, addition is performed using aseptic addition methods, as are known in the art. In addition, a small amount of anti-foaming agent may be added during the culture.

The temperature of the culture medium can be any temperature suitable for growth of the genetically modified cells and/or production of non-catabolic compounds. For example, prior to inoculation of the culture medium with an inoculum, the culture medium can be brought to and maintained at a temperature in the range of from about 20° C. to about 45° C., typically to a temperature in the range of from about 25° C. to about 40° C., and more typically in the range of from about 28° C. to about 34° C.

The pH of the culture medium can be controlled by the addition of acid or base to the culture medium. In such cases when ammonia is used to control pH, it also conveniently serves as a nitrogen source in the culture medium. Preferably, the pH is maintained from about 3.0 to about 8.0, typically from about 3.5 to about 7.0, and more typically from about 4.0 to about 6.5.

In some embodiments, the carbon source concentration, such as the maltose or glucose concentration, of the culture medium is monitored during culture. Glucose concentration of the culture medium can be monitored using known techniques, such as, for example, use of the glucose oxidase enzyme test or high pressure liquid chromatography, which can be used to monitor glucose concentration in the supernatant, e.g., a cell-free component of the culture medium, and maltose levels may be similarly monitored. As stated previously, the carbon source concentration should be kept below the level at which cell growth inhibition occurs. Although such concentration may vary from organism to organism, for glucose as a carbon source, cell growth inhibition may occur at glucose concentrations greater than at about 60 g/L, and can be determined readily by trial. Accordingly, when glucose is used as a carbon source the glucose is preferably fed to the fermentor and maintained below detection limits. Alternatively, the glucose concentration in the culture medium is maintained in the range of from about 1 g/L to about 100 g/L, typically in the range of from about 2 g/L to about 50 g/L, and sometimes in the range of from about 5 g/L to about 20 g/L. Although the carbon source concentration can be maintained within desired levels by addition of, for example, a substantially pure glucose solution, it is acceptable to maintain the carbon source concentration of the culture medium by addition of aliquots of the original culture medium. The use of aliquots of the original culture medium may be desirable because the concentrations of other nutrients in the medium (e.g. the nitrogen and phosphate sources) can be maintained simultaneously. Likewise, the trace metals concentrations can be maintained in the culture medium by addition of aliquots of the trace metals solution.

6.10 Recovery of Non-Catabolic Compounds

Once the non-catabolic is produced by the host cell, it may be recovered or isolated for subsequent use using any suitable separation and purification methods known in the art. In some embodiments, an organic phase comprising the non-catabolic is separated from the fermentation by centrifugation. In other embodiments, an organic phase comprising the non-catabolic compound separates from the fermentation spontaneously. In other embodiments, an organic phase comprising the non-catabolic derived compound is separated from the fermentation by adding a deemulsifier and/or a nucleating agent into the fermentation reaction. Illustrative examples of deemulsifiers include flocculants and coagulants. Illustrative examples of nucleating agents include droplets of the non-catabolic compound itself and organic solvents such as dodecane, isopropyl myristrate, and methyl oleate.

The non-catabolic compound produced in these cells may be present in the culture supernatant and/or associated with the host cells. In embodiments where the non-catabolic compound is associated with the host cell, the recovery of the non-catabolic may comprise a method of permeabilizing or lysing the cells. Alternatively or simultaneously, the non-catabolic in the culture medium can be recovered using a recovery process including, but not limited to, chromatography, extraction, solvent extraction, membrane separation, electrodialysis, reverse osmosis, distillation, chemical derivatization and crystallization.

In some embodiments, the non-catabolic compound is separated from other products that may be present in the organic phase. In some embodiments, separation is achieved using adsorption, distillation, gas-liquid extraction (stripping), liquid-liquid extraction (solvent extraction), ultrafiltration, and standard chromatographic techniques.

In some embodiments, the recovered non-catabolic compound is pure, e.g., at least about 40% pure, at least about 50% pure, at least about 60% pure, at least about 70% pure, at least about 80% pure, at least about 90% pure, at least about 95% pure, at least about 98% pure, or more than 98% pure, where "pure" in the context of a non-catabolic compound refers to a non-catabolic compound that is free from other non-catabolic compounds, contaminants, etc.

6.11 Production of Isoprenoids

In some embodiments, the non-catabolic compound is an isoprenoid. Isoprenoids are derived from isopentenyl pyrophosphate (IPP), which can be biosynthesized by enzymes of the mevalonate-dependent ("MEV") pathway or the 1-deoxy-D-xylulose 5-diphosphate ("DXP") pathway.

6.11.1. MEV Pathway

In some embodiments of the methods provided herein, the genetically modified microorganism comprises one or more heterologous nucleotide sequences encoding one or more enzymes of the MEV pathway, which effects increased production of one or more isoprenoid compounds as compared to a genetically unmodified parent cell.

In some embodiments, the isoprenoid producing cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

In some embodiments, the isoprenoid producing cell comprises a heterologous nucleotide sequence encoding an enzyme that can condense acetoacetyl-CoA with another molecule of acetyl-CoA to form 3-hydroxy-3-methylglutaryl-CoA (HMG-CoA), e.g., a HMG-CoA synthase. Illustrative examples of nucleotide sequences encoding such an enzyme include, but are not limited to: (NC_001145. complement 19061.20536; *Saccharomyces cerevisiae*), (X96617; *Saccharomyces cerevisiae*), (X83882; *Arabidopsis thaliana*), (AB037907; *Kitasatospora griseola*), (BT007302; *Homo sapiens*), and (NC_002758, Locus tag SAV2546, GeneID 1122571; *Staphylococcus aureus*).

In some embodiments, the isoprenoid producing cell comprises a heterologous nucleotide sequence encoding an enzyme that can convert HMG-CoA into mevalonate, e.g., a HMG-CoA reductase. Illustrative examples of nucleotide sequences encoding such an enzyme include, but are not limited to: (NM 206548; *Drosophila melanogaster*), (NC_002758, Locus tag SAV2545, GeneID 1122570; *Staphylococcus aureus*), (NM 204485; *Gallus gallus*), (AB015627; *Streptomyces* sp. KO 3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734.118898; *Saccharomyces cerevisiae*).

In some embodiments, the isoprenoid producing cell comprises a heterologous nucleotide sequence encoding an enzyme that can convert mevalonate into mevalonate 5-phosphate, e.g., a mevalonate kinase. Illustrative examples of nucleotide sequences encoding such an enzyme include, but are not limited to: (L77688; *Arabidopsis thaliana*), and (X55875; *Saccharomyces cerevisiae*).

In some embodiments, the isoprenoid producing cell comprises a heterologous nucleotide sequence encoding an enzyme that can convert mevalonate 5-phosphate into mevalonate 5-pyrophosphate, e.g., a phosphomevalonate kinase. Illustrative examples of nucleotide sequences encoding such an enzyme include, but are not limited to: (AF429385; *Hevea brasiliensis*), (NM 006556; *Homo sapiens*), and (NC_001145. complement 712315.713670; *Saccharomyces cerevisiae*).

In some embodiments, the isoprenoid producing cell comprises a heterologous nucleotide sequence encoding an enzyme that can convert mevalonate 5-pyrophosphate into IPP, e.g., a mevalonate pyrophosphate decarboxylase. Illustrative examples of nucleotide sequences encoding such an enzyme include, but are not limited to: (X97557; *Saccharomyces cerevisiae*), (AF290095; *Enterococcus faecium*), and (U49260; *Homo sapiens*).

In some embodiments, the isoprenoid producing cell comprises one or more heterologous nucleotide sequences encoding more than one enzyme of the MEV pathway. In some embodiments, the isoprenoid producing cell comprises one or more heterologous nucleotide sequences encoding two enzymes of the MEV pathway. In some embodiments, the isoprenoid producing cell comprises one or more heterologous nucleotide sequences encoding an enzyme that can convert HMG-CoA into mevalonate and an enzyme that can convert mevalonate into mevalonate 5-phosphate. In some embodiments, the isoprenoid producing cell comprises one or more heterologous nucleotide sequences encoding three enzymes of the MEV pathway. In some embodiments, the isoprenoid producing cell comprises one or more heterologous nucleotide sequences encoding four enzymes of the MEV pathway. In some embodiments, the isoprenoid producing cell comprises one or more heterologous nucleotide sequences encoding five enzymes of the MEV pathway. In some embodiments, the isoprenoid producing cell comprises one or more heterologous nucleotide sequences encoding six enzymes of the MEV pathway.

In some embodiments, the isoprenoid producing cell further comprises a heterologous nucleotide sequence encoding an enzyme that can convert IPP generated via the MEV pathway into its isomer, dimethylallyl pyrophosphate ("DMAPP"). DMAPP can be condensed and modified through the action of various additional enzymes to form simple and more complex isoprenoids (FIG. 2).

6.11.2. DXP Pathway

In some embodiments of the methods provided herein, the isoprenoid producing cell comprises one or more heterologous nucleotide sequences encoding one or more enzymes of the DXP pathway, which effects increased production of one or more isoprenoid compounds as compared to a genetically unmodified parent cell.

In some embodiments, the isoprenoid producing cell comprises a heterologous nucleotide sequence encoding an enzyme that can condense two molecules of acetyl-coenzyme A to form acetoacetyl-CoA, e.g., an acetyl-CoA thiolase. Illustrative examples of nucleotide sequences encoding such an enzyme include, but are not limited to: (NC_000913 REGION: 2324131.2325315; *Escherichia coli*), (D49362; *Paracoccus denitrificans*), and (L20428; *Saccharomyces cerevisiae*).

In some embodiments, the isoprenoid producing cell comprises a heterologous nucleotide sequence encoding an enzyme, e.g., 1-deoxy-D-xylulose-5-phosphate synthase, which can condense pyruvate with D-glyceraldehyde 3-phosphate to make 1-deoxy-D-xylulose-5-phosphate. Illustrative examples of nucleotide sequences encoding such an enzyme include but are not limited to: (AF035440; *Escherichia coli*), (NC_002947, locus tag PP0527; *Pseudomonas putida* KT2440), (CP000026, locus tag SPA2301; *Salmonella enterica Paratyphi*, see ATCC 9150), (NC_007493, locus tag RSP 0254; *Rhodobacter sphaeroides* 2.4.1), (NC_005296, locus tag RPA0952; *Rhodopseudomonas palustris* CGA009), (NC_004556, locus tag PD1293; *Xylella fastidiosa Temecula1*), and (NC_003076, locus tag AT5G11380; *Arabidopsis thaliana*).

In some embodiments, the isoprenoid producing cell comprises a heterologous nucleotide sequence encoding an enzyme, e.g., 1-deoxy-D-xylulose-5-phosphate reductoisomerase, which can convert 1-deoxy-D-xylulose-5-phosphate to 2C-methyl-D-erythritol-4-phosphate. Illustrative examples of nucleotide sequences include but are not limited to: (AB013300; *Escherichia coli*), (AF148852; *Arabidopsis thaliana*), (NC_002947, locus tag PP1597; *Pseudomonas putida* KT2440), (AL939124, locus tag SC05694; *Streptomyces coelicolor* A3(2)), (NC_007493, locus tag RSP 2709; *Rhodobacter sphaeroides* 2.4.1), and (NC_007492, locus tag Pfl_1107; *Pseudomonas fluorescens* PfO-1).

In some embodiments, the isoprenoid producing cell comprises a heterologous nucleotide sequence encoding an enzyme, e.g., 4-diphosphocytidyl-2C-methyl-D-erythritol synthase, which can convert 2C-methyl-D-erythritol-4-phosphate to 4-diphosphocytidyl-2C-methyl-D-erythritol.

Illustrative examples of nucleotide sequences include but are not limited to: (AF230736; *Escherichia coli*), (NC_007493, locus tag RSP 2835; *Rhodobacter sphaeroides* 2.4.1), (NC_003071, locus tag AT2G02500; *Arabidopsis thaliana*), and (NC_002947, locus tag PP1614; *Pseudomonas putida* KT2440).

In some embodiments, the isoprenoid producing cell comprises a heterologous nucleotide sequence encoding an enzyme, e.g., 4-diphosphocytidyl-2C-methyl-D-erythritol kinase, which can convert 4-diphosphocytidyl-2C-methyl-D-erythritol to 4-diphosphocytidyl-2C-methyl-D-erythritol-2-phosphate. Illustrative examples of nucleotide sequences include but are not limited to: (AF216300; *Escherichia coli*) and (NC_007493, locus tag RSP 1779; *Rhodobacter sphaeroides* 2.4.1).

In some embodiments, the isoprenoid producing cell comprises a heterologous nucleotide sequence encoding an enzyme, 2C-methyl-D-erythritol 2,4-cyclodiphosphate synthase, which can convert 4-diphosphocytidyl-2C-methyl-D-erythritol-2-phosphate to 2C-methyl-D-erythritol 2,4-cyclodiphosphate. Illustrative examples of nucleotide sequences include but are not limited to: (AF230738; *Escherichia coli*), (NC_007493, locus tag RSP 6071; *Rhodobacter sphaeroides* 2.4.1), and (NC_002947, locus tag PP1618; *Pseudomonas putida* KT2440).

In some embodiments, the isoprenoid producing cell comprises a heterologous nucleotide sequence encoding an enzyme, e.g., 1-hydroxy-2-methyl-2-(E)-butenyl-4-diphosphate synthase, which can convert 2C-methyl-D-erythritol 2,4-cyclodiphosphate to 1-hydroxy-2-methyl-2-(E)-butenyl-4-diphosphate. Illustrative examples of nucleotide sequences include but are not limited to: (AY033515; *Escherichia coli*), (NC_002947, locus tag PP0853; *Pseudomonas putida* KT2440), and (NC_007493, locus tag RSP 2982; *Rhodobacter sphaeroides* 2.4.1).

In some embodiments, the isoprenoid producing cell comprises a heterologous nucleotide sequence encoding an enzyme, e.g., isopentyl/dimethylallyl diphosphate synthase, which can convert 1-hydroxy-2-methyl-2-(E)-butenyl-4-diphosphate into either IPP or its isomer, DMAPP. Illustrative examples of nucleotide sequences include but are not limited to: (AY062212; *Escherichia coli*) and (NC_002947, locus tag PP0606; *Pseudomonas putida* KT2440).

In some embodiments, the isoprenoid producing cell comprises one or more heterologous nucleotide sequences encoding more than one enzyme of the DXP pathway. In some embodiments, the isoprenoid producing cell comprises one or more heterologous nucleotide sequences encoding two enzymes of the DXP pathway. In some embodiments, the isoprenoid producing cell comprises one or more heterologous nucleotide sequences encoding three enzymes of the DXP pathway. In some embodiments, the isoprenoid producing cell comprises one or more heterologous nucleotide sequences encoding four enzymes of the DXP pathway. In some embodiments, the isoprenoid producing cell comprises one or more heterologous nucleotide sequences encoding five enzymes of the DXP pathway. In some embodiments, the isoprenoid producing cell comprises one or more heterologous nucleotide sequences encoding six enzymes of the DXP pathway. In some embodiments, the isoprenoid producing cell comprises one or more heterologous nucleotide sequences encoding five enzymes of the DXP pathway. In some embodiments, the isoprenoid producing cell comprises one or more heterologous nucleotide sequences encoding seven enzymes of the DXP pathway.

In some embodiments, "cross talk" (or interference) between the host cell's own metabolic processes and those processes involved with the production of IPP are minimized or eliminated entirely. For example, cross talk is minimized or eliminated entirely when the host microorganism relies exclusively on the DXP pathway for synthesizing IPP, and a MEV pathway is introduced to provide additional IPP. Such a host organism would not be equipped to alter the expression of the MEV pathway enzymes or process the intermediates associated with the MEV pathway. Organisms that rely exclusively or predominately on the DXP pathway include, for example, *Escherichia coli*.

In some embodiments, the host cell produces IPP via the MEV pathway, either exclusively or in combination with the DXP pathway. In other embodiments, a host's DXP pathway is functionally disabled so that the host cell produces IPP exclusively through a heterologously introduced MEV pathway. The DXP pathway can be functionally disabled by disabling gene expression or inactivating the function of one or more of the DXP pathway enzymes.

In some embodiments, the isoprenoid produced by the cell is a $C_5$ isoprenoid. These compounds are derived from one isoprene unit and are also called hemiterpenes. An illustrative example of a hemiterpene is isoprene. In other embodiments, the isoprenoid is a $C_{10}$ isoprenoid. These compounds are derived from two isoprene units and are also called monoterpenes. Illustrative examples of monoterpenes are limonene, citranellol, geraniol, menthol, perillyl alcohol, linalool, thujone, and myrcene. In other embodiments, the isoprenoid is a $C_{15}$ isoprenoid. These compounds are derived from three isoprene units and are also called sesquiterpenes. Illustrative examples of sesquiterpenes are periplanone B, gingkolide B, amorphadiene, artemisinin, artemisinic acid, valencene, nootkatone, epi-cedrol, epi-aristolochene, farnesol, gossypol, sanonin, periplanone, forskolin, and patchoulol (which is also known as patchouli alcohol). In other embodiments, the isoprenoid is a $C_{20}$ isoprenoid. These compounds are derived from four isoprene units and also called diterpenes. Illustrative examples of diterpenes are casbene, eleutherobin, paclitaxel, prostratin, pseudopterosin, and taxadiene. In yet other examples, the isoprenoid is a $C_{20+}$ isoprenoid. These compounds are derived from more than four isoprene units and include: triterpenes ($C_{30}$ isoprenoid compounds derived from 6 isoprene units) such as arbrusideE, bruceantin, testosterone, progesterone, cortisone, digitoxin, and squalene; tetraterpenes ($C_{40}$ isoprenoid compounds derived from 8 isoprenoids) such as β-carotene; and polyterpenes ($C_{40+}$ isoprenoid compounds derived from more than 8 isoprene units) such as polyisoprene. In some embodiments, the isoprenoid is selected from the group consisting of abietadiene, amorphadiene, carene, α-farnesene, β-farnesene, farnesol, geraniol, geranylgeraniol, isoprene, linalool, limonene, myrcene, nerolidol, ocimene, patchoulol, β-pinene, sabinene, γ-terpinene, terpinolene and valencene. Isoprenoid compounds also include, but are not limited to, carotenoids (such as lycopene, α- and β-carotene, α- and β-cryptoxanthin, bixin, zeaxanthin, astaxanthin, and lutein), steroid compounds, and compounds that are composed of isoprenoids modified by other chemical groups, such as mixed terpene-alkaloids, and coenzyme Q-10.

In some embodiments, the isoprenoid producing cell further comprises a heterologous nucleotide sequence encoding an enzyme that can convert IPP generated via the MEV pathway into DMAPP, e.g., an IPP isomerase. Illustrative examples of nucleotide sequences encoding such an enzyme include, but are not limited to: (NC_000913, 3031087.3031635; *Escherichia coli*), and (AF082326; *Haematococcus pluvialis*).

In some embodiments, the isoprenoid producing cell further comprises a heterologous nucleotide sequence encoding a polyprenyl synthase that can condense IPP and/or DMAPP molecules to form polyprenyl compounds containing more than five carbons.

In some embodiments, the isoprenoid producing cell comprises a heterologous nucleotide sequence encoding an enzyme that can condense one molecule of IPP with one molecule of DMAPP to form one molecule of geranyl pyrophosphate ("GPP"), e.g., a GPP synthase. Illustrative examples of nucleotide sequences encoding such an enzyme include, but are not limited to: (AF513111; *Abies grandis*), (AF513112; *Abies grandis*), (AF513113; *Abies grandis*), (AY534686; *Antirrhinum majus*), (AY534687; *Antirrhinum majus*), (Y17376; *Arabidopsis thaliana*), (AE016877, Locus AP11092; *Bacillus cereus*; ATCC 14579), (AJ243739; *Citrus sinensis*), (AY534745; *Clarkia breweri*), (AY953508; *Ips pini*), (DQ286930; *Lycopersicon esculentum*), (AF182828; *Mentha×piperita*), (AF182827; *Mentha×piperita*), (MPI249453; *Mentha×piperita*), (PZE431697, Locus CAD24425; *Paracoccus zeaxanthinifaciens*), (AY866498; *Picrorhiza kurrooa*), (AY351862; *Vitis vinifera*), and (AF203881, Locus AAF12843; *Zymomonas mobilis*).

In some embodiments, the isoprenoid producing cell comprises a heterologous nucleotide sequence encoding an enzyme that can condense two molecules of IPP with one molecule of DMAPP, or add a molecule of IPP to a molecule of GPP, to form a molecule of farnesyl pyrophosphate ("FPP"), e.g., a FPP synthase. Illustrative examples of nucleotide sequences that encode such an enzyme include, but are not limited to: (ATU80605; *Arabidopsis thaliana*), (ATHFPS2R; *Arabidopsis thaliana*), (AAU36376; *Artemisia annua*), (AF461050; *Bos taurus*), (D00694; *Escherichia coli* K-12), (AE009951, Locus AAL95523; *Fusobacterium nucleatum* subsp. *nucleatum* ATCC 25586), (GFFPPSGEN; *Gibberella fujikuroi*), (CP000009, Locus AAW60034; *Gluconobacter oxydans* 621H), (AF019892; *Helianthus annuus*), (HUMFAPS; *Homo sapiens*), (KLPFPSQCR; *Kluyveromyces lactis*), (LAU15777; *Lupinus albus*), (LAU20771; *Lupinus albus*), (AF309508; *Mus musculus*), (NCFPPSGEN; *Neurospora crassa*), (PAFPS1; *Parthenium argentatum*), (PAFPS2; *Parthenium argentatum*), (RATFAPS; *Rattus norvegicus*), (YSCFPP; *Saccharomyces cerevisiae*), (D89104; *SchizoSaccharomyces pombe*), (CP000003, Locus AAT87386; *Streptococcus pyogenes*), (CP000017, Locus AAZ51849; *Streptococcus pyogenes*), (NC_008022, Locus YP_598856; *Streptococcus pyogenes* MGAS10270), (NC_008023, Locus YP_600845; *Streptococcus pyogenes* MGAS2096), (NC_008024, Locus YP_602832; *Streptococcus pyogenes* MGAS10750), (MZEFPS; *Zea mays*), (AE000657, Locus AAC06913; *Aquifex aeolicus* VF5), (NM 202836; *Arabidopsis thaliana*), (D84432, Locus BAA12575; *Bacillus subtilis*), (U12678, Locus AAC28894; *Bradyrhizobium japonicum* USDA 110), (BACFDPS; *Geobacillus stearothermophilus*), (NC_002940, Locus NP_873754; *Haemophilus ducreyi* 35000HP), (L42023, Locus AAC23087; *Haemophilus influenzae* Rd KW20), (J05262; *Homo sapiens*), (YP_395294; *Lactobacillus sakei* subsp. *sakei* 23K), (NC_005823, Locus YP_000273; *Leptospira interrogans* serovar Copenhageni str. Fiocruz L1-130), (AB003187; *Micrococcus luteus*), (NC_002946, Locus YP_208768; *Neisseria gonorrhoeae* FA 1090), (U00090, Locus AAB91752; *Rhizobium* sp. NGR234), (J05091; *Saccharomyces cerevisiae*), (CP000031, Locus AAV93568; *Silicibacter pomeroyi* DSS-3), (AE008481, Locus AAK99890; *Streptococcus pneumoniae* R6), and (NC_004556, Locus NP_779706; *Xylella fastidiosa Temeculal*).

In some embodiments, the isoprenoid producing cell further comprises a heterologous nucleotide sequence encoding an enzyme that can combine IPP and DMAPP or IPP and FPP to form geranylgeranyl pyrophosphate ("GGPP"). Illustrative examples of nucleotide sequences that encode such an enzyme include, but are not limited to: (ATHGERPYRS; *Arabidopsis thaliana*), (BT005328; *Arabidopsis thaliana*), (NM_119845; *Arabidopsis thaliana*), (NZ_AAJM01000380, Locus ZP_00743052; *Bacillus thuringiensi serovar israelensis*, ATCC 35646 sq1563), (CRGGPPS; *Catharanthus roseus*), (NZ_AABF02000074, Locus ZP_00144509; *Fusobacterium nucleatum* subsp. *vincentii*, ATCC 49256), (GFGGPPSGN; *Gibberella fujikuroi*), (AY371321; *Ginkgo biloba*), (AB055496; *Hevea brasiliensis*), (AB017971; *Homo sapiens*), (MCI276129; *Mucor circinelloides f. lusitanicus*), (AB016044; *Mus musculus*), (AABX01000298, Locus NCU01427; *Neurospora crassa*), (NCU20940; *Neurospora crassa*), (NZ_AAKL01000008, Locus ZP_00943566; *Ralstonia solanacearum* UW551), (AB118238; *Rattus norvegicus*), (SCU31632; *Saccharomyces cerevisiae*), (AB016095; *Synechococcus elongates*), (SAGGPS; *Sinapis alba*), (SSOGDS; *Sulfolobus acidocaldarius*), (NC_007759, Locus YP_461832; *Syntrophus aciditrophicus* SB), (NC_006840, Locus YP_204095; *Vibrio fischeri* ES114), (NM_112315; *Arabidopsis thaliana*), (ERWCRTE; *Pantoea agglomerans*), (D90087, Locus BAA14124; *Pantoea ananatis*), (X52291, Locus CAA36538; *Rhodobacter capsulatus*), (AF195122, Locus AAF24294; *Rhodobacter sphaeroides*), and (NC_004350, Locus NP_721015; *Streptococcus mutans* UA159).

In some embodiments, the isoprenoid producing cell further comprises a heterologous nucleotide sequence encoding an enzyme that can modify a polyprenyl to form a hemiterpene, a monoterpene, a sesquiterpene, a diterpene, a triterpene, a tetraterpene, a polyterpene, a steroid compound, a carotenoid, or a modified isoprenoid compound.

In some embodiments, the heterologous nucleotide encodes a carene synthase. Illustrative examples of suitable nucleotide sequences include, but are not limited to: (AF461460, REGION 43.1926; *Picea abies*) and (AF527416, REGION: 78.1871; *Salvia stenophylla*).

In some embodiments, the heterologous nucleotide encodes a geraniol synthase. Illustrative examples of suitable nucleotide sequences include, but are not limited to: (AJ457070; *Cinnamomum tenuipilum*), (AY362553; *Ocimum basilicum*), (DQ234300; *Perilla frutescens* strain 1864), (DQ234299; *Perilla citriodora* strain 1861), (DQ234298; *Perilla citriodora* strain 4935), and (DQ088667; *Perilla citriodora*).

In some embodiments, the heterologous nucleotide encodes a linalool synthase. Illustrative examples of a suitable nucleotide sequence include, but are not limited to: (AF497485; *Arabidopsis thaliana*), (AC002294, Locus AAB71482; *Arabidopsis thaliana*), (AY059757; *Arabidopsis thaliana*), (NM_104793; *Arabidopsis thaliana*), (AF154124; *Artemisia annua*), (AF067603; *Clarkia breweri*), (AF067602; *Clarkia concinna*), (AF067601; *Clarkia breweri*), (U58314; *Clarkia breweri*), (AY840091; *Lycopersicon esculentum*), (DQ263741; *Lavandula angustifolia*), (AY083653; *Mentha citrate*), (AY693647; *Ocimum basilicum*), (XM 463918; *Oryza sativa*), (AP004078, Locus BAD07605; *Oryza sativa*), (XM 463918, Locus XP 463918; *Oryza sativa*), (AY917193; *Perilla citriodora*), (AF271259;

*Perilla frutescens*), (AY473623; *Picea abies*), (DQ195274; *Picea sitchensis*), and (AF444798; *Perilla frutescens* var. *crispa* cultivar No. 79).

In some embodiments, the heterologous nucleotide encodes a limonene synthase. Illustrative examples of suitable nucleotide sequences include, but are not limited to: (+)-limonene synthases (AF514287, REGION: 47.1867; *Citrus limon*) and (AY055214, REGION: 48.1889; *Agastache rugosa*) and (−)-limonene synthases (DQ195275, REGION: 1.1905; *Picea sitchensis*), (AF006193, REGION: 73.1986; *Abies grandis*), and (MHC4SLSP, REGION: 29.1828; *Mentha spicata*).

In some embodiments, the heterologous nucleotide encodes a myrcene synthase. Illustrative examples of suitable nucleotide sequences include, but are not limited to: (U87908; *Abies grandis*), (AY195609; *Antirrhinum majus*), (AY195608; *Antirrhinum majus*), (NM_127982; *Arabidopsis thaliana* TPS10), (NM_113485; *Arabidopsis thaliana* ATTPS-CIN), (NM_113483; *Arabidopsis thaliana* ATTPS-CIN), (AF271259; *Perilla frutescens*), (AY473626; *Picea abies*), (AF369919; *Picea abies*), and (AJ304839; *Quercus ilex*).

In some embodiments, the heterologous nucleotide encodes an ocimene synthase. Illustrative examples of suitable nucleotide sequences include, but are not limited to: (AY195607; *Antirrhinum majus*), (AY195609; *Antirrhinum majus*), (AY195608; *Antirrhinum majus*), (AK221024; *Arabidopsis thaliana*), (NM_113485; *Arabidopsis thaliana* ATTPS-CIN), (NM_113483; *Arabidopsis thaliana* ATTPS-CIN), (NM_117775; *Arabidopsis thaliana* ATTPS03), (NM_001036574; *Arabidopsis thaliana* ATTPS03), (NM_127982; *Arabidopsis thaliana* TPS10), (AB110642; *Citrus unshiu* CitMTSL4), and (AY575970; *Lotus corniculatus* var. *japonicus*).

In some embodiments, the heterologous nucleotide encodes an α-pinene synthase. Illustrative examples of suitable nucleotide sequences include, but are not limited to: (+) α-pinene synthase (AF543530, REGION: 1.1887; *Pinus taeda*), (−)α-pinene synthase (AF543527, REGION: 32.1921; *Pinus taeda*), and (+)/(−)α-pinene synthase (AGU87909, REGION: 6111892; *Abies grandis*).

In some embodiments, the heterologous nucleotide encodes a β-pinene synthase. Illustrative examples of suitable nucleotide sequences include, but are not limited to: (−) β-pinene synthases (AF276072, REGION: 1.1749; *Artemisia annua*) and (AF514288, REGION: 26.1834; *Citrus limon*).

In some embodiments, the heterologous nucleotide encodes a sabinene synthase. An illustrative example of a suitable nucleotide sequence includes but is not limited to AF051901, REGION: 26.1798 from *Salvia officinalis*.

In some embodiments, the heterologous nucleotide encodes a γ-terpinene synthase. Illustrative examples of suitable nucleotide sequences include, but are not limited to: (AF514286, REGION: 30.1832 from *Citrus limon*) and (AB110640, REGION 1.1803 from *Citrus unshiu*).

In some embodiments, the heterologous nucleotide encodes a terpinolene synthase. Illustrative examples of a suitable nucleotide sequence include but are not limited to: (AY693650 from *Ocimum basilicum*) and (AY906866, REGION: 10.1887 from *Pseudotsuga menziesii*).

In some embodiments, the heterologous nucleotide encodes an amorphadiene synthase. An illustrative example of a suitable nucleotide sequence is SEQ ID NO. 37 of U.S. Patent Publication No. 2004/0005678.

In some embodiments, the heterologous nucleotide encodes a α-farnesene synthase. Illustrative examples of suitable nucleotide sequences include, but are not limited to DQ309034 from *Pyrus communis* cultivar *d'Anjou* (pear; gene name AFS1) and AY182241 from *Malus domestica* (apple; gene AFS1). Pechouus et al., *Planta* 219(1):84-94 (2004).

In some embodiments, the heterologous nucleotide encodes a β-farnesene synthase. Illustrative examples of suitable nucleotide sequences include, but are not limited to GenBank accession number AF024615 from *Menthaxpiperita* (peppermint; gene Tspal1), and AY835398 from *Artemisia annua*. Picaud et al., *Phytochemistry* 66(9): 961-967 (2005).

In some embodiments, the heterologous nucleotide encodes a farnesol synthase. Illustrative examples of suitable nucleotide sequences include, but are not limited to GenBank accession number AF529266 from *Zea mays* and YDR481C from *Saccharomyces cerevisiae* (gene Pho8). Song, L., *Applied Biochemistry and Biotechnology* 128:149-158 (2006).

In some embodiments, the heterologous nucleotide encodes a nerolidol synthase. An illustrative example of a suitable nucleotide sequence includes, but is not limited to AF529266 from *Zea mays* (maize; gene tps1).

In some embodiments, the heterologous nucleotide encodes a patchouliol synthase. Illustrative examples of suitable nucleotide sequences include, but are not limited to AY508730 REGION: 1.1659 from *Pogostemon cablin*.

In some embodiments, the heterologous nucleotide encodes a nootkatone synthase. Illustrative examples of a suitable nucleotide sequence include, but are not limited to AF441124 REGION: 1.1647 from *Citrus sinensis* and AY917195 REGION: 1.1653 from *Perilla frutescens*.

In some embodiments, the heterologous nucleotide encodes an abietadiene synthase. Illustrative examples of suitable nucleotide sequences include, but are not limited to: (U50768; *Abies grandis*) and (AY473621; *Picea abies*).

6.12 Production of Polyketides

In some embodiments, the non-catabolic compound is a polyketide. Polyketides are synthesized by sequential reactions catalysed by a collection of enzyme activities called polyketide synthases (PKSs), which are large multi-enzyme protein complexes that contain a coordinated group of active sites. Polyketide biosynthesis proceeds stepwise starting from simple 2-, 3-, 4-carbon building blocks such as acetyl-CoA, propionyl CoA, butyryl-CoA and their activated derivatives, malonyl-, methylmalonyl- and ethylmalonyl-CoA, primarily through decarboxylative condensation of malonyl-CoA-derived units via Claisen condensation reactions. The PKS genes are usually organized in one operon in bacteria and in gene clusters in eukaryotes. Three types of polyketide synthases have been characterized: Type I polyketide synthases are large, highly modular proteins subdivided into two classes: 1) iterative PKSs, which reuse domains in a cyclic fashion and 2) modular PKSs, which contain a sequence of separate modules and do not repeat domains. Type II polyketide synthases are aggregates of monofunctional proteins, and Type III polyketide synthases do not use acyl carrier protein domains.

Unlike fatty acid biosynthesis, in which each successive chain elongation step is followed by a fixed sequence of ketoreduction, dehydration and enoyl, reduction as described below, the individual chain elongation intermediates of polyketide biosynthesis undergo all, some, or no functional group modifications, resulting in a large number of chemically diverse products. Additional degrees of complexity arise from the use of different starter units and chain elongation units as well as the generation of new stereoisomers.

The order of complete polyketide-synthesis as directed by a polyketide synthase follows (in the order N-terminus to C-terminus): starting or loading the initial carbon building blocks onto an acyl carrier protein, elongation modules which catalyze the extension of the growing macrolide chain and termination modules that catalyze the release of the synthesized macrolide. Component domains or separate enzyme functionalities active in this biosynthesis include acyl-transferases for the loading of starter, extender and intermediate acyl units; acyl carrier proteins which hold the growing macrolide as a thiol ester; β-keto-acyl synthases which catalyze chain extension; β-keto reductases responsible for the first reduction to an alcohol functionality; dehydratases which eliminate water to give an unsaturated thiolester; enoyl reductases which catalyse the final reduction to full saturation; and thiolesterases which catalyze macrolide release and cyclization.

In some embodiments, the genetically modified microorganism useful for the methods disclosed herein comprises a heterologous nucleotide sequence encoding an enzyme that can condense at least one of acetyl-CoA and malonyl-CoA with an acyl carrier protein, e.g. an acyl-transferase.

In some embodiments, the genetically modified microorganism disclosed herein comprises a heterologous nucleotide sequence encoding an enzyme that can condense a first reactant selected from the group consisting of acetyl-CoA and malonyl-CoA with a second reactant selected from the group consisting of malonyl-CoA or methylmalonyl-CoA to form a polyketide product, e.g. a β-keto-acyl synthase.

In some embodiments, the polyketide producing cell comprises a heterologous nucleotide sequence encoding an enzyme that can reduce a β-keto chemical group on a polyketide compound to a β-hydroxy group, e.g. a β-keto reductase.

In some embodiments, the genetically modified microorganism disclosed herein comprises a heterologous nucleotide sequence encoding an enzyme that can dehydrate an alkane chemical group in a polyketide compound to produce an α-β-unsaturated alkene, e.g. a dehydratase.

In some embodiments, the polyketide producing cell comprises a heterologous nucleotide sequence encoding an enzyme that can reduce an α-β-double-bond in a polyketide compound to a saturated alkane, e.g. an enoyl-reductase.

In some embodiments, the polyketide producing cell comprises a heterologous nucleotide sequence encoding an enzyme that can hydrolyze a polyketide compound from an acyl carrier protein, e.g. a thioesterase.

In some embodiments, the polyketide producing cell comprises one or more heterologous nucleotide sequences encoding an enzyme comprising a KS catalytic region. In some embodiments, the polyketide producing cell comprises one or more heterologous nucleotide sequences encoding an enzyme comprising an AT catalytic region. In some embodiments, the polyketide producing cell comprises more than one heterologous nucleotide sequence encoding an enzyme comprising an AT catalytic region. In some embodiments, the polyketide producing cell comprises one or more heterologous nucleotide sequences encoding an enzyme comprising a CLF catalytic region. In some embodiments, the polyketide producing cell comprises one or more heterologous nucleotide sequences encoding an enzyme comprising an ACP activity. In some embodiments, the polyketide producing cell comprises more than one heterologous nucleotide sequence encoding an enzyme comprising an ACP activity.

In a particular embodiment, the polyketide producing cell comprises a minimal aromatic PKS system, e.g., heterologous nucleotide sequences encoding an enzyme comprising a KS catalytic region, an enzyme comprising an AT catalytic region, an enzyme comprising a CLF catalytic region, and an enzyme comprising an ACP activity, respectively. In a particular embodiment, the polyketide producing cell comprises a minimal modular PKS system, e.g., heterologous nucleotide sequences encoding an enzyme comprising a KS catalytic region, an enzyme comprising an AT catalytic region, and an enzyme comprising an ACP activity, respectively. In yet another particular embodiment, the polyketide producing cell comprises a modular aromatic PKS system for de novo polyketide synthesis, e.g., heterologous nucleotide sequences encoding an enzyme comprising a KS catalytic region, one or more enzymes comprising an AT catalytic region, and one or more enzymes comprising an ACP activity, respectively.

In some embodiments, the polyketide producing cell comprises a minimal PKS system, e.g., a minimal aromatic PKS system or minimal modular PKS system, further comprises additional catalytic activities which can contribute to production of the end-product polyketide. In some embodiments, the polyketide producing cell comprises one or more heterologous nucleotide sequences encoding an enzyme comprising a cyclase (CYC) catalytic region, which facilitates the cyclization of the nascent polyketide backbone. In some embodiments, the polyketide producing cell comprises one or more heterologous nucleotide sequences encoding an enzyme comprising a ketoreductase (KR) catalytic region. In some embodiments, the polyketide producing cell comprises one or more heterologous nucleotide sequences encoding an enzyme comprising an aromatase (ARO) catalytic region. In some embodiments, the polyketide producing cell comprises one or more heterologous nucleotide sequences encoding an enzyme comprising an enoylreductase (ER) catalytic region. In some embodiments, the polyketide producing cell comprises one or more heterologous nucleotide sequences encoding an enzyme comprising a thioesterase (TE) catalytic region. In some embodiments, the polyketide producing cell further comprises one or more heterologous nucleotide sequences encoding an enzyme comprising a holo ACP synthase activity, which effects pantetheinylation of the ACP.

In some embodiments, the polyketide producing cell further comprises one or more heterologous nucleotide sequences conferring a postsynthesis polyketide modifying activity. In some embodiments, the polyketide producing cell further comprises one or more heterologous nucleotide sequences encoding an enzyme comprising a glycosylase activity, which effects postsynthesis modifications of polyketides, for example, where polyketides having antibiotic activity are desired. In some embodiments, the polyketide producing cell further comprises one or more heterologous nucleotide sequences encoding an enzyme comprising a hydroxylase activity. In some embodiments, the polyketide producing cell further comprises one or more heterologous nucleotide sequences encoding an enzyme comprising an epoxidase activity. In some embodiments, the polyketide producing cell further comprises one or more heterologous nucleotide sequences encoding an enzyme comprising a methylase activity.

In some embodiments, the polyketide producing cell further comprises one or more heterologous nucleotide sequences encoding a biosynthetic enzyme including, but not limited to, at least one polyketide synthesis pathway enzyme, and enzymes that can modify an acetyl-CoA compound to form a polyketide product such as a macrolide, an antibiotic, an antifungal, a cytostatic compound, an anticholesterolemic compound, an antiparasitic compound, a coccidiostatic compound, an animal growth promoter or an insecticide. In some embodiments, the non-catabolic compound is a polyene. In some embodiments, the non-catabolic compound is a cyclic lactone. In some embodiments, the non-catabolic compound comprises a 14, 15, or 16-membered lactone ring. In some embodiments, the non-catabolic compound is a polyketide selected from the group consisting of a polyketide macrolide, antibiotic, antifungal, cytostatic, anticholesterolemic, antiparasitic, a coccidiostatic, animal growth promoter and insecticide.

In some embodiments, the polyketide producing cell comprises heterologous nucleotide sequences, for example sequences encoding PKS enzymes and polyketide modification enzymes, capable of producing a polyketide selected from, but not limited to, the following polyketides: Avermectin (see, e.g., U.S. Pat. Nos. 5,252,474; 4,703,009; EP Pub. No. 118,367; MacNeil et al., 1993, "Industrial Microorganisms: Basic and Applied Molecular Genetics"; Baltz, Hegeman, & Skatrud, eds. (ASM), pp. 245-256, "A Comparison of the Genes Encoding the Polyketide Synthases for Avermectin, Erythromycin, and Nemadectin"; MacNeil et al., 1992, Gene 115: 119-125; and Ikeda and Omura, 1997, Chem. Res. 97: 2599-2609); Candicidin (FR008) (see, e.g., Hu et al., 1994, Mol. Microbiol. 14: 163-172); Carbomycin, Curamycin (see, e.g., Bergh et al., Biotechnol Appl Biochem. 1992 February; 15(1):80-9); Daunorubicin (see, e.g., J Bacteriol. 1994 October; 176(20):6270-80); Epothilone (see, e.g., PCT Pub. No. 99/66028; and PCT Pub. No. 00/031247); Erythromycin (see, e.g., PCT Pub. No. 93/13663; U.S. Pat. Nos. 6,004,787; 5,824,513; Donadio et al., 1991, Science 252:675-9; and Cortes et al., Nov. 8, 1990, Nature 348:176-8); FK-506 (see, e.g., Motamedi et al., 1998; Eur. J Biochem. 256: 528-534; and Motamedi et al., 1997, Eur. J Biochem. 244: 74-80); FK-520 (see, e.g., PCT Pub. No. 00/020601; and Nielsen et al., 1991, Biochem. 30:5789-96); Griseusin (see, e.g., Yu et al., J Bacteriol. 1994 May; 176(9):2627-34); Lovastatin (see, e.g., U.S. Pat. No. 5,744,350); Frenolycin (see, e.g., Khosla et al., Bacteriol. 1993 April; 175(8):2197-204; and Bibb et al., Gene 1994 May 3; 142(1):31-9); Granaticin (see, e.g., Sherman et al., EMBO J. 1989 September; 8(9):2717-25; and Bechtold et al., Mol Gen Genet. 1995 Sep. 20; 248(5):610-20); Medermycin (see, e.g., Ichinose et al., Microbiology 2003 July; 149(Pt 7):1633-45); Monensin (see, e.g., Arrowsmith et al., Mol Gen Genet. 1992 August; 234(2):254-64); Nonactin (see, e.g., FEMS Microbiol Lett. 2000 Feb. 1; 183(1):171-5); Nanaomycin (see, e.g., Kitao et al., J Antibiot (Tokyo). 1980 July; 33(7):711-6); Nemadectin (see, e.g., MacNeil et al., 1993, supra); Niddamycin (see, e.g., PCT Pub. No. 98/51695; and Kakavas et al., 1997, J Bacteriol. 179: 7515-7522); Oleandomycin (see e.g., Swan et al., 1994, Mol. Gen. Genet. 242: 358-362; PCT Pub. No. 00/026349; Olano et al., 1998, Mol. Gen. Genet. 259(3): 299-308; and PCT Pat. App. Pub. No. WO 99/05283); Oxytetracycline (see, e.g., Kim et al., Gene. 1994 Apr. 8; 141(1):141-2); Picromycin (see, e.g., PCT Pub. No. 99/61599; PCT Pub. No. 00/00620; Xue et al., 1998, Chemistry & Biology 5(11): 661-667; Xue et al., October 1998, Proc. Natl. Acad. Sci. USA 95: 12111 12116); Platenolide (see, e.g., EP Pub. No. 791,656; and U.S. Pat. No. 5,945,320); Rapamycin (see, e.g., Schwecke et al., August 1995, Proc. Natl. Acad. Sci. USA 92:7839-7843; and Aparicio et al., 1996, Gene 169: 9-16); Rifamycin (see, e.g., PCT Pub. No. WO 98/07868; and August et al., Feb. 13, 1998, Chemistry & Biology, 5(2): 69-79); Sorangium (see, e.g., U.S. Pat. No. 6,090,601); Soraphen (see, e.g., U.S. Pat. No. 5,716,849; Schupp et al., 1995, J Bacteriology 177: 3673-3679); Spinocyn (see, e.g., PCT Pub. No. 99/46387); Spiramycin (see, e.g., U.S. Pat. No. 5,098,837); Tetracenomycin (see, e.g., Summers et al., J Bacteriol. 1992 March; 174(6):1810-20; and Shen et al., J Bacteriol. 1992 June; 174(11):3818-21); Tetracycline (see, e.g., J Am Chem Soc. 2009 Dec. 9; 131(48):17677-89); Tylosin (see, e.g., U.S. Pat. Nos. 5,876,991; 5,672,497; 5,149,638; EP Pub. No. 791,655; EP Pub. No. 238,323; Kuhstoss et al., 1996, Gene 183:231-6; and Merson-Davies and Cundliffe, 1994, Mol. Microbiol. 13: 349-355); and 6-methylsalicyclic acid (see, e.g., Richardson et al., Metab Eng. 1999 April; 1(2):180-7; and Shao et al., Biochem Biophys Res Commun. 2006 Jun. 23; 345(1):133-9).

6.13 Production of Fatty Acids

In some embodiments, the non-catabolic compound is a fatty acid. Fatty acids are synthesized by a series of decarboxylative Claisen condensation reactions from acetyl-CoA and malonyl-CoA catalyzed by fatty acid synthases. Similar to polyketide synthases, fatty acid synthases are not a single enzyme but an enzymatic system composed of 272 kDa multifunctional polypeptide in which substrates are handed from one functional domain to the next. Two principal classes of fatty acid synthases have been characterized: Type I fatty acid synthases are single, multifunctional polypeptides common to mammals and fungi (although the structural arrangement of fungal and mammalian synthases differ) and the CMN group of bacteria (corynebacteria, mycobacteria, and nocardia). Type II synthases, found in archaeabacteria and eubacteria, are a series of discrete, monofunctional enzymes that participate in the synthesis of fatty acids. The mechanisms fatty acid elongation and reduction is the same in the two classes of synthases, as the enzyme domains responsible for these catalytic events are largely homologous amongst the two classes.

Following each round of elongation of the fatty acid chain in the decarboxylative Claisen condensation reactions, the β-keto group is reduced to a fully saturated carbon chain by the sequential action of a ketoreductase, a dehydratase, and an enol reductase. The growing fatty acid chain moves between these active sites attached to an acyl carrier protein and is ultimately released by the action of a thioesterase upon reaching a carbon chain length of 16 (palmitidic acid).

In some embodiments, the genetically modified microorganism useful for the methods disclosed herein comprises a heterologous nucleotide sequence encoding a biosynthetic enzyme including, but not limited to, at least one fatty acid synthesis pathway enzyme, and enzymes that can modify an acetyl-CoA compound to form a fatty acid product such as a palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid. In some embodiments, the non-catabolic compound is a fatty acid selected from the group consisting of palmitate, palmitoyl CoA, palmitoleic acid, sapienic acid, oleic acid, linoleic acid, α-linolenic acid, arachidonic acid, eicosapentaenoic acid, erucic acid, and docosahexaenoic acid.

In some embodiments, the fatty acid producing cell comprises a heterologous nucleotide sequence encoding an enzyme that can covalently link at least one of acetyl-CoA and malonyl-CoA with an acyl carrier protein, e.g. an acyl-transferase.

In some embodiments, the genetically modified microorganism disclosed herein comprises a heterologous nucleotide sequence encoding an enzyme that can condense acetyl chemical moiety and a malonyl chemical moiety, each bound to an acyl carrier protein (ACP), to form acetoacetyl-ACP, e.g. a β-Ketoacyl-ACP synthase.

In some embodiments, the fatty acid producing cell comprises a heterologous nucleotide sequence encoding an enzyme that can reduce the double bond in acetoacetyl-ACP with NADPH to form a hydroxyl group in D-3-hydroxybutyryl hydroxylase-ACP, e.g. a β-Ketoacyl-ACP reductase.

In some embodiments, the fatty acid producing cell comprises a heterologous nucleotide sequence encoding an enzyme that can dehydrate D-3-Hydroxybutyryl hydroxylase-ACP to create a double bond between the beta- and gamma-carbons forming crotonyl-ACP, e.g. a β-hydroxyacyl-ACP dehydrase.

In some embodiments, the fatty acid producing cell comprises a heterologous nucleotide sequence encoding an enzyme that can reduce crotonyl ACP with NADPH to form butyryl-ACP, e.g. an enoyl ACP reductase.

In some embodiments, the fatty acid producing cell comprises a heterologous nucleotide sequence encoding an enzyme that can hydrolyze a C16 acyl compound from an acyl carrier protein to form palmitate, e.g. a thioesterase.

In some embodiments, the fatty acid producing cell comprises one or more heterologous nucleotide sequences encoding acetyl-CoA synthase and/or malonyl-CoA synthase, to effect increased production of one or more fatty acids as compared to a genetically unmodified parent cell.

For example, to increase acetyl-CoA production, one or more of the following genes can be expressed in the cell: pdh, panK, aceEF (encoding the E1p dehydrogenase component and the E2p dihydrolipoamide acyltransferase component of the pyruvate and 2-oxoglutarate dehydrogenase complexes), fabH, fabD fabG, acpP, and fabF. Illustrative examples of nucleotide sequences encoding such enzymes include, but are not limited to: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), fabF (AAC74179).

In some embodiments, increased fatty acid levels can be effected in the cell by attenuating or knocking out genes encoding proteins involved in fatty acid degradation. For example, the expression levels of fadE, gpsA, idhA, pflb, adhE, pta, poxB, ackA, and/or ackB can be attenuated or knocked-out in an engineered host cell using techniques known in the art. Illustrative examples of nucleotide sequences encoding such proteins include, but are not limited to: fadE (AAC73325), gspA (AAC76632), IdhA (AAC74462), pflb (AAC73989), adhE (AAC74323), pta (AAC75357), poxB (AAC73958), ackA (AAC75356), and ackB (BAB81430). The resulting host cells will have increased acetyl-CoA production levels when grown in an appropriate environment.

In some embodiments, the fatty acid producing cell comprises a heterologous nucleotide sequence encoding an enzyme that can convert acetyl-CoA into malonyl-CoA, e.g., the multisubunit AccABCD protein. An illustrative example of a suitable nucleotide sequence encoding AccABCD includes but is not limited to accession number AAC73296, EC 6.4.1.2.

In some embodiments, the fatty acid producing cell comprises a heterologous nucleotide sequence encoding a lipase. Illustrative examples of suitable nucleotide sequences encoding a lipase include, but are not limited to accession numbers CAA89087 and CAA98876.

In some embodiments, increased fatty acid levels can be effected in the cell by inhibiting PlsB, which can lead to an increase in the levels of long chain acyl-ACP, which will inhibit early steps in the fatty acid biosynthesis pathway (e.g., accABCD, fabH, and fabI). The expression level of PlsB can be attenuated or knocked-out in an engineered host cell using techniques known in the art. An illustrative example of a suitable nucleotide sequence encoding PlsB includes but is not limited to accession number AAC77011. In particular embodiments, the plsB D31 IE mutation can be used to increase the amount of available acyl-CoA in the cell.

In some embodiments, increased production of monounsaturated fatty acids can be effected in the cell by overexpressing an sfa gene, which would result in suppression of fabA. An illustrative example of a suitable nucleotide sequence encoding sfa includes but is not limited to accession number AAN79592.

In some embodiments, increased fatty acid levels can be effected in the cell by modulating the expression of an enzyme which controls the chain length of a fatty acid substrate, e.g., a thioesterase. In some embodiments, the fatty acid producing cell has been modified to overexpress a tes or fat gene. Illustrative examples of suitable tes nucleotide sequences include but are not limited to accession numbers: (tesA: AAC73596, from *E. Coli*, capable of producing $C_{18:1}$ fatty acids) and (tesB: AAC73555 from *E. Coli*). Illustrative examples of suitable fat nucleotide sequences include but are not limited to: (fatB: Q41635 and AAA34215, from *Umbellularia california*, capable of producing $C_{12:0}$ fatty acids), (fatB2: Q39513 and AAC49269, from *Cuphea hookeriana*, capable of producing $C_{8:0}$-$C_{10:0}$ fatty acids), (fatB3: AAC49269 and AAC72881, from *Cuphea hookeriana*, capable of producing $C_{14:0}$-$C_{16:0}$ fatty acids), (fatB: Q39473 and AAC49151, from *Cinnamonum camphorum*, capable of producing $C_{14:0}$ fatty acids), (fatB [M1417]: CAA85388, from m *Arabidopsis thaliana*, capable of producing $C_{16:1}$ fatty acids), (fatA: NP 189147 and NP 193041, from *Arabidopsis thaliana*, capable of producing $C_{18:1}$ fatty acids), (fatA: CAC39106, from *Bradvrhiizobium japonicum*, capable of preferentially producing $C_{18:1}$ fatty acids), (fatA: AAC72883, from *Cuphea hookeriana*, capable of producing $C_{18:1}$ fatty acids), and (fatA1, AAL79361 from *Helianthus annus*).

In some embodiments, increased levels of $C_{10}$ fatty acids can be effected in the cell by attenuating the expression or activity of thioesterase $C_{18}$ using techniques known in the art. Illustrative examples of suitable nucleotide sequences encoding thioesterase $C_{18}$ include, but are not limited to accession numbers AAC73596 and POADA1. In other embodiments, increased levels of $C_{10}$ fatty acids can be effected in the cell by increasing the expression or activity of thioesterase $C_{10}$ using techniques known in the art. An illustrative example of a suitable nucleotide sequence encoding thioesterase $C_{10}$ includes, but is not limited to accession number Q39513.

In some embodiments, increased levels of $C_{14}$ fatty acids can be effected in the cell by attenuating the expression or activity of endogenous thioesterases that produce non-$C_{14}$ fatty acids, using techniques known in the art. In other embodiments, increased levels of $C_{14}$ fatty acids can be effected in the cell by increasing the expression or activity of thioesterases that use the substrate $C_{14}$-ACP, using techniques known in the art. An illustrative example of a suitable nucleotide sequence encoding such a thioesterase includes, but is not limited to accession number Q39473.

In some embodiments, increased levels of $C_{12}$ fatty acids can be effected in the cell by attenuating the expression or activity of endogenous thioesterases that produce non-$C_{12}$ fatty acids, using techniques known in the art. In other embodiments, increased levels of $C_{12}$ fatty acids can be effected in the cell by increasing the expression or activity of thioesterases that use the substrate $C_{12}$-ACP, using techniques known in the art. An illustrative example of a suitable nucleotide sequence encoding such a thioesterase includes, but is not limited to accession number Q41635.

7. EXAMPLES

7.1 Example: Cell Density Measurements

This example describes an exemplary method for determining the cell density ($OD_{600}$) of a yeast cell culture.

An 8 µL sample of a cell culture was combined with 92 µL of Triton OD Diluent (20 g/L Triton X-114, 200 mL/L PEG 200, 200 mL/L 100% ethanol, rest water) in a clear 96-well plate, the solution was agitated at 1,000 RPM for 6 minutes, and the $OD_{600}$ was determined by measuring absorbance at 600 nm on an M5 spectrophotometer (Molecular Devices, Sunnyvale, Calif.).

7.2 Example: UV Methods for Measuring Farnesene Titer

This example describes an exemplary method for determining the amount of farnesene production using an UV assay method. In this UV assay method, farnesene titers are measured using the whole broth followed by direct UV absorbance or gas chromatography.

For preculture conditions, the strains were cultured were gown in sterile 96-well plates (1.1 ml working volume; Axygen) containing 360 µl of Bird Seed Media (BSM, originally described by van Hoek et al. (2000). For the preculture conditions, the carbon source was typically a mixture of 1.4% sucrose and 0.7% maltose, unless indicated otherwise. Single colonies were picked into each well and incubated for approximately 72 hours at 33.5° C., 80% humidity and 1000 rpm (Infors Multitron; ATR Biotec).

For farnesene production experiments, the aforementioned saturated cultures were diluted 1/25 into sterile 1.1 ml plates containing 145 µl of BSM and 5 µl of mineral oil. Typically, the carbon source was either 4% sucrose, or a mixture of 2.3% sucrose and 1.7% maltose, unless indicated otherwise. After 72 hours of culture, farnesene extraction was performed by adding 600 µl of isopropyl alcohol (IPA) to each well. After 30-minute incubation, 8 µl was transferred to a clear bottom assay plate containing 192 µl IPA. Farnesene concentration was measured by UV absorbance at 222 nm on a SpectraMax plate reader.

7.3 Example: Nile Red Based Method for Measuring the Farnesene Titer

This example describes an exemplary Nile Red based method useful for determining the farnesene titer of yeast cell cultures.

A 98 µL sample of a cell culture was transferred into a 96-well black polystyrene flat bottom assay plate, and 2 µL of Nile Red (Invitrogen, Carlsbad, Calif.) dissolved at 100 µg/mL in DMSO was added to each well. Fluorescence levels were immediately measured on an M5 spectrophotometer with excitation at 500 nm and emission at 550 nm.

7.4 Example: Gas Chromatography Based Method for Measuring the Farnesene Titer This example describes an exemplary gas chromatography (GC) based method useful for determining the farnesene titer of yeast cell cultures.

Sample was extracted with methanol-heptane (1:1 v/v), and the mixture was centrifuged to remove cellular material. An aliquot of the methanol-heptane extract was diluted into n-heptane with 0.001% t-caryohyllene (which served as a retention time marker to monitor successful injection and elution during the specified GC oven profile) and then injected onto a methyl silicone stationary phase using a pulsed split injection. Farnesene was separated by boiling point using GC with flame ionization detection (FID).

7.5 Example: Background Strain Engineering

A "non-switchable" farnesene production strains (e.g., Y9213 and Y9709) were derived from a wild-type *Saccharomyces cerevisiae* strain (CEN.PK2) and also comprises the following chromosomally integrated mevalonate pathway genes (shown in FIG. 15) from *S. cerevisiae* under the control of GAL promoters: acetyl-CoA thiolase, HMG-CoA synthase, HMG-CoA reductase, mevalonate kinase, phosphomevalonate kinase, and mevalonate pyrophosphate decarboxylase; and six copies of farnesene synthase mutants from Artemisinin *annua*. This non-switchable strain has GAL80 gene deleted and an additional copy of GAL4 under GAL4oc promoter, wherein the coding sequence of the GAL4 gene of *Saccharomyces cerevisiae* is under regulatory control of an "operative constitutive" version of its native promoter (PGAL4oc; see, e.g., Griggs & Johnston (1991) PNAS 88(19):8597-8601).

Farnesene production in the "non-switchable" strain was then made "switchable," that is, repressible in the presence of maltose. The maltose switchable strain (e.g., Strain H) was built on top of the constitutive strain by chromosomally integrating a copy of GAL80 (SEQ ID NO: 71) under the control of maltose-responsive promoter pMAL32 (SEQ ID NO: 34).

Strain E is also a maltose switchable strain that was built on top of the constitutive parent by chromosomally integrating a copy of GAL80 (SEQ ID NO: 71) under the control of maltose-responsive promoter pMAL32 (SEQ ID NO: 34). This strain has a URA3 marker.

7.6 Example: Tier I Mutagenesis and Screening Maltose Binding Protein ("MBP") Mutants This example describes the initial tier I mutagenesis of nucleic acids encoding wild-type MBP. MBP mutants generated from the mutagenesis were screened to obtain those, which, when fused to a protein of interest, would cause the protein of interest to become maltose dependent in terms of their expression and stability in genetically modified host cells. For example, MBP mutants that act as maltose dependent degrons would switch from a functional (e.g., stable) state in the presence of maltose to a non-functional (e.g., unstable) state in the absence of maltose. In this example, Gal80p was used as a fusion partner for MBP mutants to test whether a MBP mutant fused to Gal80p results in maltose dependent stability to Gal80p.

7.6.1. Materials and Methods

The GeneMorph II Random Mutagenesis Kit from Agilent technologies was used to mutagenize a nucleic acid sequence encoding wild-type MBP (SEQ ID NO: 27 which includes a linker sequence at the C terminus end of the wild-type MBP having SEQ ID NO: 1) by error-prone PCR, using conditions for high, medium or low mutagenesis rates. The following primers PC542 and PC543 were used for to mutagenize the wild-type MBP nucleic acids from the DNA construct (SEQ ID NO: 68), which comprises a GAL80 gene fused in frame to the wild-type MBP gene, flanked by homologous sequences consisting of the upstream nucleotide sequences of the S. cerevisiae GAS2 locus, and a portion of nucleotide sequences encoding the URA3 marker gene:

PC542: CGTTAGCAATATCTCGCATTATAG (SEQ ID NO: 66; a forward primer to mutagenize the wild-type MBP nucleic acids from the DNA construct (SEQ ID NO: 68)); and PC543: CCAAGCACAGGGCAAGATGC (SEQ ID NO: 67; a reverse primer to mutagenize the wild-type MBP nucleic acids from the DNA construct (SEQ ID NO: 68)).

The mutagenized PCR MBP fragment was assembled into the transformation vector using the Gibson Assembly® Cloning Kit from New England Biolabs. The following primers (PC540 and PC541) were designed to amplify part of the DNA construct (SEQ ID NO: 68) lacking the bulk of the MBP sequence but overlapping sequences of the mutagenized fragment, and the mutagenized MBP fragment was assembled into the amplified vector:

PC540: TGACTAACTTACCTTCTTCG (SEQ ID NO: 69; a reverse primer for vector backbone for the DNA construct (SEQ ID NO: 68) for Gibson assembly); and PC541: CAACAACTTGGGTATCGAAGG (SEQ ID NO: 70; a forward primer for vector backbone the DNA construct (SEQ ID NO: 68) for Gibson assembly).

Ten random clones from each mutagenesis reaction were sequenced to confirm that the library contained an appropriate diversity and frequency of mutations. The validated libraries were amplified, cut with PmeI, and transformed into the Y9213-based reporter strain. The Y-9213-based reporter strain PCY757 was constructed by transforming DNA construct MS71316 (SEQ ID NO: 72) into strain Y9709 and subsequently selecting for FOA-resistant colonies that had lost the URA3 marker. The reporter strain PCY757 comprised a LYS2 gene operably linked to the pGAL10 promoter as shown in FIG. 4. The transformants were plated onto CSM-ura-lysine+2% glucose agar plates to select for transformants that failed to express functional Gal80p. Colonies that grew were transferred to the standard solid α-aminoadipate plates with 1% maltose. For example, the α-aminoadipate plates contained 0.167% Bactoyeast nitrogen base without acids and without ammonium sulfate, 2% dextrose, 1% maltose, 0.2% D, L-α-aminoadipic acid, 30 m/L lysine, 2% Bacto-agar, and other standard supplements if they were required by the auxotrophic strain. The general methods for preparing α-aminoadipate plates are described in Keeney & Reed, *J. Microbiology & Biology Education*, vol. 1 (2000) and Chattoo & Sherman, *Genetics* 93: 51-65 (1979), which are incorporated herein by reference in their entirety.

Positive colonies from the counter-selection were streaked out on a plate to single colonies, and the farnesene titer measurements in the production media were measured for the cells cultured in the presence of maltose, followed by in the absence of maltose. In addition to the carbon source, lysine was added to the production media since the host cells comprising MBP mutants were selected for LYS2-phenotype conferred by functional GAL80. Thus, for this example, the production medium for the "off" state contained 2.3% sucrose, 1.7% maltose, and 0.1% lysine. The production medium for the "on" state contained 4% sucrose and 0.1% lysine. The farnesene titer was measured using the UV assay method as described in Example 7.2.

7.6.2. Results and Discussion

A genetic strategy was devised to screen for MBP mutants, which, when fused to constitutively-transcribed GAL80, would cause Gal80p to switch from a functional (e.g., stable) state in the presence of maltose to a non-functional (e.g., unstable) state in the absence of maltose. Gal80p function was reported by the phenotypes ascribed to expression or repression of LYS2 from a Gal80p-regulated promoter (pGAL10) as shown in FIG. 4. When Gal80p is unstable and non-functional, LYS2 is expressed and this confers host cells the ability to grow on media lacking lysine. Media lacking lysine would also exclude cells not expressing LYS2. When Gal80p is stable and functional, LYS2 is not expressed and this confers host cells the ability to grow on media containing α-aminoadipate as the sole nitrogen source. The α-aminoadipate media also prevent LYS2-expressing cells from growing. The expected phenotypes were validated by introducing pGAL80>GAL80 (encoding always-stable Gal80p) and pGAL80>D_GAL80 (e.g., SEQ ID NO: 71 encoding constitutively unstable Gal80p due to its fusion to the constitutive degron at its N terminus to increase protein turnover) into the reporter strain and growing the strains on the two types of media. FIG. 4 illustrates the genetic strategy as well as the validated controls for growth on the two types of selection media.

A library containing PCR-mutagenized MBP fused to GAL80 expressed from the native pGAL80 promoter was integrated into the GAS2 locus of the Y9213 background reporter strain containing pGAL10>LYS2. The transformants were first plated on media lacking lysine and maltose to select for MBP mutations that had inactivated GAL80. Cells that grew could contain MBP mutations that generally destabilized Gal80p regardless of the absence of maltose. To exclude generally destabilizing mutations, colonies that grew on the first plated on media lacking lysine and maltose were counter-selected on media containing maltose and α-aminoadipate as the sole nitrogen source. Only cells containing Gal80p that could become stable in the presence of maltose should be able to grow on the counter-selective media.

Sixty-six putative MBP mutants were obtained from the selection/counter-selection process described above. They were analyzed to assess their switchability for farnesene production in the presence or in the absence of maltose. The reporter strain (Y9213 background) produces farnesene with pathway genes under the control of GAL regulon promoters. Any real mutations that conferred conditional Gal80p stability in a maltose-dependent manner should also cause farnesene production to switch in a maltose-dependent manner.

The results are shown in FIG. 5. Each MBP mutant is indicated by a square marker, and the value of the ratio of farnesene titer in the absence of maltose to that in the presence of maltose is indicated by the size of the marker. The controls for the constitutive producer and non-producer are indicated on the graph, as is the theoretical position of a perfectly switching strain. As shown in FIG. 5, although none of the MBP mutants performed as a perfect switch (i.e., no production of farnesene in the presence of maltose and a high production of farnesene in the absence of maltose), the screen identified numerous MBP mutants that were able to produce more farnesene in the absence of maltose than in the presence of maltose. Among these mutants, MBP domains from MBP mutants L8, H8, H9, H10, M1, M5, and M13 were cloned and sequenced.

7.7 Example: Tier II Optimization: Construction of Combinatory Library

7.7.1. Materials and Methods

Primers were designed to contain degenerate bases at locations where SNPs had been identified (to encode both wild-type sequence and mutated sequence/sequences) from the MBP mutants obtained from tier I mutagenesis. The combinatorial library was constructed by using the Quickchange multi-site mutagenesis kit (Agilent Technologies) to incorporate the primer sequences randomly into a DNA construct having SEQ ID NO: 73 (containing MBP L8 mutant) or a DNA construct having SEQ ID NO: 74 (containing MBP M5 mutant). DNA construct S69250 comprises a pGAL80 promoter operably linked to fusion nucleic acids comprising a GAL80 gene fused to MBP mutant L8 nucleic acids, flanked by upstream sequences of the *S. cerevisiae* GAS2 locus and a portion of URA3 marker gene. The DNA construct comprise a pGAL80 promoter operably linked to a fusion nucleic acids comprising a GAL80 gene fused to MBP mutant M5 nucleic acids, flanked by upstream sequences of the *S. cerevisiae* GAS2 locus and a portion of URA3 marker gene. The Quickchange multi-site mutagenesis kit has been reported to be able to randomly combine up to 49 different SNPs (single nucleotide polymorphism) in one single reaction. Sequencing of random clones from the library confirmed a good rate of incorporation of mutant SNPs.

The library was transformed into the reporter strain. The transformation mix representing approximately 20,000 transformants was directly inoculated into liquid non-maltose-containing media lacking lysine and uracil (i.e., the same media as described in Example 7.6 except without agar). Transformants bearing constructs that confer better "on" states would grow faster in the absence of lysine and become enriched. The resulting culture was then re-inoculated into maltose media containing α-aminoadipate (i.e., the same media as described in Example 7.6 except without agar), which selects for cells that can impose a tight "off" state in the presence of maltose. The rounds of competitive selective/counter-selective growth scheme are illustrated in FIG. 6. After a few passages in alternating non-maltose minimal media followed by maltose-containing alpha-aminoadipate media, the positive colonies from the last round of counter-selection were streaked out on a plate to single colonies. Single colonies were cultured under pre-culture conditions, and the farnesene production from the cells in the presence or in the absence of maltose in the production media were measured as described above in Example 7.2. The farnesene production media used in this example were same as those described in Example 7.6.

7.7.2. Results and Discussion

Sixteen best MBP mutants from Example 7.6 were sequenced. These MPB mutants were best in terms of their "on" state for farnesene production and/or "off" state for shutting down farnesene production. Sixty-eight unique mutations were identified from these sixteen MBP mutants. A few of these mutations occurred multiple times and were derived from independent mutagenic PCR reactions, suggesting that they were significant causal mutations. In one case, the same codon was mutated to encode two different amino acids in two different MBP mutants. The identified mutations were mapped to the crystal structure of MBP. These mutations were analyzed using a stability prediction algorithm (e.g., http://mordred.bioc.cam.ac.uk/~sdm/sdm.php). A large number of the identified mutations were predicted to destabilize the MBP structure, in accordance with the original theory that destabilizing mutations could make the protein dependent on binding to its ligand for stability. In this example, it was tested whether combining destabilizing mutations identified from separate MBP mutants could increase the dependence of stability on binding to maltose even more, thereby increasing the differential between the stable and unstable states of the MBP mutants.

To obtain additional MBP mutants with a potentially increased differential between the stable and unstable states, a combinatorial library of identified mutations was generated. In order to identify cells with the combination of mutations that resulted in the best switching (between "on" and "off" states), the library of transformants were subjected to a growth competition regime as shown in FIG. 6 where they were alternatively grown in the liquid medium that favored growth when Gal80p was unstable in the absence of maltose followed by growth in the liquid medium that favored growth when Gal80p was stable in the presence of maltose. After rounds of selection and counter-selection, cells were plated out for growth into single colonies. These colonies represent additional MBP mutants obtained by the Tier II optimization process.

The additional MBP mutants obtained by the Tier II optimization process were cultured in the culture medium including or excluding maltose, respectively, to assess farnesene production under fermentation conditions intended to serve as "off" and "on" state. FIGS. 7A and 7B show the results when additional mutations were combined with an original MBP mutant L8, and the combinatorial library was subjected to the growth competition regime after 1 round of selection/counter-selection (FIG. 7A) or after 3 rounds of selection/counter-selection (FIG. 7B). The original MBP mutant L8 had a relatively good "on" state (i.e., a high level of farnesene production in the absence of maltose) but less than ideal "off" state. After 3 rounds of selection/counter-selection, strains derived from the original MBP mutant L8 with improved "off" states were obtained. As shown in FIG. 7B, a number of new MBP mutants (represented by squares on the graph) shifted to the left of the original L8 MBP mutant, indicating that their farnesene production during "off" state is less than the original L8 MBP mutant and close to that of the non-farnesene producing control strain. One of the best MBP mutants obtained during this Tier II optimization was L8_v4d (see, e.g., FIG. 10B). Another original MBP mutant M5, with a good "off" state but less than ideal "on" state, was combined with the identified mutations. After 3 rounds of selection/counter-selection process shown in FIG. 6, strains with improved "on" states were identified (data not shown). These results indicate that the growth competition assay can be used as a powerful strategy to select for desired mutations that can be coupled to growth phenotypes.

7.8 Example: Tier III Optimization to Engineer an Unstable MBP in the Absence of Maltose

7.8.1. Materials and Methods

A different host strain was constructed by transforming DNA construct MS85927 (SEQ ID NO: 75) into Y9709 (resulting in PCY816). DNA construct MS85927 includes a gene encoding GFP operably linked to pTHD3 promoter and a URA3 marker flanked between GAS2 upstream and downstream sequences for integration into the host genome at the GAS2 locus. A fragment containing MBP L8_v4d from DNA construct S73873 (SEQ ID NO: 76) was mutagenized using the GeneMorph II Random Mutagenesis Kit from Agilent technologies. Mutagenized DNA was transformed directly into PCY816 together with pAM2947 plasmid (SEQ ID NO: 77; F-CphI gene operably linked to pTDH3 promoter, kanmx4-marked, Cen-ARS) encoding the CphI nuclease. See FIG. 8A for the genetic strategy. The transformation mix was directly inoculated into liquid media containing 5-FOA (5-fluoro-orotic acid) lacking maltose and allowed to grow into a culture. Cells from the resulting culture were sorted for dimly fluorescing cells on the GFP channel (530/11 band) using the FACSAria (BD Sciences).

Sorted cells were inoculated into BSM media containing uracil and maltose, and the sorted cells were grown in the BSM media. Cells from this culture were then sorted for brightly fluorescing cells using the FACSAria. The brightly fluorescing cells were plated out on plates, and single colonies were picked and cultured in 96-well plates to form pre-cultures. The pre-cultures were then inoculated into uracil-supplemented production media plates containing no maltose or with maltose. After 24 hours of growth in the production media (see Example 7.2 for the description of production media), the GFP intensity was measured using the Guava flow cytometer for each of the production conditions.

7.8.2. Results and Discussions

Measurements of fluorescent intensity of GFP fused to various MBP mutants from the combinatorial library growth competition selection from the Tier II optimization process identified L8_v4d as the MBP mutant with the best maltose-dependent stability differential (see, e.g., FIG. 8B). However, in the absence of maltose, the residual GFP expression could still be detected for L8_v4d. Direct mutagenesis of MBP mutant L8_v4d was performed to obtain additional MBP mutants which could potentially reduce the residual GFP expression in the absence of maltose. MBP mutants with reduced residual GFP expression in the absence of maltose would be particularly useful in controlling expression of genes with native promoters or of genes that were already expressed at very low levels.

A MBP mutant screening was performing using cell sorting as described above in the materials and methods section. Using this strategy, additional maltose dependent MBP mutants were obtained. These include MBP mutants 3A6, 4D3, 5A2, and 5F3. MBP mutants 4-H10, 1-B9, 4-G10, 4-F11, 2-F10, 2-E8, 2-G8, 1-F7, 4-H4, and 2-A4 were also identified from Tier III mutagenesis. As shown in FIG. 8B, these MBP mutants also depend on maltose content in the culture medium for their stability.

FIG. 8C also illustrates the fluorescent intensity of GFP fused to wild-type MBP. The GFP fused to wild-type MPB was not destabilized in the absence of maltose compared to in the presence of maltose. This result is in contrast to GFP fused to various MBP mutants, which were destabilized and expressed at reduced levels in the absence of maltose compared to in the presence of maltose.

7.9 Example: Using Maltose Dependent Degrons to Control the Stability of Constitutively-Expressed Gal80 Protein and their Effects on Farnesene Production This example illustrates that MBP mutants obtained from Tier I through Tier III mutagenesis can be used as maltose dependent degrons to control the stability of constitutively expressed Gal80 protein (e.g., using native pGAL80 promoter). Each MBP domain from the mutant strains was cloned, sequenced, and re-fused to a vector containing a GAL80 gene operably linked to its native promoter pGAL80. The MBP mutant strains were tested to confirm their maltose dependent farnesene production.

7.9.1. Materials and Methods

The strains comprising MBP mutants were cultured for 72 hours under preculture conditions as described in Example 7.2. For farnesene production experiments, the aforementioned cultures were diluted and cultured in production media described in Example 7.2. In the production media, the carbon source was either 4% sucrose ("on" state) or a mixture of 2.3% sucrose and 1.7% maltose ("off" state). After 72 hours of culture, farnesene extraction was performed, and farnesene concentration was measured by UV absorbance at 222 nm on a SpectraMax plate reader as described in Example 7.2.

7.9.2. Results and Discussions

The results are shown in FIGS. 9A through 9C. The plots on the top panel represent farnesene production without any maltose in the production medium for strains that express various fusion proteins comprising Gal80p fused to wild-type MBP or MBP mutants operably linked to a pGal80 promoter. The plots on the bottom panel represent farnesene production with maltose in the production medium for the same set of strains shown on the top panel.

As shown in FIG. 9A, for the strains which express wild-type MBP fused in frame to Gal80p (second from the right), there was virtually no production of farnesene (only background measurements) either in the presence or in the absence of maltose. By contrast, for strains comprising MBP mutants H8, H9, H10, M1, M5, and M13, farnesene production in the absence of maltose ("on" state) was at least about 10% greater, typically at least about 50% greater than in the presence of maltose ("off" state). In this group, MBP mutant M5 has the best "on" state response. However, the "on" state response of host cells comprising MBP mutant M5 was reduced compared to the constitutively farnesene producing control Y9213 by about 46%.

Similarly, FIG. 9B illustrates farnesene production from strains which express Gal80p fused in frame to various MBP mutants. As shown in FIG. 9B, for strains comprising MBP mutants 3A6, 4D3, 5A2, and 5F3, farnesene production from the strains in the absence of maltose ("on" state) was at least about 50% greater than in the presence of maltose ("off" state).

FIG. 9C illustrates farnesene production from the strain which expresses Gal80p fused in frame to MBP mutant L8. As shown in FIG. 9C, farnesene production from the strain in the absence of maltose ("on" state) was at least about 280% greater than in the absence of maltose ("off" state). The farnesene production from this mutant strain during the "on" state was comparable (about 90%) to that of non-switchable farnesene producing control strain Y9213. The farnesene production from *Saccharomyces cerevisiae* strain Y17025 (CEN.PK) which does not comprise the heterologous mevalonate pathway enzyme and which contains pGAL80>GAL80 gene without MBP mutants produced virtually no farnesene (only background measurements).

These results indicate that these MBP mutants, in the presence of maltose, are stable and therefore fusion proteins comprising Gal80p fused in frame to MBP mutants repress Gal4p, reducing expression of biosynthetic pathway genes necessary to produce farnesene. In the absence of maltose, however, Gal80p fused in frame to MBP mutants is destabilized, relieving Gal4p from being repressed by the fusion protein, therefore, resulting in higher expression of biosynthetic pathway genes necessary to produce farnesene.

7.10 Example: Combining MBP Mutants that are Maltose Dependent Degrons with the Maltose-Responsive Promoter This example illustrates that MBP mutants behaving as maltose dependent degrons can be combined with maltose-responsive promoters to control farnesene production at both transcription and post-translational levels.

7.10.1. Materials and Methods

As shown in FIG. 10, two isogenic strains were generated by varying the specific switch constructs. The parent strain D is similar to strains Y9213 and Y9709 and comprises heterologous nucleic acids that encode mevalonate pathway enzymes and farnesene synthase with GAL80 gene deleted as described in Example 7.5. Strains B and C are isogenic strains as strain D, except that these strains comprise nucleic acids encoding Gal80p fused to a MBP mutant operably linked to a maltose-responsive promoter. For example, strain B is a transformant generated after introducing a DNA construct MS85487 which includes promoter pMal_32_v1 (SEQ ID NO: 78) operably linked to nucleic acids encoding Gal80p fused in frame to MBP mutant L8v4d; Strain C is a transformant generated after introducing a DNA construct MS85488 which comprises promoter pMAL32 (SEQ ID NO: 34) operably linked to nucleic acids encoding Gal80p fused in frame to MBP mutant L8_v4d. Promoter pMAL32 used in strain C is stronger than promoter pMAL_32_v1 (SEQ ID NO: 78).

The strains were cultured for 72 hours under preculture conditions as described in Example 7.2. For farnesene production experiments, the aforementioned cultures were diluted and cultured in production media as described in Example 7.2. In the production media, the carbon source was either 4% sucrose ("on" state) or a mixture of 2.3% sucrose and 1.7% maltose ("off" state). After 72 hours of culture, farnesene extraction was performed and farnesene concentration was measured by UV absorbance at 222 nm on a SpectraMax plate reader as described in Example 7.2.

7.10.2. Results and Discussions

In Example 7.9, MBP mutants were used by themselves to control the stability of constitutively-expressed GAL80 transcribed from its native promoter in host cells. In this example, the maltose control of GAL80 transcription with maltose control of GAL80 stability were combined by integrating and operably linking various MBP mutants fused to Gal80p a maltose-inducible promoter. The results shown in FIG. 10 illustrate that various combinations of maltose-responsive promoters and MBP mutants resulted in good switchability for these new strains B and C. In addition, farnesene productions from both strains B and C during "on" state in the absence of maltose were comparable to non-switchable farnesene producing control.

7.11 Example: Half-Lives of Fusion Proteins Comprising MBP Degrons

This example illustrates that MBP mutants obtained from Tier I through Tier III mutagenesis can be used as maltose dependent degrons to increase the degradation rate for their fusion partner, GFP.

7.11.1. Materials and Methods

All the GFP DNA constructs (e.g., a GFP gene fused to a MBP mutant gene operably linked to a pTDH3 promoter) were transformed into Y9709 and integrated at GAS2 locus using URA3 as selection marker. Strains were inoculated and grown in BSM 1.4% sucrose and 0.7% maltose medium at 30 degrees for 2 days to induce GFP expression. Two days later, cultures were diluted by 25 fold in BSM 2% sucrose. GFP fluorescence was measured by Guava flow cytometer during log growth phase (e.g., immediately before, 1.75, 3, 4.25, 6, 7.25, and 8.5 hours after dilution). The reduction in GFP fluorescence was reported in log scale after background subtraction, which is shown in FIG. 11A. Since GFP fluorescence decrease shown in FIG. 11A reflects the effects of both GFP protein degradation and GFP dilution by cell division during log phase. In order to obtain the true GFP degradation rate, the growth rate was subtracted from GFP fluorescence decrease rate. Growth rate of Y9213 in sucrose ($\mu$=0.15 hr$^{-1}$) was subtracted to correct the half-lives. The true GFP degradation rates were then converted to GFP half-lives as shown in FIG. 11B. Half-lives of GFP are shown in FIG. 11B without taking into account the GFP transcription change in sucrose medium.

7.11.2. Results and Discussions

Half of GFP protein decayed in 8.7 hours when it was not fused to MBP. Half of GFP protein fused in frame to wild-type MBP decayed in 11.6 hours. When GFP was fused to MBP mutants, the degradation speed was dramatically increased and the half-lives of the fusion proteins were shortened to 1.4-5.0 hours (See FIG. 11B). Among these, two MBP mutants (5A2, 5F3) had the shortest half-lives as measured by GFP intensity in the absence of maltose (see FIG. 11A). These results indicate that MBP mutants facilitate protein degradation in the absence of maltose.

7.12 Example: MBP-Based Maltose Switch Prevents Breakage Due to GAL80 Reactivation This example provides results demonstrating that host cells capable of producing the isoprenoid farnesene, and comprising the MEV pathway under negative regulation by a maltose switch and a maltose dependent degron, display improved stability of production of farnesene in a long fermentation run when the build stage of the fermentation is performed in the presence of maltose (thereby effecting an "off" state), compared to production from a constitutively producing strain that produced farnesene throughout the build stage.

7.12.1. Material and Methods

The non-switchable farnesene producing control strain and the maltose switchable strain (pMAL32>GAL80 fused to MBP_L8) were initially struck out on a solid agar medium containing 2% dextrose, 1% maltose and grown at 30° C. until colonies were visible. Seed vials were prepared by inoculating a single colony into a 15 ml tube containing 3 ml of BSM 2% sucrose, 1% maltose. After approximately 48 hours, all 3 ml was transferred into 500 mL disposable shake flask containing 125 mL of 2% sucrose, and 1% maltose BSM (seed vial medium). Cells were grown at 30° C. in a shaker at 200 rpm until an OD$_{600}$ between 4 and 7 was reached. Once the desired OD has been reached, 36 ml of a sterile 50% glycerol stock was added to 84 ml of culture, the suspension was aliquoted into seed vials, and the seed vials were slowly frozen to −80° C. at a rate of approximately 1° C./min. Biomass build prior to the fermentation was accomplished by thawing one or more seed vials into a 250 mL shake flask containing 50 mL of 1.6% sucrose, 0.4% glucose, and 1% maltose BSM (biomass build medium), and by growing the culture for 24 hours at 34° C. and 200 RPM. A portion of this culture was then transferred a 500 ml flask containing 100 ml of the same medium to reach a starting OD$_{600}$ of 0.1, and grown for an additional 24 hours. 25 ml of this culture was then used to inoculate a 0.5 L fermentor containing 225 ml of BSM media lacking any sugar. Cane syrup (without any maltose) was fed on demand and the fermentation was run for 13 days at 34° C. following a feeding protocol that maximized farnesene yield.

The total amount of farnesene produced and the total sugar consumed by the cells were monitored daily, and the cumulative farnesene yield was measured and plotted against time as shown in FIG. 12A. The cumulative farnesene yield shown in FIG. 12A was normalized against the cumulative farnesene yield value of the maltose switchable strain measured at 168 hours.

The total amount of farnesene produced and the total sugar consumed by the cells were updated daily, and the ratio of these two values was determined for each 24 hour interval, normalized by the highest yield observed in any interval, and plotted as normalized fermentor interval yield, as shown in FIG. 12B. The normalized farnesene interval yield shown in FIG. 12B was normalized against the interval farnesene yield value of the maltose switchable strain measured at 168 hours.

7.12.2. Results and Discussion

As shown in FIG. 12A, the normalized cumulative yield of the non-switchable parent strain declined continuously from its peak at about 120 hours to below about 20% of the peak yield of the switchable child strain at 168 hours. By contrast, the maltose switchable strain maintained the normalized cumulative yield into about 216 hours. Similarly, as shown in FIG. 12B, the normalized interval farnesene yield of the non-switchable parent strain declined continuously from its peak at about 100 hours to well below 40% of the peak yield of the maltose switchable strain at 168 hours. By contrast, the maltose switchable strain maintained a normalized yield that was about 80% of its peak into 216 hours. Thus, these results demonstrate that a maltose switchable strain (pMAL32>GAL80 fused to MBP_L8) that turns off farnesene production in the presence of maltose during the build stage of a two-stage fermentation process results in improved production stability of farnesene production during the production stage.

7.13 Example: Construction of pGMAL Promoters

This example illustrates construction of synthetic pGMAL promoters. In this example, exemplary pGMAL promoters were constructed using pGAL1, pGAL2, and/or pGAL7 promoters as background promoters with their Gal4p binding sites removed and different copy numbers of MAL activator binding sequences (e.g., Malx3p) added at different locations within the background promoters.

7.13.1. Materials and Methods

There are four Gal4p binding sites in pGAL1 and pGAL2, and two Gal4p binding sites in pGAL7. All Gal4p binding sites were removed from these promoters. The resulting "empty" promoters were called pGAL1_0, pGAL2_0, and pGAL7_0. One to eight copies of the following MAL activator binding sequences were inserted in these empty GAL promoters: AGAAATAT-TATCTAAAAGCGAGAGTTTAAGCGAGTTGCAAGA (SEQ ID NO: 80); and GTCCGCGAAAATTTCCGGA-TAAATCG (SEQ ID NO: 81). Thirty-four new synthetic promoters were created, and they were named as pGMAL, pG2MAL, and pG7MAL (see FIGS. 14A and 14B) Four hybrid promoters were also constructed by joining partial sequences of pGAL1_0, pGAL2_0, and pGAL7_0 with a few MAL binding sites. These promoters were named as pG721 MAL_v11, pG271 MAL_v12, pG172 MAL_v13, and pG712 MAL_v14. Some of these and other new synthetic promoters were used to drive GFP expression at GAS2 locus in the farnesene production strain Y9213.

7.13.2. Results and Discussions

For a genetic switch system, it is desirable to have an inducible promoter which does not express any genes operably linked thereto without an inducing agent. It is also desirable to have inducible promoters with a varying degree of strength to control gene expression so that production of gene products can be adjusted to an appropriate level.

Synthetic pGMAL promoters were generated because host cells comprising a natural pMAL promoter operably linked to a gene of interest tend to express the gene product at a low level in the culture medium without any maltose. In addition, it was found that the activity of natural pMAL promoters was up-regulated in a culture medium without maltose when host cells were growing at a low growth rate. As illustrated in FIGS. 14A and 14B, synthetic pGMAL promoters were found to be maltose inducible and were not affected by the cell growth rate when host cells were grown in a culture medium which does not include maltose. The results shown in FIGS. 14A and 14B are described in further detail in Example 7.14.

7.14 Example: pGMAL Promoters are Maltose Inducible

This example illustrates that synthetic pGMAL promoters obtained from Example 7.13 are maltose inducible. The promoters are also not affected by the growth rate of host cells in the absence of maltose.

7.14.1. Materials and Methods

Synthetic pGMAL promoters produced from Example 7.13 were used to drive GFP expression at GAS2 locus in Y9213 using URA3 as selection marker. Strains were inoculated and grown in BSM 1.45 sucrose and 0.7% maltose media at 30 degrees for 2 days and then were diluted by 25 fold in the same medium. After 48 hours, GFP fluorescence was measured using Guava flow cytometer. pGAL1, pTDH3, pMAL11, pMAL12, pMAL31, and pMAL32 were used as controls in this experiment. GFP fluorescence data were normalized to the background signal generated by Y9213 without GFP expression. A ladder of maltose inducible promoters was created with promoter strength ranging from slightly above the background (pG7MAL_v2, 108%) to twice of pTDH3 (pGMAL_v16, 9000% of background). Strains with the empty promoters pGAL1_0, pGAL2_0, and pGAL7_0 driving GFP were also measured, and they did not exhibited any GFP fluorescence (data not shown). Leakiness of these promoters at high growth rate (0.15 h$^{-1}$) in BSM 2% sucrose and low growth rate (0.03 hr$^{-1}$) in BSM 2% raffinose plus 0.1% of glucose were also examined.

7.14.2. Results and Discussions

The GFP fluorescence data from various synthetic pGMAL promoters are illustrated in FIGS. 14A and 14B. As shown in FIGS. 14A and 14B, a ladder of synthetic pGMAL promoters with different promoter strength induced by maltose was obtained. In addition, the promoter strength of synthetic pGMAL promoters were relatively unaffected by the cell growth rate. By contrast, pMAL promoters exhibited a relatively large difference in the promoter strength when the cells were cultured in 2% sucrose (providing high cell growth rate) versus in 2% raffinose (providing low cell growth rate). As shown in FIGS. 14A and 14B, some of the promoters (e.g. pGMAL_v5 and pG2MAL_v8) exhibited extremely low leakiness at both high and low growth rates under un-induced condition.

7.15 Example: First Round of Screening of Essential Amino Acid Biosynthesis Genes to Test its Suitability in a Stabilization Construct This example describes screening various combinations of essential amino acid biosynthesis genes operably linked to four native GAL regulon promoters (i.e., pGAL3, pGAL2, pGAL7 and pGAL10) to determine their suitability as stabilization constructs in genetically modified host cells.

TABLE 1

List of GAL regulon promoters and amino acid biosynthesis genes screened during the first round of screen

| pGAL promoters tested | Lysine biosynthesis genes tested | Methionine biosynthesis genes tested |
| --- | --- | --- |
| pGAL3 | LYS1 | HOM2 |
| pGAL2 | LYS2 | HOM3 |
| pGAL7 | LYS4 | HOM6 |
| pGAL10 | LYS9 | MET2 |
| | LYS12 | MET17 |
| | LYS14 | |
| | LYS20 | |

Forty eight combinations of GAL regulon promoters and amino acid biosynthetic genes were transformed into yeast host cells using URA3 as a selective marker. For each combination, a pGal promoter was inserted immediately upstream of the initiation codon of a selected amino acid biosynthetic gene at its endogenous locus by homologous recombination. Two different strains were used for transformation: Y9213 and Y9213 containing native GAL80, which represses expression of enzymes in the biosynthetic pathway for producing farnesene, and therefore, turns off the production of farnesene. A construct useful as a stabilization construct would exhibit differential cell growth in the two strains when essential amino acid (methionine or lysine) is not added to culture medium. If a construct behaves as a suitable stabilization construct, strain Y9213 transformed with such a construct would grow without added essential amino acid (methionine or lysine) in culture media since constitutively expressed transcriptional activator Gal4p in Y9213 would activate expression of the amino acid biosynthesis gene operably linked to a pGal promoter. On the other hand, strain Y9213 containing native GAL80 transformed with the same construct would not grow as well since Y9213 containing native GAL80 will repress the GAL regulon.

The transformants comprising a lysine biosynthetic gene operably linked to a pGAL promoter were plated onto CSM+2% glucose agar plates with 0.2% lysine or onto the plates without lysine. The transformants comprising a methionine biosynthetic gene operably linked to a pGAL promoter were plated onto CSM+2% glucose agar plates with 20 mg/L methionine or onto the agar plates without methionine. The plates were cultured for 4 to 5 days at 30° C. The colonies that grew on the plates were visually compared.

The transformants comprising a lysine biosynthetic gene operably linked to a pGAL promoter were cultured in a 96-well plate in BSM liquid medium comprising 2% sucrose with 0.1% lysine or the BSM liquid medium without lysine. The transformants comprising a methionine biosynthetic gene operably linked to a pGAL promoter were cultured in a 96-well plate in BSM liquid media comprising 2% sucrose with 20 mg/L methionine or the BSM liquid medium without methionine. The plates were cultured for about 1 to 2 days at 30° C. The cell densities of the transformants grown with and without their respective essential amino acids were also compared visually.

Based on the visual comparison, it was found that several combinations of amino acid biosynthesis genes, when coupled to the GAL regulon, were able to prevent cell growth in strain Y9213 containing native GAL80 strain but not in strain Y9213. For example, MET2, LYS2, LYS1 and LYS4 genes coupled to all 4 pGAL promoters prevented cell growth in Y9213 containing native GAL80 strain but not in Y9213 strain when cultured in culture media lacking lysine (or methionine for MET2 construct). LYS9, when coupled to pGAL2 or pGAL3, was able to prevent cell growth in strain Y9213 containing native GAL80 but not in strain Y9213. These results indicated that various combinations of amino acid biosynthetic genes operably linked to pGAL promoters are suitable in generating GAL regulon based conditional auxotrophy in yeast cells.

7.16 Example: Second Round of Screening of Essential Amino Acid Biosynthesis Genes This example describes a second round of screening of essential amino acid biosynthesis genes from Example 7.15, operably linked to additional pGAL promoters to determine their suitability as a stabilization construct in genetically modified host cells.

As shown in Table 2 below, a more comprehensive promoter swap library was generated for the eight amino acid synthesis genes selected. pGALx_v # promoters are engineered pGAL promoters that have increased or reduced promoter strength by altering the number and location of Gal4p-binding sites; these are derived from native pGAL promoters (denoted by x in the name), and the engineered versions of the promoters have a version number in their names following the name of the original native promoter from which they were derived. Each of lysine or methionine biosynthesis gene for *Saccharomyces cerevisiae* is publicly available and can be obtained from, e.g., the yeast genome database (world wide web address:yeastgenome.org) or from GENBANK. The nucleotide sequences of lysine and methionine biosynthesis genes used in the examples section are also provided in the Sequence Listing.

TABLE 2

List of promoters and genes screened in the second round

| pGAL promoters tested | Lysine or methionine biosynthesis genes tested |
| --- | --- |
| pGAL3 | LYS1 |
| pGAL2 | LYS2 |
| pGAL7 | LYS9 |
| pGAL10 | LYS20 |
| pGCY1 | LYS4 |
| pGAL80 | LYS12 |
| pGAL2_v3 | LYS14 |
| pGAL7_v1 | MET2 |
| pGAL2_v4 | |
| pGAL1_v3 | |
| pGAL10_v3 | |
| pGAL2_v2 | |
| pGAL7_v2 | |

During the second round of screening, promoter swap libraries containing various combinations of 13 pGAL promoters (6 native promoters and 7 engineered synthetic promoters) and seven different biosynthesis genes shown in Table 2 were transformed into maltose switch strain H. Strain H contains same nucleic acid elements described above for non-switchable strain Y9213, and was made into a "switchable" strain, that is, repressible in the presence of maltose by chromosomally integrating a copy of GAL80 under the control of maltose-responsive promoter pMAL 32 (SEQ ID NO: 34). For each combination, a pGAL promoter was inserted immediately upstream of the initiation codon of a selected amino acid biosynthetic gene at its endogenous locus by homologous recombination.

The second round of screening for transformants comprising a lysine biosynthetic gene operably linked to a pGAL promoter was performed under four different conditions on CSM+2% glucose agar plates: 1) CSM agar plates containing 2% glucose and 1% maltose but no lysine; 2) CSM agar plates containing 2% glucose, 1% maltose and 0.1% lysine; 3) CSM agar plates containing 2% glucose but no lysine; and 4) CSM agar plates containing 2% glucose and 0.1% lysine. For transformants comprising a methionine biosynthetic gene operably linked to a pGAL promoter, the CSM agar plates contained 20 mg/L methionine instead of lysine in conditions 2) and 4). The plates were cultured for 4 to 5 days at about 30° C. The size and/or densities of colonies grew on plates were visually compared for transformants cultured under four different conditions.

Similar sets of experiments were performed in BSM liquid medium containing 2% sucrose. The transformants comprising a lysine biosynthetic gene operably linked to a pGAL promoter were cultured under the following four conditions: 1) BSM culture medium containing 2% sucrose and 1% maltose but no lysine; 2) BSM culture medium containing 2% sucrose, 1% maltose and 0.1% lysine; 3) BSM culture medium containing 2% sucrose but no lysine; and 4) BSM culture medium containing 2% sucrose and 0.1% lysine. The transformants were cultured for 1 to 2 days at about 30° C. The cell densities of the transformants grown under four different conditions were visually compared.

An optimal combination of promoter and gene would allow transformed cells to grow during the "on" state (production stage) without lysine (or methionine), but would prevent cell growth during the "off" state (build stage) in the absence of lysine (or methionine). The "off" state without lysine (or methionine) condition mimics the reactivation of GAL80, which may occur due to spontaneous mutations in genetically modified yeast during a long fermentation run. Cells containing an optimal combination of promoter and gene should not be able to grow when GAL80 is expressed.

FIG. 18 illustrates the screening strategy and growth phenotypes of Strain H transformed with pGAL10_v3 operably linked to LYS2 (pGAL v3>LYS2). As shown on the top left quadrant of FIG. 18, transformed cells cultured in a culture medium containing maltose but lacking lysine (GAL80 expressed) did not grow on agar plates or in a liquid medium. As shown on the bottom left quadrant of FIG. 18, transformed cells cultured in a culture medium containing dextrose but lacking lysine (no GAL80 expression) grew on agar plates and in a liquid medium. As shown on the top right quadrant of FIG. 18, transformed cells cultured in a culture medium containing maltose and lysine (GAL80 expressed) grew. As shown on the bottom right quadrant of FIG. 18, transformed cells cultured in a culture medium containing dextrose and lysine (no GAL 80 expressed) grew.

Using the screening strategy shown in FIG. 18, transformants comprising various combinations of an amino acid biosynthetic gene operably linked to a pGAL promoters were tested. Among the combinations, the following constructs exhibited a discernable growth phenotype differential: pGAL10_v3>LYS9, pGAL2_v2>LYS1, pGAL2_v3>LYS1, pGAL7_v2>LYS1, pGAL80>LYS1, pGCY1>LYS1. Overall, it was found that synthetic pGAL promoters with low promoter strengths performed best in terms of providing differential cell growth during the "on" versus "off" state of the GAL regulon.

7.17 Example: Additional Testing of Differential Growth Phenotypes Exhibited by Two Stabilization Constructs This example describes additional testing of differential growth phenotypes exhibited by two stabilization constructs in Y9213 strain background.

During the second round of screening, there were a few constructs that showed very low growth, when cultured in a culture medium containing maltose but no added lysine, while retaining good growth when cultured in a culture medium containing sucrose but no added maltose. pGAL2_v3>LYS1 was chosen as a representative construct from this group for further testing. The constructs chosen for further testing in fermentation tanks were pGAL10_v3>LYS9 and pGAL2_v3>LYS1.

Each stabilization construct was transformed into strains were transformed into strain Y9213. For preculture conditions, the strains were cultured were gown in sterile 96-well plates (1.1 ml working volume; Axygen) containing 360 µl of Bird Seed Media (BSM, originally described by van Hoek et al. (2000). For the preculture conditions, the carbon source was typically a mixture of 1.4% sucrose and 0.7% maltose, and 0.1% lysine was added to the culture medium. Single colonies were picked into each well and incubated for approximately 72 hours at 33.5° C., 80% humidity and 1000 rpm (Infors Multitron; ATR Biotec).

For the production stage experiments, the aforementioned saturated cultures were diluted 1/25 into sterile 1.1 ml plates containing 145 µl of BSM and 5 µl of mineral oil. The carbon source was a mixture of 2.3% sucrose and 1.7% maltose. The presence of maltose in the culture medium activates GAL80 expression and therefore is expected to repress expression of LYS1 or LYS9 operably linked to a GAL promoter. During the production stage, the strains were cultured in the presence of 0.1% lysine or in the absence of lysine in a culture medium to determine whether added lysine can alleviate conditional auxotrophy in these strains. After 72 hours of culture, cell densities in the production stage cultures were measured according to techniques described in Example 7.1.

As shown in FIG. 19, both strains containing stabilization constructs showed very low growth in the culture medium without added lysine, whereas they showed good growth in the culture medium with added lysine. The results shown in FIG. 19 indicates that both constructs pGAL10_v3>LYS9 and pGAL2_v3>LYS1 are good candidates as stabilization constructs for stabilizing production of heterologous non-catabolic compounds in genetically modified host cells.

7.18 Example: Stabilization Constructs in Farnesene Producing Strains Stabilize Production of Farnesene in a Long Fermentation Run This example provides results demonstrating that the host cells capable of producing the isoprenoid farnesene, and comprising the MEV pathway under negative regulation by a maltose switch, display improved stability of production of farnesene in a long fermentation run when the host cells were transformed with a stabilization construct (e.g., conditional essential LYS1 or LYS9 gene operably linked to a pGAL promoter).

Both control maltose switchable strain E and these strains transformed with stabilization constructs (pGAL10_v3>LYS9 and pGAL2_v3>LYS1) were initially struck out on a solid agar medium containing 2% dextrose, 1% maltose and 2 g/L of lysine and grown at 30° C. until colonies were visible. Seed vials were prepared by inoculating a single colony into a 15 ml tube containing 3 ml of BSM 2% sucrose, 1% maltose, and 1 g/L of lysine. After approximately 48 hours, all 3 ml was transferred into 500 mL disposable shake flask containing 125 mL of 2% sucrose, 1% maltose, and 1 g/L of lysine BSM (seed vial medium). Cells were grown at 30° C. in a shaker at 200 rpm until an $OD_{600}$ between 4 and 7 was reached. Once the desired OD has been reached, 36 ml of a sterile 50% glycerol stock was added to 84 ml of culture, the suspension was aliquoted into seed vials, and the seed vials were slowly frozen to −80° C. at a rate of approximately 1° C./min. Biomass build prior to the fermentation was accomplished by thawing one or more seed vials into a 250 mL shake flask containing 50 mL of 1.6% sucrose, 0.4% glucose, 1% maltose, 1 g/L of lysine BSM (biomass build medium), and by growing the culture for 24 hours at 34° C. and 200 RPM. A portion of this culture was then transferred a 500 ml flask containing 100 ml of the same medium to reach a starting $OD_{600}$ of 0.1, and grown for an additional 24 hours. 25 ml of this culture was then used to inoculate a 0.5 L fermentor containing 225 ml of BSM media lacking any sugar. Cane syrup (without any maltose or lysine) was fed on demand and the fermentation was run for 13 days at 34° C. following a feeding protocol that maximized farnesene yield.

The total amount of farnesene produced and the total sugar consumed by the cells were updated daily, and the ratio of these two values was determined for each 24 hour interval, normalized by the highest yield observed in any interval, and plotted as normalized as farnesene fermentor interval yield, as shown in FIG. 20. The normalized farnesene interval yield shown in FIG. 20 was normalized against the interval farnesene yield value of strain F measured at 96 hours of the production stage.

As shown in FIG. 20, the normalized interval farnesene yield of the parent maltose switchable strain E peaked at about 120 hours, and the normalized interval farnesene yield declined from its peak to well below about 40% of the peak yield of the switchable child strain with a stabilization construct at 200 hours. By contrast, the child strains comprising a stabilization construct (Strain F comprising pGAL10_v3>LYS9; Strain G comprising pGAL2_v3>LYS1) maintained the normalized interval yield that was at least about 70% of its peak from 120 to about 300 hours. Thus, these results demonstrate that a stabilization construct in genetically modified host cells have a stabilization effect on the production of heterologous compound farnesene during a long fermentation run.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed:

1. A method for producing a heterologous non-catabolic compound, the method comprising:

(a) culturing a population of genetically modified host cell in a culture medium comprising an essential compound, wherein the genetically modified host cell comprises:
   i. a heterologous nucleic acid for producing the heterologous non-catabolic compound, wherein the heterologous nucleic acid is operably linked to a first promoter;
   ii. a nucleic acid encoding a conditional essential gene product of a biosynthetic pathway for producing the essential compound, wherein the nucleic acid is operably linked to a second promoter; and
   iii. a nucleic acid encoding a transcriptional regulator, wherein the first promoter and the second promoter are both regulated by the transcriptional regulator, and wherein expression of the heterologous nucleic acid encoding the enzyme of the biosynthetic pathway and expression of the nucleic acid encoding the conditional essential gene product are limited, and wherein the nucleic acid encoding a transcriptional regulator is operably linked to an inducible promoter, and wherein the inducible promoter is a maltose-responsive promoter; and (b) culturing the population or a subpopulation thereof in a culture medium comprising a sufficiently low amount of or no essential compound under a culture condition which promotes expression of the nucleic acid encoding the conditional essential gene product resulting in production of the essential compound necessary for cell growth, and which culture condition promotes expression of the heterologous nucleic acid operably linked to the first promoter, resulting in increased production of the heterologous non-catabolic compound compared to step (a).

2. The method of claim 1, wherein the heterologous nucleic acid operably linked to the first promoter encodes an enzyme of a biosynthetic pathway for producing the heterologous non-catabolic compound.

3. The method of claim 1, wherein the heterologous nucleic acid operably linked to the first promoter encodes the heterologous non-catabolic compound.

4. The method of claim 3, wherein the heterologous nucleic acid encoding the heterologous non-catabolic compound and the nucleic acid encoding the conditional essential gene product for the biosynthetic pathway for producing the essential compound are regulated as a GAL regulon.

5. The method of claim 1, wherein the transcriptional regulator is transcriptional activator Gal4p.

6. The method of claim 5, wherein the culture medium in step (b) comprises an inducer to induce transcription of the heterologous nucleic acid encoding the transcriptional activator Gal4p.

7. The method of claim 1, wherein the transcriptional regulator is transcriptional repressor Gal80p.

8. The method of claim 7, wherein the culture medium in step (a) comprises an inducer to induce transcription of the heterologous nucleic acid encoding the transcriptional repressor Gal80p.

9. The method of claim 1, wherein the first promoter and the second promoter are selected from the group consisting of pGAL1, pGAL2, pGAL3, pGAL7, pGAL10, pGCY1, pGAL80, and pGAL synthetic promoters.

10. The method of claim 9, wherein the pGAL synthetic promoters are selected from the group consisting of: pGAL2_v3 (SEQ ID NO: 84), pGAL7_v1 (SEQ ID NO: 85), pGAL2_v4 (SEQ ID NO: 86), pGAL1_v3 (SEQ ID NO: 87), pGAL10_v3 (SEQ ID NO: 88), pGAL2_v2 (SEQ ID NO: 89), pGAL7_v2 (SEQ ID NO: 90), a portion thereof that retains promoter function, or a sequence that has at least about 90%, sequence identity to thereof.

11. The method of claim 1, wherein the essential compound is selected from an amino acid, a nucleotide and a fatty acid, and wherein the conditional essential gene product is an enzyme of a biosynthetic pathway for producing the amino acid, the nucleotide, or the fatty acid.

12. The method of claim 11, wherein the essential compound is lysine and the conditional essential gene product is an enzyme in a lysine biosynthetic pathway.

13. A method for producing a heterologous non-catabolic compound, the method comprising:
(a) culturing a population of a genetically modified host cell in a culture medium comprising an essential compound and a carbon source comprising a maltose based inducer, wherein the genetically modified host cell comprises:
  i. a heterologous nucleic acid for producing the heterologous non-catabolic compound, wherein the heterologous nucleic acid is operably linked to a first Gal4p-responsive promoter;
  ii. a heterologous nucleic acid encoding a conditional essential gene product of a biosynthetic pathway for producing an essential compound, wherein the heterologous nucleic acid is operably linked to a second Gal4p-responsive promoter;
  iii. a nucleic acid encoding Gal4p;
  iv. a heterologous nucleic acid encoding Gal80p, operably linked to a maltose-responsive promoter,
wherein the maltose based inducer in the culture medium limits the amount of the non-catabolic compound produced by the genetically modified host cell, and wherein an amount of the essential compound produced by the genetically modified host cell is limited;
(b) culturing the population or subpopulation thereof in a culture medium comprising no added essential compound or a sufficiently low amount of the added essential compound and the carbon source wherein the maltose based inducer is absent or in sufficiently low amounts such that the activity of the maltose-responsive promoter is limited, which, in turn, increases production of the heterologous non-catabolic compound compared to step (a).

14. The method of claim 13, wherein the heterologous nucleic acid operably linked to the first Gal4p-responsive promoter encodes the heterologous non-catabolic compound.

15. The method of claim 13, wherein the heterologous nucleic acid operably linked to the first Gal4p-responsive promoter encodes an enzyme of a biosynthetic pathway for producing the heterologous non-catabolic compound.

16. A method for producing a heterologous non-catabolic compound, the method comprising culturing a genetically modified host cell in a culture medium, wherein the genetically modified host cell comprises:
(a) a heterologous nucleic acid encoding a fusion protein comprising a transcriptional regulator fused in frame to a maltose dependent degron;
(b) one or more heterologous nucleic acids encoding one or more enzymes of a biosynthetic pathway for producing the heterologous non-catabolic compound, wherein each of the heterologous nucleic acids is operably linked to a promoter regulated by the fusion protein; and
(c) a heterologous nucleic acid encoding a cell-growth-affecting protein, wherein the heterologous nucleic acid is operably linked to a promoter regulated by the fusion protein.

17. The method of claim 16, wherein the maltose dependent degron comprises an amino acid sequence having at least about sequence identity to SEQ ID NO: 2 or SEQ ID NO: 28, and comprises one or more variant amino acid residues selected from the group consisting of K7R, I10T, W11G, L21S, V24A, F28Y, D42V, K43E, A64T, F68S, D83G, D88N, P92T, W95R, V98I, N101I, A110T, I117V, P134S, A135T, L136M, M149I, Y168C, Y168N, Y177H, N186S, A187P, L193S, D198V, D210E, A216V, A217D, G229C, I236N, D237N, N242D, L263M, L291V, A304S, T321N, M322L, A339T, A351T, T357S, T367S, S370P, and N374S, wherein positions of one or more variant amino acid residues correspond to amino acid positions of SEQ ID NO: 2 or SEQ ID NO: 28.

18. The method of claim 17, wherein the maltose dependent degron comprises at least one set of variant amino acid residues compared to SEQ ID NO: 2 or SEQ ID NO: 28, and wherein the at least one set of variant amino acid residues is selected from the group of sets of variant amino acid residues consisting of:
(d) I10T, V24A, D42V, K43E, D83G, P92T, M149I, Y168N, N186S, A216V, and T357S;
(e) I10T, V24A, D42V, K43E, D83G, M149I, Y168N, N186S, A216V, and D237N;
(f) I10T, V24A, D42V, K43E, D83G, M149I, Y168N, N186S, A216V, and A339T;
(g) I10T, V24A, D42V, K43E, D83G, M149I, Y168N, N186S, A216V, and N242D;
(h) I10T, V24A, D42V, Al 10T, M149I, and A216V;

(i) I10T, V24A, D42V, K43E, D83G, M149I, Y168N, N186S, and A216V;
(j) L21S, A64T, L136M, Y177H, A187P, A304S, T321N, and A351T;
(k) K7R, D83G, V98I, L193S, I236N, and N374S;
(l) W11G, D88N, P134S, A135T, D210E, and M322L;
(m) I117V, Y168N, G229C, L263M, T367S, and S370P;
(n) F68S, W95R, N186S, and D198V; and
(o) F28Y, K43E, N101I, Y168C, A217D, and L291V.

19. The method of claim 1, wherein the first promoter and the second promoter are identical.

20. The method of claim 1, wherein the first promoter and the second promoter are different.

21. The method of claim 1, wherein the maltose-responsive promoter is selected from the group consisting of pMAL1 (SEQ ID NO: 29), pMAL2 (SEQ ID NO: 30), pMAL11 (SEQ ID NO: 31), pMAL12 (SEQ ID NO: 32), pMAL31 (SEQ ID NO: 33), pMAL32 (SEQ ID NO: 34), pMAL32 v1 (SEQ ID NO:78), pGMAL v5 (SEQ ID NO: 35), pGMAL v6 (SEQ ID NO: 36), pGMAL v7 (SEQ ID NO: 37), pGMAL v9 (SEQ ID NO: 38), pGMAL v10 (SEQ ID NO: 39), pGMAL v11 (SEQ ID NO: 40), pGMAL v12 (SEQ ID NO: 41), pGMAL v13 (SEQ ID NO: 42), pGMAL v14 (SEQ ID NO: 43), pGMAL v15 (SEQ ID NO: 44), pGMAL v16 (SEQ ID NO: 45), pGMAL v17 (SEQ ID NO: 46), pGMAL v18 (SEQ ID NO: 47), pG2MAL v1 (SEQ ID NO: 48), pG2MAL v2 (SEQ ID NO: 49), pG2MAL v3 (SEQ ID NO: 50), pG2MAL v5 (SEQ ID NO: 51), pG2MAL v6 (SEQ ID NO: 52), pG2MAL v7 (SEQ ID NO: 53), pG2MAL v8 (SEQ ID NO: 54), pG2MAL v9 (SEQ ID NO: 55), pG2MAL v10 (SEQ ID NO: 56), pG7MAL v2 (SEQ ID NO: 57), pG7MAL v9 (SEQ ID NO: 58), pG7MAL v6 (SEQ ID NO: 59), pG7MAL v8 (SEQ ID NO: 60), pG7MAL v9 (SEQ ID NO: 61), pG172 MAL v13 (SEQ ID NO: 62), pG271 MAL v12 (SEQ ID NO: 63), pG721 MAL v11 (SEQ ID NO: 64), pG712 MAL v14 (SEQ ID NO: 65), a portion thereof that retains promoter function, and a sequence that has at least about 90% sequence identity to thereof.

22. The method of claim 1, wherein the genetically modified host cell is selected from the group consisting of a fungal cell, a bacterial cell, a plant cell, and an animal cell.

23. The method of claim 22, wherein the genetically modified host cell is a microbial host cell.

24. The method of claim 23, wherein the genetically modified host cell is a yeast cell.

25. The method of claim 24, wherein the genetically modified host cell is *Saccharomyces cerevisiae*.

* * * * *